US006531123B1

(12) United States Patent
Chang

(10) Patent No.: US 6,531,123 B1
(45) Date of Patent: *Mar. 11, 2003

(54) LENTIVIRAL VECTORS

(76) Inventor: Lung-Ji Chang, 3102 57th Ter., NW., Gainesville, FL (US) 32606

( * ) Notice: Subject to any disclaimer, the term of this patent is extended or adjusted under 35 U.S.C. 154(b) by 0 days.

This patent is subject to a terminal disclaimer.

(21) Appl. No.: 09/318,138

(22) Filed: May 25, 1999

Related U.S. Application Data

(63) Continuation-in-part of application No. 08/935,312, filed on Sep. 22, 1997, now Pat. No. 6,207,455, which is a continuation-in-part of application No. 08/848,760, filed on May 1, 1997, now Pat. No. 6,248,721.
(60) Provisional application No. 60/086,635, filed on May 26, 1998.

(51) Int. Cl.⁷ ...................... A61K 48/00; C12N 15/867; C12N 15/63; C12N 5/10
(52) U.S. Cl. ................ 424/93.2; 435/235.1; 435/320.1; 435/325; 435/366; 435/455; 435/456; 435/457; 435/5; 435/6; 536/23.1; 536/23.72; 536/24.1; 424/93.1; 424/93.2; 424/93.6
(58) Field of Search ........................... 435/235.1, 320.1, 435/325, 366, 455, 456, 457, 5, 6; 536/23.1, 23.72, 24.1; 424/93.1, 93.2, 93.6

(56) References Cited

U.S. PATENT DOCUMENTS

| 5,665,557 A | 9/1997 | Sodroski et al. |
| 6,207,455 B1 * | 3/2001 | Chang ........................ 435/457 |

FOREIGN PATENT DOCUMENTS

| WO | WO-91/02805 | 3/1991 |
| WO | WO-99/04026 | 1/1999 |
| WO | WO-99/19501 | 4/1999 |

OTHER PUBLICATIONS

Amendt B. A. et al., "Presence of Negative and Positive cis–Acting RNA Splicing Elements eihtin and Flankin the First tat Coding Exon of Human Immunodificiency virus Type 1" Molecular and Cellular Biology, vol. 14, No. 6, Jun. 1994, p. 3960–3969.
Ashe MP, et al., "Poly(A) site selection in the HIV–1 Provirus: inhibition of promoter—proximal polyadenylation by the downstream major splice donor site." Genes Dev Dec. 1, 1995; 9(23):3008–25.
Ashe MP, et al., "The HIV–1 5' LTR poly(A) site is inactivated by U1 snRNP interaction with the downstream major splice donor site" Embo J Sep. 15, 1997; 16(18):5752–63.
Borg KT, et al., "Involvement of human immunodeficiency virus type–1 splice sites in the cytoplasmic accumulation of viral RNA" Virology Sep. 15, 1997; 236(1):95–103.
McCann E. M., et al., "Location of cis–Acting Sgnals Important for RNA Ecapsidation in the leader sequence of human immunodficiency virus type 2" Journal of Virology, vol. 71, No. 5, May 1997, pp. 41334133–4137.
Chang DD. et al., "Messenger RNA transport and HIV rev regulation" Science Aug. 10, 1990, 249(4969):614–615.
Borg KT. et al., "Activation of a cryptic splice donor in human immunodeficiency virus type–1." J Biomed Sci Jan. 1999; 6(1):45–52.
Dull T et al., A third–generation lentivirus vector with a conditional packaging system: Journal of Virology, US, The American Society for Microbiology, vol. 72, No. 11, Nov. 1998.
Cui Yan et al., "Contributions of viral splice sites and cis–regulatory elements to lentivirus vector function." Journal of Virology Jul., 1999, pp. 6171–6176.
Iwakuma T. et al., "Self–Inactivating Lentiviral Vectors with U3 and U5 Modifications" Virology, US, Academic Press, Orlando vol. 261, No. 1, 1999, pp. 120–132.
Elder et al., Advances in Virus Research, vol. 45, pp. 225–247, 1995.*
J.M. Coffin in "Retroviridiae:The Viruses and Their Replication", in Fields' Virology, Third Edition, vol. 2, (B.N. Fields et al., Eds., Lippincott–Raven, Philadelphia, PA, 1996), p. 1778.*
Joag et al. in "Retroviridiae:The Viruses and Their Replication", in Fields' Virology, Third Edition, vol. 2, (B.N. Fields et al., Eds., Lippincott–Raven, Philadelphia, PA, 1996), pp. 1980–1982.*

* cited by examiner

Primary Examiner—David Guzo
(74) Attorney, Agent, or Firm—Fulbright & Jaworski, LLP

(57) ABSTRACT

The present invention contemplates novel lentiviral vectors which exhibit strong promoter activity in human and other cells. Vectors are provided which are packaged efficiently in packaging cells and cell lines to generate high titer recombinant virus stocks. The present invention further relates to HIV vaccines and compositions for gene therapy. In particular, the present invention provides attenuated replication-competent HIV vaccines and replication defective HIV vectors.

37 Claims, 26 Drawing Sheets

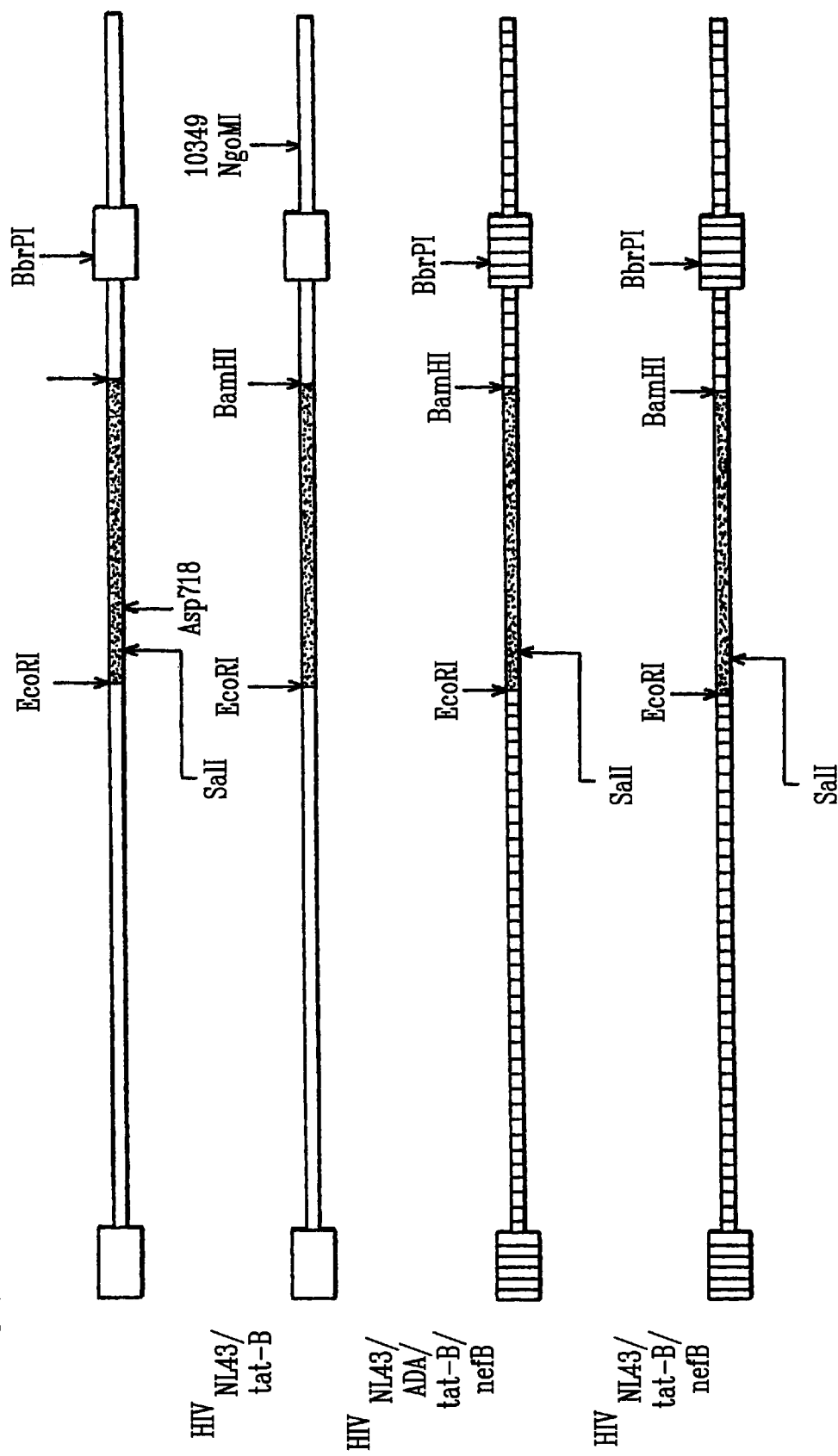

FIG. 12A
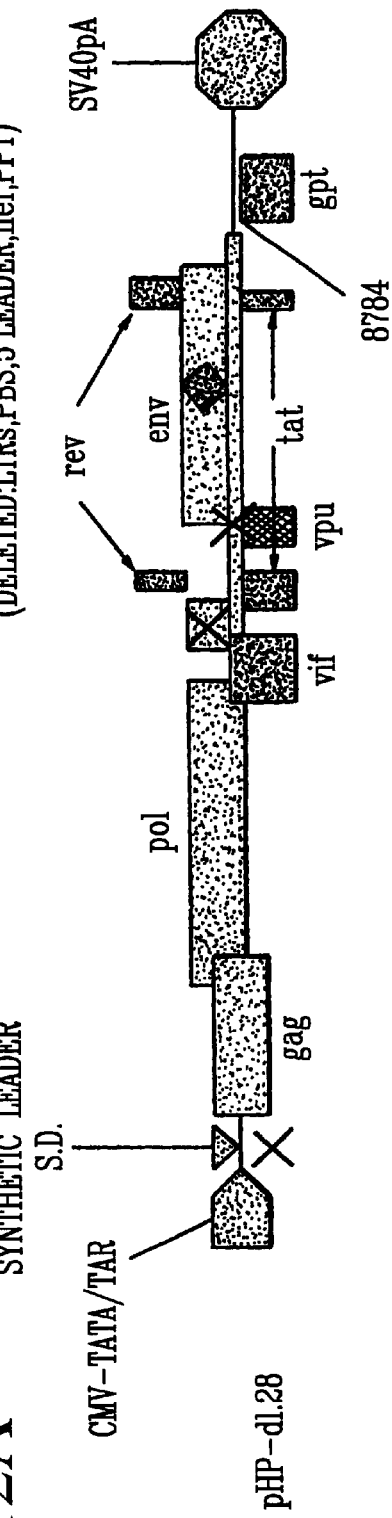
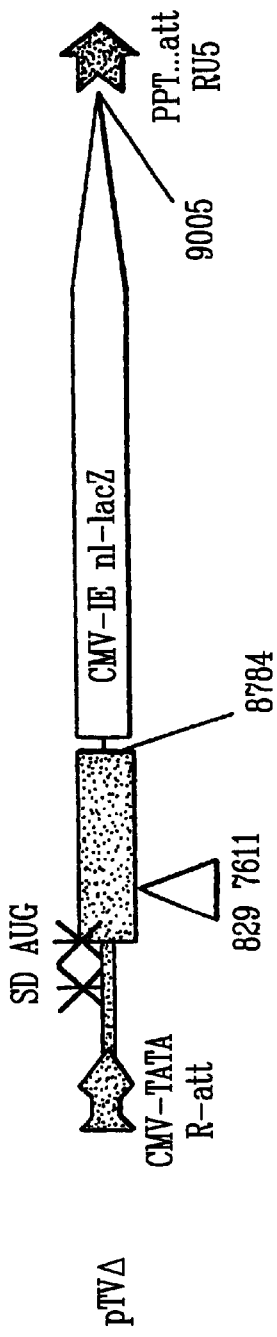

FIG. 13A

```
              tat starts
         5801      5811      5821       ↱5831      5841      5851      5861
WT:      AGGCGTTACTCGACAGAGGAGAGCAAGAAATGGAGCCAGTAGATCCTAGACTAGAGCCCTGGAAGCATCC
tat-B:   ------------------------------------------------------T--G-----------
                                                              ↰
                                                            vpr ends 5871      5881      5891      5901      5911      5921      5931
WT:      AGGAAGTCAGCCTAAAACTGCTTGTACCAATTGCTATTGTAAAAAGTGTTGCTTTCATTGCCAAGTTTGT
tat-B:   ----------T----------T-----------------------------------------------
```

FIG. 13B

```
           nef starts
         ↱8781      8791      8801      8811      8821      8831      8841
WT:      TATAAGATGGGTGGCAAGTGGTCAAAAAGTAGTGTGATTGGATGGCCTGCTGTAAGGAAAGAATGAGAC..
nef-A:   ---C-T---------------------------------------------------------------..
nef-B:   ---C-T---------------------------------------------------------------..
              ↰env ends ...9001      9011      9021      9031      9041      9051      9061
WT:      CTCAGGTACCTTTAAGACCAATGACTTACAAGGCAGCTGTAGATCTTAGCCACTTTTTAAAGAAAAAGGG
nef-A:   ---------------------------------------------------------------------
nef-B:   ---------------------------TCTA--TC--G-------------------------------
```

FIG. 17

```
         5801       5811       5821       5831       5841       5851       5861
WT:      AGGGCGTTACTCGACAGAGGAGAGGAGCAAGAAATGGAGCCAGTAGATCCTAGACTAGAGACCCTGGAAGCATCC
tat-A:   ------------------------------------------------------T--G-----------------
tat-B:   ------------------------------------------------------T--G-----------------
tat-C:   --------------------------------------C---C---TCGC-TAG-----//////CGGCCGCCCG 5871       5881       5891       5901       5911       5921       5931
WT:      AGGAAGTCAGCTAAAACTGCTTGTACCAATTGCTATTGTAAAAAGTGTTGCTTTCATTGCCAAGTTTGT
tat-A:   ---------------------------------------------------------------------
tat-B:   -------T-----T-------------------------------------------------------
tat-C:   GGATCGATACGC//////////-----------------------------------------------
```

FIG. 20

| pTV | Mutation site | N | Avg | S.E. | P Value |
|---|---|---|---|---|---|
| pTVdlnLacZ | | 5 | 1.000 | 0.000 | |
| AUG-Age I | Gag AUG → ACC | 3 | 0.351 | 0.073 | 0.018 |
| AUG-TAG | Gag AUG → TAG | 3 | 0.718 | 0.129 | 0.215 |
| SD Pst I | Splice donor GGTG → GCAG | 4 | 0.977 | 0.063 | 0.786 |
| SDG | Splice donor GGTG → GCGG | 4 | 0.854 | 0.166 | 0.500 |
| SD-TAG | Splice donor and Gag AUG (SD PstI+AUG-TAG) | 3 | 0.610 | 0.165 | 0.192 |
| BamHI 2'-6 | Deletion between RRE and CMV 231 bp | 1 | 0.650 | | |
| BamHI 2'-8 | Deletion between RRE and CMV 271 bp | 4 | 0.469 | 0.057 | 0.004 |
| BamHI 2'-12 | Deletion between RRE and CMV 183 bp SA8 intact | 4 | 0.475 | 0.050 | 0.003 |
| BamHI 5'-3 | Deletion between RRE and CMV 443 bp | 4 | 0.602 | 0.125 | 0.071 |
| BamHI 5'-8 | Deletion between RRE and CMV 505 bp | 4 | 0.635 | 0.109 | 0.062 |
| BamHI 5'10 | Deletion between RRE and CMV 572 bp | 5 | 0.442 | 0.069 | 0.002 |
| INTR deletion 1 | Deletion between SL4 and RRE 180 bp | 4 | 1.077 | 0.092 | 0.521 |
| INTR deletion 2 | Deletion between SL4 and RRE 361 bp | 4 | 0.900 | 0.109 | 0.482 |
| INTR deletion 3 | Deletion between SL4 and RRE 591 bp | 4 | 0.812 | 0.139 | 0.326 |
| INTR deletion 4 | Deletion between SL4 and RRE 824 bp | 4 | 0.936 | 0.077 | 0.516 |
| INTR deletion 5 | Deletion between SL4 and RRE 1039 bp | 5 | 0.653 | 0.076 | 0.014 |
| RRE dl alone | Deletion of RRE only 234 bp | 4 | 0.097 | 0.024 | 0.000 |
| RRE Full length dl | Deletion from SL4 to CMV.IE(dl 2.2 Kb) | 4 | 0.018 | 0.015 | 0.000 |

FIG. 21

HIV-1:RUS-5' Leader sequence TAR → 3'

```
      531 HindIII            ←R)U5→
WT:1  AAGCTTGCCTTGAGTGCTCAAAGTAGTGTGTGCCCGTCTGTTGTGTGACTCTG
pHP:2 AAGCTT//...deletion............................
pTV:3 AAGCTTGCCTTGAGTGCTCAAAGTAGTGTGTGCCCGTCTGTTGTGTGACTCTG 584
                                                   U5 ←(
   1  GTAACTAGAGATCCCTCAGACCCTTTTAGTCAGTGTGGAAAATCTCTAGCAGT
   2  ..deletion.......................................
   3  GTAACTAGAGATCCCTCAGACCCTTTTAGTCAGTGTGGAAAATCTCTAGCAGT )637→    PBS     ←(
   1  GGCGCCCGAACAGGGACTTGAAAGCGAAAGTAAAGCCAGAGGAGATCTCTC
   2  ..deletion.......................................
   3  GGCGCCCGAACAGGGACTTGAAAGCGAAAGTAAAGCCAGAGGAGATCTCTC 688
   1  GACGCAGGACTCGGCTTGCTGAAGCGCGCACGGCAAGAGGCGAGGGGCGGC
   2  ..deletion...............//insertion of RSV 5'SD sequence.....TGGT
   3  GACGCAGGACTCGGCTTGCTGAAGCGCGCACGGCAAGAGGCGAGGGGCGGC 5'SD(744)
      739  ↓
   1  GACTGGTGAGTACGCCAAAAATTTTGACTAGCGGAGGCTAGAAGGAGAGAG
   2  CGCCCGGTGGATCAAGACCGGTAGCCGTCATAAAGGTGATTTCGTCGGATCC
   3  GACTGCAGAGTACGCCAAAAATTTTGACTAGCGGAGGCTAGAAGGAGAGAG 790
      |gag→
   1  ATGGGTGCGAGAGCGTCGGTATTAAGCGGGGGAGAATTAGATAAATGGGAA
   2  ATGGGTGCGAGAGCGTCGGTATTAAGCGGGGGAGAATTAGATAAATGGGAA
   3  TAGGGTGCGAGAGCGTCGGTATTAAGCGGGGGAGAATTAGA//nt830//nt7611//
```

LENTIVIRAL VECTORS

This application is a continuation-in-part of Ser. No. 08/935,312, filed Sep. 22, 1997, now U.S. Pat. No. 6,207,455, which is incorporated by reference to the extent that it does not directly conflict with the teachings of the present application. That application is a continuation-in-part of Ser. No. 08/848,760, filed May 1, 1997 now U.S. Pat. No. 6,248,721.

This application is also a nonprovisional of Ser. No. 60/086,635, filed May 26, 1998, which likewise is incorporated by reference.

MENTION OF GOVERNMENT GRANT

The inventions disclosed herein may have arisen in part from work done under one or more U.S. government grants, including NIH grant No. P50 HL-59412. Consequently, the U.S. Government may have certain rights in the inventions.

FIELD OF THE INVENTION

The present invention relates to improved lentivirus-derived packaging and transducing vectors useful for the expression of genes at high levels in eukaryotic cells. The improved vectors are safer, yet permit increased efficiency of packaging the recombinant viral genome and increased long-term gene expression.

BACKGROUND OF THE INVENTION

1. Gene Transfer; Gene Therapy

Viral vectors transduce genes into target cells with high efficiencies owing to specific virus envelope-host cell receptor interaction and viral mechanisms for gene expression. Consequently, viral vectors have been used as vehicles for the transfer of genes into many different cell types including whole embryos, fertilized eggs, isolated tissue samples, and cultured cell lines. The ability to introduce and express a foreign gene in a cell is useful for the study of gene expression and the elucidation of cell lineages (J. D. Watson et al., *Recombinant DNA*, 2d Ed., W. H Freeman and Co., NY [1992], pp. 256–263). Retroviral vectors, capable of integration into the cellular chromosome, have also been used for the identification of developmentally important genes via insertional mutagenesis (J. D. Watson et al., supra, p. 261). Viral vectors, and retroviral vectors in particular, are also used in therapeutic applications (e.g., gene therapy), in which a gene (or genes) is added to a cell to replace a missing or defective gene or to inactivate a pathogen such as a virus.

In view of the wide variety of potential genes available for therapy, it is clear that an efficient means of delivering these genes is sorely needed in order to fulfill the promise of gene therapy as a means of treating infectious, as well as non-infectious diseases. Several viral systems including murine retrovirus, adenovirus, parvovirus (adeno-associated virus), vaccinia virus, and herpes virus have been developed as therapeutic gene transfer vectors (For review see, A. W. Nienhuis et al., *Hematology*, Vol. 16:*Viruses and Bone Marrow*, N. S. Young (ed.), pp. 353–414 [1993]).

Factors affecting viral vector usage include tissue tropism, stability of virus preparations, genome packaging capacity, and construct-dependent vector stability. In addition, in vivo application of viral vectors is often limited by host immune responses against viral structural proteins and/or transduced gene products.

One of the key issues in human gene therapy is the toxicity and safety to the treatment subjects. Gene therapy applications in humans have met with problems associated with the host immune responses against the gene delivery vehicles or the therapeutic gene products. Viral vectors (e.g., adenovirus) which co-transduce several viral genes together with the therapeutic gene(s) are particularly problematic. For example, readministration is necessary for adenovirus vectors because of the transient nature of viral gene expression. As such, a host immune response to the vector or the therapeutic gene product may be detrimental (B. C. Trapnell and M. Gorziglia, Curr. Op. Biotechnol., 5:617–625 [1994]; and S. K. Tripathy et al., Nature Med., 2:545–550 [1996]).

Although MLV vectors have not been reported to induce cytotoxicity and do not elicit strong host immune responses, lentiviral vectors such as HIV-1 which carry several immunostimulatory gene products have the potential to cause cytotoxicity and induce strong immune responses in vivo. The latter are known to induce strong cell-mediated immune responses upon transient exposure (M. Clerici et al., J. Inf. Dis., 165:1012–1019 [1992]; M. Clerici et al., J. Amer. Med. Assoc., 271:42–46 [1994]; L. A. Pinto et al., J. Clin. Invest., 96:867–876 [1995]; and S. Rowland-Jones et al., Nature Med., 1:59–64 [1995]). However, this may not be a concern for lentiviral derived transducing vectors, as the latter need not encode any viral genes in the transducing vector.

Of course, in some instances, the purpose of the vector is to provoke a clinically useful immune response against an encoded protein.

Another important issue related to the lentiviral vector usage is that of possible cytopathogenicity upon exposure to some cytotoxic viral proteins. Exposure to HIV-1 proteins may induce cell death or functional unresponsiveness in T cells (N. Chirmule et al., J. Virol., 69:492–498 [1995]; C. J. Li et al., Science 268:429–431 [1995]; J. D. Lifson et al., Science 232:1123–1127 [1986]; I. G. Macreadie et al., Mol. Microbiol., 19:1185–1192 [1996]; and T. Nosaka et al., Exp. Cell. Res., 209:89–102 [1993]). During the development of the present invention, it was observed that direct gene transfer into tissue culture cells by the calcium-phosphate DNA co-precipitation method could induce more than 80% cell death which is caused mainly by necrosis and a residual percentage, approximately 2–4%, by programmed cell death A final concern is the possibility of generating replication-competent, virulent virus by recombination.

Safety concerns have prompted much effort towards the development of non-viral vector systems, such as liposome-mediated gene transfer, naked DNA injections and gene gun technology. However, all of these non-viral gene transfer methods lack the ability to allow permanent integration of foreign genes into the host cell chromosomes, and are relatively inefficient. For long term expression of therapeutic genes in target cells, efficient means of transduction and genome integration are essential.

2. Retroviruses; Retroviral Vectors

The term "retrovirus" is used in reference to RNA viruses that utilize reverse transcriptase during their replication cycle. The retroviral genomic RNA is converted into double-stranded DNA by reverse transcriptase. This double-stranded DNA form of the virus is capable of being integrated into the chromosome of the infected cell; once integrated, it is referred to as a "provirus." The provirus serves as a template for RNA polymerase II and directs the expression of RNA molecules which encode the structural proteins and enzymes needed to produce new viral particles. At each end of the provirus are structures called "long terminal repeats" or "LTRs." The LTR contains numerous regulatory signals including transcriptional control elements, polyadenylation signals and sequences needed for replication and integration of the viral genome. There are several genera included within the family Retroviridae, including Cisternavirus A, Oncovirus A, Oncovirus B, Oncovirus C, Oncovirus D, Lentivirus, and Spumavirus. Some of the retroviruses are oncogenic (i.e., tumorigenic), while others are not. The oncoviruses induce sarcomas, leukemias, lymphomas, and mammary carcinomas in susceptible species. Retroviruses infect a wide variety of species, and may be transmitted both horizontally and vertically. They are integrated into the host DNA, and are capable of transmitting sequences of host DNA from cell to cell. This has led to the development of retroviruses as vectors for various purposes including gene therapy.

Retroviral vectors derived from the amphotropic Moloney murine leukemia virus (MLV-A), use cell surface phosphate transporter receptors for entry and then permanently integrate into proliferating cell chromosomes. The amphotropic MLV vector system has been well established and is a popular tool for gene delivery (See e.g., E. M. Gordon and W. F. Anderson, Curr. Op. Biotechnol., 5:611–616 [1994]; and A. D. Miller et al., Meth. Enzymol., 217:581–599 [1993]).

Other retroviruses, including human foamy virus (HFV) and human immunodeficiency virus (HIV) have gained much recent attention, as their target cells are not limited to dividing cells and their restricted host cell tropism can be readily expanded via pseudotyping with vesicular stomatitis virus G (VSV-G) envelope glycoproteins (See e.g., J. C. Burns et al., Proc. Natl. Acad. Sci. USA 90:8033–8037 [1993]; A. M. L. Lever, Gene Therapy. 3:470–471 [1996]; and D. Russell and A. D. Miller, J. Virol., 70:217–222 [1996]). However, a useful lentiviral vector system has not been well established, mainly because of the lack of sufficient studies on lentiviral vectorology and safety concerns.

While many viral vector systems are available, virtually all of the current human gene therapy trials use retroviral vectors derived from the amphotropic Moloney murine leukemia virus (M-MuLV), such as pLNL6 (Genbank M63653), see Baker, et al., J. Virol. 61:1639 (1987), for gene transfer (see also A. D. Miller and C. Buttimore, Mol. Cell. Biol., 6:2895 [1986]). Among the vectors known in the art, special note may be taken of Chang, U.S. Pat. No. 5,693,508 (1997) which discloses retroviral vectors contining chimeric MoMLV/CMV-IE/HIV-TAR LTRs. The elements essential to the retroviral vector system are viral structural proteins Gag, Pol and Env, the long terminal repeats (LTR), the reverse transcription templates including primer binding site (PBS) and polypurine tract (PPT), and the packaging signals (psi [ψ]). The MLV-A vector system is comprised of a packaging cell line expressing Gag, Pol and Env, and a vector construct containing LTRs, PBS, PPT and the packaging signal sequences. Up to 8 kbp of foreign sequences can be inserted into the MLV vector and packaged into virus particles. The commonly used amphotropic MLV packaging cell lines such as PA317, PG-13, ψ-CRIP, GP-AM12 and FLY-A13 produce $10^5$–$10^7$ transducing units per ml after vector DNA transfection (F.-L. Cosset et al., J. Virol., 69:7430–7436 [1995]; H. Kotani et al., Human Gene Ther., 5:19–28 [1994]; J. S. Lam et al., Human Gene Ther., 7:1415–1422 [1996]; D. Markowitz et al., J. Virol., 62:1120–1124 [1988]; A. D. Miller and F. Chen, J. Virol., 70:5564–5571 [1996]).

The M-MuLV system has several advantages: 1) this specific retrovirus can infect many different cell types; 2) established packaging cell lines are available for the production of recombinant M-MuLV viral particles; and 3) the transferred genes are permanently integrated into the target cell chromosome. The established M-MuLV vector systems comprise a DNA vector containing a small portion of the retroviral sequence (the viral long terminal repeat or "LTR" and the packaging or "psi" [ψ] signal) and a packaging cell line. The gene to be transferred is inserted into the DNA vector. The viral sequences present on the DNA vector provide the signals necessary for the insertion or packaging of the vector RNA into the viral particle and for the expression of the inserted gene. The packaging cell line provides the viral proteins required for particle assembly (D. Markowitz et al., J. Virol., 62:1120 [1988]).

The vector DNA is introduced into the packaging cell by any of a variety of techniques (e.g., calcium phosphate coprecipitation, lipofection, electroporation, etc.). The viral proteins produced by the packaging cell mediate the insertion of the vector sequences in the form of RNA into viral particles which are shed into the culture supernatant. The M-MuLV system has been designed to prevent the production of replication-competent virus as a safety measure. The recombinant viral particles produced in these systems can infect and integrate into the target cell but cannot spread to other cells. These safeguards are necessary to prevent the spread of the recombinant virus from the treated patient and to avoid the possibility of helper virus-induced disease (A. D. Miller and C. Buttimore, supra; and D. Markowitz et al., supra).

After selection, producer cell clones can be established to generate $10^4$–$10^6$ transducing units per ml. Increased transduction efficiencies may be achieved by modification of the transduction protocols through means such as repetitive infection steps, cocultivation with the producer cell line, centrifugation, and modification of the culture conditions using growth factors and fibronectin etc. (H. Kotani et al., Human Gene Ther., 5:19–28 [1994]; and T. Moritz et al., Blood 88:855–862 [1996]).

Despite these advantages, existing M-MuLV-based retroviral vectors are limited by several intrinsic problems: 1) they do not infect non-dividing cells (D. G. Miller et al., Mol. Cell. Biol., 10:4239 [1990]); 2) they produce only low titers of the recombinant virus (A. D. Miller and G. J. Rosman, BioTechn., 7: 980 [1989]; and A. D. Miller, Nature 357: 455 [1992]); 3) they express foreign proteins at low levels and often get "turned-off" or inactivated after integration (A. D. Miller, Nature 357: 455 [1992]); (4) the instability of the enveloped virus particles, as it is both difficult to concentrate in vitro and difficult to manipulate in vivo (A. D. Miller, Nature 357:455–460 [1992]); 5) the MLV LTR activity is also known to be suppressed in embryonal cells (P. M. Challita et al., J. Virol., 69:748–755 [1995]; and T. P. Loh et al., J. Virol., 62:4086–4095 [1988]); and 6) long term expression after viral integration is often restricted by transcription repression, likely due to DNA methylation (J. Boyes and A. Bird, Cell 64:1123–1134 [1991]; and M. Szyf et al., Mol. Cell. Biol., 10:4396–4400 [1990]).

The low production of recombinant virus produced by the M-MuLV system (e.g., 106/ml) compared to the adenoviral system (up to $10^{12}$/ml) means that human cells are infected at a very low efficiency. This low efficiency is particularly problematic when the target cell type is represented at very low numbers in the tissue to be infected. Although the hematopoietic stem cell is a preferred target for gene therapy in a large number of disorders, these cells are present at very low frequencies. For example, totipotent embryonic stem cells have been reported to occur at a frequency of $10^{-4}$ to $10^{-6}$ in bone marrow (B. R. Glick and J. J. Pasternak, Molecular Biotechnology, American Society for Microbiology, Washington, D.C., p. 412 [1994]). Thus, the low titer produced by existing M-MuLV vector systems is highly problematic for stem cell infection.

The promoter present in the M-MuLV LTR is quite weak compared with other viral promoters such as the human cytomegalovirus immediate early (CMV-IE) enhancer/promoter. In order to increase expression of the genes carried on the retroviral vector, internal promoters possessing stronger activities than the M-MuLV promoter have been utilized. However, the inclusion of an internal promoter to drive the expression of the inserted gene does not always lead to increased levels of expression (D. Robinson et al., Gene Therapy 2:269 [1995]). Apparently, the activity of the internal promoter is significantly decreased because of interference from the upstream M-MuLV promoter (i.e., transcriptional read-through interference). The dual transcription-unit construct is, however, a common feature in almost all M-MuLV vectors.

To create an improved retroviral vector suitable for a wide variety of gene expression studies and gene therapy applications, the clinically approved gene therapy vector pLNL6 has been modified to allow synthesis of high basal levels of mRNA, and increased packaging efficiency (See e.g., co-pending U.S. patent application. Ser. No. 08/336,132, now U.S. Pat. No. 5,693,508, and PCT/US95/14576, to Chang, herein incorporated by reference). However, other limitations remain.

Given these limitations, it is clear that improved vector systems are urgently needed to provide a means of delivering and expressing genes efficiently in mammalian cells, particularly human cells. Improved vectors will aid the study of gene expression and development and are necessary if the promise of gene therapy is to be realized.

The major limitation in the use of the simple retroviral vectors in gene transfer is that use of the MLV-based vector is restricted to dividing cells. This led to the development of the present invention, in which lentiviruses, capable of infecting non-dividing cells are provided.

3. Lentiviruses; Lentiviral Vectors

As used herein, the term "lentivirus" refers to a group (or genus) of retroviruses that give rise to slowly developing disease. Viruses included within this group include HIV (human immunodeficiency virus; including HIV type 1, and HIV type 2), the etiologic agent of the human acquired immunodeficiency syndrome (AIDS); visna-maedi, which causes encephalitis (visna) or pneumonia (maedi) in sheep, the caprine arthritis-encephalitis virus, which causes immune deficiency, arthritis, and encephalopathy in goats; equine infectious anemia virus, which causes autoimmune hemolytic anemia, and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which cause immune deficiency and encephalopathy in sub-human primates. Diseases caused by these viruses are characterized by a long incubation period and protracted course. Usually, the viruses latently infect monocytes and macrophages, from which they spread to other cells. HIV, FIV, and SIV also readily infect T lymphocytes (i.e., T-cells).

Lentivirus virions have bar-shaped nucleoids and contain genomes that are larger than other retroviruses. Lentiviruses use tRNA$^{lys}$ as primer for negative-strand synthesis, rather than the tRNA$^{pro}$ commonly used by other infectious mammalian retroviruses. The lentiviral genomes exhibit homology with each other, but not with other retroviruses (See, Davis et al., Microbiology, 4th ed., J. B. Lippincott Co., Philadelphia, Pa. [1990], pp. 1123–1151). An important factor in the disease caused by these viruses is the high mutability of the viral genome, which results in the production of mutants capable of evading the host immune response. It is also significant that they are capable of infecting non-dividing cells.

Lentiviruses including HIV, SIV, feline immunodeficiency virus (FIV) and equine infectious anemia virus (EIAV) depend on several viral regulatory genes in addition to the simple structural gag-pol-env genes for efficient intracellular replication. Thus, lentiviruses use more complex strategies than classical retroviruses for gene regulation and viral replication, with the packaging signals apparently spreading across the entire viral genome. These additional genes display a web of regulatory functions during the lentiviral life cycle. For example, upon HIV-1 infection, transcription is up-regulated by the expression of Tat through interaction with an RNA target (TAR) in the LTR. Expression of the full-length and spliced mRNAs is then regulated by the function of Rev which interacts with RNA elements present in the gag region and in the env region (RRE) (S. Schwartz et al., J. Virol., 66:150–159 [1992]). Nuclear export of gag-pol and env mRNAs is dependent on the Rev function. In addition to these two essential regulatory genes, a list of accessory genes, including vif, vpr, vpx, vpu, and nef, are also present in the viral genome and their effects on efficient virus production and infectivity have been demonstrated, although they are not absolutely required for virus replication (K. and F. Wong-Staal, Microbiol. Rev., 55:193–205 (1991]; R. A. Subbramanian and E. A. Cohen, J. Virol. 68:6831–6835 [1994]; and D. Trono, Cell 82:189–192 [1995]).

HIV-1 virions contain 60% protein and 2% nucleic acid. The genome consists of two molecules of linear positive-sense single stranded RNA (held together by hydrogen bonds to form a dimer). Even within a single virion, these molecules need not be identical. Hence, genetic variation can occur through recombination between the two viral RNAs of a single virion.

The HIV-1 genome is about 9.7 kb in length. Many HIV-1 proviral genome sequences have been sequenced in their entirety. The sequence GenBank M19921, LOCUS HIVNL43, Human immunodeficiency virus type 1, NY5/BRU (LAV-1) recombinant clone pNL4-3, 9709 bp ss-RNA, is used as a reference sequence in this discussion. The construction of pNL4-3 has been described in Adachi, A., Gendelman, H. E., Koenig, S., Folks, T., Willey, R., Rabson, A. and Martin, M. A., Production of acquired immunodeficiency syndrome-associated retrovirus in human and non-human cells transfected with an infectious molecular clone, J. Virol. 59, 284–291 (1986). pNL4-3 is a recombinant (infectious) proviral clone that contains DNA from HIV isolates NY5 (5' half) and BRU (3' half). The site of recombination is the EcoRI site at positions 5743–5748. The final sequence is set forth in Dai, L. C., Littaua, R., Takahashi, K. and Ennis, F. A., Mutation of human immunodeficiency virus type 1 at amino acid 585 on gp41 resultis in loss of killing by CD8+ A24-restricted cytotoxic T lymphocytes, J. Virol. 66, 3151–3154 (1992).

For several reasons, the HIV-1 genome has a high mutation rate. First, there can be recombination between the two RNAs of a single virion. Secondly, a single cell can be infected by more than one viral particle simultaneously, and recombination occur between the two viral genomes. Finally, the HIV reverse transcriptase has a high frequency of misincorporation (:1700 to 1:4000). The replication error rate for HIV is such that each newly synthesized HIV genome carries on average approximately one mutation. For all of these reasons, there is not one HIV-1 sequence, but rather a family of closely related sequences. Different HIV-1 sequences may be identified even in different samples isolated from a single individual. The degree of genetic variation observed is phenomenal—up to 20% within an infected individual. This is essentially due to remorseless cycles of viral replication, most probably due tochronic activation of the immune system. It can be estimated that the number of variants in existence worldwide must be in excess of 10(14) –10(18), and given the nature of RNA viruses even more novel variants should emerge.

HIV-1's are currently divided into two genetic groups based on phylogenetic reconstruction using DNA sequences. The majority of these sequences fall into the M (major) group, while a smaller, but growing, number of sequences are classified as O (outlier). Most HIV-1 strains from around the world can be placed into one of nine nucleotide sequence-defined clades; these clades have been given the letter designations A through I. However, more than a dozen HIV-1 strains isolated from patients have now been shown to have chimeric genomes in that their gag and env genomic regions cluster with different clades. Interclade recombination is relatively easy to demonstrate because strains from different clades typically differ substantially in their nucleotide sequence identities. For example, the env gene sequences of HIV-1 strains of different clades may differ by 20% or more. As might be expected, interclade HIV-1 recombinants have most often been detected in geographic regions where two or more clades are prevalent. At least 17 HIV clades have now been reported in humans: nine HIV-1 clades in the major grouping (A through I), three HIV-1 group O group "outlier" clades, and five HIV-2 clades. An additional three lentiviruses are known in nonhuman primate species (African green monkeys, mandrils, and Syke's monkeys). Thus the potential gene pool for primate lentivirus recombination is on the order of 20, e.g., 20 gag genes and 20 pol genes. The current HIV-1 clades may have arisen in part through past recombination between some of these genes. Viable recombinants between SIV and HIV ("SHIV" strains) have been genetically engineered in research laboratories.

The principal elements of the HIV-1 genome are set forth below, in the 5' to 3' direction. For further information, see Vaishnav and Wong-Staal, Ann. Rev. Biochem., 60: 577–630 (1991). The positions of each element are given according to the Genbank numbering of the complete genome sequence (M19921) cited above. That means that the numbering begins with the first base of the 5' LTR, not with the cap site. The exact positions will vary from strain to strain, and some elements are better defined than others. Note that some genetic elements overlap, and that two (Tat and Rev) are interrupted. For a compilation of numerous sequences and alignments, at both the nucleic acid and amino acid levels, for many lentiviruses and othe retroviruses, see the HIV Sequence Database at http://hiv-web.lanl.gov.

5' LTR (1-634)

Each end of the DNA provirus contains the so-called long terminal repeats (LTRs). The 5' LTR and 3' LTR regions are essentially identical in the wild-type HIV-1 genome. These LTRs are 634-bp non-coding sequences, located at the extreme 5' and 3' ends of the proviral genome, that contain enhancer and promoter regions. The LTRs consist of three distinct coding regions, U3, R, and U5, which can be subdivided into the separate enhancer and promoter regions. The U3 region is 450, the R sequence 100 and the U5 region some 85 nt long. Transcription initiates at the first base of the R region in the 5' LTR, and polyadenylation occurs immediately after the last R region base in the 3' LTR. The primary transcript is thus about 600 bases shorter than the provirus.

The U3 region includes several features of interest: the integration attachment site (att) at the far 5' end, the promoter TATA box (a segment of DNA, located approximately 19–27 base pairs upstream from the start point of eukaryotic structural genes, to which RNA polymerase binds), promoter (SP1) regions (promoter binding site for RNA polymerase and reverse transcriptase), the kappa-enhancer (contains two imperfect 11-bp repeats, GGGACTTTC(SEQ ID NO.58), and IL-1 and IL-2 homologous enhancers.

The R region (454–550) contains the transcription initiation site, the TAR (Tat-activating) region and the poly A signal (—AATAAAA—); the latter is significant only in the 3' LTR). The primary transcript corresponds to bases 455 to 9626.

The U5 region contains a polyA downstream element and a second integration attachment site at the 3' end. These are significant only in the 3' LTR. PBS Immediately downstream of the 5' LTR is the primer binding site (637–651) for minus-strand DNA synthesis, called the RNA cap. The primer binding site is complementary to the 3' end of a Lys transfer RNA.

5' Leader (L)

The 5' leader (L), the untranslated region between the primer binding site and the initiation codon for gag, has two elements worthy of note.

The first is the major 5' splice donor (SD) site (the splice point is at 748) which is used for the processing of full-length genomic RNA to subgenomic mRNA for the syntheses of various viral proteins. The major splice donor site is so called because it acts as the donor site during splicing of the vif, vpr, tat, rev, vpu-env and nef subgenomic RNAs (The Gag-Pol polyprotein is translated from genomic RNA.) There are also minor splice donor sites in the vicinity of the first exon of the rev gene.

The other is the major packaging signal (psi) (651–669) which serves as a contact point for the Gag nucleocapsid (Ncp7) protein to bind the RNA and to incorporate it into virus particles. Note that one can define an extended packaging signal extending into the gag gene, to about 820.

The 5' leader also contains a sequence which participates in the dimer-linkage structure of 70S RNA. This DLS overlaps with the major packaging signal.

A secondary structure model of the leader, and the 5' end of gag, was prepared by Baudin, et al., J. Mol. Biol., 229: 382–97 (1993).

Structural Genes

The gag gene encodes a polyprotein (55 kDa) (CDS 790..2292) which is cleaved by the viral protease (see pol) to yield various core and nucelocapsid proteins. The gag coding region extends from the ATG initiation codon at nucleotide 337 to nucleotide 1837 relative to the RNA cap site. The polyprotein is translated from unspliced viral RNA. The precursor Gag protein is cleaved by protease to produce p17 (the major matrix MA protein, involved in membrane anchoring, env interaction, and nuclear transport of viral core), p24 (the core capsid CA protein), p7 (the nucleocapsid NC protein, which binds RNA), and p6 (which binds Vpr). A pair of zinc finger motifs in the NC protein binds to the major packaging signal in the viral RNA.

The gag gene is believed by some authors to contain one or more minor packaging signals.

The pol gene (CDS est. 2085..5096) codes for a large polyprotein which is a precursor to the virion proteins providing the viral enzyme functions: protease, reverse transcriptase, and integrase. The gag and pol genes overlap by 241 nucleotides, and are in different reading frames. A slippage sequence in or upstream of the gag-pol overlap region induces an occasional ribosomal frameshift at a frequency (about 5%) which ensures that Gag proteins are made in large amounts and Pol proteins in small amounts. Initially, a gag-pol fusion protein (p190) is created as a result of the ribosomal frameshift, which does not interrupt translation. The viral protease cleaves Gag from Pol, and further digests Gag and Pol to separate the various mature proteins. In the case of Pol, the cleavage products are protease (p10), reverse transcriptase (p50), Rnase H (p15) and integrase (p31). Roughly 50% of the RT remains linked to Rnase H as a single polypeptide (p66). The principal functional form of RT is actually a heterodimer of p66 and p50. All pol gene products are found within the capsid of free HIV-1 virions.

Reverse transcriptase is responsible for the synthesis of double-stranded DNA from the viral RNA. Activity of RT is localized to the N-terminus. RT in HIV has an extremely high error rate, 1/1700 nucleotides. At the 3' end of the pol coding region is the coding region for viral endonuclease/integrase. Integrase functions to integrate the proviral DNA in the host genome.

The env gene (CDS 6221..8785) is located at the 3' end of the genome. It encodes the envelope protein gp160, some of which is cleaved to yield the envelope proteins gp120 and gp41. Both function in cell recognition on the outer envelope of a released virus. The C-terminus of gp120 interacts with the viral receptor CD4 of human T lymphocytes to facilitate the viral entry into the host cell. Only a 12 amino acid sequence in gp120 is necessary for binding to CD4; the rest of the protein is mutable. The gp120 polypeptide contains nine conserved intrachain disulfide bridges and, within this scaffolding, folds into five globular domains (I–V). There are five hypervariable regions (V1–V5) whose sequences vary especially widely among HIV-1 isolates.

Regulatory Genes

The tat gene (CDS 5830..6044, 8369..8414) encodes Tat, a trans-activating protein, the most important activator of of the LTR promoter region. Three functional domains have been identified: an amino terminal amphipathic helix, a cluster of seven cysteine residues, and a stretch of basic amino acids involved in nuclear localization. It is known that conservative mutations of the acidic amino acids of the amphipathic helix are tolerated. Tat mediates the 5' LTR by interacting with its R region, in a segment termed the "TAR" (trans-activating response) element (bases 436–497). The "TAR" element forms a stable stem loop structure that interacts with the Tat protein to prevent premature termination of transcription initiation. Tat is reported in the literature to be absolutely essential for HIV transcription and consequently for viral replication.

The rev gene (CDS 5969..6044, 8369..8643) encodes Rev, another transactivator. Rev is phosphorylated at serine residues, but serine substitution mutants which are not phosphorylated are fully active. The amino terminal 20 amino acids and the carboxy terminal 25 amino acids are known to be dispensable. There are two important domains, a stretch of basic amino acids, which is involved in nuclear localization and in interaction with RRE RNA, and a leucine-rich region, presumed to be involved in transactivation, whose leucines are intolerant of mutation.

Rev is a protein whose target is termed RRE (Rev-response element), on the env protein coding region of the mRNA. Interaction of Rev with the RRE region apparently allows for transport of unspliced RNA from the nucleus to the cytoplasm. RRE (7758–7992) is an RNA secondary structure element. Proviruses lacking Rev function remain transcriptionally active but fail to generate new viral particles.

Accessory Genes

The nef gene (CDS 8787..9407) encodes Nef, and overlaps the env gene and the 3' LTR. Nef may be involved in signal transduction, although this is controversial. There has also been speculation that Nef down-regulates viral expression. The Nef protein does not appear to be essential to the HIV life cycle in tissue culture.

The vif gene (CDS 5041..5619) encodes Vif, the virion infectivity factor. Vif-deficient mutants are typically much less efficient than wild type HIV at cell-free (as opposed to cell-to-cell) virus transmission. It is not a virion component and the mechanism by which it affects infectivity is unclear.

The vpr gene (CDS 5559..5849) encodes Vpr, a virion protein which accelerates the replication and cytopathic effect of HIV-1 in CD4+ T-cells. About 100 copies of Vpr are associated with each virion.

The vpu gene (CDS 6061..6306) encodes Vpu. The vpu gene encodes part of a polycistronic transcript which also includes the env gene. Vpu is a cytoplasmic protein which is thought to facilitate assembly and/or release of viral particles.

PPT (Bases 9059–9075)

Immediately upstream from the 3' LTR is the polypurine tract vital to initiation of positive-strand DNA synthesis.

3 'LTR (9076..9709)

The 3' LTR is identical to the 5' LTR, but is significantly mainly by virtue of its poly-A signal (9602..9607), and the "R" repeat sequence (9529..9626) allowing RT jumping during DNA synthesis.

Infectivity

HIV-1 infects activated and resting lymphocytes, terminally differentiated monocytes and neuronal cells through cellular receptors and co-receptors such as CD4, chemokine receptors and galactosyl ceramide (J. M. Harouse et al., Science 253:320–323 [1991]; and R. A. Weiss, Science 272:1885–1886 [1996]). The restricted lentiviral host cell tropism can be expanded by pseudotyping the virus particles with broadly tropic viral envelope proteins from human T cell leukemia virus type I (HTLV-I), amphotropic MLV envelope protein or the vesicular stomatitis virus G glycoprotein (J. C. Burns et al., Proc. Natl. Acad. Sci. USA. 90:8033–8037 [1993]; N. R. Landau et al., J. Virol., 65:162–169 [1991]; K. A. Page et al., J. Virol., 64:5270–5276 [1990]; and D. H. Spector et al., J. Virol., 64:2298–2308 [1990]). Alternatively, a CD4 receptor can be introduced into target cells by adenovirus transduction before HIV vector transduction in a two-step transduction protocol (K. Miyake et al., Human Gene Ther., 7:2281–2286 [1996]). Naldini et al. have demonstrated that HIV-1 vectors pseudotyped with MLV-A or VSV-G envelope could produce up to $5 \times 10^5$ transducing units/ml of vectors capable of infecting nondividing cells such as macrophages and terminally differentiated neurons (L. Naldini et al., Science 272:263–267. [1996]).

Infection of nondividing cells by lentiviruses such as HIV-1 is mediated by the nuclear localization signal (NLS) in the Gag MA protein (M. I. Bukrinsky et al., Nature 365:666–669 [1993]). Efficient viral entry and integration into non-dividing cells may also require some of the accessory gene products such as Vpr (T. M. Fletcher et al., EMBO J., 15:6155–6165 [1996]; and N. K. Heinzinger et al., Proc. Natl. Acad. Sci. USA. 91:7311–7315 [1994]).

Cytotoxicity

One difficulty related to HIV vector development encountered during the development of the present invention is the cytotoxicity of many HIV gene products to human cells. In particular, it has been difficult to establish continuous cell lines expressing the essential structural proteins Gag, Pol and Env for particle assembly. Cell lines expressing Tat, Rev, Nef have been established. However, expression of Gag, Rev and Vpr has been shown to induce cytopathology, cell death and cell cycle arrest in human cells (See, M. Emerman, Curr. Biol., 6:1096–1103 [1996]; G. Miele and A. M. L. Lever, Gene Ther., 3:357–361 [1995]; and T. Nosaka et al., Exp. Cell. Res,. 209:89–102 [1993]). The development of a tightly inducible system was favored for a lentiviral packaging cell line (H. Yu et al., J. Virol., 70:4530–4537 [1996]). HIV-1 Vpr also induces apoptosis in human cells. The expression of VSV-G protein induces syncytium formation which again is problematic for establishing a packaging cell line.

Other Safety Issues

Unlike other retroviruses, the lentiviruses are able to infect non-dividing cells. Hence, lentiviral vectors have the potential to overcome this limitation of prior vectors systems. However, there is an understandable concern as to the safety of lentiviral vectors, especially those derived from HIV-1. The foremost safety consideration is the risk that either packaging vector and transducing vector will recombine, either with themselves or with defective virus endogenous to the host cell genome, to produce a replication-competent, infectious lentivirus, in particular, replication-competent HIV (RC-HIV). While the vector constructs are replication-defective, the risk of generating RC-HIV is increased with the DNA co-transfection procedure, when a high frequency of recombination events can occur at both DNA and RNA levels. Thus, the packaging constructs and the transducing vectors of lentiviruses could potentially recombine and generate replication-competent viruses (RCV) as do the MLV vectors during co-transfection. However, the chances of generating RCV are reduced if multiple recombination steps are necessary, and if the key envelope gene of HIV-1 is deleted.

Due to the restricted tissue tropism of the native lentiviral env gene, lentiviral vectors were developed that use a pan-tropic envelope gene such as amphotropic MLV env or VSV-Gs. This reduced the possibility of producing a wild-type lentiviral RCV (e.g., an HIV-1 Env-trophic virus). However, it is still possible that an RCV could be generated via recombination with these pan-tropic env genes or endogenous retrotransposon env genes. The fact that human genomes carry numerous human endogenous retroviral sequences (HERVs) further increases the probability of generating a fortuitous recombinant RCV (T. P. Loh et al., J. Virol., 62:4086–4095 [1988]). For example, a recent study demonstrated that a member of the HERV family encodes a protein resembling the lentivirus rev gene product with a nucleolar localization signal, a putative RNA binding domain, and a sequence similar to the Rev effector domain consensus sequence (R. Lower et al., J. Virol., 69:141–149 [1995]).

Some human tissues and cell lines such as the placenta, syncytiotrophoblasts, brain, differentiated U-937 cells, teratocarcinomas, and the mammary carcinoma T47D cells have been shown to express complete human endogenous retrovirus env gene and release retrovirus-like particles. These endogenous retroviruses may form defective particles which lack infectivity. Although the possibility of generating a recombinant RC-HIV with an HERV env gene is low, it is worth examining.

Discussion of Particular Lentiviral Vector Systems

Page, et al., J. Virol., 64: 5270–6 (1990) prepared a noninfectious transducing vector HIV-gpt in which the env gene was replaced with SV-gpt, and a helper vector providing either the HIV-1 gp160 env gene (the HXB2-env vector) or the amphotropic MLV env gene (the SV-A-MLV-env vector).

Shimada, et al., J. Clin. Investig., 88: 1043–7 (1991) describes a recombinant HIV-1 gene transfer system employing two vectors. The packaging vector has a CMV promoter, and an insertion mutation in the packaging signal. The transducing vector replaces part of gag, and all of pol, with a reporter gene cassette. The vector system uses wild type HIV-1 Env proteins to target CD cells. It is worth noting that Shimada et al. state that sequences upstream of gag AUG are important for gag expression, implying that they cannot be modified.

Corbeau, et al, Proc. Nat. Acad. Sci. (USA), 93: 14070–5 (1996) constructed an HIV-1 derived packaging vector by deleting the major packaging signal (37 nucleotides, starting from 6 nt downstream of the 5' major splice donor site to 7 nucleotides upsteam of the beginning of gag). The genome, which was derived from HIV-1-MN-ST.1 because of its high efficiency of infection in both monocytes and T cells, was otherwise intact. Their transducing vector had the components LTR-gag-RRE-reporter gene (SL3-gpt)-env-LTR. Titers of 10E5 transducing units (TU)/mL were reported.

Corbeau et al. suggest that the first 500 nt of the gag gene may be directly or indirectly involved in the binding of the viral RNA to the nucleocapsid of the virion, and that a stretch within the env gene, including the RRE, also contains a packaging signal.

Corbeau et al. also criticize prior vectors. They attribute the alleged deficiencies of these vectors to the truncation of the vpr gene from the packaging vector, and/or to the deletion of gag and/or env sequences which may contain additional packaging signals from the transducing vector.

Akkina, et al., J. Virol., 70: 2581–5 (1996) demonstrated that an HIV-1 based retroviral vector containing the firefly luciferase reporter gene can be pseudotyped with a broad host range VSV G envelope glycoprotein. The luciferase gene replaced the HIV-1 nef gene. The authors suggested that such a vector should be able to infect CD34+ hematopoietic progenitor cells with high efficiency.

Markowitz, et al, J. Virology 62: 1120–4 (1988) had suggested that viral genes could be separated onto two different plasmids, to provide a safer packaging line for gene transfer Markowitz et al. Placed the gag and pol genes of MLV on one plasmid, and the env gene on the other. The plasmids had deletions of the 3'LTRs and the packaging signal as well. Hence, to generate intact retrovirus, there would need to be several recombination events. Markowitz' strategy was adapted to HIV-1 by Naldini et al., as described below.

Naldini, et al., Science, 272: 263 (1996) describes a lentiviral vector-based system for gene delivery. There are three vectors in the system. The first packaging vector (pCMVΔR9) provides the HIV gag, pro, pol, vif, nef, tat, rev, and vpr genes, but the env and vpu genes, and the packaging signal, were inactivated. (A later paper, cited below, makes it clear that the env gene was inactivated by insertion of a linker containing multiple stop codons.) The human cytomegalovirus (CMV) immediate early promoter was substituted for the 5' LTR, while the 3' LTR was replaced with a polyA site from the human insulin gene. The major splice donor site was preserved. A second packaging vector was used to broaden the tropism of the vector system. In one variant, this vector expressed the amphotropic envelope of Moloney leukemia virus (MLV), under control of the MLV LTR, and in the other, it expressed the G glycoprotein of vesicular stomatitis virus (VSV) under the direction of the CMV promoter. (The lternative Env protein was the only expression product of the second vector.) The final element of the system was a transducing vector (pHR'), providing, in order, the 5'LTR, the major splice donor site, the major packaging signal, nearly 350 base pairs of gag, the env sequence encompassing the RRE element, a splice acceptor site, an internal CMV promoter, a reporter gene (luciferase or beta-galactosidase), and a 3' LTR.

Naldini et al., Proc. Nat. Acad. Sci. (USA), 93: 11382–8 (1996) discuss the use of VSV-G-pseudotyped lentiviral vector particles to achieve "long-term" expression of a transgene in adult rat brains injected with the particles. The packaging vector differs from that described above in that 1.4 kbp was deleted from the env gene, downstream of the functional vpu gene, and replaced with an inframe stop codon. See also Blomer et al., J. Virol., 71: 6641–9 (September 1997).

Sodroski, U.S. Pat. No. 5,654,195 (1997) describes a hybrid virus in which the 5' DNA segment encodes functional SIV or HIV-2 gag, pol, pro, vif, and vpx proteins, and the 3' DNA segment encodes functional HIV-1 env, tat and rev proteins, and a functional SIV or HIV-2 nef protein. The 5' and 3' LTRs are from SIV or HIV-2.

Sodroski, U.S. Pat. No. 5,665,577 (1997) discloses an HIV vector which comprises the gag, pol and env genes but lacks the HIV major packaging, signal identified therein as AAAAATTTTGACTAGCGGA(SEQ ID NO: 4). When introduced into a eukaryotic host cell, these express the structural proteins to form HIV virions that do not contain sufficient HIV RNA to result in a replication-competent HIV virion.

SUMMARY OF THE INVENTION

The present invention contemplates attenuated lentiviruses, and improved viral packaging and transducing vectors derived from lentiviruses, especially HIV-1, and useful for the delivery of nonlentiviral genes to target cells. It also contemplates the use of these vectors in delivering transgenes to target cells, especially nondividing cells, in organisms, especially humans.

Packaging Vectors

The packaging vectors of the present invention differ from those known previously in that they contain less in the way of lentiviral sequences from a single lentivirus, and hence present a reduced risk of recombination. In particular, the packaging vectors of the present invention are characterized by either the use of a modified but functional major splice donor site, substantially incapable of serving as a site for homologous recombination, or by the complete omission of the major splice donor site. In a preferred embodiment, the modified major splice donor site is modified so that it is substantially identical to the major splice donor site of a non-lentiviral retrovirus, especially that of Rous Sarcoma Virus (RSV).

Preferably, other non-essential sequences, such as the accessory genes, of the source lentivirus are also deleted in the course of the construction of the packaging vector. Preferably, in the 5' LTR region of the packaging vector, the wild-type promoter and enhancer are replaced with a non-homologous promoter (and, optionally, a nonhomologous enhancer). These changes likewise serve to reduce the risk of generating replication-competent virus through recombination with the transducing vector or a defective provirus endogenous to the host or target cell.

Preferably, the 5' LTR promoter is an tightly inducible promoter, so that expression of Gag, Pol and Env proteins is under the control of the biologist. This, together with the inactivation of certain accessory genes, tends to reduce cytotoxicity.

Preferably, the Gag and Pol functions are encoded by one vector and the Env functions (preferably, a non HIV-1-like envelope protein) by another vector.

Preferably, gag expression is enhanced by the operable linking of the gag gene to a Kozak sequence.

Transducing Vectors

In a preferred embodiment, the transducing vector likewise is characterized by a functional major splice donor site which differs from that of its source lentivirus. In the latter case, its major splice donor site need not be identical to that of the packaging vector(s). The modification should leave a functional packaging signal, too.

Preferably, it likewise has a strong nonlentiviral promoter/enhancer in place of the normal 5' LTR.

Preferably, the gag (except for packaging signals) and pol sequences are deleted. Desirably, the env sequences are deleted to the extent that this can be done without a substantial loss in yield.

While there may still be regions of sequence identity between the packaging and transducing vectors which are sufficiently long to present a meaningul risk of homologous recombination, a characteristic of the preferred vector system is that homologous recombination alone, among only the packaging and transducing vectors, cannot create a recombinant virus which possesses, simultaneously, a functional packaging signal, a functional major splice donor site, and a gag AUG, even if the recombined virus possesses a 5' promoter/enhancer and genes otherwise encoding equivalents of the Gag, Pol and Env proteins. The first region of significant homology is in the gag gene, after the initiation codon. Hence, if the recombinant virus derives a functional packaging signal and a functional major splice donor site from the transducing vector, it will lack the gag AUG, since it can crossover to the packaging vector only after the AUG. Contrariwise, if it has the 5' sequence of the packaging vector through the gag AUG, it will lack a functional packaging signal and a functional major splice donor site. Of course, a replication-competent virus could still be generated by nonhomologous recombination, or by further recombination with a defective endogenous retrovirus.

Certain speculative vector systems are also described herein which further increase safety.

BRIEF DESCRIPTION OF THE DRAWINGS

FIGS. 3A–3C show the organization of the HIV-1 genome and a series of HIV-1 mutants containing LTR, tat, and nef mutations

FIG. 12A similarly illustrates possible crossover with the same packaging vector and a different transducing vector, pTVΔ.

FIG. 13A provides a schematic showing a portion of the wild-type HIV-1 sequence (SEQ ID NO:60), as well as the tat-B the tat-B sequence is provided in SEQ ID NO:1).

FIG. 13B provides a schematic showing of a portion of the wild-type HIV-1 sequence (SEQ ID NO:61), as well as the nef-A (SEQ ID NO:16) mutations and nef-B (SEQ ID NO:17) mutations

FIG. 17 provides the sequence of a portion of the wild-type HIV-1 sequence (SEQ ID NO:60), and tat-A (SEQ ID NO:19), tat-B (SEQ ID NO:1), and tat-C (SEQ ID NO:19).

FIG. 20 is a table setting forth the relative titers for the transducing vectors of FIGS. 19A–19C, but further indicating the number of constructs tested in each sample group, the standard error, and the paired P value.

FIG. 21 is a table comparing a portion of the wild-type HIV-1 (SEQ ID NO:62), pHP (SEQ ID NO:20) and pTV5' (SEQ ID NO:21) sequences.

DETAILED DESCRIPTION OF THE PREFERRED EMBODIMENTS OF THE INVENTION

Figure 1A:
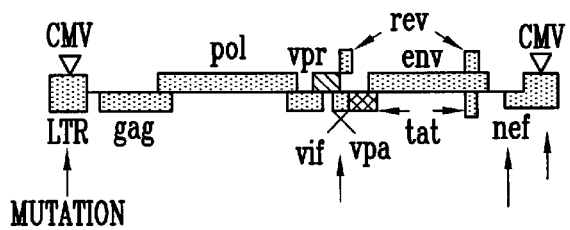
FIG. 1A is a simplified schematic illustration showing the HIV-1 genomic structure.
Figure 1B:
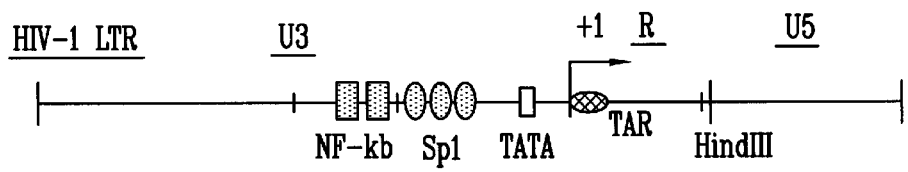
FIG. 1B is a simplified schematic illustration of the HIV-1 LTR.
Figure 1C:
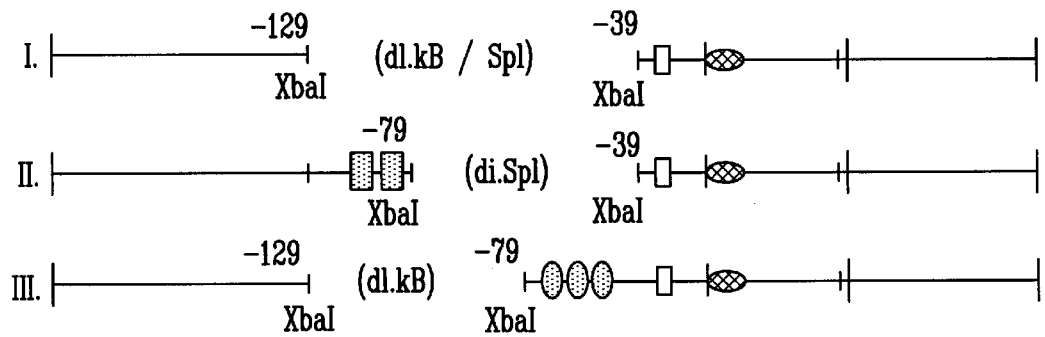
FIG. 1C provides simplified schematic illustrations of three HIV-1 LTR deletion constructs.
Figure 1D:
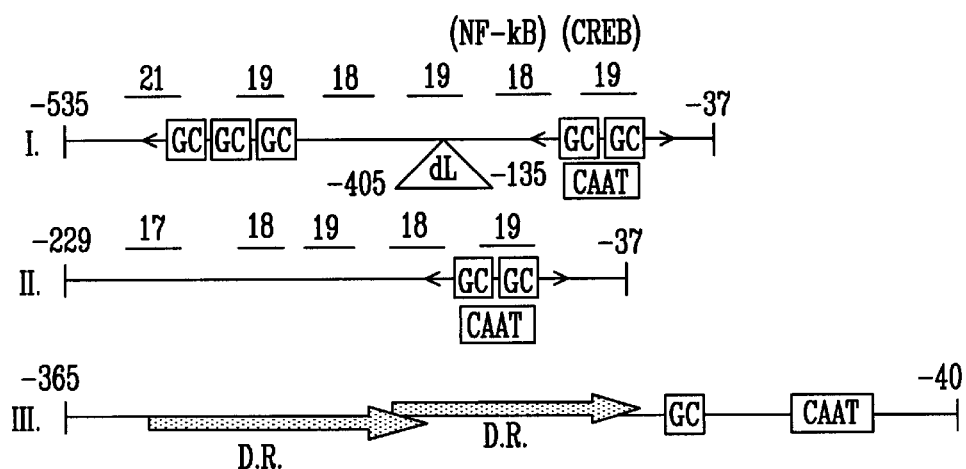
FIG. 1D provides simplified schematic illustrations of three heterologous enhancer/promoter inserts (I. Human CMV IE(a), II. Human CMV IE(b), and III. Mo-MLV).

The present invention relates to attenuated and/or replication-defective lentiviruses, and to packaging and transducing vectors derived in whole or in part from a lentivirus.

The Lentivirus

A "source" or "original" lentivirus is a wild-type lentivirus from which an attenuated and/or replication-defective lentivirus is derived, or which is used as a starting point, during construction of the packaging or transducing vector, for the preparation of one or more of the genetic elements of the vector. The genetic element may be employed unchanged, or it may be mutated (but not beyond the point where it lacks a statistically significant sequence similarity to the original element). A vector may have more than one source lentivirus, and the different source lentiviruses may be, e.g., HIV-1 and HIV-2, or HIV and SIV, and so forth.

One may also speak of a "source" or "original" gene, genetic element or protein for a vector gene, genetic element or protein. (The term "genetic element" includes but is not limited to a gene.)

The cognate lentivirus is the wild-type lentivirus with which the vector in question has the greatest percentage sequence identity at the nucleic acid level. Normally, this will be the same as the source lentivirus. However, if a source lentivirus is extensively mutated, it is conceivable that the vector will then more closely resemble some other lentivirus. It is not necessary that the cognate lentivirus be the physical starting point for the construction; one may choose to synthesize a genetic element, especially a mutant element, directly, rather than to first obtain the original element and then modify it.

One may also speak of a "cognate" protein, gene, or genetic element (e.g., splice donor site or packaging signal). When referring to a cognate protein, percentage sequence identities are of course determined at the amino acid level.

The term "cognate" lentivirus may be difficult to interpret in the extreme case, i.e., if all lentiviral genetic elements have been replaced with surrogate non-lentiviral genetic elements. In this case, the preferred source HIV-1 strain mentioned previously is arbitrarily considered to be the cognate lentivirus.

HIV type 2 (HIV-2) is known to be less pathogenic than HIV-1 in humans, and HIV-2 infection is associated with natural protection against HIV-1 infection. Simian immunodeficiency virus (SIV) also infects human cells; however, it is unclear whether it can cause AIDS in humans. Thus, both HIV-2 and SIV may be better candidates than HIV-1 for developing lentiviral vectors. It may be advantageous to derive both the packaging and transducing vectors from a lentivirus other than HIV-1, or to derive one from HIV-1 and the other from a lentivirus other than HIV-1. Use of different sources for the two vectors reduces the risk of homologous recombination to generate RCV, and use of a source other than HIV-1 reduces the health risk if recombination, homologous or otherwise, occurs. Applicant's preliminary work was with HIV-1 derived vectors and attenuated viruses because much more is known about the HIV-1 genome and proteins than about those of other lentiviruses. However, in the long run, it may be preferable to derive the instant vector system from a less threatening lentiviral source virus, such as HIV-2 or SIV.

The term "replication" as used herein in reference to a virus or vector, refers not to the normal replication of proviral DNA in a chromosome as a consequence of cell reproduction, or the autonomous replication of a plasmid DNA as a result of the presence of a functional origin of replication, but rather to the completion of a complete viral life cycle wherein infectious viral particles containing viral RNA enter a cell, the RNA is reverse transcribed into DNA, the DNA integrates into the host chromosome as a provirus, the infected cell produces virion proteins and assembles them with full length viral genomic RNA into new, equally infectious particles.

The term "replication-competent" refers to a wild-type virus or mutant virus that is capable of replication, such that replication of the virus in an infected cell result in the production of infectious virions which, after infecting another, previously uninfected cell, causes the latter cell to likewise produce such infectious virions. The present invention contemplates the use of replication-defective virus.

As used herein, the term "attenuated virus" refers to any virus (e.g., an attenuated lentivirus) that has been modified so that its pathogenicity in the intended subject is substantially reduced. Preferably, the virus is attenuated to the point it is nonpathogenic from a clinical standpoint, i.e., that subjects exposed to the virus do not exhibit a statistically significant increased level of pathology relative to control subjects.

The present invention contemplates the preparation and use of an attenuated lentivirus. In some embodiments, the attenuated lentivirus is selected from the group consisting of attenuated mutants of human immunodeficiency virus type 1, human immunodeficiency virus type 2, feline immunodeficiency virus, simian immunodeficiency virus, visna-maedi, caprine arthritis-encephalitis virus, equine infectious anemia virus, and bovine immune deficiency virus. Thus, the attenuated virus may be an attenuated HIV-1, attenuated HIV-2, attenuated SIV, or a virus comprised of portions of more than one lentiviral species (e.g., a hybrid, comprised of portions of HIV-1 and HIV-2, or HIV-1 and SIV, etc.)

A reference virus is a virus whose genome is used in describing the components of a mutant virus. For example, a particular genetic element of the mutant virus may be said to differ from the cognate element of the reference virus by various substitutions, deletions or insertions. It is not necessary that the mutant virus actually be derived from the reference virus.

The preferred reference HIV-1 was mentioned previously. For HIV-2, see LOCUS HIV2ROD, 9671 bp ss-RNA, Human immunodeficiency virus type 2, isolate ROD, complete proviral genome, ACCESSION M15390, see Clavel, F., Guyader, M., Guetard, D., Salle, M., Montagnier, L. and Alizon, M, Molecular cloning and polymorphism of the human immunodeficiency virus type 2, Nature 324, 691–695 (1986).

The preferred reference SIV sequence is LOCUS SIVMM239, 13068 bp ss-RNA, a Simian immunodeficiency virus isolated from a macaque, isolate 239 (Macaca mulatta Mm239–82); complete proviral genome and flanking sequence, GenBank ACCESSION M33262, see Regier, D. A. and Desrosiers, R. C., The complete nucleotide sequence of a pathogenic molecular clone of simian immunodeficiency virus, AIDS. Hum. Retroviruses 6, 1221–1231 (1990).

The preferred reference RSV sequence is Genbank locus/accession # AP052428, 9396 bp DNA, the Rous sarcoma virus strain Schmidt-Ruppin B, complete genome.

Lentiviral Vector System

The present invention contemplates a gene amplification and transfer system comprising a transducing vector (TV), one or more compatible packaging vectors (HP), and a suitable host cell, the transducing vector and at least one packaging vector being derived from a lentivirus, which allow (1) transfection of the packaging vectors into the host cell to form a packaging cell line which produces essentially (packaging vector RNA)-free viral particles, (2) transfection of the transducing vector into the packaging cell line, (3) the packaging of the transducing vector RNA by the packaging cell line into infectious viral particles, and (4) the administration of the particles to target cells so that such cells are transduced and subsequently express a transgene carried by the transducing vector.

Either the particles are administered directly to the subject, in vivo, or the subject's cells are removed, infected in vitro with the particles, and returned to the body of the subject.

The basic characteristics of the packaging vector and the transducing vector are summarized in the following table:

| Lentiviral Genetic Element | Packaging Vector | Transducing Vector |
|---|---|---|
| 5' LTR U3: integration attachment site (att) | preferably deleted | preferably deleted (not in mRNA transcript) |
| 5' LTR U3: promoter/enhancer | preferably replaced by any sufficiently strong heterologous promoter (opt. incl. enhancer) functional in the packaging cell line | as for packaging vector, but must be functional in the packaging cells; preferably CMV or EF-1α promoter/enhancer, or an inducible promoter |
| 5' LTR R: TAR site | may be deleted | may be replaced with an alternative R of another retrovirus (Note 1) |
| 5' LTR R: Poly-A | preferably deleted | see above |
| 5' LTR U5 | preferably deleted | may be deleted |
| 5' LTR U5-3' att site | preferably deleted | functional att required |
| L: PBS | preferably deleted | may be replaceable with a mutant PBS or with the PBS of another retrovirus if reverse transcriptase also replaced |
| L: major splice donor site | replaced with an alternative splice donor site, the RSV site is preferred (see text); or deleted totally | may be mutated, e.g., GGTG to GCAG or GGGG to reduce homology to source sequence and retain packaging function and 5' poly A suppression |
| L: major packaging signal | inactivated | functional packaging signal required; need not be wild-type |
| L: genomic RNA dimer linkage site | inactivated | functional DLS required; need not be wild-type |
| L: region upstream of gag initiation codon | preferably insert Kozak sequence | no preference |
| gag | a gene or genes encoding proteins substantially identical to the wild-type Gag proteins is/are required; the identity or similarity is preferably sufficient so that the protein retains the nuclear translocation function, and (if the target cell is a nondividing cell) the function of entering the nucleus of nondividing cells | the gene is inactivated vis-a-vis production of functional Gag proteins, e.g., by replacing the initiation codon with a stop codon (e.g., TAG) and/or deleting at least part of the gene, but the minor packaging signal in bases 1–40 of the gag gene is preferably retained in functional form |
| pol | a gene or genes encoding compatible protease, integrase, and reverse transcriptase is/are required (see text) | inactivated, preferably by deletion |

-continued

| Lentiviral Genetic Element | Packaging Vector | Transducing Vector |
| --- | --- | --- |
| env | a gene encoding a retroviral envelope protein, or a chimera of an envelope protein and one or more foreign binding moieties, is required. | inactivated, preferably by deletion of part of the gene; the RRE region is preferably retained in functional form to maintain its packaging and nuclear transport functions |
| tat | may be deleted or otherwise inactivated | preferably inactivated, preferablyby deletion |
| rev | may be deleted or otherwise inactivated if INS's in gag and pol inactivated, and RRE in env inactivated | preferably inactivated, preferably by deletion |
| vif | preferably deleted | preferably deleted |
| vpr | may be deleted; may inactivate its cell cycle arrest function and maintain its nuclear transport function | preferably deleted |
| vpx (HIV-2) | preferably deleted; may inactivate its cell cycle arrest function and maintain its nuclear transport function | preferably deleted |
| vpu | preferably deleted | preferably deleted |
| nef | preferably deleted | preferably deleted |
| PPT | preferably deleted | preferable to have a functional PPT; may be possible to replace with the PPT of another retrovirus |
| 3' LTR-U3 | enhancer-promoter region preferably deleted | preferably deleted, except that a functional att site is required |
| 3' LTR - R | preferably deleted and replaced by a functional, non-HIV polyA site | may be replaced with the R region of another retrovirus (see Note 1) |
| 3' LTR-U5 | preferably replaced with any polyA signal compatible with host cell | may be deleted; if it contains a polyA element, it may be preferable to retain that element at least |

Notes:
(1) In the transducing vector, The 5' LTR and 3' LTR R regions must be sufficiently identical so that ssDNA jumping by the reverse transcriptase will occur.
(2) there can be more than one packaging vector, carrying separate structural genes. For example, one vector can encode gag and pol functions, and another vector, env functions.

The packaging vectors and transducing vectors of the present invention are each replication-incompetent viruses. Moreover, the vectors chosen for incorporation into a given vector system of the present inventionare such that it is not possible, without further mutation of the packaging vector(s) or transducing vector, for the cotransfected cells to generate a replication-competent virus by homologous recombination of the packaging vector(s) and transducing vector alone.

Packaging Signal

As used herein, the term "packaging signal" or "packaging sequence" refers to sequences located within the retroviral genome or a vector which are required for, or at least facilitate, insertion of the viral or vector RNA into the viral capsid or particle. The packaging signals in an RNA identify that RNA as one which is to be packaged into a virion. The term "packaging signal" is also used for convenience to refer to a vector DNA sequence which is transcribed into a functional packaging signal. Certain packaging signals may be part of a gene, but are recognized in the form of RNA, rather than as a peptide moiety of the encoded protein.

The major packaging signal is the signal having the predominant effect on whether viral RNA is inserted into the particle. This signal is located in the 5' leader region (spanning the SD site and the gag AUG) of the wild-type lentiviral genome. It is not equivalent to the conventional site of the MLV vectors, in that the latter alone allows efficient MLV vector packaging.

There are also minor packaging signals with a lesser effect on packaging efficiency. Several studies have shown that many sequences in HIV-1, including LTR, TAR, RRE, and in the 5' and 3' gag ORF, the pol ORF, and in the sequences flanking the RRE, contribute to efficient genome packaging, pointing to the complex nature of HIV-1 packaging signals (See e.g., A. Aldovini and R. A. Young, J. Virol., 64:1920–1926 [1990]; J. F. Kaye et al., J. Virol., 69:6593–6599 [1995]; A. Lever et al., J. Virol., 63:4085–4087 [1989]; J. Richardson et al., J. Virol., 67:3997–4005 [1993]).

Earlier studies of the HIV packaging signal demonstrated that a 46 nt (751–796) stem-loop structure derived from the splice donor site to the 5' gag coding region is sufficient to allow packaging of a heterologous Sendai virus RNA but the efficiency was not determined and the location of the insertion was critical to the stem-loop conformation. See Hayashi T, Shioda T, Iwakura Y, Shibuta H. RNA packaging signal of human immunodeficiency virus type 1. Virology 1992; 188:590–9. They further showed that the 46 nt sequence must be inserted in the 5' end of the Sendai RNA to serve as a packaging signal; inserting in the midst of the Sendai RNA destroyed the packaging signal. Secondary structure analysis showed that several stem-loop structrual domains can be identified in the 5' untranslated leader region andlin the 5' gag coding region. See Baudin F, Marquet R, Isel C, Darlix J L, Ehresmann B, Ehresmann C. Functional sites in the 5' region of human immunodeficiency virus type 1 RNA form defined structural domains. J Mol Biol 1993; 229:382 97. McBride et al. further showed that the packaging signals in the 5' end of the HIV genome include TAR and four stem-loops from upstream of the major 5' splice donor site extending into the first 7 amino acid codons in the gag coding region. See McBride MS, Panganiban AT. The human immunodeficiency virus type 1 encapsidation site is a multipartite RNA element composed of functional hairpin structures. J. Virol. 1996; 70:2963–2973; McBride M S, Schwartz M D, Panganiban A T. Efficient encapsidation of humna immunodef iciency virus, type 1 vectors and further characterization of cis elements required for encapsidation. J. Virol. 1997; 71:4544–4554. Parolin et al. demonstrated that up to 653 nt in the gag coding region can enhancer RNA packaging efficiency. See Parolin C, Dorfman T, Palu G, Gottlinger H, Sodroski J. Analysis in human immunodeficiency virus type 1 vectors of cis-acting sequences that affect gene transfer into human lymphocytes. J. Virol. 1994;

68:3888–3895. Luban and Goff showed that the first 40 nt of gag coding sequence is strongly influential on the packaging function, see Luban J, Goff SP. Mutational analysis of cis-acting packaging signals in human immunodeficiency virus type 1 RNA. J. Virol. 1994; 68:3784–3793, and the Goff group further reported that the HIV-1 packagng signal requires the very 5' edge of the RNA and sequences downstream of the 170th nt of gag or sequences in pol, see Berkowitz R D, Hammarskjold M-L, Helga-Maria C, Rekosh D, Goff SP. 5' regions of HIV-1 RNAs are not sufficient for encapsidation: implications for the HIV-1 packaging signal. Virology 1995; 212:718–723. Their studies indicate that for efficient packaging function, the four stem-loop structure may not be sufficient. Instead, the packaging signal as well as its sequence context consist of the entire packaging signal. This is consistent with the study of Kaye et al. who have reported that the RRE and env sequences, although not essential to render RNA packaging, may have a positive effect on enhancing the packaging efficiency, see Kaye J F, Richardson J H, Lever AML. cis-Acting sequences involved in human immunodeficiency virus type 1 RNA packaging. J. Virol. 1995; 69:6593–6599. This latter group also reported that the mutation of the gag AUG is detrimental to RNA packaging. It is thus clear that the packaging signal of HIV is not as simple as MLV and RSV.

A further reason for including the major packaging signal in a transducing vector is because it overlaps with the dimer linkage sequence (DLS) which is also essential for genome packaging (See, J. L. Clever et al., J. Virol., 70:5902–5908 [1996]; J.-C. Paillart et al., J. Virol., 70:8348–8354 [1996]; and J.-C. Paillart et al., Proc. Natl. Acad. Sci. USA. 93:5572–5577 [1996]).

The key distinction between a packaging vector and a transducing vector is that in the packaging vector, the major packaging signal is inactivated, and, in the transducing vector, the major packaging sign al is functional. Ideally, in the packaging vector, all packaging signals would be inactivated, and, in the transducing vector, all packaging signals would be functional However, countervailing considerations, such as maximizing viral titer, or inhibiting homologous recombination, may lender such constructs less desirable.

Using a precise quantitative assay for vector function, we have found that the 5' major splice donor site, the gag AUG and the extended gag sequences are dispensable for the packaging of a functional HP/TV vector. The highly conserved sequences essential to HIV replication (the SD and gag AUG, and additional coding sequence) have now been deleted from the pTV vector which has greatly improved the safety of the HP/TV vector system and totally eliminated the possibility of generating RCV via homologous recombination at the gag region.

Packaging System; Packaging Vectors; Packaging Cell Line

A packaging system is a a vector, or a plurality of vectors, which collectively provide in expressible form all of the genetic information required to produce a virion which can encapsidate suitable RNA, transport it from the virion-producing cell, transmit it to a target cell, and, in the target cell, cause the RNA to be reverse transcribed and integrated into the host genome in a such a manner that a transgene incorporated into the aforementioned RNA can be expressed. However, the packaging system must be substantially incapable of packaging itself. Rather, it packages a separate transducing vector which is described below. The general abbreviation for a packaging vector in this specification is HP or pHP.

In the case of an HIV-1 vector, the packaging system will provide functional equivalents of the gag, pol and env genes as discussed below. One may use a single vector which provides all three genes (a "GPE" vector), or a two vector system wherein one vector provides the gag-pol genes (a "GP" vector) and the other vector (an "E" vector) provides the env gene. In theory, a three vector system ("G", "P", and "E" vectors) is possible if one is willing to construct distinct gag and pol genes on separate vectors, and operably link them to different regulatable promoters (or one to a regulatable and the other to a constitutive promoter) such that their relative levels of expression can be adjusted appropriately.

The vector or vectors which together compose the packaging system are called the packaging vectors.

A packaging cell line is a suitable host cell transfected by a packaging system which, under achievable conditions, produces viral particles. As used herein, the term "packaging cell lines" is typically used in reference to cell lines that express viral structural proteins (e.g., gag, pol and env), but do not contain a packaging signal. For example, a cell line has been genetically engineered to carry at one chromosomal site within its genome, a 5'-LTR-gag-pol-3'-LTR fragment that lacks a functional psi$^+$ sequence (designated as Δpsi), and a 5'-LTR-env-3'-LTR fragment which is also Δpsi located at another chromosomal site. While both of these segments are transcribed constitutively, because the psi$^+$ region is missing and the viral RNA molecules produced are less than full-size, empty viral particles are formed.

If a host cell is transfected by the packaging vector(s) alone, it produces substantially only viral particles without the full-length packaging vector Preferably less than 10% of the viral particles produced by the packaging cell contain full length packaging vector-derived RNA. However, since the packaging vector lacks a functional primer binding site, even if these particles infect a new cell, the packaging vector RNA will not be reverse transcribed back into DNA and therefore the new cell will not produce virion. Thus, by itself, the packaging vector is a replication-incompetent virus.

Preferred packaging vectors include vectors identical or otherwise substantially indentical to HP vectors disclosed herein, including but not limited to those selected from the group consisting of pHP-1, pHP-dl.2 and pHP-dl.28, pHP-VSVG, pHP-CMV, pHP-CMVdel.TAR/SD, pHP-CMV-EF1α intron, and pHP-EF.

The pHP construct was made by first replacing the 5' LTR with the CMV-TATA-TAR chimeric promoter, obtained from the BbrPI to HindIII fragment of the chimeric LTR containing CMV IE promoter-TATA box and TAR seqence, which was derived from a recombinant HIV-1 LTR as described previously, see Chang L-J, Zhang C. Infection and replication of Tat-minus human immunodeficiency viruses: genetic analyses of LTR and tat mutants in primary and long-term human lymphoid cells. Virology 1995; 211:157–169; Chang L-J, McNulty E, Martin M. Human immunodeficiency viruses containing heterologous enhancer/promoters are replication competent and exhibit different lymphocyte tropisms. J Virol 1993; 67:743–752, then deleting the rest of the 5' leader sequence extending from the HindIII site in the end of TAR region to the gag AUG using a synthetic oligonucleotide containing a splice donor site of Rous sarcoma virus and a conserved Kozak sequence —CCACC— adjacent to the gag AUG. The Kozak sequence serves to increase the translational efficiency. The gag-pol coding sequence is kept intact. Alternatively, the conserved reverse transcriptase (RT) domain of the pol sequence is replaced with RSV RT domain by PCR amplification and cloning. The vif, vpr, vpu and env genes were mutated by site-specific mutagenesis to eliminate the AUG initiation codon and some of the coding sequence but not affecting Gag-Pol or Tat/Rev syntheses. The tat coding sequence can also be mutated as described below either by inserting multiple stop codons (e.g. tat-B mutant) or by deleting the initiation AUG codon and part or all of the coding sequence (e.g. tat-C mutant) because the pHP can be tat-independent. A rev independent gag-pol construct can also be made by mutating the nuclear retention signals in the gag-pol coding region as indicated by Schneider R, Campbell M, Nasioulas G, Felber B K, Pavlakisl G N. Inactivation of the human immunodef iciency virus type 1 inhibitory elements allows Rev-independent expression of Gag and Gag/protease and particle formation. J. Virol. 1997; 71:4892–4903, and in the env coding region including the RRE element. In this rev-independent pHP construct, the rev open reading frame is mutated by removing the intiation codon AUG and deleting the coding sequence. The 3' nef-PPT-LTR of HIV-1 was entirely deleted from the nef initiation AUG codon which was mutated to contain a new HindIII site and replaced with a selective marker gene gpt and an SV40 polyadenylation signal.

In some embodiments, the packaging cell and/or cell line contains a transducing vector. The packaging cell line will package the transducing vector into infectious particles. Such a cell line is referred to herein as a "transgenic virion production cell line".

It is contemplated that packaging may be inducible, as well as non-inducible. In inducible packaging cells and packaging cell lines, lentiviral particles are produced in response to at least one inducer. In non-inducible packaging cell lines and packaging cells, no inducer is required in order for lentiviral particle production to occur.

The packaging vectors necessarily differ from wild-type, replication-competent lentiviral genomes by virtue of the inactivation of at least one packaging signal of the cognate wild-type genome. More than one packaging signal may be inactivated. Preferably, the only lentiviral genes provided by the packaging vector are those encoding structural, or essential regulatory, proteins.

Transducing Vectors

A transducing vector is an expression vector which bears an expressible nonlentiviral gene of interest and includes at least one functional lentiviral packaging signal, so that, after said transducing vector is transfected into a packaging cell line, the transducing vector is transcribed into RNA, and this RNA is packaged into an infectious viral particle. These particles, in turn, infect target cells, their RNA is reverse transcribed into DNA, and the DNA is incorporated into the host cell genome as a proviral element, thereby transmitting the gene of interest to the target cells.

As used herein, the term "transduction" refers to the delivery of a gene(s) using a viral or retroviral vector by means of infection rather than by transfection. In preferred embodiments, retroviral vectorsiare transduced. For example, an anti-HIV gene carried by a retroviral vector can be transduced into a cell through infection and provirus integration. Thus, a "transduced gene" is a gene that has been introduced into the cell via lentiviral or vector infection and provirus integration. In preferred embodiments, viral vectors (e.g., "transducing vectors") transduce genes into "target cells" or host cells.

It may be convenient to classify transducing vectors as follows:

Generation 0 pTV: pTV vectors containing non-replication essential genes or genetic elements. (e.g vectors previously reported by Naldini et al. and Shimada et al. [Naldini, 1996 #2755; Shimada, 1991 #470]?) Generaion 1 pTV: pTV vectors with deletions of all the accessory genes and non-replication essential genetic elements (e.g. vif, vpr, vpu, nef, NF-kB/Sp1)

Generation 2 pTV: pTV vectors with deletions of replication-essential genetic elements (e.g., gag AUG, SD site, env sequences, RRE, TAR, such elements are also missing on pHP)

Generation 3 pTV: pTV vectors with substitutions of vector-essential genetic elements (complementary substitutions are also present on pHP).

In the present invention, various transducing vectors may be used, including those identical or otherwise substantially identical to TV vectors disclosed herein, including but not limited to those selected from the group consisting of pTVψ, pTVψ100, pTVψ140, pTV.ψ.nlacZ, and pTVψCMV-nlacZ-hyg-dl.SmaI, pTVΔ, pTVΔ-X, pTVΔEFnlacZ, PTVΔEFGFP, pTVΔCMV-X, pTVΔCMVnlacZ, pTVΔSVneo, pTVΔSVhyg, pTVΔCMV-GFP, pTVΔCMV-nlacZ, and pTVΔCMV-nlacZ-hyg. However, it is not intended that the present invention be limited to these specific transducing vectors. For example, the "pTVΔ-X," indicates that the vector may be comprised of "pTVΔ" in combination with any gene ("X"). Thus, the present invention encompasses transducing vectors that are suitable for use in the present invention that are linked to any gene of interest (or a "marker gene" or "reporter gene," used to indicate infection or expression of a gene).

One preferred transducing vector pTV is made of a chimeric CMV-TATA-TAR-U5/att-PBS-packaging signal-mutated SD-portion of gag-portion of env-mutated nef-PPT-U3/att-R-U5 which exhibits packaging function like the wild type HIV. The U5 sequence was mutated such that all of it was deleted except for the 3' 24 nt att site. The 5' chimeric promoter is derived from the NF-kB/Sp1 deleted CMV-TATA construct of the HIV LTR mutant described previously which directs transcription at the native HIV transcriptional initiation site. The TAR is in the R region which can be mutated at both ends to maintain the repeatitive function of the R but significantly different from the wild type HIV R. Alternatively, the R sequence can be replaced with RSV R so it is completely different from HIV R sequence. Alternatively, the PBS can be modified to become RSV PBS such that the chimeric pHP RT (gag-RSV-RT-pol) can initiate minus-strand DNA synthesis using the appropriate tRNA primer. The packaging signal will have conserved stem-loop secondary structure as described by McBride et al. as SL1 to SL4 but with mutations in SD (GGTG to GCAG or GGGG) and gag AUG (replaced with ACC or UAG) We showed that the latter mutations have minimal effect on packaging efficiency. The mutant SD/gagAUG pTV RNA genome is packaged into transducing particles at near 70% wild type efficiency.

In preferred embodiments, the vectors of the present invention are capable of "high efficiency transduction." This is intended to encompass transducing vectors capable of transduction at a level of at least $10^5$/ml, although in particularly preferred embodiments, the vectors are capable of transduction levels of up to $10^{10}$/ml. As used herein, the term "low efficiency transduction" refers to transducing vectors capable of transduction at levels less than or equal to $10^3$/ml.

As used herein, the term "long-term transduction" refers to vectors that are capable of remaining transduced in host or target cells for time periods that are longer than those observed with other vectors. For example, the present invention provides lentiviral vectors that are capable of remaining transduced for at least 120 days, more preferably at least one year, most preferably for the life of the subject or the necessary time course of treatment. Long-term gene transduction and high efficiencies of transduction of human cells by the HIV vectors of the present invention were compared with the conventional MLV vector (See, Table 5). The duration of expression is a function of the choice of promoter and the target cell type, more so than the choice of vector.

The term "stable transduction" or "stably transduced" refers to the introduction and integration of foreign DNA into the genome of the transducted cell. The term "stable transductant" refers to a cell which has stably integrated foreign DNA into the genomic DNA.

The term "transient transduction" or "transiently transduced" refers to the introduction of foreign DNA into a cell where the foreign DNA fails to integrate into the genome of the transducted cell. The foreign DNA persists in the nucleus of the transducted cell for several days. During this time the foreign DNA is subject to the regulatory controls that govern the expression of endogenous genes in the chromosomes. The term "transient transductant" refers to cells which have taken up foreign DNA but have failed to integrate this DNA.

In some preferred embodiments, the target and/or host cells of the present invention are "non-dividing" cells. These cells include cells such as neuronal cells that do not normally divide. However, it is not intended that the present invention be limited to non-dividing cells (including, but not limited to muscle cells, white blood cells, spleen cells, liver cells, eye cells, epithelial cells, etc.).

In particularly preferred embodiments, the vector and the vector progeny are capable of transducing a plurality of target cells so as to achieve vector titers of at least $10^5$ cfu/ml. The preferred multiplicity of infection (MOI) would be at least one (i.e., one hit on average per cell), more preferably at least two.

Adaptations for HIV-2 and SIV Derived Vectors

Based upon the experiments conducted during development of the HIV-1 vector system, HIV-2 and SIV vector systems may be developed (pH2P and PSIVP). To establish a lentiviral vector based on HIV-2 or SIV, the 5' LTR and the untranslated leader sequences of HIV-2ROD and SIV-mac239 may be replaced with the recombinant HP-1 enhancer/promoter and a synthetic leader sequence with or without a splice donor site, both obtainable from the pHP vectors. The 3' LTR may be replaced by the SV40 polyadenylation signal. The nef and env genes may both be deleted from the vector. The expression of vpx is preferably included in the HIV-2/SIV packaging cells because it has been shown that the HIV-2/SIV vpx (or SIVagm vpr) is necessary and sufficient for nuclear import function and does not inhibit cell cycle progression as does vpr. The VSV-G envelope gene is preferably expressed from a separate expression vector.

Previous studies suggested that SIV or HIV-2 genomes can be assembled into the HIV-1 particles, indicating that the packaging signals of SIV or HIV-2 can be recognized by HIV-1 nucleocapsids. Thus, one may construct a hybrid vector which is essentially an HIV-1 derived vector with SIV or HIV-2 packaging signals (from 3' of the PBS to the extended gag sequences). These HIV-2 and SIV transducing vectors (pTV2 and pTVS) may be tested in co-transfection experiments using pH2P or pSIVP.

Alternatively, one may construct transducing vectors wherein the lentiviral genetic elements are derived solely from HIV-2 (pTV2) and SIV (pTVS). However, instead of using modified LTRs, a strong heterologous promoter is preferably used and the transcription initiation site is placed at the beginning of the R-U5 sequence. Sequences in gag-pol and env genes are deleted and the major SD and the gag AUG are mutated. A CMV-driven reporter gene cassette such as the CMV-IE-nlacZ-IRES-hyg from the pTVΔ-nlacZ-hyg vector may be inserted in the nef ORF of the HIV-2 and the SIV vectors. The 3' LTR resembles the native LTR but with a deletion in the U3 except for the 5'att site.

Genetic Elements of the Packaging and Transducing Vectors

These are discussed in detail below.

Modified Major Splice Donor Sites

A splice donor site is a sequence which directs the splicing of one exon to another exon. Typically, the first exon lies 5' of the second exon, and the splice donor site overlapping and flanking the first exon on its 3' side recognizes a splice acceptor site flanking the second exon on its 5' side. Splice donor sites have a characteristic consensus sequence represented as (A/C) AG GURAGU (R=purine). See Jackson, Nucleic Acids Res., 19: 3715–98 (1991). The first three bases of the splice donor consensus are the last three bases of the exon.

A splice acceptor site is a sequence which acts in conjunction with a splice donor site, so that the intron separating the two sites is removed. The characteristic splice acceptor site is YYYYYYYYYYNYAG (Y=pyrimidine, N=any).

In a preferred embodiment, the HIV-1 major SD is replaced with the cognate RSV SD. The synthetic RSV SD sequence is split into two parts with an AgeI site inserted in place of the RSV gag AUG site:

```
Synthetic RSV SD: (sequence derived from RSV, Gene Bank ACCESION # AF052428,
is underlined and in bold)

5'-AGCTTGGTCGCCCGGTGGATCAAGACCGGTAGCCGTCATAAAGGTGATTTCGTCGGATC-3'(SEQ ID NO:23)

(AgeI) The original RSV SD:

5'-ATTCTGGTCGCCCGGTGGATCAAGCATGGAAGCCGTCATAAAGGTGATTTCGTCCGCGT-3'(SEQ ID NO:24)

The HIV-1 LTR consensus A 5' leader sequences (5'sj is in bold and underlined, the construct was
made from HIV-1NL4-3, Access # M19921):

5'-GGCTTGCTGAGGTGC--?CACAGCAAGAGGCGAGAG----CGGCGACTGGTGAGTACGCC-??AAATTTT-3' (SEQ ID NO:25)

The entire 5' leader sequence of HIV-1 consensus A:

GCCTTGAG?TGCTT?AAGTA-GTGTGTGCCCGTCTG?TT?T?TGACTCTGGTAACTAGAGATCCCT
```

```
                                                 -continued
CAGACCACT?TAGACTGTGT--AAAAATCTCTAGCAGTGGCGCCCGAACAGG?????????????

???GACTCGAAAGCGAAAG----------------------TTCCAGAGAAG?----TCTCTCG

ACGCA?-GGACTCGGCTTGCTGAGGTGC--?CACAGCAAGAGGCGAGAG----CGGCGACTGGT

GAGTACGCC-??AAATTTT??-GACTAGCGGAG------GCTAGAAGGAGAGA?A (SEQ ID NO:26)

For reference, the corresponding HIV-2 and SIV sites are as follows:
HIV-2ROD 5' splice junction: (ACCESSION # M15390)

CAAAAACTGTAGCCGAAAGGGCTTGCTATCCTACCTTTAGACAGGTAGAAGATTGTGGGAG-3' (SEQ ID NO:27)

SIV 239 (ACCESSION # M33262 M61062-M61093)

ACGGCGTGAGGAGCGGGAGAGGAAGAGGCCTCCGGTTGCAGGTAAGTGCAACACAAAAAA

GAAATAGCTGTCTTTTATCCAGGAAGGGGTAATAAGATACAGTGGGAGATG (SEQ ID NO:28)
```

The artificially engineered splice donor (SD) site from Rous sarcoma virus (RSV) in the pHP-1 construct, a site that is unrelated to HIV sequences, was found to work like the wild-type SD site (i.e., allowing partition of spliced tat and rev, and unspliced gag-pol mRNAs into the cytoplasm). This is a critical factor in some embodiments of the present invention (i.e., the replacement of the HIV SD site with the RSV SD site), as the native leader sequences and the major splice donor site must both be deleted from the HP constructs to decrease the probability of homologous recombination with the transducing vectors (TV).

The splicing junction sequences have been previously studied, see Ezzell C. Eukaryotic mRNA processing. The Journal of NIH Research, 1995; 7:101–104; Mount SM. AT-AC introns: an ATtACk on dogma. Science 1996; 271:1690–1692. In our previous studies, we showed that the first tat coding exon contains positive and negative splicing regulatory elements and the splicing signals can be hundreds of nucleotides away from the splice junciton sites. Amendt B A, Hesslein D, Chang L J, Stoltzfus C M. Presence of negative and positive cis-acting RNA splicing elements within and flanking the first tat coding exon of human immunodeficiency virus type 1. Mol Cell Biol 1994; 14:3960–3970. Therefore, the success of inserting a functional splice site in the leader region of HP construct using an oligonucleotide sequence containing a small number of nucleotide sequences from RSV 5' splice junction site was surprising.

The splice donor site in the packaging constructs is used solely for the expression of tat and rev genes downstream and serves to stabilize the gag-pol transcript. It is possible that tat and rev functions can be provided in trans and the 5' splice donor site can be totally eliminated. For example, an SV40 promoter with a replication origin can be used in the packaging constructs and the DNA can be transfected into a SV40 large T antigen expressing cell lines such as COS7 cells (African green monkey kidney cells expressing SV40 T Ag).

Modified Packaging Signals

The packaging signal is of course inactivated in the packaging vectors. In the transducing vectors, a functional packaging signal is required, but need not be identical to the source signal.

The packaging signals have a secondary structure; they may be mutated so as to alter the primary sequence while substantially retaining the secondary structure. Applicant has found it possible to mutate the HIV-1 major packaging signal by replacing GGTG with GCAG or GGGG.

Lentiviral packaging signals may be replaced with non-lentiviral packaging signals, or functional mutants thereof, such as the cognate packaging signal of another virus, such as RSV or MLV. If so, it will generally be necessary to make corresponding mutations in the Gag nucleocapsid protein so that it recognizes the new packaging signal. Thus, one could make a chimera of the Gag nucleocapsid protein and the cognate nucleocapsid protein of the other virus.

Finally, in the case of the packaging vector(s), one may delete the HIV-1 major packaging signal altogether.

Structural Genes/Proteins

The terms "Gag protein" and "Gag proteins" refer to any or all proteins, respectively, encoded by the gag gene, including both the ultimate virion proteins and their precursors (i.e., proteins which are processed intracellularly into the ultimate virion proteins.) The terms "Pol protein(s)" and "Env protein(s)" are analogously defined. These terms can be further modified by "-like" or "-equivalent" as elsewhere defined.

As noted above, the structural virion genes are the gag, pol and env genes. At least one, and preferably all of these genes is inactivated in the transducing vector. The only part of gag or env necessary to keep is the part that play essential roles in packaging. We have identified the first 39 nucleotides of the gag coding sequence excluding the initiation codon and the RRE in the beginning of gp41 coding region of the env sequence are essential to keep. However, site-specific mutagenesis can be performed to further change these sequences to introduce stop codons in the gag gene and in the env gene and to kill the RRE function of interacting with Rev. This latter changes can further improve the safety of the HP/TV vector system.

However, the packaging vectors must collectively provide genes encoding the functions of the gag, pol and env genes in order to provide a functional virion. Nonetheless, these genes may differ from the source genes by silent and other functional mutations.

Silent Mutations

These may be made almost freely throughout the gene. The only areas where caution is required is where the choice of sequence has regulatory significance, e.g., the slippage region in gag-pol, or the RRE region in env. In some instances, such as in the case of an INS element, it may actually be desirable to inactivate the regulatory element. In other instances, the regulatory element may be useful, and only silent mutations which leave it functional are desirable.

Functional Mutations

These are mutations which affect the amino acid sequence of one or more of the encoded polypeptides, but which do not substantially abolish the relevant biological activity of the affected polypeptide(s).

The comments which follow apply not only to mutation of lentiviral proteins, but also to mutation of naturally occurring, nonlentiviral proteins which are acting as the equivalent of a lentiviral protein. For example, instead of using wild-type VSV G protein in place of HIV-1 gp120, one may use a functional mutant of VSV G protein.

As explained below, while the result of a mutation is not absolutely predictable, some mutations are clearly more likely to be tolerated than others. The accuracy of these predictions is dependent in part on whether a 3-D structure for the protein is known, whether homologous proteins (i.e., functional mutants, naturally occurring or otherwise) have been sequenced, and whether the biologically relevant binding sites of the protein have been identified.

The tremendous natural variation of the HIV-1 genome suggests that it is quite tolerant of multiple mutations in many genes. The following specific guidance is offered:

A general source of 3D structures is the Protein Data Bank, whcih is searchable on the Internet.

Gag: The overall sequence variability of Gag proteins in HIV-1 isolates is more than 20%. With deliberate mutations, it is likely that a higher degree of sequence variation can be tolerated. The 3D structure of the nucleocapsid protein of Gag, complexed to human cyclophilin A, has been determined; Gamble, et al., Cell, 87: 1285–94 (1996); see also PDB structures 1atv and 1ncp. Mutational analysis reveals that the zinc finger domains in the NC protein play important roles in RNA encapsidation and HIV infectivity. Mizuno, et al., AIDS Res. Hum. Retroviruses, 12: 793–800 (1996). Charged amino acids have also been shown to be involved in RNA packaging and infectivity. Poon, et al., J. Virol., 70: 6607–16 (1996). Mutational studies have also been made of the CA proteins, using deletion mutants and chimeras. Carriere, et al., J. Virol., 69: 2366–77 (1995). For structure-function relationships in general, see Wills, AIDS, 5: 639–54 (1991). 3D structures are available for the CA (PDB 1afv) and MA (PDB 1hiw) proteins.

Pol: The overall sequence variability among HIV-1 isolates is more than 20%; in the protease domain, a variability of more than 40% has been observed. The 3D structure of the reverse transcriptase, complexed to an inhibitor, is known, see Kohlstaedt, et al., Science, 256:1783–90 (1992), and a structural model for the protease has been proposed, see Pearl and Taylor, Nature, 329: 351–4 (1987). The polymerase and protease functional domains have been studied by mutagenesis, see Loeb et al., Nature, 329: 351–4 (1989); Le Grice, et al, EMBO J., 10: 3905–11 (1991). For 3D structures, see also PDB entries 1hnv and 1rtl (RT), 1itg (integrase), and 1hvk (protease).

Env: For the Env proteins gp120 and gp41, the overall sequence variability among HIV-1 isolates exceeds 60%. For 3D structures, see PDB entries 1aik (gp41) and lacy (gp120 fragment) For discussion of functional domains, see Moulard M, Challoin L, Canarelli S, Mabrouk K, Darbon H, Retroviral envelope glycoprotein processing: structural investigation of the cleavage site, Biochemistry 1998 Mar 31;37(13):4510–4517.

Pseudotyping studies have shown that the Env proteins can be entirely replaced by the retroviral but non-lentiviral MoMLV Env proteins, or the unrelated VSV-G protein.

The envelope proteins encoded by the packaging vector may be lentiviral or non-lentiviral proteins. The advantage of a non-lentiviral protein is that it can confer on the produced particles the ability to bind to a cell surface receptor of a class of cells not normally infected by the lentivirus. An example of a non-lentiviral envelope protein of interest is the vesicular stomatitis virus (VSV) G protein. VSV-G pseudotyped particles are rigid and can be concentrated more than 1000-fold. They also bind to different cells than those bound by HIV-1 gp120 typed particles.

Where one of the packaging vectors encodes a non-lentiviral envelope protein, it is referred to as an envelope pseudotyping vector. In preferred embodiments, the pseudotyping vector is selected from the group consisting of PHEF-VSVG, pHEF.A-env, Gibbon ape leukemia virus env, and MLV-Amphotropic env.

Alternative Env proteins: The Env proteins of HIV-1 may be replaced with Env proteins of other lentiviruses, of nonlentiviral retroviruses, of nonretroviral viruses, or with chimeras of these proteins with other peptides or proteins. Examples are the Env proteins of VSV (G protein), the hemagglutinin protein of influenza virus, the surface antigen (S and preS) of hepatitis B virus, and the Env protein of RSV. These mdofications increase the range of cells which can be transduced with HIV-1 derived vectors.

Chimeric Env Proteins: A chimera may be constructed of an env protein and of a ligand that binds to a specific cell surface receptor in order to target the vector to cells expressing that receptor. Examples are chimeras including FLA16 (a 6 a.a. peptide which binds integrin receptors), erythropoietin (which binds the erythropoietin receptor), human heregulin (which binds the EGF and related receptors). Alternatively, the chimera could include an antibody variable light or heavy domain, or both domains joined by suitable peptide linker (a so-called single chain antibody). Such an antibody domain could target any desired cell surface molecule, such as a tumor antigen, the human low-desnity lipoprotein receptor, or a determinant on human MHC Class I molecules.

Derivatized Env Proteins: Virions may be chemically, enzymatically or physically modified after production in order to alter their cell specificity. Examples of modifications include chemical or enzymatic addition of a ligand which would be recognized by a cell surface receptor (e.g., addition of lactose so that the virions will transduce human hepatoma cells which express asialoglycoprotein receptors), or incubation of the virus with a biotinylated antibody directed against the vector's Env protein, followed by addition of a streptavidin-linked ligand recognized by the cell-surface receptor. A heterobispecific antibody could be used to link the virion's Env protein to such a ligand, too.

Regulatory Genes

The vector system may provide the regulatory proteins, or surrogates therefor, or wholly omit them. If Tat or Rev equivalents are provided, the corresponding genes may be placed on the transducing vector, or on the same or different helper vector(s). These genes need not be placed on the packaging vectors. Again, silent mutations may be made almost freely.

Functional mutation of Tat and Rev should be feasible. For the 3D structure of Rev, see PDB entry 1rpv; for RRE, see 1etf and 1etg; fFor Tat, see 1tiv; for TAR, see 1kis.

Tat is a transcriptional factor which acts to bind the polII transcription elongation complex and increases the processivity of transcription. The amino acid sequence of Tat is highly conserved amongst different HIV-1 strains with more than 80% homology. Mutational analysis has shown that the functional domain is in the first coding exon because deletion of the second exon does not affect its transactivation function. The N-terminal domain is highly charged and contains a long stretch of basic amino acids such as arginine which is the characteristic of RNA binding domain. Tat has been shown to bind to the TAR sequence at the loop of a stem-loop structure in the 5' end of the genome. In addition to its transcriptional activation function, Tat has also been shown to enhance reverse transcription and in our laboratory, we have shown that Tat can enhance gag protein precursor processing. Therefore, the multiple functions of Tat may indicate that it may be required for high titer vector production. However, Tat may be substituted with different lentiviral transactivators to avoid recombination of HIV sequences.

Rev is also a transcriptional regulator which acts at a post transcriptional step in the nucleus to enhance the export of RRE-containing RNA to the cytoplasm. Its amino acid sequence is highly conserved amongst different HIV-1 strains. Human T cell leukemia virus type 1 (HTLV-1) encodes a similar protein named Rex. Rex and Rev share low sequence homology (less than 40%) but have similar functions. Mutational analysis have shown that rev function requires both coding exons. Rev binds to RRE in env and interacts with cellular proteins in the nucleus to mediate the nuclear export of the RRE-containing transcripts. The function of Rev is dispensable if RRE and the inhibitory sequences in the gag-pol and env are mutated.

Although TAR and RRE are known for their functions in mediating Tat and Rev interaction with the viral RNA, these two RNA elements may have other functions unrelated to Tat and Rev interaction which may be important for gene transfer ector function. It is possible that RRE or TAR may contain minor packaging signal to enhance viral RNA encapsidation. The example of RRE mutation on vector function is presented later.

With regard to complete deletion, Tat and Rev have been reported to be absolutely required for viral replication in vitro or in vivo Vaishnav Y N, Wong-Staal F. The biochemistry of AIDS. Ann Rev Biochem 1991; 60:577–630; Greene W C. Regulation of HIV-1 gene expression. Annu Rev Immunol 1990; 8:453–475.

However, a small element from the Mason-Pfizer monkey virus genome can make human immunodeficiency virus type 1 expression and replication Rev-independent, Bray M, Prasad S, Dubay J W, et al. A small element from the Mason-Pfizer monkey virus genome makes human immunodeficiency virus type 1 expression and replication Rev-independent. Proc Natl Acad Sci Usa 1994; 91:1256–1260, and this strategy has been used to develop a rev-independent HIV vector system, see Srinivasakumar N, Chazal N, Helga-Maria C, Prasad S, Hammarskjold M-L, Rekosh D. The effect of viral regulatory protein expression on gene delivery by human immunodeficiency virus type 1 vectors produced in stable packaging cell lines. J. Virol. 1997; 71:5841–5848.

Also, we have reported that HIV tat mutants with stop codon mutations or deletions in the tat open reading frame can still infect human lymphocytes and macrophages, Chang L-J, Zhang C. Infection and replication of Tat-minus human immunodeficiency viruses: genetic analyses of LTR and tat mutants in primary and long-term human lymphoid cells. Virology 1995; 211:157–169. The requirement for Tat transactivation of HIV-1 LTR can be, diminished if the LTR enhancer promoter elements are replaced with a chimeric CMV-IE-HIV LTR. Robinson D, Elliott J F, Chang L-J. Retroviral vector with a CMV-IE/HIV-TAR hybrid LTR gives high basal expression levels and is upregulated by HIV-1 Tat. Gene Therapy 1995; 2:269–278.

LTR and tat mutants of HIV-1 have been shown to have iminished replication phenotypes (See e.g., L.-J. Chang et al., J Virol., 67:743–752 [1993]; L.-J. Chang and C. Zhang, Virol., 211:157–169 [1995]; and J. C. Leonard et al., J Virol. 63:4919–4924 [1989]).

Accessory Genes

The accessory proteins of HIV-1 may have important functions in viral pathogenesis, see Trono D. HIV accessory proteins: leading roles for the supporting cast. Cell 1995; 82:189–192; but they are dispensable for viral replication in tissue culture. We and others have shown that the accessory genes are not essential to the creation of functional packaging and transducing vectors, i.e., they may be completely deleted. Hence, it is unnecessary to consider in detail the guidance offered by the art as to which mutations of the accessory proteins might be functional. Of course, if one chooses to retain an accessory gene, such guidance can be found in the literature on, e.g., sequences of HIV-1 isolates.

In general, it is preferable to delete all lentiviral accessory genes when constructing the transducing vector, in order to reduce the risk of homologous recombination to form RCV. However, certain accessory genes, such as vpr or vpx, may increase transduction efficiency of nondividing cells, in which case there is a countervailing advantage to retaining them in a form in which they encode functional protein. If so, silent mutations, and other functional mutations, may be introduced to reduce the risk of homologous recombination without loss of gene function.

Other Genetic Elements

In the packaging vectors (pHP-likes), the 5' LTR can be totally eliminated but a functional promoter will be needed to drive RNA transcription and gag-pol gene expression. Preferably, a strong enhancer/promoter will be used to replace the 5' LTR.

Tat may be needed for high efficiency of Gag-Pol synthesis. In this case, HIV-1 TAR seqeunce may be retained in the 5' end for enhanced promoter function. In the transducing vectors (pTV-likes), the necessary functions for vector production in the 5' LTR are the repetitive sequence R, which serves as annealing sequence for minus-strand DNA jumping to the 3' R, and the attachment site (att) in the 3' end of U5 adjacent to the PBS for provirus integration. The R can be made different from the native HIV R but have the same mutated R in the 3' end. The att site is necessary for integrase recognition and binding and therefore cannot be changed.

Preferably the lentiviral promoter/enhancer elements of the 5 Ltr are replaced with a nonlentiviral promoter/enhancer in at least one (a) the packaging vectors or (b) the transducing vector. Both the HP 5' LTR and TV 5'LTR promoter/enhancers may be replaced with the same or with different promoter/enhancers, e.g., CMV IE in one and EF-1α in the other.

In the 5' leader region, no HIV functional elements are necessary for the packaging construct. However, for the transducing vector, several elements are needed, in an order from 5' to 3' including PBS, packaging signal, and dimer linkage sequence (DLS). HIV uses lysine tRNA PBS which may be mutated to a different retroviral PBS such as histidine tRNA or proline tRNA of RSV or MLV. However, a coupled change in the RT domain which recognizes the corresponding PBS will also be needed. The packaging signal for HIV RNA has been shown to include different areas in the genome. It is possible that site-specific mutations can be made to change the primary sequence but maintain the secondary structure. The major 5' splice donor site and the gag AUG have been shown by others to be essential for genome packaging. However, we have demonstrated that both the SD and the gag AUG can be mutated and the modified transducing vector can still be packaged in high efficiency (see examples below). The DLS is not well defined. However, both primary sequence and secondary structure may be necessary for a functional DLS which overlaps the packaging signal between SD and the gag AUG.

In one embodiment, the packaging vector replaces the HIV-1 SD with an RSV SD. The splicing junction sequences have been previously studied. Ezzell C. Eukaryotic mRNA processing. The Journal of NIH Research 1995; 7:101–104; Mount SM. AT-AC introns: an ATtACk on dogma. Science 1996; 271:1690–1692. In our previous studies, we showed that the first tat coding exon contains positive and negative splicing regulatory elements and the splicing signals can be hundreds of nucleotides away from the splice junciton sites. Amendt BA, Hesslein D, Chang L J, Stoltzfus C M. Presence of negative and positive cis-acting RNA splicing elements within and flanking the first tat coding exon of human immunodeficiency virus type 1. Mol Cell Biol 1994; 14:3960–3970. Therefore, the success of inserting a functional splice site in the leader region of HP construct using an oligonucleotide sequence containing a small number of nucleotide sequences from RSV 5' splice junciton site was a surprise.

Coordinated Mutations

In a number of instances, a mutation of one genetic element is preferably complemented by a mutation of another genetic element in the same or a different vector:

(a) transducing vector PBS and packaging vector RT;

(b) transducing vector packaging signal, or dimer linkage site, and packaging vector Gag nucleocapsid protein;

(c) packaging vector Rev deletion, and, in transducing vectors, inactivation of INS's in gag and pol, and RRE; and (d) vector tat and vector TAR.

Wild-Type, Mutant and Surrogate Proteins

Fom time to time this specification has cause to characterize a protein, or a gene encoding a protein, as being (a) identical to a naturally occurring protein; (b) a mutant which is substantially similar in amino acid sequence to the naturally occurring protein, and retaining a substantial portion of the biological function of the naturally occurring protein, or (c) substantially dissimilar in amino acid sequence to the naturally occurring protein, but nonetheless capable of substituting for the naturally occurring protein. It is convenient to develop a concise terminology for the various possibilities.

Hence, the term "wild-type" X implies that the protein is identical to a naturally occurring form of protein X.

The term X "-like" protein implies that the protein is either identical to X, or is a mutant as described in (b) above. The precise scope of this term will vary depending on how narrowly X is defined. If the reference is to an "HIV-1 gp120-like protein", the amino acid sequence and biological activity of the X-like protein will be compared to that of the HIV-1 gp120 proteins. If it is to a "lentiviral Env-like protein", it will be compared to that of the most similar of the lentiviral envelope proteins. And so forth.

A mutant is more likely to be considered substantially identical to a reference protein if (a) the overall sequence identity is within the natural range of variation of homologous proteins (e.g, of all HIV-1 gp120 variants, if the referent is a particular gp120); (b) most or all of the sites of mutation are sites of high variability in that family; and (c) most or all of the substitutions, especially at low variability sites, are at least semiconservative, and more preferably conservative or highly conservative substitutions in general, or favored by experimental data. The term "X-like protein mutant" implies that the protein is not identical to X.

The term "X-equivalent protein" includes all of the possibilities (a)–(c) above. Possibility (a) is excluded by the phrasing "X-equivalent protein mutant". Possibilities (a) and (b) are both excluded by the phrasing "x surrogate".

Similarly, we may speak of a gene encoding a "wild-type X", an "X-like protein", an "X-like protein mutant", an "X-equivalent protein", an "X-equivalent protein mutant", or an "X-surrogate". The gene may encode a precursor of the protein in question, rather than the mature protein per se.

Similar terminology applies to genetic elements other than genes.

If not otherwise defined for use in the particular context in question, a mutant is considered substantially similar in sequence ito a reference sequence if it is at least 50% identical with the reference sequence, with percentage identity being calculated by the default procedure set forth below.

Inactivation

This invention contemplates that certain genetic elements of the lentiviral genome will be substantially inactivated to render the genome more suitable (e.g., safer) for use as a vector in the delivery of therapeutic genes to a patient. The inactivation may, but need not be, absolute. Preferably, the level of inactivation is at least 50%, more preferably at least 9%, still more preferably at least 95%, most preferably at least 99%.

There are two fundamental methods of inactivating a protein. First, one may delete the corresponding gene so that the protein is simply not produced. Secondly, one may alter the corresponding gene so that the expressed polypeptide is a nonfunctional mutant.

A gene is substantially inactivated if it is mutated so that it substantially is no longer capable of being transcribed and translated into a polypeptide retaining a substantial amount of the objectionable biological activity of the originally encoded polypeptide. A gene may be inactivated by (1) completely deleting it, (2) removing its initation codon so that it is not translated, (3) inserting one or more stop codons into the coding sequence, preferably immediately after or in place of the initiation codon, so as to stop translation prior to production of a functional polypeptide, (4) inserting or deleting a number of bases, other than a multiple of three, so as to cause a frameshift, and thus the production of an erroneous polypeptide sequence downstream of the frameshift mutation, (5) inserting or deleting one or more whole codons, at either end or internally, so that a nonfunctional polypeptide (or a polypeptide of substantially different function) is encoded, (6) making one or more base substitutions (point mutations) in the gene which alter the encoded amino acid, so that a nonfunctional polypeptide is encoded, or (7) a combination of any of (2) to (6) above.

Preferably, if there is no reason to preserve any of the sequence of the gene, it is inactivated by completely deleting it. In the lentiviral genome, some genes overlap, so that it is not possible to inactivate one gene by complete deletion without inactivating the overlapping gene. And some genes contain regulatory elements (like RRE in env), and so cannot be completely deleted without loss of a regulatory function. Hence, in these circumstances, methods (2)–(6) above are appropriate. If point mutations are employed, preferably these are multiple mutations.

This specification explains how to identify which mutations of a gene are likely to be functional. By disregarding such advice, one may obtain inactivating mutations.

A genetic element other than a gene is inactivated if it is mutated so that it is no longer capable of performing its normal biological function. Normally, this means that it is mutated so that it is no longer recognized by a nucleic acid-binding protein. In some cases, the protein recognizes the primary structure (nucleotide sequence) of the genetic element, in other cases, it recognizes a secondary structure arises from the folding of the strand. A single nucleic acid strand can fold upon itself to bring complementary regions into proximity; these are then held together by hydrogen bonding between the complementary G:C or A:T bases. The HIV major packaging signal is an example of a genetic element recognized on the basis of its secondary structure. (Of course, the secondary structure of a genetic element is a consequence of its primary sequence.)

The secondary structure of a nucleic acid sequence may be predicted by conventional methods, such as those of Tinoco, and one or more segments predicted to have a secondary structure (e.g., a stem loop) deleted or modified until an acceptable level of inactivation is obtained.

Complete deletion is the preferred method of inactivation, if a genetic element is not at all desirable. However, it is possible that a genetic element A which is to be inactivated lies between two genetic elements B and C which are to be retained, and which preferably are at a particular distance from each other, or that all or part of the sequence forming the genetic element to be inactivated is also part of another genetic element which is to be retained. In these situations, complete deletion is not desirable. If so, single or multiple insertions, deletions or substitutions, whether consecutive or nonconsecutive in the primary sequence, may be used to alter the sequence sufficiently so that the objectionable genetic element is inactivated without substantial adverse consequences.

A vector may be said to comprise an inactivated genetic element even if the inactivation is accomplished by completely deleting the element, so it is not present in the vector; the phrase then indicates that at least one of the differences between the vector and a source (or cognate) lentivirus is that the element in question, which is missing in the former, is found in the latter.

Homologous Recombination

Homologous recombination is the formation of a hybrid of two sequences, wherein the point of crossover between one sequence and the other lies at a region of significant length wherein the two sequences are substantially identical. This region is called a region of homology.

Preferably, the packaging vector(s) and transducing vector are chosen so that the frequency of homologous recombination between them is less than that experienced with the vector systems of Naldini, et al., Science, 272: 263 (1996) or of Corbeau, et al., PNAS USA 93:14070–5 (1996). Preferably, if homologous recombination so occurs, it is not enough by itself to form a replication-competent virus.

It should be noted that mutations which inactivate a gene do not necessarily prevent that gene from being a site for a crossover event, and, conversely, mutation of a gene in one vector to eliminate homology with a corresponding gene in another vector will not necessarily inactivate the gene. For example, insertion of a stop codon does not prevent crossover within the untranslated downstream sequence, and silent mutations may be used to destroy homology, without affecting the nature of the encoded polypeptide. Of course, it a gene is entirely deleted, it is both inactivated and incapable of participating in homologous recombination.

The probability of a recombination occurring between the packaging vector and the transducing vector increases as the number, length and degree of identity of the two sequences increases. Cell GeneSys, WO91/06667, which relates to the deliberate induction of homologous recombination of a transgene, states that homologous sequences as short as 14 bases may provide for homologous recombination, but that its preferred flanking sequences are at least about 150 bp. They cite Rubnitz and Subramani, Mol. And Cell. Biol., 4:2253–8 (1984), as describing the minimum amount of homology required for homologous recombination in mammalian cells, and Kim and Smithies, Nucleic Acids Res., 16: 8887–8903 (1988) as describing a PCR-based assay for homologous recombination. Chappel, U.S. Pat. No. 5,272, 071, states that it has been suggested that the minimum requirement for homologus recombination is 25 base pairs, citing Ayares et al., ONAS USA 83:5199–5203 (1986). It has been reported in studies of bacterial recombination that a 10% divergence in sequence between two incompletely homologous sequences reduces the frequency of recombination between them by a factor of about 40. See Shen and Huang, Genetics, 112: 441–457.

Watt, et al., PNAS USA 82:4768–72 (1985) states that, for *E. Coli* recombination, a minimum of about 20 base pairs of completely homologous segment is required for significant recombnation, that there is an exponential increase in frequency over the range 20–74 bp, and a linear increase in frequency with length for longer perfectly homologus segments. There was a 100-fold increase in recombination frequency from 30 bp to 150 bp homology. Other relevant papers include Smokik-Utlaut, et al., Mol. Cell. Biol., 3:1204–11 (1983); Watt et al., PNAS USA 82:4768–72 (1985).

Homologus recombination begins with a hybridization step, and it is therefore worthwhile to consider studies of hybridization probes. Typically, even perfectly homologous probes must be 15–20 bases long to exhibit reasonable specificity against the mammalian genome. A published formula relating Tm (deg C) to, inter alia, probe length, indicates that the Tm should decrease according to the term (600/N), where N is the probe length. Moreover, each 1% divergence in sequence is expected to reduce Tm by 1–2 deg C. Finally, the Tm increases with increasing GC content, and hence it is more helpful to eliminate GC than AT pairs.

Therefore, the likelihood of recombination can be decreased by minimizing the lengths of identical segments in the two vectors. In practice, this means that it is preferable to (1) completely delete any genes or other genetic elements which do not substantially contribute to the functionality of the vector (packaging or transducing) in question, (2) when a function of a genetic element does make such a contribution, replace it, where possible, in one of the vectors (or differently in both vectors) with a genetic element which is different in sequence but similar in function, and substitutable for the original element (e.g., the cognate element in another strain or lade, in another lentivirus, in another retrovirus, in another virus, or in a microbial cell, or a functional mutant of the original element or a cognate element of another organism). In some instances, such as the PBS and the RT, Rev and RRE, and Tat and TAR, it may be necessary to make coordinated changes in two or more genetic elements.

In the case of a gene, silent mutations may be introduced so as to reduce its sequence identity with the original gene, even though both the mutated and original genes encode the same protein. In many codons, the third base of the codon is a wobble position in which any of 2–4 different bases can appear without alteration of the encoded amino acid. While there are a few codons (Met and Trp) which do not allow silent alteration of the third base, these are counterbalanced by the codons which allow some variation of the first base, too. Thus, one can reasonably expect to be able to make silent alterations to perhaps one-third of the total sequence, with the alterations being fairly evenly distributed. Care must be taken that such silent mutations do not substantially interfere with any important regulatory element of the gene, such as the slippage region in gag-pol, unless a functional substitute for that regulatory element is provided.

In the case of a genetic element which is recognized by virtue of its secondary structure,. paired bases may be identified and swapped, i.e., if a G at position 1 pairs to a C at position 10, forming part of a stem, position 1 may be changed to C and position G to C. Indeed, it may also be possible to replace G:C with A:T, and A:T with G:C, pairs, although such changes are less certain to be tolerated in view of the difference in strength between the two interactions.

In case of a genetic element which is recognized by virtue of its primary sequence, it is relatively rare that the recognition is absolutely specific, that is, only one functional primary sequence exists. The specificity of the recognition may be explored by combinatorial mutagenesis, e.g., as taught by Reidhaar-Olsen and Ladner, in a system which screens or selects for recognition of the mutated element. Alternatively, if the gene encoding the binding protein is accessible to manipulation, e.g., it is a viral or host cell gene, one may attempt to modify that gene so that a modified binding protein is produced, either in place of or in addition to the wild-type protein, and the cognate recognition sequence may then be modified as well for recognition by the mutant protein. It may be possible to simultaneously explore mutations of both the binding protein and the target sequence by combinatorial mutagenesis. (These methods are of course applicable, although less urgently, to the case of genetic elements recognized by virtue of their secondary structure, too.)

Default Definition of Percentage Sequence Identity

For the purpose of this specification and claims, unless otherwise stated, the percentage sequence identity between two sequences is to be determined by (1) aligning to maximize the local similarity score (as hereafter defined) between the two sequences, and (2) expressing the number of identical aligned pairs as a percentage of (a) the total length of the overlap region, including nulls (gaps), or (b) the original length of the shorter sequence, whichever of (a) or (b) is larger.

The two sequences are to be aligned by a rigorous (linear programming) based local alignment algorithm in which the overall similarity score for a given alignment is obtained by summing the pairwise alignment scores, for each aligned pair of bases or amino acids, and a gap penalty for each gap introduced into either sequence in an attempt to improve the overall similarity score for the alignment. The pairwise alignment scores are der ved from a 20×20 scoring matrix for amino acids and a 4×4 scoring matrix for nucleotides. The gap penalties are a linear combination of a gap initiation penalty imposed for the first null of a given gap, and a gap extension penalty for each additional null added to that gap. Only internal gaps will be penalized. The alignment must be statistically significant as elsewhere defined in order to be considered.

In the case of an amino acid sequence alignment, the scoring matrix will be the PAM250 matrix, in the form wherein the scores range from +17 to −8; the gap initiation penalty will be −12; and the gap 'extension penalty will be −4.

For nucleotide sequence alignments, the scoring matrix will be an identity matrix in which all identities are scored 6 and non-identities are scored zero, the gap initiation penalty will be −12, and the gap extension penalty will be −4.

Functional Mutation

In certain instances, we have indicated that it is required, or at least desirable, that the function of a particular lentiviral gene be retained. This does not mean that the gene cannot be mutated, or even that the mutations be limited to silent mutations. Functional mutations, which substantially preserve the relevant biological activity of the corresponding protein(s), are permissible.

Most residues of a protein can tolerate some degree of mutation. Mutations may take the form of single or multiple substitutions, insertions, or deletions. Preferably, insertions or deletions are directed to the termini of the molecule, or to surface loops or interdomain boundaries. Preferably, internal insertions and deletions are of no more than five residues, absent evidence (such as an example in a homologous protein) that a larger internal insertion or deletion could be tolerated.

There is no preferred maximum with respect to an insertion at a terminus, which is more aptly termed an "addition" or "fusion". It is routine to fuse one protein to another to facilitate expression, or to provide a fusion protein which has the combined biological activities of its components. A fusion protein may be useful as a precursor, which can be cleaved to liberate an active protein, even if the fusion protein itself lacks activity.

With regard to deletion at a terminus, more aptly termed "truncation", the purpose of the modification is important. It is routine to extensively truncate a protein when one is interested only in its immunological properties. One may abstract from a protein an epitope as small as five amino acids, and use it by itself to elicit a T cell response, or conjugated to copies of itself or to an immunogenic carrier to elicit a B cell response. When it is a biological activity which must be preserved, the limits on truncation may be more stringent.

Preferably, after considering substitutions, and any internal deletions and insertions, the mutant is at least 50%, more preferably at least 80%, identical in sequence to the original protein.

A protein is more likely to tolerate a mutation which
 (a) is a substitution rather than an insertion or deletion;
 (b) an insertion or deletion at the termini, than internally, or, if internally, at a loop or an interdomain linker;
 (c) affects a surface residue rather than an interior residue;
 (d) affects a part of the molecule distal to the binding site;
 (e) is a substitution of one amino acid for another of similar size, charge, and/or hydrophobicity; and
 (f) is at a site which is subject to substantial variation among a family of homologous proteins to which the protein of interest belongs.

These considerations can be used to design functional mutants of lentiviral proteins, and of naturally occurring nonlentiviral surrogates of lentiviral proteins.

The preferred mutants are those which comprise an amino acid sequence which is
 (I) at least 50% identical in amino acid sequence with the corresponding amino acid sequence of a first reference protein, after the mutant protein and the first reference protein are aligned to maximize local similarity as hereafter defined, and
 (II) which differs from the corresponding amino acid sequence of the first reference protein solely by one or more of the following mutations:
  (A) conservative substitutions as hereafter defined,
  (B) nonconservative substitutions at positions shown to be tolerant of at least one nonconservative substitution by one or more of the following criteria:
   (1) retention of at least 10% of the biological activity of the first reference protein in a mutant which differs from the first reference protein by a single alanine substitution at such position, (2) existence of a second reference protein which is a member of a recognized protein family to which the first reference protein also belongs, and having at least 10% of the biological activity of the first reference protein, which differs from said first reference protein by a nonconservative substitution at such position, (3) existence of a known 3D structure for the first reference protein, or of a predicted 3D structure on the homology between the first reference protein and a second reference protein of known 3D structure, on the basis of which such position is known or predicted to lie on the surface of the protein, or (4) retention of at least 10% of the biological activity of the first reference protein in a second mutant protein which differs from said first reference protein at least by a nonconservative amino acid substitution at such position, (B) a truncation or extension at the amino terminal, (C) an internal deletion or insertion of residues where
(1) the residues lie within an interdomain region of the first reference protein,
(2) the residues correspond to a loop of the first reference protein, or
(3) the internal deletion or insertion corresponds to a difference between the first reference protein and a homologous second reference protein.

If the first reference protein is an HIV-1 protein, the second reference protein is any corresponding lentiviral protein. In some instances, it may be appropriate to consider the possible second reference proteins as including corresponding nonlentiviral proteins, especially retroviral proteins, as well.

Preferably, for the framework residues, and more preferably for the whole chain, the predicted or experimentally determined 3D structure of the modified protein has a main chain ($C^\alpha$-carbon) conformation whose root-mean-square deviation from the predicted or experimentally determined 3D structure of the original protein is preferably less than 5 Å, more preferably less than 3 Å, Istill more preferably less than 2 Å, most preferably less than 1 Å.

"Conservative modifications" are defined as
(a) conservative substitutions of amino acids as hereafter defined; and
(b) single or multiple insertions or deletions of amino acids at the termini, at interdomain boundaries, in loops or in other segments of relatively high mobility.

Preferably, except at the termini, no more than about five amino acids are inserted or deleted at a particular locus, and the modifications are outside regions known to contain binding sites important to activity.

Conservative substitutions are herein defined as exchanges within one of the following five groups:

I. Small aliphatic, nonpolar or slightly polar residues: Ala, Ser, Thr (Pro, Gly)

II. Polar, negatively charged residues, and their amides Asp, Asn, Glu, Gln

III. Polar, positively charged residues: His, Arg, Lys

IV. Large, aliphatic, nonpolar residues: Met, Leu, Ile, Val (Cys)

V. Large, aromatic residues: Phe, Tyr, Trp

Residues Pro, Gly and Cys are parenthesized because they have special conformational roles. Cys participates in formation of disulfide bonds. Gly imparts flexibility to the chain. Pro imparts rigidity to the chain and disrupts α helices. These residues may be essential in certain regions of the polypeptide, but substitutable elsewhere.

"Semi-conservative substitutions" are defined herein as being substitutions within supergroup I/II/III or within supergroup IV/V, but not within a single one of groups I–V. If a substitution is not conservative, it preferably is semi-conservative. Highly conservative substitutions are Arg/Lys, Asp/Glu, Met/Ile/Leu/Val, and Phe/Tyr/Trp.

Surface vs. Interior Residues

Charged residues almost always lie on the surface of the protein. For uncharged residues, there is less certainty, but in general, hydrophilic residues are partitioned to the surface and hydrophobic residues, to the interior. Of course, for a membrane protein, the membrane-spanning segments are likely to be rich in hydrophobic residues.

Surface residues may be identified experimentally by various labeling techniques, or by 3-D structure mapping techniques like X-ray diffraction and NMR. A 3-D model of a homologous protein can be helpful.

Binding Site Residues

Residues forming the binding site may be identified by (1) comparing the effects of labeling the surface residues before and after complexing the protein to its target, (2) labeling the binding site directly with affinity ligands, (3) fragmenting the protein and testing the fragments for binding activity, and (4) systematic mutagenesis (e.g., alanine-scanning mutagenesis) to determine which mutants destroy binding. If the binding site of a homologous protein is known, the binding site may be postulated by analogy.

Protein libraries may be constructed and screened that a large family (e.g., $10^8$) of related mutants may be evaluated simultaneously.

3-D Structure Determination

The determination of the 3-D structure of a protein can provide considerable guidance to one seeking to modify that protein for a useful purpose, or at least to avoid inactivating modifications. If the full 3-D structure is known, the practitioner knows which residues are on the surface and which are on the interior, which residues have side chains pointing toward the outside, which residues are packed closely together and which are not, where the chain is flexible and where it is constrained, which residues are in secondary structures, which residues are brought into proximity as a result of chain folding, and which may be interacting in the form of H-bonding and salt bridges.

A protein may be modified at an interior residue, a surface residue distant from the binding site of interest, or at a surface residue which is part of, or close enough to affect, the binding site of interest.

Mutations at surface residues are more likely to be tolerated than at internal residues. Mutations at the latter positions have greater potential to destabilize the protein, thereby, by denaturing the protein, affecting all of its binding activities. Mutation at a surface residue may have no effect on binding activity at all, or it may affect some activities but not others. In any event, they are unlikely to denature the protein.

The principal methods of determining the complete 3-D structure of a protein are X-ray crystallography and NMR spectroscopy.

Amino acid-specific chemical affinity labels may be used to ferret out which residues are in fact exposed. The most useful labels are likely to be those which react with charged residues, as those are most likely to appear on the surface. Sample labels include the following:

| Amino Acid | Affinity Label |
|---|---|
| Asp, Glu | diazo compounds (with nonionized AA) or epoxides (with ionized AA) |
| Lys | 2,4,6-trinitrobenzene sulfonic acid; acetic, succinic, maleic and citraconic anhydrides |
| Arg | cyclohexanedione, hydrazine |

Labeled and unlabeled protein are then separately subjected to a fragmentation reagent such as cyanogen bromide, pepsin, papain, chymotrypsin, trypsin or iodosobenzoic acid. The peptides resulting from cleavage of the labeled protein are compared to those derived from the native protein, using two-dimensional electrophoresis. Peptides that have altered mobility are sequenced and modified amino acids are determined.

Surface residues may also be identified by means of photoaffinity labels which, upon exposure to light, form highly reactive intermediates, e.g. nitrenes and carbenes. These species are capable of insertion into C-H bonds, and therefore can react with any accessible amino acid. For this reason, photoaffinity labeling has been used to study membrane topography. Some proteins lie at the periphery of the membrane, others are integral to it. To identify a protein at the membrane surface, a label is used which ideally is indiscriminate, so that any accessible component would be labeled, and which is itself membrane impermeant. Of course, such a reagent will not only identify a membrane surface protein, but also the exposed amino acids of any soluble protein.

Another example of a nonspecific labeling reagent is tritium. A folded protein may be tritiated (by hydrogen exchange with tritiated water), denatured, and fragmented, and the fragments sequenced and tested for the presence of tritium (which is radioactive).

All of these labeling methods may also be used to determine whether residues, besides being on the surface, are part of a binding site. The distribution of label obtained when free protein is labeled is compared with that obtained when the complexed protein is labeled. Since in the complex, the binding partner occludes the binding site residues of the binding protein, binding site residues should be labeled in the free protein and not in the complexed protein.

Prediction of 3D Structure

The most accurate method for the prediction of a protein structure is model building from a protein or proteins of known structure that have been identified as homologous from sequence analysis. Surprisingly, proteins with very little detectable sequence identity can still fold into very similar structures.

The coordinates of protein structures can be obtained from Protein Data Bank or the Cambridge Crystal Structure Data Centre. Sequence databases include the Protein Identification Resource (National Biomedical Research Foundation), GENBANK (Los Alamos National Laboratory), EMBL (European Molecular Biology Laboratory) and SBASE (International Center for Genetic Engineering and Biotechnology). Derived alignment databases, in which 3D structure and amino acid sequence have been correlated, include NRL-3D (U.S. Naval Research Lab), HSSP (EMBL), 3D-ALI (EMBL), FSSP (EMBL), and the Overington database (J.P. Overington, Pfizer Central Research). For complete addresses see Table 2 in Johnson et al., Crit. Rev. Biochem. & Mol. Biol. 29(1):1–68 (1994).

The basic approach is to (1) identify related sequences and structures; (2) identify structurally equivalent residues; (3) model structurally conserved regions (SCRs); and (4) model structurally variable regions (SVRs). The model of the SCRs acts, to a greater or lesser degree, as a constraint in the modeling of the SVRs. Because the core residues are usually more structurally conserved than surface residues, they are usually modeled first. For similar reasons, helices and strands are usually modeled before loops. Typically, the main chain (C$\alpha$ atom) conformation is determined first, and then the side chain conformations. Modeling steps may be iterated to arrive at successively improved approximations of the true structure. Typically, the predicted structures are more accurate for protein cores than for protein loops.

It is not necessary that more than one 3-D structure be available for model building. However, if the 3-D structures of two or more homologous proteins are known, the accuracy of the model can be improved. Preferably, the 3-D structures are "weighted" to reflect the relatedness of the homologous protein to the protein of interest. One popular scheme is to weight by the square of the percentage sequence identity.

Moreover, information regarding homologous substructures of nonhomologous proteins may be used in addition to, or even in lieu of, a 3-D structure of a homologous protein. See Jones and Thirup, Curr. Comm. Molec. Biol., EMBO J. 1986 April (5) (4) 819-22:75–76 (1986); Unger, et al., Proteins, 5:335 (1989); Claesseus, et al., Protein Eng., 4:335 (1989); Levitt, et al., J. Mol. Biol., 226:507 (1992) for the building of models by combining "spare parts" from different proteins.

It is not necessary for a molecular biologist to be an expert in protein modeling, as several programs exist which automate the modeling process. These include COMPOSER (Tripos Associates).

If a 3-D structure is available for the binding partner, as well as for a binding protein of interest, molecular modeling software may be used to predict potential binding sites, or to predict the effect of a proposed mutation on a binding site, by attempting to "dock" the binding partner to the site. See, e.g., Guruprasad, et al., Protein Eng., 9:849–56 (1996); Constantino and Pelliccian, J. Med. Chem. 39:3998–4006 (1996).

Surface Residues

In general, within families of proteins of similar sequence and function, surface residues are more likely to vary than are interior residues. This is most likely because the surface residues are unlikely to be involved in interactions with other residues which are necessary to maintain the overall conformation of the protein.

Some surface residues are directly involved in the binding surface by which a protein exercises a particular binding activity. Mutation of such residues is likely to affect binding; however, it is not necessarily undesirable to make such mutations. For example, mutation of the binding site of a serine protease can alter what is bound, as opposed to simply rendering the protein inactive altogether.

The most reliable method of identifying the surface residues of a protein is to determine the protein's 3-D structure by X-ray diffraction. Even an incomplete 3D structure can be useful in designing mutants. Residues with high mobility, as evidenced by a higher than average crystallographic thermal factor, are those least susceptible to destabilizing mutations. See Alber, et al., Biochemistry, 26:37–54–8 (1987).

Interior Residues

Although many amino acid substitutions can be made at surface positions with no adverse effects, substitutions at internal positions tend to be severely destabilizing. Within families of homologous proteins, the most conserved residues, apart from functional amino acids, are those which are buried.

The main contribution to the free energy of protein folding, and hence to protein stability, comes from burying hydrophobic side chains in the interior, thereby shielding them from solvent. Packing densities are typically high. In general, the ability of a protein to tolerate mutations which alter the volume of core residues is dependent more on the net change in the total core residue volume, then on the magnitude of the individual residue volume changes. In other words, an increase in the volume of one core position can compensate for a decrease in the volume of another core position. Preferably, the net change in the total core residue volume is not more than 10%, more preferably, not more than 5%. See Lim and Sauer, Nature, 339:31–36 (1989); Lim et al., Biochemistry, 31:4324–33 (1992).

In the absence of evidence to the contrary, all residues identified as interior residues may be assumed to be part of a single core. However, if it is likely that the protein folds to form several distinct cores, the above-stated volume conservation rule should be applied separately to each core.

Amino acids differ in terms of their propensity to be buried residues. The following table shows, for each residue, the percentage which were in buried positions, based on a study of the 3D structures of a collection of unrelated proteins:

| Amino Acid | % Buried |
|---|---|
| Gly | 36 |
| Ala | 38 |
| Val | 54 |
| Ile | 60 |
| Leu | 45 |
| Phe | 50 |
| Pro | 18 |
| Ser | 22 |
| Thr | 23 |
| Cys | 48 |
| Met | 40 |
| Tyr | 15 |
| Trp | 27 |
| His | 17 |
| Asn | 12 |
| Gln | 7 |
| Asp | 15 |
| Glu | 18 |
| Lys | 3 |
| Arg | 1 |

The makeup of the buried core of a protein is dependent, not only on the propensity of each amino acid, if present, to be buried, but also on the overall frequency of occurrence of that amino acid in the protein. The most commonly buried residues are, in descending order, Val, Gly, Leu, Ala, Ile and Ser.

Lim et al., Biochemistry, 31:4324–33 (1992) reported that replacing a single hydrophobic amino acid (Leu, Val) in the protein core with a hydrophilic amino acid (Asn, Gln) prevented the complete folding of the protein and destroyed biological activity.

Buried Cys, (—S—S— form), Asp, Gly, His, Pro, and Trp are more than 70% likely to be unchanged in a homologous protein. Therefore, if these residues occur in a buried position in the protein of interest it is preferable to leave them unchanged. Their conservation is probably explainable as follows: Cys (disulfide bonding), Asp (charged but rigid side chain), Gly (chain flexibility), His (charged and uncharged states both available at physiological pH), Pro (unique chain geometry), and Trp (largest side chain).

The other residues, with the exception of Met, are 40–60% likely to left unchanged when buried (Met is unchanged only 26% of the time, but it is 25% likely to be replaced by Leu).

The following buried residue substitution probabilities exceed 10%:

Ala→Val, Glu→Gln, Phe→Leu, Ile→Leu, Ile→Val, Lys→Arg, Leu→Ile, Leu→Val, Met→Leu, Met→Val, Asn→Asp, Asn→Ser, Arg→Lys, ArgGln, Ser→Ala, Thr→Ser, Val→Ile, Val→Leu, Tyr→Phe, Cys(-SH)→Ala.

These further substitutions have probabilities in the 5–10% range:

Ala→Ser, Asp→Asn, Glu→Arg, Glu→Val, Phe→Ile, Phe→Val, Phe→Tyr, His→Val, Leu→Phe, Met→Ala, Met→Ile, Gln→Glu, Gln→His, Gln→Met, SerGly, Ser→Thr, Thr→Val, Val→Ala, Trp→Phe, Tyr→Leu, Cys(-SH)→Ser.

See Overington, et al., Protein Science, 1:216–226 (1992), Table 5.

The most consistent exchange groups appear to be (Arg, Lys), (Leu, Ile, Met, Val, Phe), and (Ser, Thr, Ala). However, Ala and Val appear to be fairly promiscuous.

In general, therefore, it is preferable to avoid mutating buried residues at all. However, if they are mutated, one should limit the overall change in the volume of the core, and most preferably should limit the mutation to the replacement of one residue with another whose typical substitution probability exceeds zero, more preferably is at least 5%, and most preferably at least 10%. Mutation of buried Cys(—S—S), Asp, Gly, His, Pro and Trp should be avoided, absent justification by other evidence. The safest core mutations are exchanges of one hydrophobic amino acid for another, and of Arg for Lys (or vice versa).

Nonetheless, judicious mutation at internal residues may be used to improve protein stability. Such mutations could introduce additional stabilizing interactions (hydrogen bonds, ion pairs) compatible with the native structure, or could reduce the mobility of nearby interacting groups by replacing smaller amino acids with larger ones, or linear side chains with branched or aromatic ones. See Alber, et al., Biochemistry, 26:3751–8 (1987).

Identification of Naturally Occurring Homologous Proteins

The most useful information for determining which residues are safely mutatable is knowledge of the sequence of proteins of similar sequence which have similar activity. The sequences of these homologous proteins may then be aligned, and residues which are not conserved are more likely to be safely mutatable. The degree of confidence which one has as to the tolerance of a residue to mutation is a function of the degree of variation of amino acid type at that site among the protein family, as well as the extent to which all of the proteins in the family, despite their differences, retain the desired activity.

While studies of homologous proteins are useful in identifying sites which, by virtue of their variability, are likely to be tolerant of mutation, it is less certain that sites which are strongly conserved are necessarily invariant. According to Shenkin, et al., (1991), random mutagenesis studies indicate that "proteins are able to accommodate, both structurally and functionally, a far greater variety of mutations than occur naturally".

Homologous proteins are those which are similar in structure to the protein of interest, to a statistically significant degree, and which perform the same or an analogous biological function. Examples are human growth hormone and human prolactin, and human alpha globin and human myoglobin. When homologous proteins occur in nature, the similarities may imply that they have a common evolutionary origin, and the time of origin may be estimated by calculating the number of mutations which would give use to the observed sequence divergence and dividing by the mutation rate.

Cognate proteins are homologous proteins, expressed in a different species of organism, which perform the same biological function as: that performed by the protein of interest, although they may differ in activity, specificity, timing of expression, etc. Examples of cognate proteins are human and fish growth hcrmones, or human and other vertebrate alpha (or beta) globins.

The possession of the cDNA or genomic DNA (the "starting DNA") encoding the protein of interest (the "starting protein") greatly facilitates the isolation of homologous proteins. For the use of probes to identify homologous genes in other species, see, e.g., Schwinn, et al., J. Biol. Chem., 265:8183–89 (1990) (hamster 67-bp CDNA probe vs. human leukocyte genomic library; human 0.32kb DNi probe vs. bovine brain CDNA library, both with hybridization at 42° C. in 6×SSC); Jenkins et al., J. Biol. Chem., 265:19624–31 (1990) (Chicken 770-bp CDNA probe vs. human genomic libraries; hybridization at 40° C. in 50% formamide and 5×SSC); Murata et al, J. Exp. Med., 175:341–51 (1992) (1.2-kb mouse CDNA probe v. human eosinophl cDNA library; hybridization at 65° C. in 6×SSC); Joziasse, et al., European Journal of Biochemistry (1990) July 20:191 (1):75–83 (various bovine cDNAs v. human genomic library); Guyer et al., J. Biol. Chem., 265:17307–17 (1990) (2.95-kb human genomic DNA probe vs. porcine genomic DNA library;

hybridization at 42° C. Ln 5×SSC).

Alignment of Homologous Sequences

In order to deiive guidance from the sequences of homologous proteins, it is necessary to identify which proteins are homologous and to align the sequence of the protein of interest with that of the homologous proteins. Such alignment is guided by calculating a homology or alignment score for each possible alignment, and determining the highest such score for each pair of potentially homologous proteins. Homologous proteins are distinguished from nonhomologous proteins by having an alignment score which is significantly higher.

Global alignment algorithms consider both complete sequences in generating similarity scores for a given alignment, and, in general, allow "gapping". They are most appropriate when the sequences are known or expected to be similar over their entire length.

Local alignment algorithms search for similar fragments of two sequences, and, in general, do not allow gaps. They are useful in locating comion subdomains between long sequences that otherwise share little similarity.

Scoring of "Gaps"

The justification or "gapping" is that the introduction of a gap can improve the apparent homology between two sequences so extensively that there is no reasonable doubt that the gap reflects evolutionary history.

In general, overhangs (terminal gaps) are not counted. The simplest method of scoring for internal gaps is to count each deleted residue as a simple mismatch. Another approach is to impose an initiatLng gap penalty and an extension gap penalty. Typically, if the reward for an identity is R, the cost of initiating a gap is at least R and more usually at least 2*R. In FASTA, the default penalties are −12 for the initiating gap, and −4 for each extension gap, on a scale where an identity is +6.

Scoring of Mismatches

A mismatch occurs when the amino acid residues at the same site in two different aligned amino acid sequences are different. Several systems are used in the art for scoring matches (identities) and mismatches.

The simplest, the Identity Matrix, gives a score of one to each match and zero to each mismatch. The other schemes give more weight to "similar" though nonidentical pairings of residues.

The Genetic Code Matrix (GCM) scores amino acid similarity based on the maximum number of common nucleotide bases (which can range from 3 to 0) between their closest matching representative codons. The original scoring system awarded 3 points for three common bases, 2 for 2, etc., (i.e., a 3/2/1/0 system) and u!sed a gap penalty of −3. Feng, et al. (1985) reported that best results are obtained with a 4/2/1/0 system and a gap penalty of −4. The file Codaa.mat accompanying FASTA uses the system 6/2/−2/−6.

A Mutation Data Maltrix (MDM) scores amino acid similarity on the basis of the frequency of the exchange of the two amino acids in question between two members of a family of homologous proteins, or of a member and the inferred ancestor of that protein. It is customary for an MDM to take into account the apparent evolutionary distance, too. Thus, it calculates the probability that one residue will be mutated into another residue in a specified unit of a evolutionary time. To calculate this matrix, proteins of known sequences are clustered into families of homologous proteins, a phylogenetic type is constructed for each protein, and an ancestral sequence inferred the amino acid exchanges which apparently occurred between each modem sequence and the ancestral sequence are tailied, and the minimum number of base changes which could explain those exchanges are calculated. The assumption is made that mutations are strictly Markovian processes. The basic unit of molecular evolution expressed in an MDM is the "accepted point mutation" (PAM). In sequence analysis, the most commonly used MDM is the 250 PAM matrix, i.e., one characterizing the amino acid exchanges that would be expected to occur between sequences separated by 250 PAMS.

The Structural Similarity Matrix weighs pairings according to the similarity of the amino acids in size, hydrophilicity, and/or other structural measures.

Hybrid matrixes have also been devised.

It is important that the mutation matrix values and gap penalties be scaled so that identities have appropriate positive scores relative to the gap penalties.

In FASTA, the standard matrix is the Dayhoff PAM 250 matrix. In BLAST, the default matrix is the PAM120 matrix, which is more selective.

Statistical Significance

Two random amino acid sequences (of equimolar amino acid composition) would have, an average, an identity of 5% if gapping is not allowed. If gapping is permitted, two random sequences can be 10–20% identical. In general, if two sequences are longer than 100 residues, and are more than 25% identical after suitable gapping, it is likely that they are genuinely related, i.e., that the similarity is not due to chance. The "twilight zone" is 15–25% identity.

The statistical significance of an alignment may be determined by comparing the alignment score obtained when the two authentic sequences are aligned, with the mean and standard deviation of the alignment scores obtained when both sequences are repeatedly randomized, and each "jumbled" sequence in one set is aligned with the jumbled sequences in the other set. The score of the authentic sequence is then expressed as so many standard deviations above the mean of the jumbled group. See, e.g., Doolittle, Science, 214:149 (1981); Lipman and Pearson, Science, 277:1435 (1985). However, since similarity scores are distributed according to the extreme value distribution, not the normal distribution, the extreme value statistical form of the z-value should be used. See Altschul, et al., Nature Genetics, 6:119–129 (1994).

Lipman and Pearson are of the opinion that the z value of the optimized alignment similarity score obtained with FASTP hould be evaluated as follows: >3, possibly significant; >6, probably significant; >10, significant. Doolittle used a more stringent identity matrix scoring system and considered a score of 3.0 S.D. or more to be significant.

A second approach to determining significance of a particular alignment is to compare the alignment score for that alignment with the mean and standard deviation of the alignment scores for the alignments of the query sequence with all sequences in a sequence library. Once again, a z value is calculated. See Wilbar and Lipman Proc. Nat. Acad. Sci. USA 80:726–30 (1983). Most of these sequences will be unrelated to the query sequence. Of course, the choice of sequences in the library will reflect the interests of the scientific community, e.g., it will tend to favor the sequences of those organisms which are most closely studied, e.g., humans, fruit flies, *S. cerevisiae*, and *E. coli*.

Measures of Variability

The variability index ($V_k$) is a simple method of quantifying the degree of variation of amino acid residues at a particular aligned site. It is the ratio of the number of different amino acid types which appear at the position, to the fraction of the time which the site is occupied by the most common of these types. Wu, et al., J. Exp. Med. 132:211–49 (1970). $V_k$ ranges from 1 to 400 for proteins. Preferably, mutations are directed to sites having a variability index which is within the upper 50%, more preferably the upper 20%, of all sites of the protein.

A more sophisticated approach involves calculating the informational entropy of the site. This is $$s = -\Sigma P_i \log_2 P_i \text{ (for all } P_i > 0)$$

where there i different amino acid residues appearing at the site, and $P_i$ is the fraction of the total number of aligned sequences in which residue i appears at the site. See Shenkin, et al., Proteins: Structure, Function and Genetics, 11:297–313 (1991). If only one residue appeared at a site, the entropy would be zero. If all 20 enetically encoded residues appeared with equal frequency, the entropy would be $-\log_2(0.05)$, or about 4.32. The informational entropy is less likely to "jump" than the variability index when a new sequence is added. Preferably, mutations are directed to sites which have an informational entropy S greater than 1.0, more preferably greater than 2.0. (A related measure, $V_s$, is defined as $6 \times 2^S$; it ranges from 6 to 120 for proteins. The factor 6 was chosen empirically to make the $V_k$ and $V_s$ scales roughly comparable.

Shenkin et al. (1991) reported that for all immunoglobulin light chains, $V_k$ ranged from 1 to 96, S from 0 to 3.4792, and Vs from 6 to 66.91.

The two methods dEscribed above do not take into account either the normal equivalency of the different residues (the appearance of both Arg and Gly at a site is more revealing of tolerance than the appearance of both Arg and Lys) or the degree of relationship between the source organisms (the conservation of a residue between human and chimpanzee should be less significant than the conservation of the same residue between human and fruit fly). Various weighting schemes can be used to adjust for these subtleties.

Mutagenic Analysis of Binding Sites

Binding sites may also be identified by mutagenesis strategies designed to locally perturb the protein. One such strategy is alanine scarning mutagenesis. In this technique, all non-alanine residues. of the protein (or of a region of the protein suspected to contain the binding site are replaced, one-by-one, with alanine, yielding a collection of single substitution mutants. Alanine is used because (1) it is the most common amino acid residue in proteins, (2) it has a small side chain, and therefore is not likely to sterically hinder other residues, and (3) its side chain (—$CH_3$) does not form H-bonds, but is not especially hydrophobic. Cunningham and Wells (1989) conducted an Ala scanning mutagenesis study of residues 2–19, 54–74, and 167–191 in hGH. A total of 62 Ala mutations were produced. Of these, fourteen mutants could not be produced in quantities sufficient for affinity testing. Presumably, these mutations globally destabilized the protein, rendering it vulnerable to proteolysis. Eleven mutants seemingly enhanced binding, although it is unclear which improvements were significant. Of the remaining 37 mutants, only four impaired biniding by 10-fold or more, and only nine by 5-fold or more. See generally Genentech, WO90/04788.

For other uses of Ala-scan mutagenesis, see Yu, et al., J. Mol. Biol., 249:388–97 (1995) (complete scan of a single disulfide derivative of the 58-residue protein BPTI); Allen, et al., Nature, 327:713 (1987) (Ala-scan of residues 52–61 of hen egg white lysozyme).; Ruf, et al., Biochemistry, 33:1565–72 (1994) (Ala-scan of residues other than Gly, Pro and Cys; multiple Ala mutants examined first, then single Ala mutants); Williams, et al., J. Biol. Chem., 270:3012–6 (1995) (Ala-scan in insulin receptor of (1) charged amino acids, (2) aromatic residues, and (3) residues adjacent to (1) or (2), other than prolines, cysteines, or potential N-linked glycosylation sites); Kelly and O'Connell, Biochemistry, 32:6828–35 (Ala-scan of antibody CDR). Ala-scanning mutagenesis may be applied to all residues of a protein, or to residues selected on some rational basis, such as amino acid type (e.g., charged and aromatic residues), degree of variability in a homologous protein family, or relevance to function as shown by homologue-scanning mutagenesis.

Preferably, further mutations (especially nonconservative mutations) are made at siltes where an alanine substitution does not worsen the activity of interest by more than 20-fold, more preferably, by more than 10-fold, even more preferably, by more than 5-fold, still more preferably, by more than 2-fold. Most preferably, mutations are made at sites at which an alanine substitutions improves activity.

Preferably, if multiple mutations are made, the expected (additive) effect of the mutations is one which does not worsen the activity more than 10-fold, more preferably, by more than fold, still more preferably, by more than two fold. Most preferably, the expected effect is to improve activity. The expected effect of a conservative substitution is the effect of that mutation as a single substitution if known, or otherwise neutral. The expected effect of a nonconservative substitution is the effect of that mutation as a single ubstitution if known, or otherwise the effect of a single substitution of a different residue of the same exchange group as the actual replacement residue, if known, or otherwise the effect of a single Ala substitution.

Another approach is homologue-scanning mutagenesis. This involves identifying a homologue which can be distinguished in an activity assay from the protein of interest, and screening mutants in which a segment of the protein of interest is replaced by corresponding segments of the homologue (or vice versa). If the replacement alters the activity of the modified protein, the segment in question presumably contributes to the observed difference in activity between the protein of interest and the homologous protein, and comparison of the interchanged segments helps to explain the character of the binding site involved in that activity. For example, segments of prolactin, which does not bind the GH receptor, have been used to replace segments of growth hormone, which does. If a substitution disrupts GH binding, it implies that the replaced segment was part of the GH receptor binding site, and one may then focus on how the replaced and replacing segments differ. See WO90/04788.

If a residue is determined to be a part of the binding site, one may prepare all possible single substitution mutants of that site.

Multiple Mutation

It is possible to incorporate two or more tolerable mutations into a protein.

Generally speaking, as a first approximation, it is reasonable to assume that the effect of two mutations will be additive in nature. See Wells, Biochemistry, 29:8509–17 (1990); Sandberg and Terwilliger, Proc. Nat. Acad. Sci. (USA), 90:8367–71 (1993); Gregoret and Sauer, Proc. Nat. Acad. Sci. (USA), 90:4240–50 (1993); Schreiber and Fersht, J. Mol. Biol., 248:478–86 (1995); Lowman and Wells, J. Mol. Biol. 234: 564–78 (1993); Lawman, et al., J. Biol. Chem., 266:10982–8 (1991); Lin, et al., Proc. Nat. Acad. Sci. (USA), 91:10265–9 (1994); Venkatachalam, et al., J. Biol. Chem., 269:23444–50 (1994); Akasako, et al., Biochemiistry, 34:8115–22 (1995); Behravar, et al., Eur. J. Biochem., 198:589–92 (1991); Lin, et al., Proc. Nat. Acad. Sci. (USA), 91:10265–9 (1994); Zuckerman, et al., Proc. Nat. Acad. Sci. (USA), 89:4505–9 (1992). Gregoret, et al., Proc. Nat. Acad. Sci. (USA), 90:4246–50 (1993) assumed that, under selective conditions, the frequency of occurrence of a mutation in an active mutant was an indication of whether the mutant conferred resistance, and found that an additive model (multiplying the mutational frequencies of a pair of single Ala substitution mutants) was about 90% effective in predicting the activity class of a binomial (multiple Ala substitution) mutant.

The most common reason for combining mutations is to benefit from their additive or synergistic effect in combination. For example, if a mutation has both favorable and unfavorable activities, it may be possible to combine it with a second mutation that neutralizes the unfavorable activity of the first mutation.

One use of multiple mutation is to achieve, by combining mutations which individually have a small but favorable effect on activity, a mutant with a more substantial improvement in activity. It is not necessary that the mutations be strictly additive; it is sufficient that they be at least partially additive for the combination to be advantageous. See Blacklow, et al., Biochemistry, 30:8470–6 (1991) (improved catalytic effectiveness of triosephosphate isomerase); Akasako, et al., Biochemistry, 34:8115–22 (1995) (multiple thermostabilizing mutations in ribonuclease HI); Lowman et al., J. Biol. Chem., 266:10982–8 (1991) (HGH-receptor binding properties of human placental lactogen improved about 500-fold by five simultaneous, mutations, with "reasonably additive" effects); Lowman and Wells, J. Mol. Biol., 234:564–78 (1993) (HGH-receptor binding properties of HGH improved about 400-fold by combination of 15 substitutions. Sandberg and Terwilliger, Proc. Nat. Acad. Sci. (USA), 90:8367–71 (1993), reported that there was only a weak correlation between changes in DNA binding protein stability and changes in DNA binding affinity, and hence that it was possible to combine mutations so as to selectively change one property without changing the other.

In binomial Ala-scanning mutagenesis, one constructs a library in which, at each position of interest of a given protein molecule, the residue is randomly either the native residue, or Ala. See Gregoret and Sauer, Proc. Nat. Acad. Sci. (USA), 90:4246–50 (1993). If it is feasible to screen a library of $10^{10}$ mutants, then the combined effects of up to 30 different Ala substitutions ($2^{27} \sim 10^{10}$) can be studied in one experiment. It should be noted that the Ala:non-Ala ratio at each position may be, but need not be equal. The choice made for this ratio will determine the degree of substitution will predominate, according to a binomial distribution.

If the protein is too large for all sites of interest to be sampled by binomial Ala-scanning mutagenesis in a single experiment, one may divide the protein into segments and subject each segment in turn to such mutagenesis, and then, as a cross-check, similarly mutate one residue from each segment.

Design of Chimeric Proteins

The term "chimera" implies a protein which is a hybrid of two or more different parental proteins which are associated with two or more different organisms.

Functional chimera may be identified by a systematic synthesize-and-test strategy. It is not necessary that all theoretically conceivable chimeras be evaluated directly.

One strategy is described schematically below. We divide the aligned protein sequences into two or more testable units. These units may be equal or unequal in length. Preferably, the units correspond to functional domains or are demarcated so as to correspond to special features of the sequence, e.g., regions of unusually high divergence or similarity, conserved or unconserved regions in the relevant protein family or the presence of a sequence motif, or an area of unusual hydrophilicity or hydrophobicity. Let "1" represent a unit of the protein 1, and "2" a corresponding unit of protein 2. If there are five units (the choice of five instead of two, three, four, six, ten, etc. is arbitrary), we can synthesize and test any or all of the following chimeras, which will help us rapidly localize the critical regions:

(a) progressive C-terminal substitution of exogenous sequence for host sequence, e.g., 1 1 1 1 1
1 1 1 1 2
1 1 2 2 2
1 2 2 2 2
2 2 2 2 2

(b) progressive N-terminal substitution of exogenous sequence for host sequence 1 1 1 1 1
2 1 1 1 1
2 2 1 1 1
2 2 2 1 1
2 2 2 2 1

(c) dual terminal substitutions, e.g., 2 2 2 2 2
1 2 2 2 1
1 1 2 1 1
1 1 1 1 1 and 1 1 1 1 1
2 1 1 1 2
2 2 1 2 2
2 2 2 2 2, and (d) single replacement "scans," such as
2 1 1 1 1
1 2 1 1 1
1 1 2 1 1
1 1 1 2 1
1 1 1 1 2
and
1 2 2 2 2
2 1 2 2 2
2 2 1 2 2
2 2 2 1 2
2 2 2 2 1

Based on the data these tests provide, it may appear that, e.g., the key difference between the exogenous and host sequences vis-a-vis, say, display on the host cell membrane, is in the fifth unit. One can then subdivide that unit into subunits and test further, e.g.

2 2 2 2 (11)
2 2 2 2 (12)
2 2 2 2 (21)
2 2 2 2 (22)

where the parenthesized entries refer to the two subunits into which the original fifth unit was subdivided Transgene The transgene is a gene encoding a polypeptide which is foreign to the lentivirus(es) from which the vector is primarily derived, and which has a useful biological activity into the organism which is ultimately infected with the transducing vector in its virion-packaged form.

The transgene may be identical to a wild-type gene, or it may contain one or more mutations. The transgene may be derived from genomic DNA, cDNA, synthetic DNA, or a combination thereof. Intronless "minigenes", which are normal genes from which introns have been removed, have been especially popular. Intron-containing genes may be employed, but they may be inserted into the vector in the reverse orientation if removal of the introns is not desired. Silent mutations may be introduced to facilitate gene maipulation, to avoid undesirable secondary structure in the mRNA, to inhibit recombination, to control splicing, etc. Nonsilent mutations alter the encoded protein, and may be either gratuitous, or aimed at beneficially altering the biological activity of the protein.

One example of a transgene is a remedial gene. As used herein, the term "remedial gene" refers to a gene whose expression is desired in a cell to correct an error in cellular metabolism, to inactivate a pathogen or to kill a cancerous cell. For example, the adenosine deaminase (ADA) gene is the remedial gene when carried on a retroviral vector used to correct ADA deficiency in a patient.

The applications of transgenes include the following:

cell marking: for some purposes, it is useful to follow cells after they have been introudced into a patient.

anti-pathogen or anti-parasite: anti-pathogen genes or anti-parasite can be introduced into a host infested, or especially vulnerable to infestation, by the pathogen or parasite in question.

genetic disease: an inherited genetic defect may be ameliorated by supplying a functional gene.

It is not necessary that the endogenous gene be repaired by homologous recombination. Monogenetic genetic diseases are of particular interest. Suitable approaches include providing genes encoding the enzyme adenosine deaminase (ADA), especially to hematopoietic stem cells so as to provide longterm treatment of ADA deficiency; and correcting familial hypercholesterolemia with a vector encoding the low density lipoprotein (LDL) receptor.

Gene therapy has been used to successfully correct inborn errors of metabolism using existing vector systems. For example, the adenosine deaminase gene has been introduced into peripheral blood lymphocytes and cord blood stem cells via retroviral vectors in order to treat patients with severe combined immunodeficiency due to a lack of functional adenosine deaminase (K. W. Culver et al., Human Gene Ther., 2:107 [1991]). Partial correction of familial hypercholesterolemia has been achieved using existing retroviral vectors to transfer the receptor for low density lipoproteins (LDL) into hepatocytes. However, it was estimated that only 5% of the liver cells exposed to the recombinant virus incorporated the LDL receptor gene with the vector utilized (M. Grossman et al., Nat. Genet., 6:335 [1994]).

A number of single-gene disorders have been targeted for correction using gene therapy. These disorders include hemophilia (lack of Factor VIII or Factor IX), cystic fibrosis (lack of cystic fibrosis transmembrane regulator), emphysema (defective $\alpha$-1-antitrypsin), thalassemia and sickle cell anemia (defective synthesis of $\beta$-globin), phenylketonuria (deficient phenylalanine hydroxylase) and muscular dystrophy (defective dystrophin) (for review see A. D. Miller, Nature 357:455 [1992]). Human gene transfer trials have been approved for a number of these diseases.

The molecular genetics of cystic fibrosis (CF) has been studied and gradually understood in recent years. Approximately 70t of the CF patients carry a single amino acid deletion ((F508) mutation in one of the two nucleotide-binding domains in the CF transmembrane regulator (CFTR) protein [Miller, 1993 #535]. Other forms of genetic mutations in the CFTR genes have also been identified. This rich genetic information makes CF an ideal gene therapy candidate.

The target cells for CF patients are undifferentiated, proliferating and differentiated, non-proliferating lung epithelial cells. It is hoped that both of the dividing and non-dividing lung epithelial cell types can be efficiently targeted by VSV-G pseudotyped lentiviral vectors carrying a wild type CFTR cDNA.

CF patients have CFTR mutations which leads to basic chloride flux defect in the respiratory ciliated epithelial cells. This CFTR dysfunction causes chronic infection and inflammation of the respiratory tract and leads to high morbidity and mortality in CF patients. The CFTR CDNA gene transfer by adenoviral vectors or liposomes has demonstrated partial correction of the defective CFTR channel activity in the nasal epithelium of CF patients [Zabner, 1993 #3700; Cplen, 1995 #3701]. An important indication that CFTR dysfunction in CF patients could be treated by gene therapy protocols came from the study of Johnson et al. who demonstrated that overexpression of CFTR which numerically corrected 6–10% of a mutant CF epithelial monolayer resulted in a bioioelectric phenotype similar to sheets of 100% corrected cells [Johnson, 1992 #3702]. In a recent study, Dorin et al. further showed in a mouse model that 5% of the normal level of CFTR gene expression resulted in a correction of the chloride ion transport defect up to 50% of normal level and obtained 100% survival [Dorin, 1996 #3013]. These studies suggest that gene therapy may offer great benefits to CF patients even if only partial correction of CFTR gene function is achieved with the current gene transfer tools.

cancer: cancers may be treated with vectors carrying genes which express cancer antigens, or immunomodulatory proteins, and thereby stimulate an immune response against the cancer cells, or which express a normal tumor suppressor gene to replace the function of a mutated, tumor-rpone gene, such as a p53 mutant.

In addition to replacement of defective genes, it has been proposed that viral vectors could be used to deliver genes designed to stimulate immunity against or to otherwise destroy tumor cells. Although the integration of therapeutic genes into tumor cells is not required for cancer gene therapy application in most cases, sustained expression of the therapeutic genes in tumor cells may be required, for example, to elicit a long lasting in vivo anti-tumor immunity.

Gene therapy, originally developed for treating inherited and acquired diseases by introducing therapeutic genes to somatic cells, has great potential for cancer treatment. With the rapid advances in molecular medicine and gene delivery technology during the past decade, gene therapy approaches have brought excitement aid new hopes to fighting cancers. Currently, more than 70% of approved clinical trial gene therapy protocols worldwide are designed for treating cancers. The list is growing rapidly because of the ineffectiveness of conventional cancer treatments, especially to those late stage, metastatic cancers. There are three major components to be considered in the design and development of a gene therapy regimen: the therapeutic genes, the mode of gene delivery (ex vivo or in vivo), and an appropriate preclinical study model for the assessment of the therapeutic efficacy. Various therapeutic genes have been utilized in cancer treatments. The common examples include: (1) genes that are capable of changing the cellular sensitivity to chemo- or radiation therapy in cancer patients either to sensitize tumor cells, or to minimize the damage of chemotherapy to normal cells such as the hematopoietic stem cells, (2) genes that interfere with proliferating tumor cell cycle by either replacing the mutated genes (i.e. tumor suppresser genes and apoptotic genes), or inactivating the oncogenes to prevent further tumor development, and (3) genes that can augment a systemic anti-tumor immunity in cancer patients; this can be accomplished by the injection of modified tumor infiltrating lymphocytes (TIL) or immunomodulatory gene-modified tumor cells, or by the modification of antigen presenting cells (APC). Retroviral vectors containing genes encoding tumor necrosis factor (TNF) or interleukin-2 (IL-2) have been transferred into tumor-infiltrating lymphocytes in patients (A. Kasid et al., Proc Natl Acad Sci USA. 87:473–477 [1990]; and S. A. Rosenberg, Human Gene Therapy 5: 140 [1994]). It is postulated that the secretion of TNF or IL-2 stimulates a tumor-specific immune response resulting in the destruction of the tumor or the recruitment of effective tumor infiltrating lymphocytes from nearby lymph nodes. Other proposed anti-tumor gene therapy strategies include the delivery of toxin genes to the tumor cell.

Applications of antisense genes or antisense oligonucleotides in inhibition of oncogenes and modulation of growth factors have the potential to reduce the mortality of cancer, in particular, human leukemia (For review see, A.M. Gewirtz, Stem Cells 3:96 [1993]; and L. Neckers and L. Whitesell, Amer. J. Physiol., 265:L1 [1993]).

HIV: vectors may be used to deliver transgenes which protect susceptible cells against HIV by synthesizing proteins, antisense RNAs, or ribozymes that block HIV binding and entry, reverse transcription, integration, or replication. Of course, the transgenes must be regulated so they do not interfere with the packaging of the transducing vector.

Selectable and Screenable Markers

A vector may contain one or more selectable or screenable markers. Such markers are typically used to determine whether the vector has been successfully introduced into a host or target cell. A selectable marker is a gene whose expression substantially affects whether a cell will survive under particular controllable conditions. A selectable marker may provide for positive selection (cells with the marker are more likely to survive), negative selection (cells with the marker are less likely to survive), or both (the choice of environmental condition dictating whether positive or negative selection occurs).

Selectable markers include those which confer antibiotic resistance (or sensitivity), the ability to utilize a particular nutrient, and resistance (or sensitivity) to high (or low) temperature. Suitable selectable markers include the bacterial neomycin and bygromycin phosphotransferase resistance genes, which confers resistance to G418 and hygromycin, respectively, the bacterial gpt gene, which allows cells tog row in a medium containing mycophenolic acid, xanthine and aminopterin; the bacterial hisD gene which allows cells to grow in a medium lacking histidine but containing histidinol; the multidrug resistance gene mdr; the hprt and HSV thymidine kinase genes, which allow otherwise hprt- or tk- cells to grow in a medium containing hypoxanthine, amethopterin and thymidine, and the bacterial genes conferring resistance to puromycin or phleomycin. Positive or negative selection may require the use of a particular strain of host cell for the selection to be effective.

Screenable markers are genes which encode a product whose presence is readily detectable, directly or indirectly, but which do not necessarily affect cell survival. The green fluorescent protein (GFP) is an example. Any cell surface protein not native to the host cell can be used as an immunoscreenable marker. Transformed cells may be segregated out by using a fluorescent antibody to the protein and a cell sorter. Many enzyme-encoding genes are useful as screenable markers, especially those encoding enzymes which can act upon a substrate to provide a colored or luminescent product. The luciferase and beta-galactosidase genes have been especially popular.

A dominant marker encodes an activity which can be detected in any eukaryotic cell line. Examples of dominant selectable markers include the bacterial aminoglycoside 3' phosphotransferase gene (also referred to as the neo gene) which confers resistance to the drug G418 in mammalian cells, the bacterial hygromycin G phosphotransferase (hyg) gene which confers resistance to the antibiotic hygromycin and the bacterial xanthine-guanine phosphoribosyl transferase gene (also referred to as the gpt gene) which confers the ability to grow in the presence of mycophenolic acid. Other selectable markers are not dominant in that their use must be in conjunction with a cell line that lacks the relevant activity. Examples of non-dominant selectable markers include the thymidine kinase (tk) gene which is used in conjunction with tk cell lines, the CAD gene which is used in conjunction with CAD-deficient cells and the mammalian hypoxanthine-guanine phosphoribosyl transferase (hprt) gene which is used in conjunction with hprt-cell lines.

A review of the use of markers in mammalian cell lines is provided in Sambrook, J. et al., *Molecular Cloning: A Laboratory Manual*, 2nd ed., Cold Spring Harbor Laboratory Press, New York [1989] pp.16.9–16.15.

Regulation of Gene Expression

The transgene(s) of the transducing vector, and the marker (s) and viral genes (or replacements) of the packaging and transducing vectors, are expressed under the control of regulatory elements.

As used herein, the term "regulatory element" refers to a genetic element whictL controls some aspect of the expression of nucleic acid sequEnces. For example, a promoter is a regulatory element which facilitates the initiation of transcription of an operably linked coding region. Other regulatory elements are splicing signals, polyadenylation signals, termination signals, etc. (defined infra). A constitutive promoter is one which is always active at essentially a constant level.

Transcriptional control signals in eukaryotes comprise "promoter" and "enhancer" elements. Promoters and enhancers consist of short arrays of DNA sequences that interact specifically with cellular proteins involved in transcription (T. Maniatis et al., Science 236:1237 [1987]). Promoter and enhancer elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (for review, see, S. D. Voss et al., Trends Biochem. Sci., 11:287 [1986]; and T. Maniatis et al., supra [1987]). For example, the SV40 early gene enhancer is very active in a wide variety of cell types from many mammalian species and has been widely used for the expression of proteins in mammalian cells (R. Dijkema et al., EMBO J. 4:761 [1985]). Two other examples of promoter/enhancer elements active in a broad range of mammalian cell types are those from the human elongation factor 1α gene (T. Uetsuki et al., J. Biol. Chem., 264:5791 [1989]; D. W. Kim et al., Gene 91:217 [1990]; and S. Mizushima, and S. Nagata, Nuc. Acids. Res., 18:5322 [1990]) and the long terminal repeats of the Rous sarcoma virus (C. M. Gorman et al., Proc. Natl. Acad. Sci. USA 79:6777 [1982]) and the human cytomegalovirus (M. Boshart et al., Cell 41:521 [1985]).

As used herein, the term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) such that transcription of that gene is directed by the linked enhancer/promoter.

A regulatable promoter is one whose level of activity is subject to regulation by a regulatory molecule. An inducible promoter is one which is normally substantially inactive, but which is activated by the binding of an inducer to an operator site of the promoter. A repressible promoter is one which is normally active, but which is substantially inactivated by the binding of a repressor to an operator site of the promoter. Similar terminology applies to enhancers.

The inducer or repressor molecules are typically expressed only in particular tissues, at a particular developmental stage, or under particular environmental conditions (e.g., damage to the cell, infection, overproduction of a metabolite, absence of a nutrient, etc.). In the absence of an inducer an inducible promoter may be inactive or may produce a low level of The level of activity in the presence of the inducer will be higher than the basal rate. A tightly inducible promoter is one whose basal level of activity is very low, e.g., less than 10% of its maximum inducible activity.

Different promoters may have different levels of basal activity in the same or different cell types. When two different promoters are compared in a given cell type in the absence of any inducing factors, if one promoter expresses at a higher level than the other it is said to have a higher basal activity.

The activity of a promoter and/or enhancer is measured by detecting directly or indirectly the level of transcription from the element(s). Direct detection involves quantitating the level of the RNA transcripts produced from that promoter and/or enhancer. Indirect detection involves quantitation of the level of a protein, often an enzyme, produced from RNA transcribed from the promoter and/or enhancer. A commonly employed assay for promoter or enhancer activity utilizes the chloramphenicol acetyltransferase (CAT) gene. A promoter and/or enhancer is inserted upstream from the coding region for the CAT gene on a plasmid; the plasmid is introduced into a cell line. The levels of CAT enzyme are measured. The level of enzymatic activity is proportional to the amount of CAT RNA transcribed by the cell line. This CAT assay therefore allows a comparison to be made of the relative strength of different promoters or enhancers in a given cell line. When a promoter is said to express at "high" or "low" levels in a cell line this refers to the level of activity relative to another promoter which is used as a reference or standard of promoter activity.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is one which is isolated from one gene and placed 3' of another gene. A commonly used heterologous poly A signal is the SV40 poly A signal. The SV40 poly A signal is contained on a 237 bp Bam HI/Bcl I restriction fragment and directs both termination and polyadenylation (J.Sambrook et al., supra, at 16.6–16.7).

The cytomegalovirus immediate early promoter-enhancer (CMV-IE) is a strong enhancer/promoter. See Boshart M, Weber F, Jahn G, Dorsch-Hasler K, Fleckenstein B, Schaffner W. A very strong enhancer is located upstream of an immediate early gene of human cytomegalovirus. Cell 1985; 41:521–530. For its incorporation into HIV-1 derived viruses, see Chang L-J, McNulty E, Martin M. Human immunodeficiency viruses containing heterologous enhancer/promoters are replication competent and exhibit different lymphocyte tropisms. J Virol 1993; 67:743–752.

Another strong promoter-enhancer for eukaryotic gene expression is the elongation factor 1 alpha promoter enhancer. Kim DW, Uetsuki T, Kaziro Y, Yamaguchi N, Sugano S. Use of the human elongation factor 1a promoter as a versatile and efficient expression system. Gene 1996; 91:217–223; Mizushima S, Nagata S. pEF-BOS, a powerful mammalian expression vector. Nucleic Acids Res. 1990; 18:5322.

The internal promoter for a transgene may be the promoter native to that transgene, or a promoter native to the target cell (or viruses infecting the target cell), or another promoter functional in the target cell.

The preferred promoters and enhancers are those exhibiting tissue or cell type sepecificity which can direct the transgene expression in the target cells at the right time(s). For example, a promoter to control human preproinsulin must be operable under control of carbohydrate in the liver. An example of such a promoter is the rat S-14 liver-specific promoter.

Promoters (and enhancers) may be naturally occurring sequences, or functional mutants thereof, including chimeras of natural sequences and mutants thereof. For example, a tissue-specific, development-specific, orotherwiseregulatable element of one promoter may be introduced into another promoter.

Chen et al, Proc. Nat. Acad Sci USA 93: 10057–62 (1996) placed a VSV G gene under the control of a tetracycline-inducible promoter and also expressed a fusion of the ligand binding domain of the estrogen receptor to a chimeric transcription factor, tTA, obained by fusing the tet repressor (tetR) and the activation domain of HSV virion protein 16.

For the ability to replace the endogenous 5' LTR promoters and enhancers with heterologous ones, such as CMV immediate-early enhancer-promoter, see Chang, et al., J. Virol., 67: 743–52 (1993). *Vector; Transfection of Vectors*

As used herein, the term "vector" is used in reference to nucleic acid molecules that can be used to transfer nucleic acid (e.g., DNA) segment(s) from one cell to another. The term "vehicle" is sometimes used interchangeably with "vector." It is intended that any form of vehicle or vector be encompassed within this definition. For example, vectors include, but are not limited to viral particles, plasmids, transposons, etc.

The term "transfection" as used herein refers to the introduction of foreign DNA into eukaryotic cells. Transfection may be accomplished by a variety of means known to the art including but not limited to calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

Vectors may contain "viral replicons" or "viral origins of replication." Viral replicons are viral DNA sequences which allow for the extrachromosomal replication of a vector in a host cell expressing the appropriate replication factors. Vectors which contain either the SV40 or polyoma virus origin of replication replicate to high copy number (up to $10^4$ copies/cell) in cells that express the appropriate viral T antigen. Vectors containing the replicons from bovine papillomavirus or Epstein-Barr virus replicate extrachromosomally at low copy number (~100 copies/cell).
Expression Vector The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals. In some embodiments, "expression vectors" are used in order to permit pseudotyping of the viral envelope proteins.
Host Cells The host cell is a cell into which a vector of interest may be introduced and wherein it may be replicated, and, in the case of an expression vector, in which one or more vector-based genes may be expressed.

It is not necessary that the host cell be infectable by the transducing vector virions of the present invention. Indeed, it is preferable that they not be so infectable, so the hos cells do not bind the virions and thereby reduce the vector production titer. This can be achieved by choosing (or engineering) cells which do not functionally express the receptor to the vector particle envelope protein.
Target Cells and Organisms The transducing vector may be administered to a target organism by any route which will permit it to reach the target cells. Such route may be, e.g., intravenous, intramuscular, subcutaneous, or, with an enteric coating, oral. Alternatively, target cells may be removed from the organism, infected, and they (or their progeny) returned to the organism. Or the transducing vector may simply be administered to target cells in culture.

The target cells into which the transgene is transferred may be any cell which the transducing vector, after packaging into a virion, is capable of infecting, and in which the control sequences governing expression of the transgene are functional. Generally speaking, it will be a eukaryotic cell, preferably a vertebrate cell, more preferably a cell of a mammal or bird. If a mammal, the mammal will preferably belong to one of the orders Artiodactyla (e.g., cows, pigs, goats, sheep), Perissodactyla (e.g., horses), Rodenta (e.g., rats, mice), Lagomorpha (e.g., rabbits), Carnivora (e.g., dogs, cats) or Primata (e.g., humans, apes, monkeys, lemurs). If a bird, it will preferably be of the orders Anseriformes (e.g., ducks, geese, swans) or Galliformes (e.g., quails, grouse, pheasants, turkeys, chickens). Most preferably it will be a human cell.

The cells in question may be dividing or non-dividing cells. Non-dividing cells of particular interest include neuronal cells and astrocytes. Dividing cells of particular interest include hematopoietic stem cells, muscle cells, white blood cells, spleen cells, liver cells, epithelial cells and eye cells.

TE671, HepG2, HeLa, 293T, and MT4 are of particular interest for experimental studies. TE671 rhabdomyosarcoma cells can be induced to differentiate into muscle cells by HIV-1 Vpr. HepG2 hepatoma, HeLa cervical carcinoma, 293T human kidney carcnoma and MT4 lymphoma cells are all transformed by HTLV-I human T cell leukemia virus type I. MT4 cells are very susceptible to wild-type HIV-1 NL4-3 and hence have been used as indicator cell for RCV.
Miscellaneous Definitions As used herein, the term "endogenous virus" is used in reference to an inactive virus which is integrated into the chromosome of its host cell (often in multiple copies), and can thereby exhibit vertical transmission. Endogenous viruses can spontaneously express themselves and may result in malignancies.

The term "gene" refers to a DNA sequence of a vector or genome which comprises a coding sequence and which is operably linked to one or more control sequences such that, in a suitable host cell, under suitable conditions, a biologically active gene product, or a gene product which is a precursor of a biologically active molecule, is produced which is encoded by the coding sequence. This gene product may be a transcriptional product, i.e., a messenger RNA, as in the case of an antisense RNA or a ribozyme. Or it may be a translational product, i.e., a polypeptide (the term "polypeptide" as used herein includes oligopeptides), which is either biologically active in its own right, or further processed by the cell to generate one or more biologically active polypeptide products. In the case of retroviruses, where the genome is RNA, the term "gene" also refers to the RNA sequence of the retroviral genome which a suitable host cell reverse transcribes into a DNA sequence which acts as a gene in the classic sense.

Depending on context, the term "gene" may refer to the DNA sequence encoding a single mRNA transcript, or only to that portion of the DNA sequence which is ultimately expressed as a single polypeptide chain.

In the vectors of the present invention, each gene may be constructed from genomic DNA, complementary DNA (DNA reverse transcribed from mRNA), synthetic DNA, or a combination thereof. The gene may duplicate a gene which exists in nature, or differ from it through the omission of introns (noncoding intervening sequences), a so-called minigene, silent mutations (i.e., mutations which do not alter the amino acid sequence of the encoded polypeptide), or translated mutations (i.e., mutations which do alter that sequence). In the latter case, the mutations may be functional mutations (ones which preserve at least a substantial portion of at least one of the biological activities or functions of the encoded polypeptide) or nonfunctional (inactivating) mutations.

As used herein, the term "transcription unit" refers to the segment of DNA between the sites of initiation and termination of transcription and the regulatory elements necessary for the efficient initiation and termination. For example, a segment of DNA comprising an enhancer/promoter, a coding region and a termination and polyadenylation sequence comprises a transcription unit.

Assays

From time to time, one may wish to ascertain various information concerning the packaging and transducing vectors of the present invention.

One might like to know whether the vectors have become established in the cell; whether particular vector genes have integrated into the genome; whether the packaging cell line is producing viral proteins; whether those viral proteins are being assembled into viral particles; whether, in the absence of the transducing vector, those viral particles are essentially free of RNA, especially lentiviral RNA (e.g., packaging vector RNA); whether recombination occurs between the packaging vector and the transducing vector, or between these two vectors and defective retroviruses endogenous to the host (or target) cell; whether such recombination, if any, produces replication-competent virus; whether recombinant virus is packaged by the packaging cell line; the efficiency with which the packaging cell line packages the transducing vector into the viral particles; whether the transducing vector-containing viral particles are infectious vis-a-vis the target cells; whether the latter particles are cytotoxic to the target cells; whether the latter particles are immunogenic to the target organism; whether infected target cells themselves produce viral RNA-containing particles, infectious or otherwise; and the level and duration of expression of the transgene in the target cells.

The successful establishment of the packaging or transducing vector in the host (or target) cell may be verified by selecting for the presence of a selectable marker, or screening for the presence of a screenable marker, carried by the vector. The integration of the relevant packaging or transducing vector genes may be determined by collecting genomic DNA, amplifying the gene of interest by PCR, and detecting the amplified sequence with a suitable hybridization probe. The production of viral proteins may be detected by an immunoassay; the sample may be a cell lysate or a cell supernatant. An immunoassay by itself cannot determine whether the viral proteins are produced in functional form, although there is greater assurance of this if the antibody used is directed to a conformational epitope, or is an activity-neutralizing antibody. One may alternatively detect the appropriate messenger RNA by means of a hybridization probe.

The functionality of the produced Gag and Env protein may be determined by examining the cell lysate or supernatant for the presence of viral particles; these may further be examined for proper morphology by means of an electron microscope. It is also possible that antibodies could be used which bind to the formed viral particles, but not to gp120 or gp41 by itself. The functionality of the Pol reverse transcriptase may be determined by assaying the viral particles for RT activity. The functionality of the Pol integrase is apparent only in assays which examine whether RNA from viral particles is integrated into the target cell.

Viral particles produced by the packaging cell line may be collected and assayed for total RNA content. If more specific information is desired as to the nature of any packaged RNA, a suitable hybridization probe may be employed.

In an infectivity assay, the vector is introduced into a first culture of susceptible cells. Then, either a second culture is layered onto the first, so that infectious particles may travel by cell-to-cell contact, or the second culture is exposed to the supernatant of the first culture. The cells of the first and second culture are examined for a least one of the following indicia: RT activity, p24 Gag antigen expression, production of viral particles, and cytotoxic effects. The stringency of the assay is dependent on the susceptible of the cells to infection and to cytotoxicity, and the time allowed for the recombination and spread of the virus in the first and second cultures. Typically, the infectivity of the vector or vector system will be compared with that of a wild-type, unattenuated, replication-competent lentivirus.

Animal studies may be used to ascertain the immunogenicity and pathogenicity of the vector system.

Some of these assays are described in greater detail below.
Measurement of Infectivity of Packaging Vector per se The ability of a packaging vector to generate transmissible virus, as opposed to defective virus, may be measured. One method is described by Mann, et al., Cell, 33: 153–9 (1983). The packaging vector and its wild-type counterpart are independently transfected into suitable host cells, and reverse transcriptase activity in the culture supernatants is assayed over a period of days or weeks. A rapid increase in RT activity over 24–48 hrs is indicate of gene expression after transient transfection. A continued increase is indicative of the efficient spread of virus from the initially transfected cells to the remaining cells on the plate.

A slow or delayed increase could be indicative of either a steady but attenuated spread of virus, or to generation of competent virus by mutation, or by recombination with a cellular sequence capable of providing the missing function. To differentiate these possibilities, one may use various dilutions of culture supernatants from cells previously transfected (days or weeks before) with the vector (or with the control virus), use them to infect fresh cells, and monitor RT activity in the latter. If the latter cells develop high levels of RT activity, it suggests that nondefective virus was present in the transferred culture supernatant.
Measurement of Packaging Efficiency The packaging efficiency of a packaging cell line in the presence or absence of the packageable transducing vector may be measured in a variety of ways. One method is described by Mann, et al., Cell, 33: 153–9 (1983). In esssence, total cellular RNA is purified from the culture supernatant of the test and control cell lines, and viral RNA is extracted from purified viral particles released from the test and control cell lines. The two virion preparations are normalized by reference to their reverse transcriptase activity just prior to RNA extraction. The purified RNAs are probed with a virus-specific hybridization probe (e.g., a plasmid containing the entire viral genome) in a slot-blot assay, and the amount of viral RNA in the particles and in the cells is thereby quantified.

It is not unusual for the packaging efficiency of a packaging cell line to be less than 1% that of a host cell infected by wild-type virus.

Measurement of Packaging Specificity

It is also desirable that the packaging cell line be able to efficiently package the highly defective transducing vector into viral particles, and bud the particles into the culture supernatant (in vitro) or extracellular environment (in vivo) without also budding helper virus (the packaging vectors).

One method of measuring this packaging specificity is described by Mann, et al., Cell, 33: 153–9 (1983). In essence, the transducing vector is transfected into the packaging (helper) cell line. After 24 hours, the culture supernatants are used to infect fresh potential host cells (reporter cells). Two days later, selection pressure for the transferred gene is applied, and 8–10 days later, the transferred gene-positive colonies or cells are counted. In addition, one determines the reverse transcriptase activity of the supernatant colelcted from the packaging cell lines, and the reverse transcriptase activity of the fresh cells. A transducing vector-specific packaging cell line will produce a high transfer gene activity and a low reverse transcriptase activity in the reporter cells. In addition, the reporter cells will not produce reporter gene-positive colony-forming units (cfus).

Measurement of Helper Activity

The ability of a packaging vector to provide all viral functions required in trans may be assayed by cotransfecting host cells with the packaging vector (or control virus) and with a reporter vector carrying a selectable reporter gene. After 24 hours, culture supernatants of the transfected cells are used to infect a second plate of host cells. Selection pressure for the reporter gene is applied, and reporter-positive colonies are counted. If the helper activity is of wild-type magnitude, the count for the packaging vector should be of the same order of magnitude as that for the control virus, and no reporter activity should be detectable in the second plate when the reporter vector or the control wild-type virus expressing all viral functions is transfected into the host cells of the first plate by itself.

Measurement of Generation of Replication-Competent Virus

Several sensitive assays are available for the detection of RCV in the present lentiviral vector systems. These include: (1) co-cultivation with a sensitive cell line such as MT4, AA2 or PBLs; (2) the CD4 HeLa MAGI cell assay which relies on Tat transactivation of an integrated LTR-lacZ gene; and (3) a sensitive immunohistochemical staining method for the detection of HIV antigen expression at the individual cell level. As described in the Examples below, the latter method was modified and developed for the characterization of "Tat-minus" HIV-1 infection, although all three methods are suitable for the routine titration of infectious HIV-1.

RC-HIV can also be studied in an in vivo model by transduction of humanized SCID/beige mice. In the latter model, a long in vivo incubation time can be performed, mimicking the situation that exists in a human clinical trial. In addition, the possibility of generating HIV/HERV recombinants may be carefully tested using an artificially constructed HIV/HERV-env recombinant.

Virion Stability

Since one class of the therapeutic agents of the present invention would be the packaged transducing vectors, the stability of the packaged transducing vectors under adverse conditions, especially those which might be encountered during storage, is of interest. Thermostability may be ascertained by subjected them to elevated (e.g., 37 deg. C.) or depressed (e.g., 4 deg. C.) temperatures for various periods of time (e.g., 2, 4, 6 or 8 hrs., or overnight), or to a number (e.g., 1–6) freeze-thaw cycles, and determining the number of infectious particles remaining as a percentage of the number of such particles prior to treatment. See Burns et al. 1993.

Assays for Immunogenicity

A preferred method for determining whether the contemplated vectors, or their gene products, could elicit an immune response in a subject involves evaluating cell-mediated immunity (CMI) using either an immunocompetent mouse model or a a humanized SCID/beige mouse model.

Using a modified hu-PBL-SCID mouse reconstitution protocol, an in vivo model for evaluating CMI against HIV-1 in humans has been developed. SCID/beige mice lacking T, B and natural killer (NK) cell functions are severely immunodeficient. This strain of mice can be successfully reconstituted with fresh human peripheral blood lymphocytes (PBLs), and exhibits functional human naive, memory and activated T cell markers for more than 2–3 months (See e.g., copending U.S. patent application Ser. Nos. 08/848,760, and 08/838,702, both of which are herein incorporated by reference). In these experiments, spleen and peripheral blood lymphocytes were harvested 38 days after reconstitution from reconstituted SCID/beige mice, and red blood cells were lysed prior to incubation with anti-mouse 2Kd, anti-human CD45, anti-human CD3, anti-human CD4 and anti-human CD8 labeled antibodies. Reconstituted human lymphoid cell populations in the spleen and in the peripheral blood of the SCID/beige mice can reach up to 50–80% and 5–12%, respectively.

For the immune response study, mice repetitively injected with the viral vectors will be analyzed. Their sera will be assayed for Ab response to viral antigens, such as p24 Gag or the pseudotype env (e.g., VSV-G). For cell-mediated immune response study, the mouse splenocytes will be isolated and an in vitro assay for cellular immunity will be performed as described below. T cell response to recall antigen is normally characterized by the production of interferon gamma (IFNγ). This assay requires activation of lymphocytes with the test Ags, such as Gag p24 or Gag-Pol or VSV-G env proteins of the vector.

Upon activation, the Th1 lineage of T cells produce interferon gamma (IFN-g) and the measurement of IFN-g production has been shown to be a reliable assay for CMI. Thus, to determine CMI against HIV-1 using the in vivo humanized SCID/beige mouse model, a sensitive ELISPOT assay for the detection of IFN-g producing cells was developed. With the computer assisted imaging system integrated into this protocol, the ELISPOT method was shown to be very convenient and more sensitive than the conventional limiting dilution assay for the determination of the effector T cell precursor frequency. This in vivo model and the ELISPOT assay system were developed for the evaluation of in vivo CMI after lentiviral gene transfer. (See, e.g., PCT/US98/06944).

EXAMPLES

Abbreviations

The following examples serve to illustrate certain preferred embodiments and aspects of the present invention and are not to be construed as limiting the scope thereof.

In the experimental disclosure which follows, the following abbreviations apply: RCR (replication-competent retrovirus); RCV (replication-competent virus); WT (wild-type); PBL (peripheral blood lymphocyte); M (molar); mM (millimolar); μM (micromolar); mol (moles); mmol (millimoles); μmol (micromoles); μmol (nanomoles); g (gravity); gm (grams); mg (milligrams); μg (micrograms); pg (picograms); L (liters); ml (milliliters); μl (microliters); cm (centimeters); mm (millimeters); μm (micrometers); nm (nanometers); hr (hour); min (minute); msec (millisecond); ° C. (degrees Centigrade); AMP (adenosine 5'-monophosphate); cDNA (copy or complimentary DNA); DTT (dithiothreitol); ddH$_2$O (double distilled water); dNTP (deoxyribonucleotide triphosphate); rNTP (ribonucleotide triphosphate); ddNTP (dideoxyribonucleotide triphosphate); bp (base pair); kb (kilo base pair); TEM (transmission electron microscope); SEM (scanning electron microscope); TLC (thin layer chromatography); tRNA (transfer RNA); nt (nucleotide); VRC (vanadyl ribonucleoside complex); RNase (ribonuclease); DNase (deoxyribonuclease); poly A (polyriboadenylic acid); PBS (phosphate buffered saline); OD (optical density); HEPES (N-[2-Hydroxyethyl] piperazine-N-[2-ethanesulfonic acid]); HBS (HEPES buffered saline); SDS (sodium dodecyl sulfate); Tris-HCl (tris [Hydroxymethyl]aminomethane-hydrochloride); rpm (revolutions per minute); ligation buffer (50 M Tris-HCl, 10 mM MgCl$_2$, 10 mM dithiothreitol, 25 μg/ml bovine serum albumin, and 26 μM AND+, and pH 7.8); EGTA (ethylene glycol-bis(β-aminoethyl ether) N, N, N', N'-tetraacetic acid); EDTA (ethylenediaminetetracetic acid); ELISA (enzyme linked immunosorbant assay); ELISPOT (enzyme-linked immunosorbent spot assay); LB (Luria-Bertani broth: 10 g tryptone, 5 g yeast extract, and 10 g NaCl per liter, pH adjusted to 7.5 with 1N NaOH); superbroth (12 g tryptone, 24 g yeast extract, 5 g glycerol, 3.8 g KH$_2$PO$_4$ and 12.5 g, K$_2$HPO$_4$ per liter); DMEM (Dulbecco's modified Eagle's medium); ABI (Applied Biosystems Inc., Foster City, Calif.); Amersham (Amersham Corporation, Arlington Heights, Ill.); ATCC (American Type Culture Collection, Rockville, Md.); AIDS Research and Reference Reagent Program (AIDS Research and Reference Reagent Program of the National Institutes of Health, Bethesda, Md.); Beckman (Beckman Instruments Inc., Fullerton Calif.); BM (Boehringer Mannheim Biochemicals, Indianapolis, Ind.); Bio-101 (Bio-101, Vista, Calif.); BioRad (BioRad, Richmond, Calif.); Brinkmann (Brinkmann Instruments Inc. Wesbury, N.Y.); BRL, Gibco BRL and Life Technologies (Bethesda Research Laboratories, Life Technologies Inc., Gaithersburg, Md.); CRI (Collaborative Research Inc. Bedford, Mass.); Eastman Kodak (Eastman Kodak Co., Rochester, N.Y.); Eppendorf (Eppendorf, Eppendorf North America, Inc., Madison, Wis.); Falcon (Becton Dickenson Labware, Lincoln Park, NJ); IBI (International Biotechnologies, Inc., New Haven, Conn.); ICN (ICN Biomedicals, Inc., Costa Mesa, Calif.); Invitrogen (Invitrogen, San Diego, Calif.); New Brunswick (New Brunswick Scientific Co. Inc., Edison, N.J.); NEB (New England BioLabs Inc., Beverly, Mass.); NEN (Du Pont NEN Products, Boston, Mass.); Nichols Institute Diagnostics (Nichols Institute Diagnostics, San Juan Capistrano, Calif.); Pharmacia (Pharmacia LKB Gaithersburg, Md.); Promega (Promega Corporation, Madison, Wis.); Stratagene (Stratagene Cloning Systems, La Jolla, Calif.); UVP (UVP, Inc., San Gabreil, Calif.); USB (United States Biochemical Corp., Cleveland, Ohio); Taconic (Taconic, Germantown, N.Y.); and Whatman (Whatman Lab. Products Inc, Clifton, N.J.).

Sources

Unless otherwise indicated, all restriction enzymes were obtained from New England Biolabs and used according to the manufacturers directions. Unless otherwise indicated, synthetic oligonucleotides were synthesized using an ABI DNA synthesizer, Model No. 391.

In the following Examples, non-attenuated HIV strains used include the NL4-3 HIV-1 strain, HIV-1 primary isolates covering the different HIV clades (e.g., 92RW008, 92HT593, etc.), the ROD strain of HIV-2, and the SIV-mac239 strain of SIV, all of which are available from the AIDS Research and Reference Reagent Program.

Methods

Plasmid DNA construction. HIV-1 LTR and tat mutations were constructed as described previously (Chang et al.1993; Chang and Zhang, 1995). Cloned HIV proviruses with heterologous enhancer/promoters were constructed by ligating three fragments from an HIV-1 molecular clone HIVNL4-3(Adachi et al.1986), two fragments isolated from the U3-R-CAT plasmids containing inserted heterologous enhancer/promoters and the BamHI plus PstI digested pT7T318U vector. The proviral segments used in the ligation were as described before (Chang et al.1993). The structures of the reconstructed HIV proviral DNAs were verified by extensive restriction enzyme mapping, and the LTR regions were checked by nucleotide sequencing.

RT assay and p24 ELISA for the detection of HIV gag and pol products. RT assays detect functional reverse transcriptase activity which were performed as described below. The supernatants from transfected cells were spun in a microfuge at 3000 rpm for 5 min before being added to the reaction mixture. Supernatants from virus infections were removed from cultures after the cells had settled. Each reaction mixture contained 10 ml of supernatant and 50 ml of RT cocktail (60 mM Tris-HCl, pH 7.8, 75 mM KCl, 5 mM MgCl2, 0.1% Nonidet P-40, 1 mM EDTA, 5 mg/ml poly rA and 0.16 mg/ml oligo-dT) and was incubated at 37° C. for 1 h. The radioactive products generated in the CAT and RT assays were quantitated by using a Fuji phosphoimager. The results obtained were comparable to those derived by scintillation counting. p24 antigen is derived from p55 gag precursor. The p24 antigen expression was quantified using a commercial ELISA kit from Coulter (Coulter Corp., Hialeah, Fla.).

RT-PCR and sequencing of the packaged viral genomic RNA. Cell-free particles, present in the supernatants of vector producing cells, were harvested (100 microl), centrifuged at top speed for 5 min in a microcentrifuge at room temperature, and filtered through a 0.45 mm-pore-size Eppendorf spin filter. The particles present in the filtrate was dissociated by vortexing in the presence of an equal volume of 8 M LiCl, placed on dry ice for 20 min, transferred to a −20° C. freezer for at least 2 h, and centrifuged at top speed in a microcentrifuge at 4° C. for 20 min. The RNA pellet was then rinsed with 70% ethanol, dried briefly under vacuum, resuspended in water and reverse transcribed by using an appropriate primer and the RiboClone cDNA Synthesis System (Promega) for the synthesis of the first DNA strand. A control reaction excluding the reverse transcriptase was performed in parallel. The cDNA was amplified by PCR using the polymerase and reagents obtained from Perkin Elmer Cetus; 5' and 3' primers (0.1 micromole each) were added to a reaction mixture containing the cDNA (1/20 of the RT product) and amplified for 30 cycles under the following conditions: 94° C. for 1 min, 58° C. for 1 min and 72° C. for 3 min. The product obtained was then subjected to asymmetric PCR amplification (i.e., two primers at 10:1 molar ratio) to generate single stranded DNA for sequencing as described by Meltzer et al. (39). Excess primers were removed with a centricon 100 filtration device (Amicon) after each amplification step. Nucleotide sequencing was performed using Sequenase and protocols supplied by USB.

Immunofluorescent and Immunohistochemical Staining.

For immunofluorescent staining, non-adherent cells were attached to the surface of a microscope cover glass (12 mm circle, Fisher Scientific, Pittsburgh, Pa.) which had been pretreated with poly-D-lysine (1 mg/ml, Sigma) at room temperature for 10 min. The attached cells were washed with phosphate buffered saline (PBS) three times, fixed in cold acetone and methanol (1:1) for 5 min, washed three times in PBS, and incubated in blocking (20% FBS, 0.1% TritonX100 in PBS) solution for 30 min. An HIV patient's serum was used as the primary antibody, which was diluted at 1:2000 in blocking solution, and the cells were incubated at room temperature for 1 h or at 4° C. overnight with constant shaking. After washing in PBS 4 times for 5 min each, the cells were incubated with normal goat or sheep antisera (1:200 dilution) at room temperature for 30 min to block non-specific binding. The secondary antibody was FITC-labeled goat anti-human IgG (Fab specific, Sigma Chemical Company, St. Louis, Mo.). After staining, the cover glass was washed four times in PBS and examined using a fluorescent microscope. For direct immunohistochemical staining, a peroxidase-linked sheep anti-human Ig (Amersham) was used as the secondary antibody. Alternatively, a biotinylated sheep anti-human antibody (Amersham) was used at 1:2000 dilution and incubated at room temperature for 1 h. The latter step provided a more sensitive method for detection of low level of HIV antigens which was described in detail elsewhere (Chang and Zhang, 1995).

RNA and Protein Analyses.

Northern analysis was performed as previously described (Robinson et al.1995). For protein analysis, cells were lysed in a buffer containing 50 mM Tris pH 7.4, 300 mM NaCl, 0.5% Triton X100, 1% (v/v) aprotinin and 1 mM PMSF at 4° C. for 10 min and freeze-thawed once. Virus particles were collected by centrifugation in a refrigerated micro centrifuge in a small volume (200 microliters) at 23,000 g for 1 hr. The supernatant was carefully removed and to the pellet, 20 ml of SDS sample buffer (final 2% SDS, 5% glycerol, 0/001% BPB, 0.5% NP-40) was added and the denatured protein was resolved by polyacrylamide gel electrophoresis (PAGE) as described previously (Chang et al.1990). For Western blot analysis, the protein was transferred to a 0.2 micron nitrocellulose filter, stained with Ponceau S to identify the molecular weight marker, and blocked with 10% dried milk in TBS-T (Tris-buffered saline with 0.3% Tween 20) at room temperature for 30 min to 1 hr. After washed briefly at room temperature, the blot was placed into a "seal-a-meal" bag and incubated with an AIDS patient's serum (diluted at 1:2,000, or a rabbit polyclonal anti-Vpr antibody at 1:1,000, or a monoclonal anti-Nef antibody at 1:1000) in TBS-T containing 2% dry milk at 4° C. overnight. After four washes with TBS-T, the blot was blocked with normal goat sera (the same species as the secondary Ab) at 1:200 dilution in a shallow tray or in a bag at room temperature for 30 min. The blot was then transferred to a second bag containing a horse radish peroxidase (HRP) conjugated goat anti-human (or goat anti-rabbit, or goat anti-mouse) antibody and incubated at room temperature for 1 hr. The blot was washed four times in TBS-T and developed using the chemiluminescence ECL immunodetection reagents from Amersham. The blot was then exposed to a hyperfilm (Amersham) normally for 1 min and developed.

Cells and Culture Conditions

HeLa cells were propagated in Dulbecco's modified Eagle's medium (DMEM) supplemented with 10% fetal bovine serum (FBS). H9, CEM, MT4, C8166 and AA2 were obtained from NIH AIDS Research and Reference Reagent Program. Maintenance of the continuous human lymphoid cell lines H9, CEM, MT4, AA2 and the primary human PBLs were as described (Chang et al.1993). The Molt3 and THP-1 were obtained from the American Type Culture Collection (Rockville, Md.). HeLa clone HL3T1, C8166 and U937 cells were kindly provided by G. Pavlakis, K.-T. Jeang, and K. Peden, respectively. HeLa CD4+ clones 1022 and HT-6C (Chesebro and Wehrly, 1988) were obtained through the AIDS Research and Reference Reagent Program, Division of AIDS, NIAID, NIH, from Dr. Bruce Chesebro. The macrophage culture was prepared from HIV-sero-negative donors by adherence of PBLs to plastic flasks as described previously with minor modifications (Hassan, et al. 1986). PBLS was prepared using lymphocyte separation medium (Organon Teknika Corp., Durham, N.C.) bydensitygradient. The PBLs were resuspended in RPMI 1640 medium supplemented with 20% heat-inactivated human serum. Approximately 5×107 PBLs were attached to a T-75 flask and incubated overnight at 37° C. The next day cells were washed three times with phosphate buffered saline and the attached cells were incubated with 0.02% EDTA in PBS for 5–10 min. The cells were collected with a cell scraper and plated onto a 48-well plate at 5×104 cells per well. The viability approached 100% as determined by trypan blue staining. The initial monocytes were characterized by Wright's staining and the mature macrophages by both Wright's staining and microscopic examination.

Plasmid Construction and Site-directed Mutagenesis The tat-A, tat-B and tat-C site-directed mutations were generated by the "Megaprimer" method of Sarkar and Sommer (Sarkar and Crissman, 1990) using the following mutagenic oligos:

5'-GAATTGGGTGTCGACATAGCGGCCGCTTGTAC-CAATTGCTATTG-3'(SEQ ID NO:29).

5'-GGTACAAGCAGTTTAAGGCTAACTTCCTGGTG-CTTCC-3'(SEQ ID NO:30), and

5'-CGACAGAGGAGAGCAAGAAACGGCGCCTCG-CGTAGCTAGCGG-3'(SEQ ID NO:31), respectively.

A fragment containing the tat mutation [EcoRI-SacI (260 nt)] generated by PCR mutagenesis was used to construct the full-length two LTR HIV plasmids. Construction of the tat-A and tat-C mutations have been described elsewhere (Dimitrov, et al. 1993; Amendt, et al. 1994). The dl.Sp1/CMV tat-B macrophage-tropic virus was made by replacing the EcoRI to BamHI fragment in a T-cell tropic construct (pNL4–3, Adachi, et al. 1986) with the same fragment from a macrophage-tropic construct (pNLAD8, kindly provided by Eric Freed). Sequences of the PCR fragment and its flanking region in the final constructs were verified by DNA sequencing.

Transfection and Northern Analysis

HeLa Cells were transfected using the original Ca3(PO4) 2-DNA co-precipitation procedure with modifications (Graham and van der Eb, 1973). In brief, HeLa cells were split into 6-well plates 20 h prior to transfection. The plasmid DNA was in 90 ml of ddH2O and mixed with 10 ml of 2.5 M CaCl2 (Mallinckrodt) in a polycarbonate tube. To the DNA mixture, a 100 ml of BES-buffered solution (50 mM N,N-bis[2-hydroxyethyl]-2-aminoethanesulfonic acid

[Calbiochem], 280 mM NaCl, 1.5 mM Na2HP04, pH 6.95) was added dropwise. The solution was allowed to sit at room temperature for 45 min to 1 hr before being added to the 2 ml growth culture (pH. 7.1). After adding the DNA, the culture was maintained in a 3% CO2 incubator at 37° C. overnight. For the CAT assay, HeLa cells were transfected with 3 mg of CAT plasmid in the presence or absence of 0.1 mg of a tat plasmid pSVtat (Peterlin et al.1986) or pCEP-tat (Robinson et al. 1995). For the assay of Tat function using HL3T1 cells, transfection was done using 10 mg of DNA of different HIV-1 constructs. To generate virus stocks, HeLa cells were transfected with 10 mg of cloned HIV-1 plasmids and virus was harvested, filtered through a 0.45 m filter (MILLEX-HV, Millipore Products Division, Bedford, Mass.) and frozen at −80° C. for later use. All transfections were performed in the presence of a control human growth hormone plasmid pXGH5 (Nichols Institute Diagnostics). Northern analysis of viral RNA was done as described previously (Chang et al.1993) and analyzed using a phosphoimager (Fuji, BAS1000).

Quantitative Immunostaining of HIV-infected Cells

Adherent cells were washed with phosphate buffered saline (PBS) three times, fixed in cold acetone and methanol (1:1) for 2 min, washed three times in PBS, and incubated in blocking solution (20% FBS, 0.1% TritonX100 in PBS) for 30 min. Non-adherent cells were attached to the surface of a 24-well plate which had been pretreated with poly-D-lysine (1 mg/ml, Sigma) at room temperature for 10 min. We used an HIV patient serum which was diluted at 1:2000 in a blocking solution containing 20% FBS, 0.1% TritonX100 and 2% dry milk in PBS as the first antibody and the incubation was done at room temperature for 1 h or at 4° C. overnight with constant shaking. After being washed in PBS for 5 min 4 times, the cells were incubated with a 1:200 dilution of normal sheep antisera at room temperature for 30 min to block non-specific signals. The secondary antibody was a biotinylated sheep anti-human antibody (Amersham) which was used at 1:2000 dilution and incubated at room temperature for 1 h. The cells were washed four times in PBS-Tween 20 (0.3%) and incubated in the ultra-sensitive ABC staining solution (containing avidin and biotinylated horseradish peroxidase, Pierce Chemical Co.) at room temperature for 30 min. After four more washes in PBS-Tween 20, the cells were incubated in 3, 3'-Diaminobenzidine tetrahydrochloride (DAB) solution (Sigma) containing 0.3% NiCl2 for 2–3 min. The reaction was stopped by washing cells with tap water for 1–2 min. Cell staining was scored under an inverted microscope and photographed. To reduce background staining, both the primary and the secondary antisera were preabsorbed with fixed human PBLs. Pretreatment of fixed cells with 0.01w H2O2 at room temperature for 5 min essentially eliminated all nonspecific background signals. The percentages of positive cells were determined by taking the average of more than three representative counts of 1,000 or 10,000 cells.

Example 1A

Construction of Attenuated Recombinant HIV-1 Constructs

As described below, several modified HIV-1 constructs which exhibit reduced cytopathic effects in tissue culture were chosen for use in the development of the present invention.

HIV-1 LTR Mutants. Investigation of virus attenuation was essential to the understanding of viral pathogenesis, the development of preventive vaccines, and development of a safe lentiviral vector system. For production of a safe HIV vector, attenuated mutant molecular constructs of HIV-1 were viewed as better starting materials than wild-type constructs.

One approach to developing these attenuated constructs was establishing mutations in the LTRs of HIV-1. For example, the function of HIV-1 LTR enhancer/promoter elements has been studied using recombinant LTRs containing heterologous enhancer/promoters (See, FIG. 1). After deleting the regulatory elements including the NF-kB, Sp1 binding sites, and/or the TATA box, and inserting a minimal cytomegalovirus enhancer element, delayed replication kinetics has been observed in some CD4+ human lymphoid cell lines (See e.g., L.-J. Chang et al., J Virol., 67:743–752 [1993]). However, these LTR mutations do not severely affect the replication of the full-length HIV-1 constructs in tissue culture. Although NF-kB and Sp1 binding sites in the HIV-1 LTR are not absolutely required for viral replication and pathogenicity in vivo, a correlation of LTR mutations with low viral load and prolonged asymptomatic state has been observed for isolates of long term survivors of HIV-1 infection.

It was also found that several LTR deletion mutants containing a cytomegalovirus enhancer element were capable of attenuating HIV-1 (i.e., the mutants were capable of infecting human lymphocytes with reduced cytopathic effects when the tat gene also was deleted). Instead of killing the entire culture, infection with these LTR and tat mutants led to rapid cell recovery and establishment of persistent infection. The replication efficiency was not markedly affected by these mutations. By mutating the tat gene, it was also found that the recombinant LTRs (CMV-IE-HIV-LTR) exhibited increased basal levels of promoter activity which could support virus replication without Tat (L.-J. Chang, and C. Zhang, Virol., 211:157–169 [1995]; and D. Robinson et al., Gene Ther., 2:269–278 [1995]). These different HIV-1 mutant constructs were useful for the development of lentiviral vectors.

Replication-Competent tat-Minus Mutants. LTR mutants with kB/Sp1 or Sp1 deletion and CMV-IE enhancer/promoter insertion have been shown to replicate with delayed kinetics in human lymphocyte culture, including primary PBLS (peripheral blood lymphocytes) and macrophages (L.-J. Chang et al., J Virol., 67:743–752 [1993]; and L.-J. Chang and C. Zhang, Virol., 211:157–169 [1995]). AS they still exhibit cytopathic effects in culture and thus may be pathogenic in vivo, these constructs are not safe for vaccine use in the present form.

The tat gene was also a target, as it is a gene that is essential for efficient HIV-1 replication. HIV-1 Tat has been implicated in the induction of Kaposi's sarcoma, repression of MHC Class I gene promoter, induction of functional unresponsiveness of T cells, modulation of monocyte function, induction of IL-10 expression, potentiating TNF-induced NF-kB activation and cytotoxicity, and sensitizing T cells to Fas-mediated apoptosis (L.-J. Chang et al., J Virol., 67:743–752; N. Chirmule et al., J Virol. 69:492–498 [1995]; B. Ensoli et al., Nature. 371:674–680 [1994]; T. K. Howcroft et al., Science. 260:1320–1322 [1993); R. M. Lafrenie et al., J. Immunol., 156:1638–1645 [1996]; M.O. Westendorp et al., Nature 375:497–500 [1995]; and M. O. Westendorp et al., EMBO J., 14:546–554 [1995]). To examine whether Tat could be dispensable during HIV-1 replication, a series of tat mutants (two stop-codon mutants, tat-A & B, and a deletion mutant tat-C) were investigated (See, FIG. 13A). In FIG. 13A, the that are deleted in the mutant sequence, but are present in the wild-type sequence.

Mutant constructs containing both LTR and tat mutations were established. These LTR/tat double mutants were generated using the LTR mutant constructs which exhibited enhanced transcriptional activity after inserting heterologous enhancer elements. The recombinant LTR (CMV-IE-HIV-LTR), which has been shown to exhibit increased basal level of promoter activity, can support HIV-1 replication without Tat (L.-J. Chang and C. Zhang, Virol., 211:157–169 [1995]; D. Robinson et al., Gene Therap., 2:269–278 [1995]).

During the development of the present invention, it was determined that the tat-C mutant is more defective than the tat-A and -B mutants, and the dl.Sp1/CMV tat-B double mutant is more defective than the dl.Sp1/CMV LTR mutant or the dl.Sp1/CMV tat-A double mutant reported previously (L.-J. Chang and C. Zhang, Virol., 211:157–169 [1995]). The dl.Sp1/CMV tat-B double mutant infects human lymphoid cell lines with delayed kinetics and exhibited reduced cytopathic effects.

In addition, this double mutant HIV-1 infected primary human PBLs poorly and replicated in primary macrophage culture with reduced kinetics. Based on these results, these already attenuated HIV-1 constructs, dl.Sp1/CMV tat-B and dl.Sp1/CMV tat-C, were chosen for HIV vector development.

Figure 2:
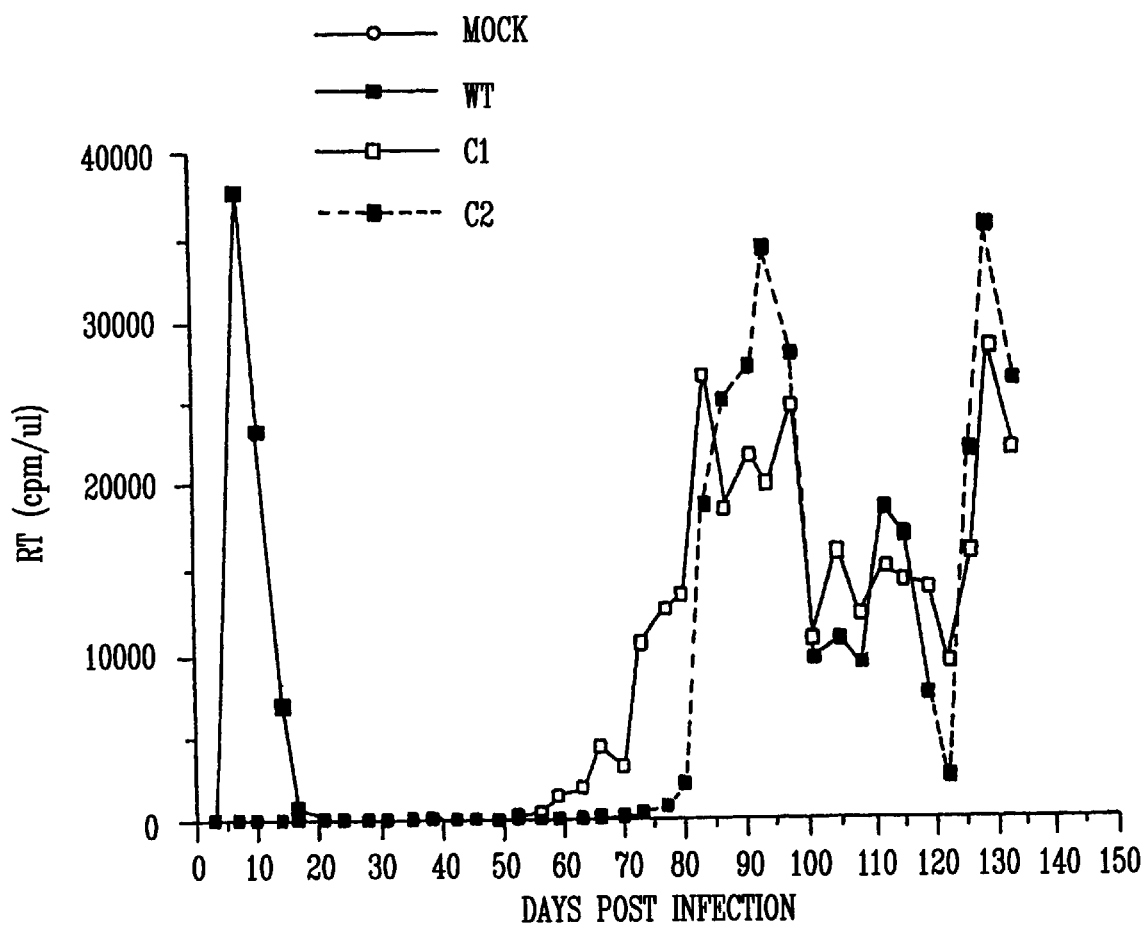
FIG. 2 is a graph showing the reverse transcriptase activity of a representative attenuated recombinant HIV-1 tat mutants over time (days post-infection).

Attenuated LTR/tat Double Mutants. The phenotypes of the LTR/tat mutants were further characterized in human lymphoid cell culture. The tat-A or tat-B LTR double mutants (Sp1 deleted and CMV-IE enhancer inserted) infected human MT4 cells with slightly reduced cytopathic effects. Further, these mutants exhibited delayed replication kinetics when compared with wild-type HIV-1. On the other hand, when cells were infected with the tat-C LTR mutant (Sp1/CMV mutant), the cytopathic effect was not so apparent and interestingly, the infected culture recovered rapidly and a persistent infection was established (See, "chr.1" and "chr. 2," in FIG. 2 and Table 1). In this table, as well as other Figures, descriptions, etc., "chr." indicates chronic infection, while the 1 and 2 indicate that the experiment was repeated twice (i.e., the "1" refers to the results of the first experiment, and the "2" refers to the results of the second experiment). In this table, the first column lists the cell line used and the virus used to infect the cells. For example, "MT4/mock" means that MT4 cells were tested without infection with HIV-1 virus (i.e., it was a control). "WT" refers to wild-type virus.

Immunofluorescent staining of cells in the persistent culture using an HIV-1 patient's sera showed that every cell was infected. Continuous output of attenuated infectious virus from these cultures was illustrated by a titration assay on CD4 HeLa cells, and the virus particles were visualized by electron microscopy (TEM and SEM). The persistently infected culture produced large quantities of fully assembled HIV particles. Virions produced from these high producer cells are tat-minus and exhibit greatly diminished infectivity. No cytopathic effect has been observed when they were further passed onto human lymphocyte cultures. Interestingly, some cultures recovered from wild-type HIV-1 infection after long term passage also became persistently infected (See, Table 1, AA2/WT [chr.] and Molt3/WT [chr.]). It is possible that the latter persistent cultures were survivors of mutant HIV-1 infection (e.g., vpr-minus).

TABLE 1

Viability and Doubling Time of Tat +/– HIV-1 Infected Cultures

| Cell Line/Virus | % Viability (± 5%) | Doubling Time (± 2 hrs) |
| --- | --- | --- |
| MT4/(mock) | 88 | 40 |
| MT4/WT (acute) | 0 | —[a] |
| MT4/tat-A (dl.Sp1/CMV) | 0 | — |
| MT4/tat-B (Dl.Sp1/CMV) | 0 | — |
| MT4/tat-C (chr.1) | 97 | 35 |
| MT4/tat-C (chr.2) | 86 | 32 |
| AA2/WT (chr.) | 73 | n.d.[b] |
| Molt3/WT (chr.) | 80 | n.d. |

[a]"—," No survivors;
[b]n.d., not determined.

HIV-1 LTR/tat/nef Triple Mutants. Prolonged asymptomatic survival of macaques infected with a nef-deleted SIV strain SIVmac239 suggested that the nef gene is a pathogenesis factor (H.W. Kestler et al., Cell 65:651–662 [1991]). Evidence to strongly support this suggestion came from studies of a cohort of long term survivors infected with HIV-1 through blood transfusion from a single donor in Australia. All the survivors were found to ca rry HIV-1 strains with multiple deletions in nef and in the U3 region of the 3' LTR (N. J. Deacon et al., Science 270:988–991 [1995]).

The LTR/tat-minus HIV-1 constructs were further modified by mutating the nef gene. To generate nef mutations, site specific mutagenesis was performed in the nef ORF to destroy its initiation codon, and a HindIII restriction site was generated (—AAGCTT—, nef-A mutant). Also, an additional stop codon was inserted in the nef ORF upstream of the polypurine tract (PPT) in the nef-A mutant, to generate a more defective nef-minus mutant (nef-B mutant, see below). The nucleotide sequence of pNL4–3 (HIV-1) from 9001 to 9031 (WT) was 5'-CTCAGGTACCTTTAAGACCAATGACTTACAA-3' (SEQ ID NO:2), while the nef-B mutant sequence generated by site-specific mutagenesis was 5'-CTCAGGTACCTTTAAGACTCTAGATCTAGAA-3' (SEQ ID NO:3). FIG. 13B provides a schematic showing of a portion of the wild-type HIV-1 sequence (SEQ ID NO:61), as well as the nef-B mutations (SEQ ID NO:26).

Figure 3A:
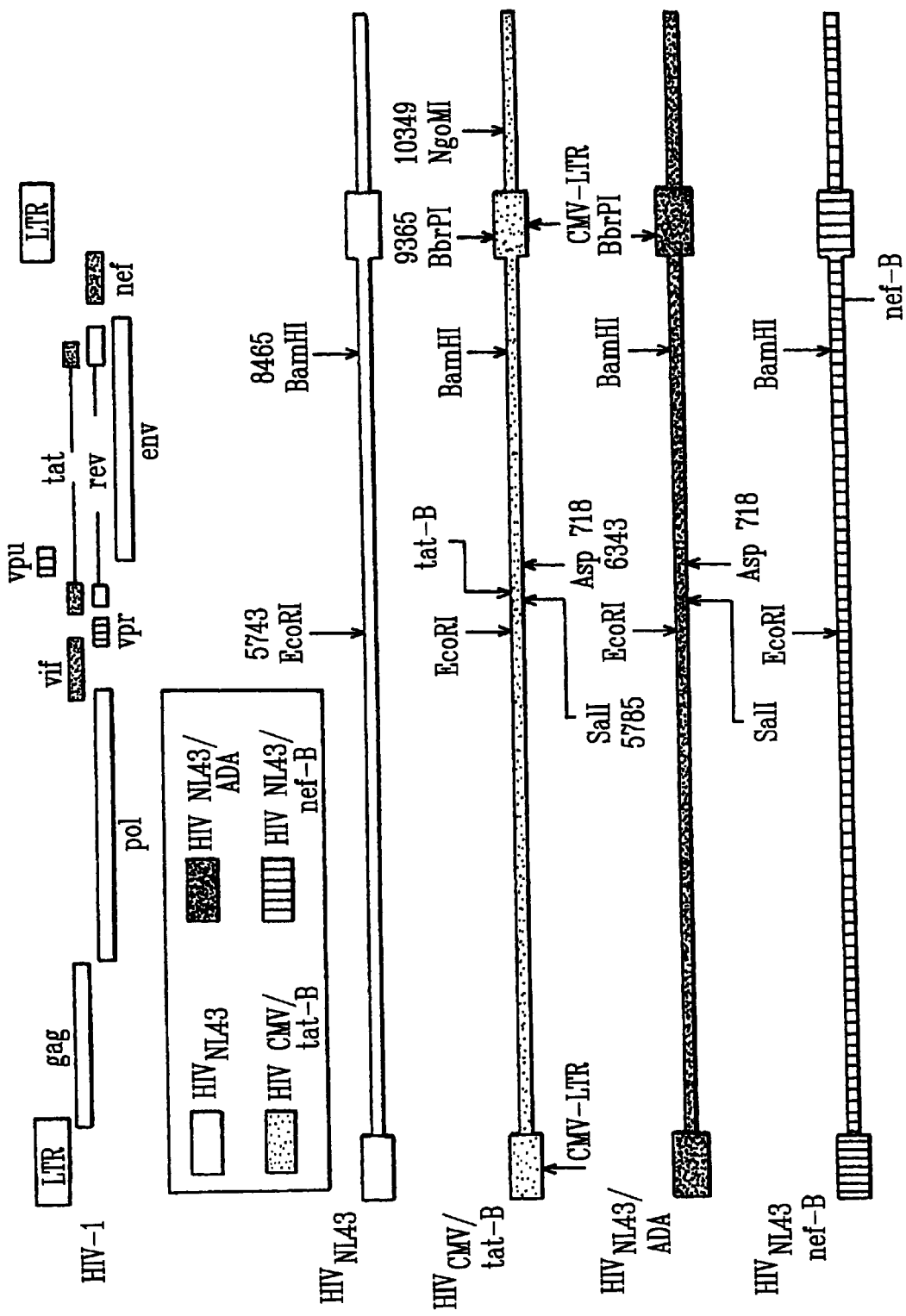
Figure 3C:
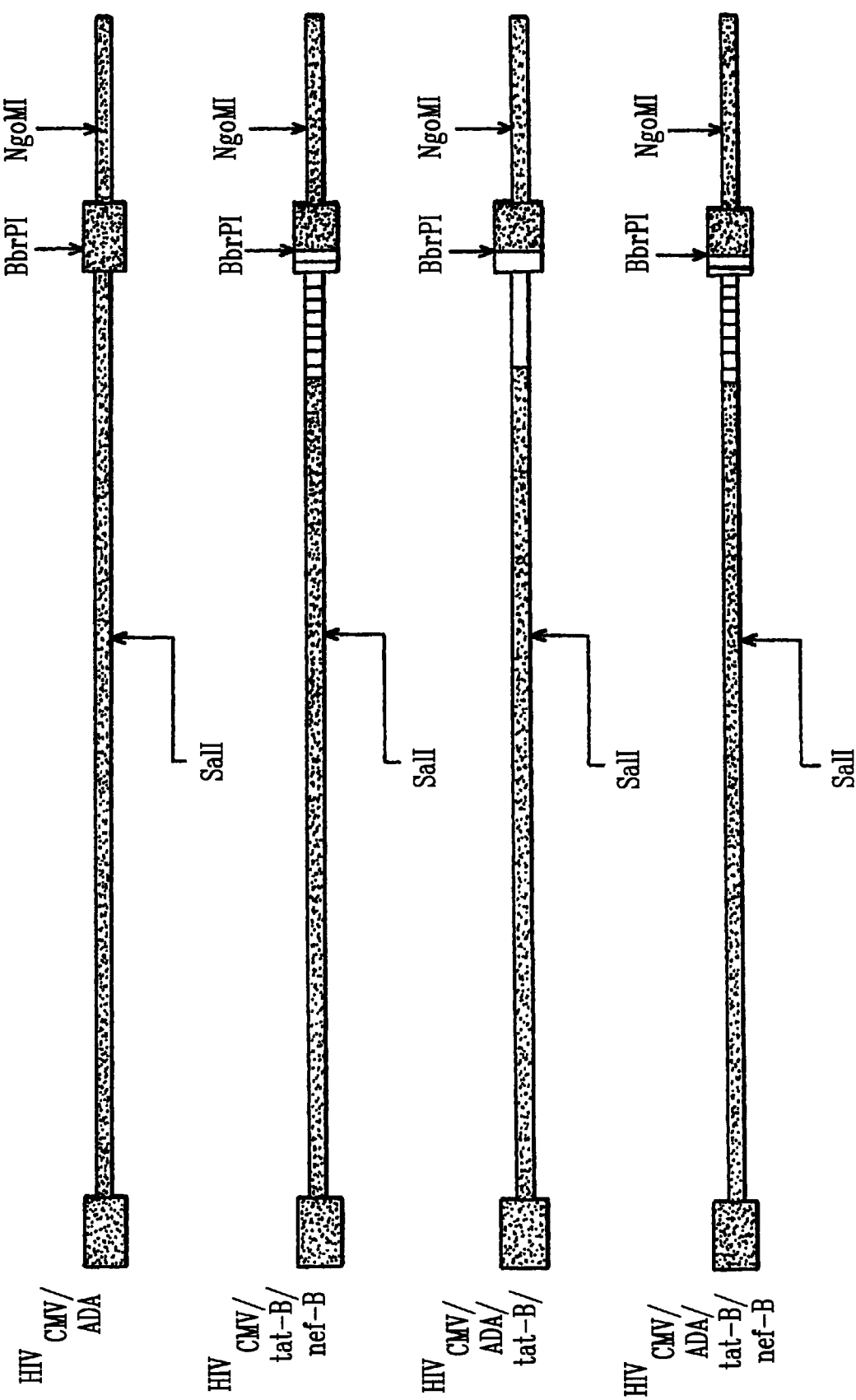

Since it is the non-syncytium-inducing, rather than the syncytium-inducing isolates of HIV-1 that are preferentially transmitted during primary infection, the T cell-tropic env gene of the LTR/tat/nef mutant was also substituted with a macrophage-tropic env (HIVADA). A schematic diagram of these HIV-1 mutants is shown in FIG. 3. These infectious molecular clones are further modified and attenuated by mutating other accessory genes including vpr, vif and vpu, as well as the U3 transcriptional regulatory elements NF-AT, NRT-1, USF and TCF-1a. A safe HIV-1 vector construct is developed from these attenuated HIV-1 LTR/tat/nef mutant constructs with a total deletion of U3 except for the att site.

Additional packaging and transducing vectors derived from mutant HIV-1 LTR, tat and nef constructs established during the development of the present invention were generated and tested for vector function.

Based on the results of experiments with the HIV-1 vectors, HIV-2 and SIV vectors will be constructed using two molecular clones, HIV-2ROD and SIVmac.

Continued experiments will establish an inducible packaging cell line using the tetracycline (TET-OFF) inducible system.

Example 1B

Replication-Competent HIV-1 Vectors Carrying Heterologous Foreign Genes

Earlier reports of HIV-1 vector systems demonstrated difficulties in generating high vector titers. This was likely due to multiple modifications in the viral genome during vector construction and the lack of a full understanding of the packaging mechanisms of HIV-1. In addition, vector titers are often construct-dependent. To analyze the ability of HIV-1 vectors carrying heterologous genes to express them at high levels, several "replication-competent" HIV-1 vectors containing different foreign genes which were inserted in the nef open reading frame (ORF) in the 3' end of the viral genome were constructed.

The nef gene has been shown to play an important role in viral pathogenesis (Z. Du et al., Cell 82:665–674 [1995]; B. D. Jamieson et al., J. Virol., 68:3478–3485 [1994]). Thus, it was considered to be safer to delete the nef allele from the lentiviral vector system to produce useful vectors. Since the nef gene of HIV is dispensable for viral replication in tissue culture, and since the nef ORF does not overlap with other genes, a foreign gene can be inserted into the nef ORF without inactivating the virus.

Figure 4:
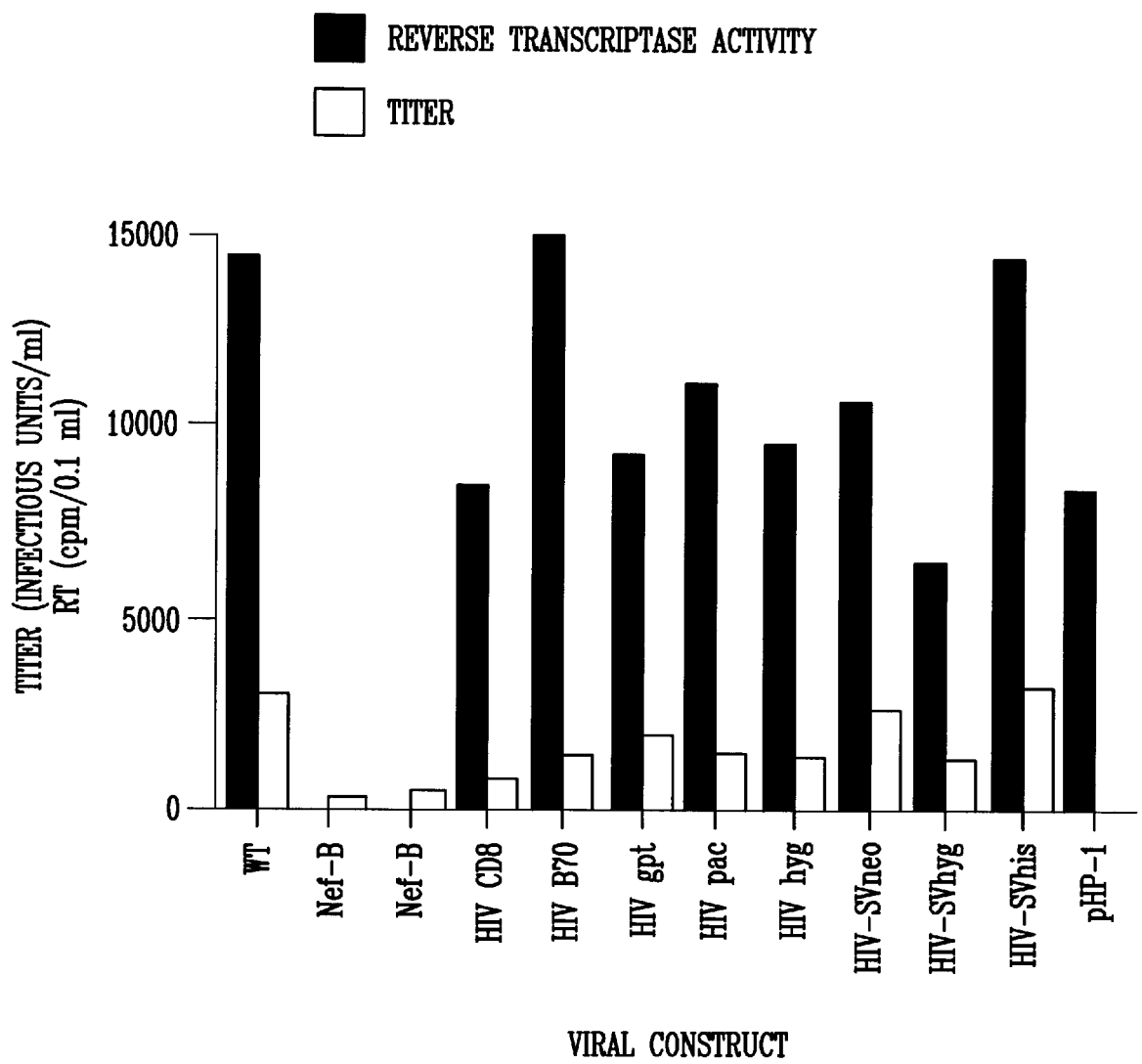
FIG. 4 shows replication efficiencies of several HIV-1 recombinants carrying heterologous genes.

FIG. 4 shows a comparison of the replication efficiencies of recombinant HIV-1 constructs carrying heterologous foreign genes. In these experiments, TE671 cells were transfected with plasmid DNA; 48 hours later, culture supernatants were used for the in vitro RT (reverse transcriptase) assay. Virus titer (i.e., transduction efficiency) was determined by infecting CD4 HeLa MAGI cells, and blue cell foci were counted under an inverted microscope after X-gal staining. The MAGI cells carry an integrated LTR-lacZ gene which can be transactivated by transduced HIV-1 Tat (J. Kimpton and M. Emerman, J Virol., 66:2232–2239.30 (1992]). The two scales in this Figure are numerically identical.

In addition, reporter genes including human T cell receptor CD8, T cell costimulator B7–2 (B70), the bacterial hygromycin-B-phosphotransferase (hyg), neomycin-phosphotransferase (neo), xanthine-guanine phosphoribosyltransferase (gpt), puromycin-resistant gene, and histidinol dehydrogenase (hisD) with or without an internal promoter (SV40) were inserted into the nef ORF at the new HindIII site or a downstream XhoI site in the nef-A mutant. These heterologous HIV-1 vector constructs were assessed by transfecting human TE671 cells, and quantitatively measuring viral RT expression and transduction efficiencies on a human CD4 cell line. Transduction efficiency was determined by counting the blue nucleated cell foci after X-gal staining. Two independent transfections were done. Representative results are shown in FIG. 4 (the standard deviation is not shown). An insertion of up to 1.5 kb of nucleotide sequences, such as B70 and SV-his, seemed to have no effect on RT production. Furthermore, the infectivity of HIV-SVhis is as high as wild-type HIV-1.

However, it was surprising to find that the nef-B mutation appeared to have an adverse effect on RT production (See, nefb tested in duplicate, FIG. 4). The cause of this adverse effect is unclear (i.e., it may have been caused by interference with packaging or reverse transcription of the RNA genome), although an understanding of this mechanism is not required in order to use the present invention. Several vectors derived from the nef-B mutant construct showed the same deficiency and thus were reconstructed. A good correlation between RT activity and virus titer was observed in this study, except for pHP-1, which is a packaging vector construct lacking the HIV-1 packaging signals (see below).

These early experiments led to some embodiments of the methods of the present invention for manipulation of the HIV-1 genome for gene expression. For example, it appeared that HIV-1 can sustain extensive changes in the enhancer and promoter region. Indeed, the replacement of the entire U3, except for att, can be tolerated. Partial substitution of the intron region for the regulatory genes (tat and rev) in the env ORF with foreign sequences can affect the splicing efficiency of the singly-spliced messages, although the nearest splice acceptor site is almost 1 kb away (See e.g., B. A. Amendt et al., Mol. Cell. Biol., 14:3960–3970 [1994]). These results suggested that: 1) a modified LTR with reduced homology to wild-type HIV-1 could be used in the vector design; and 2) deletion of the env sequence might interfere with expression of the tat and rev regulatory genes. In HIV-1 vector system, the env gene function may be deleted and replaced by the VSV-G envelope gene. As indicated herein, in some cases, it may be desirable to provide additional tat and rev functions for efficient Gag-Pol synthesis. Although an understanding of the mechanism(s) involved is not necessary in order to use the present invention, the study of heterologous replication competent HIV-1 constructs indicated that insertion of foreign sequences in the nef ORF is well tolerated and has minimal effects on viral replication. These advantages led to the development of various embodiments of the lentiviral vector systems of the present invention.

Example 1C

Construction of HIV-1 Packaging Vectors

Figure 7:
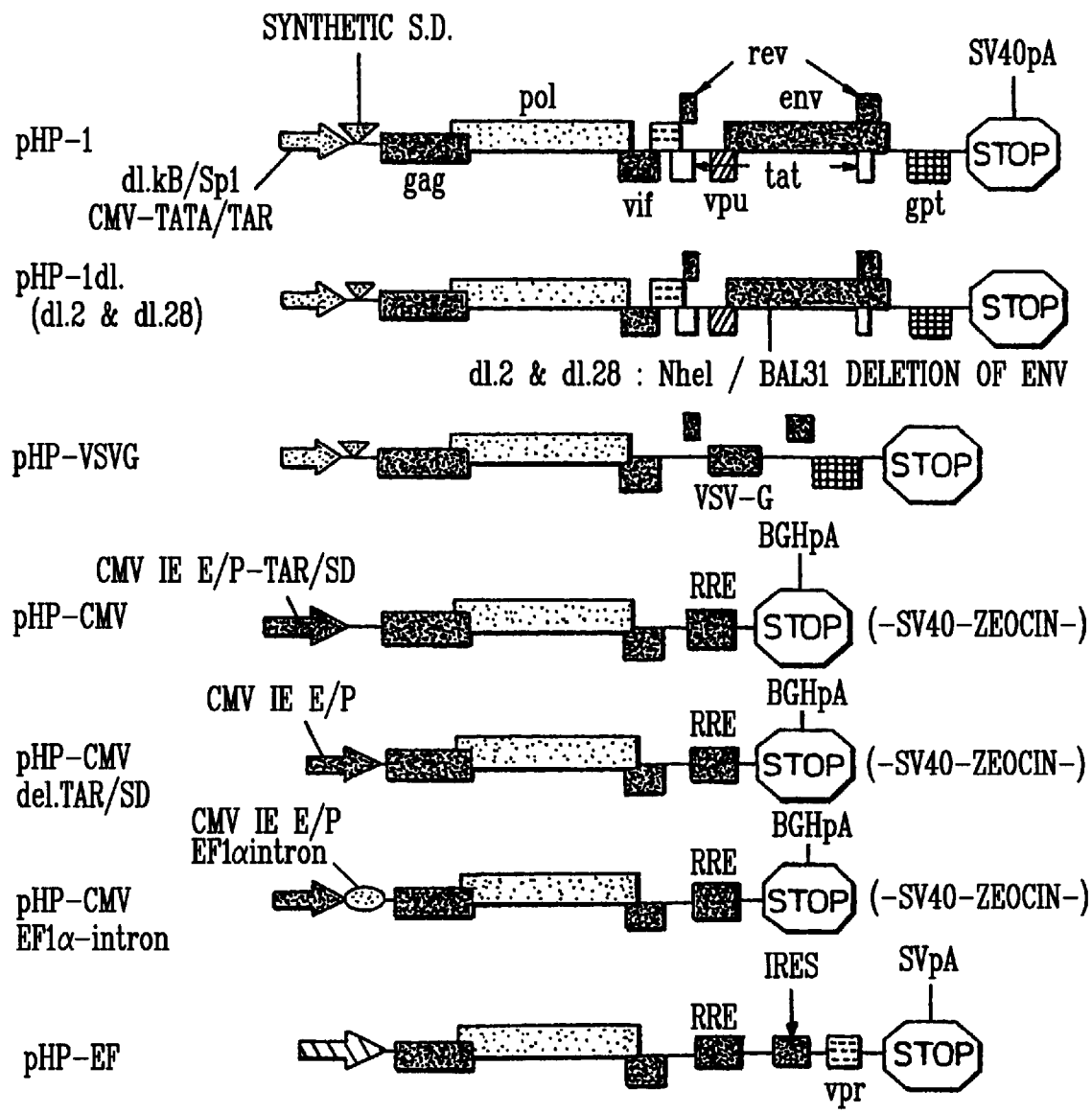
FIG. 7 shows seven pHP-1-derived packaging vector constructs.

In this Example, HIV-1 packaging and transducing vectors were constructed. Two packaging plasmids, "pHP-1" and "pHP-VSVG," containing HIV-1 env and VSV-G envelope gene respectively, were constructed. FIG. 7 is a structural diagram of seven different pHP vector constructs, including pHP-1 and pHP-VSVG.

In this Example, attenuated HIV-1 constructs were modified to produce the "pHP-1" expression vector capable of synthesizing all viral structural proteins, but lacking the packaging signal function. This vector included a strong promoter (in preferred embodiments, it is preferably not a native HIV-1 LTR), the gag-pol gene, the RRE element, the tat, and the rev gene. The RRE-Rev interaction is of great importance to the efficient synthesis of the Gag-Pol protein. This dependency may be compensated for if the INS's are deleted and RRE is replaced by a surrogate regulatory element such as the CTE of the Mason-Pfizer monkey virus.

Figure 5:
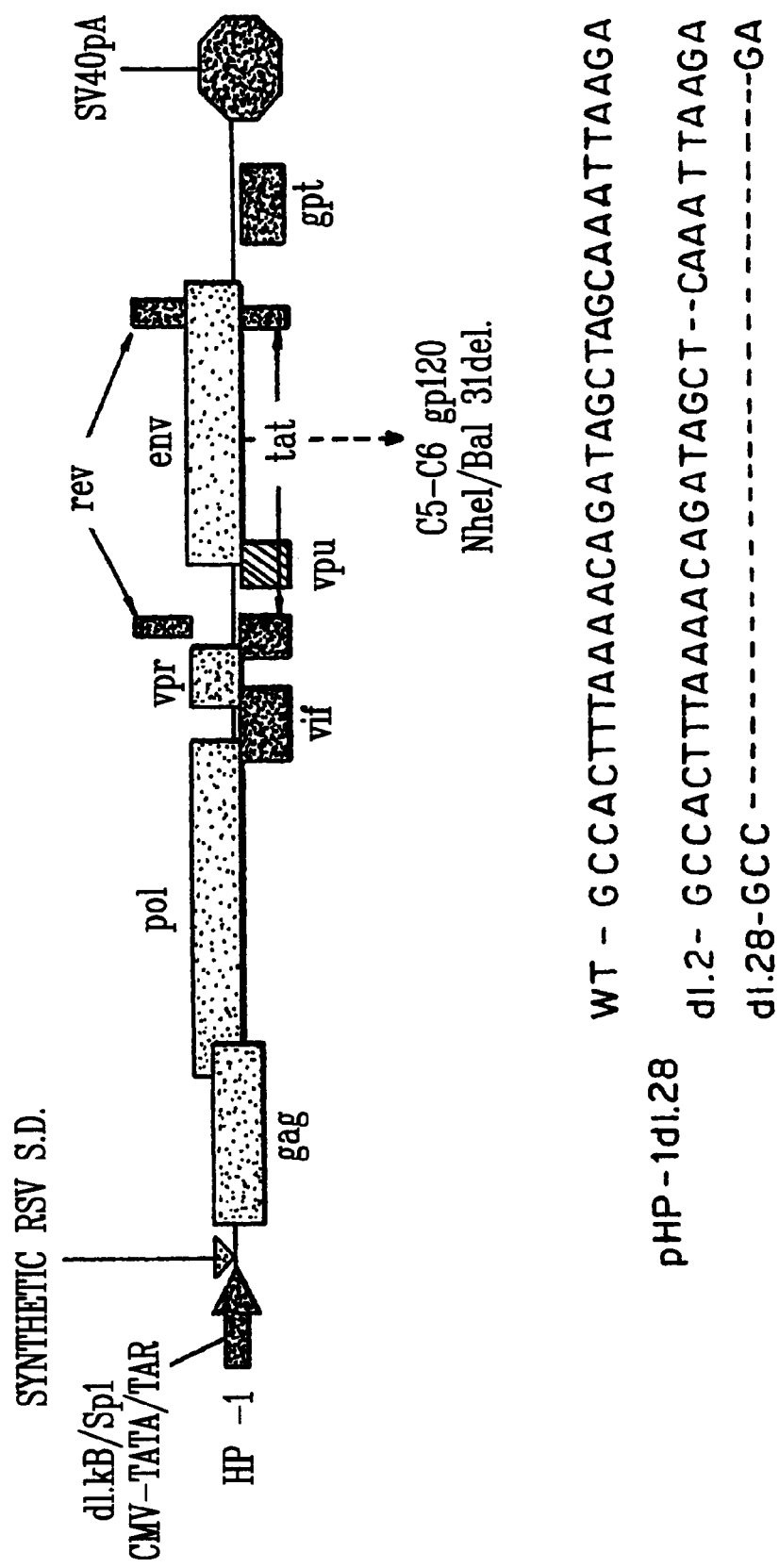
FIG. 5 shows an HIV-1 transducing vector diagram for the HIV packaging construct 1-del.env (pHP-1dl) SEQ ID NO:59. The vector pHP-1dl.2 differs from pHP-1dl in that the bases corresponding to bases 22–23 of SEQ ID NO:59 are omitted. Similarly, in pHP-1dl.28 those corresponding to bases 4–31 are omitted.

Two approaches to designing the vectors were considered, namely 1) dissecting down the wild-type genome while carefully monitoring vector titers following each modification step, and 2) starting with an over-simplified, inefficient vector construct and building back to restore wild-type function gradually. The goal was to achieve the best efficiency of vector production yet have the vector remain replication-defective to minimize the chance of generating a replication-competent recombinant HIV-1 (RC-HIV). To achieve this, the expression construct pHP-1, which contained a modified 5' HIV-1 LTR, a novel major splice donor site derived from RSV, the entire gag-pol-env,vif, vpr, vpu, tat, and rev genes, a selectable gpt marker gene, and an SV40 polyadenylation signal as shown in FIG. 5 was developed.

The wild type HIV-1 genome contains genetic elements in the 5' to 3' order:

5'LTR(U3RU5)-PBS-Psi-SD-gag-pol-vif-vpr-tat-rev-vpu-env-nef-PPT-3'LTR (U3RU5), and the pHP construct contains from 5' to 3':

a chimeric CMV-TAR promoter sequence-gag-pol-tat-rev-PPT-SV40 polyA signal.

pHP-1 lacks the native HIV-1 U3 TATA box, the primer binding site (PBS), polypurine tract (PPT), 3' LTR and most of the untranslated 5' leader sequences including the conventional retroviral packaging signal (ψ) and the major HIV-1 splice donor (SD) site. pHP-1 contains all HIV structural and accessory genes except for the nef gene and thus is capable of expressing the vast majority of the viral proteins, and also contains the bacterial gpt gene. pHP-1 provides a provirus capable of mimicking HIV-1 infection in terms of the viral proteins expressed yet this virus cannot be packaged into viral particles.

Further mutations introduced by derivatives of the pHP-1 provirus, including deletion in the env and in the 5' LTR, vpr, vif, and vpu, greatly reduce the possibility that wild-type HIV will be produced by recombination. Thus, pHP-1 and its derivatives provide excellent HIV packaging vectors. Examples of th pHP-derived packaging vectors include: pHP-dl.Vpr, pHP-Vpr/ala/leu. pHP-dl.env/Vpu I, and pHP-dl.env/Vpu II.

pHP-1 was constructed as follows. First, the Tat-responsive enhancer promoter CMV-TATA-TAR fragment (approximately 400 bp) was isolated from dl.kB/Sp1-CMV-TATA-TAR HIV (Chang et al., J. Virol. 67:743 [1993]) by BbrpI-HindIII digestion, and cloned into EcoRV-BamHI digested pSP72 (Promega) via a linker providing HindIII and BamHI cohesive sites which contains a modified gag AUG with Kozak translation initiation context and a major splice donor site of Rous sarcoma virus. This linker was formed by annealing the following oligonucleotides:

5 -AGCTTGGTCGCCCGGTGGATCAAGACCGGTA-GCCGTCATAAAGGTGATrTCGTCG-3' (SEQ ID NO:9) and

5' -GATCCGACGAAATCACCTTTATGACGCTACCG-GTCTTGATCCACCGGGCGACCA-3' (SEQ ID NO:10).

This first subclone was called pSP-CMV-TAR-SD.

Secondly, the gag coding sequence was obtained by PCR from pNL4-3 (a full-length HIV-1 plasmid) using a 5' primer (5'-CGGGATCCACCATGGGTGCGAGAG CGTC-3' [SEQ ID NO:11])

and a 3' primer downstream, of the SphI site in the gag gene (5'-ATCCTATTTGTTCCTGAAGG-3' [SEQ ID NO:12]).

The PCR product was digested with BamHI-SphI (-660 bp) and this fragment was ligated with BamHI-SphI digested pSP-CMV-TAR-SD to obtain pSP-CMV-TAR-SD-dl.gag.

Next, the poly-A minus subclone pHP-dl.pA was constructed by ligating the following three fragments: a 1112 bp HpaI-SphI fragment isolated from pSP-CMV-TAR-SD-dl.gag (contains the 30 promoter-TAR-SD-dl.gag), a 7922 bp SphI-XhoI fragment (dl.gag-pol-env-gpt) of pNLgpt, and a plasmid vector backbone provided by EcoRV-XhoI digested pBS-KS(-) (Stratagene).

Lastly, pHP-I was made by the following ligation: NotI-XhoI (9059 bp) of pHP-dl.pA containing dl.CMV-TATA-TAR-SD-gag-pol-env-gpt, a 422 bp poly-A site from XhoI-PstI digested pREP9 (Invitrogen), and NotI-PstI digested pBS-KS(-). The sequence of pHP-1 (12,479 kb) is provided in SEQ ID NO:13; this sequence begins at the promoter of the half-BbrPI site from pNL4-3 (an HIV clone available from the AIDS Research and Reference Reagent Program; the sequence of this recombinant clone is shown in Genbank Accession No. M19921). Additional mutations of pHP-1 to generate pHP-1dl2 and pHP1-dl.28 are described above (See also, FIG. 5).

Several additional HP constructs were also made ("pHP-VSVG," "pHP-CMV," "pHP-EF," "pHP-CMVdel.TAR/SD, ", "pHP-CMV-EF1α-intron", "pHP-dl.Vpr", "pHP-Vpr/ala/leu", "pHP-dl.env/Vpu I", and "pHP-dl.env/Vpu II"), each with additional changes (See, FIG. 7).

pHP-VSVG was derived from pHP-1, with the HIV-1 env gene being replaced by the VSV-G gene, and with wild-type vpr and tat, or the vpr and tat genes mutated by site-specific mutagenesis.

pHP-CMV was derived from pHP-1 with the promoter being replaced by the cytomegalovirus immediate early promoter (CMV-IE) and the tat, rev, env, vpr and vpu deleted.

pHP-CMVdel.TAR/SD was derived from pHP-CMV, with the TAR and RSV SD deleted. In other words, this construct lacks any major SD site.

pHP-CMV-EF1α-intron was derived from pHP-CMVdel.TAR/SD, with an insertion of the EF1α-intron between the promoter and the Gag AUG.

pHP-EF was derived from pHP-CMV by replacing the CMV-IE promoter-enhancer and the synthetic SD site with the human elongation factor 1α (EF1α)'s promoter and enhancer-containing intron (the latter being of course proceeded by a splice donor site). The intron-containing EF1α has been shown to be a stronger promoter than the CMV-IE promoter. The TAR sequence was also deleted. It also contains a poliovirus-derived internal ribosomal entry site (IRES)and the vpr gene. The expression of Vpr may increase the vector transduction efficiency in non-dividing cultures.

These constructs were tested for their expression of HIV-1 proteins.

Both packaging constructs (i.e., pHP-1 and pHP-VSVG) used a recombinant CMV/HIV-TAR as promoter and a synthetic major splice donor site. No sequence homology was observed with the HIV-1 genome between TAR (in the 5' end of the RNA) and the gag AUG in these two constructs. A BamHI site was generated near the gag AUG for the purpose of inserting recombinant HIV-2 and SIV gag-pol sequences in subsequent experiments.

The pHP-VSVG construct with vpr and tat mutations lacks vpr and tat genes, and the VSV-G gene is substituted for the env gene exactly at the env AUG by PCR mutagenesis. These two constructs were the first two packaging plasmids tested.

The construction of these pHP-1 derivatives is described in greater detail below. The three pHP-CMV derivatives were tested, and found to be inefficient in synthesizing HIV proteins, indicating that the pHP-1, pHP-VSVG and pHP-1 dl derivatives are the preferred embodiments of the efficient HIV vector system of the present invention.

pHP-VSVG. This clone was made to delete the HIV-1 env gene and replace it with the VSV-G gene, as well as delete the HIV-1 vpr and tat genes. It was constructed by combining the following four pieces of DNA fragments: 1) the recombinant LTR (dl.kB/Sp1-CMV-TATA-HIV-TAR) gag-pol from NotI to EcoRI fragment of pHP-1; 2) a fragment from HIV-1 with deletion in the C-terminal of vpr and the N-terminal of Tat by PCR using the following two primers 5'-TAA GAA TTC TAG TAG GTT GCT TTC ATT GCC-3' (SEQ ID NO:14), and 3'-CTT CTC CTT CAC TCT CGA GTG ATC ACT GTC TTC TGC TCT TTC-3' (SEQ ID NO:15), with the second sequence encompassing the env AUG with a new XhoI and a BclI site); 3) the VSV-G gene fragment cut by SalI-XbaI from PBS-VSV-G (obtained from Tom Hobman of the University of Alberta); and 4) a deleted env-gpt-SVpA and plasmid vector backbone from NheI-NotI digested pHP-1.

pHP-CMV. This clone was derived from pHP-1, with the 5' recombinant LTR replaced by a CMV-IE enhancer-promoter and the entire env, tat, vpu, rev, vpr, nef deleted, but with the vif gene remaining intact. This clone was constructed by ligation of the following 3 pieces of DNA: 1) the vector pcDNA3.1Zeo(+) from Invitrogen cut with NheI-XhoI; 2) the TAR/SD-gag-pol from pHP-1 digested with XbaI-EcoRI; and 3) the RRE element from pBS-RRE digested with EcoRI-XhoI. PBS-RRE was constructed by ligating BglII (nt. 7611) to HindIII (nt. 8131) of pNL4-3 of HIV-1 with BglII-HindIII digested pBS-EF. pBS-EF was from the PCRed EF1a enhancer promoter cloned into pBS (−).

pHP-CMV-del.TAR/SD: This clone is the same as pHP-CMV except that the 5' TAR and splice donor site are deleted. This construction was made by ligating the following two fragments: 1) a 702 bp fragment of MluI-BamHI digested pcDNA3.1Zeo(+) containing the CMV enhancer; and 2) the vector containing MluI-BamHI digested pHP-CMV which has deleted TAR and contains the RSV splice donor site.

pHP-CMV-EF1α-intron. This clone is similar to pHP-CMV-del.TAR/SD but with an intron from human EF-1a gene inserted between the CMV promoter and the gag AUG. It was made by ligating the following three DNA fragments: 1) pHP-1 BamHI-EcoRI fragment containing gag-pol and vif; 2) the MluI-EcoRI of pcDNAZeonlacZ-RRE containing the vector backbone of pcDNA3.1Zeo(+), HIv-1 RRE and part of the CMV promoter; and 3) the rest of the CMV enhancer promoter was obtained from BamHI-MluI digested pcDNAZeoHGHP2EF, a pcDNAZeo3.1(+) vector containing EF1α intron and the human growth hormone gene. The hGH cloned sequence is available from GenBank. See co-pending U.S. patent application. Ser. No. 08/848,760 (incorporated by reference) for additional information regarding this construct.

pHP-1 dl2 and pHP-1 dl28: To further mutate pHP-1 for safety reasons (as discussed below), portions of the env gene were deleted by Bal31 excision. To generate HIV-1 env deletions, pHP-1 was digested at the unique restriction enzyme site NheI in the env gene, and treated with Bal31 exonuclease for 1, 2 or 5 minutes. The digested product was self-ligated after T4 DNA polymerase treatment. The self-ligated plasmid DNA was then transformed into competent *E. coli* DH5α and the plasmid clones containing env deletion were selected. More than six env-deleted pHP-1 clones of different lengths were selected and sequenced.

pHP-1dl.2 and pHP-1dl.28 have 2 and 28 nucleotide deletions in the env gene respectively (See, FIG. 5). We have further modified pHP-1 dl.28 to produce various derivatives.

First, the vpr gene was mutated by site-specific mutagenesis so it retains the nuclear localization function but loses its cell cycle arrest function. Specifically, a mutation was made at amino acid 30, changing from ala to leu, as described in Mahalingam S, Ayyavoo V, Patel M, Kieber-Emmons T, Weiner D B.Nuclear import, virion incorporation, and cell cycle arrest/differentiation are mediated by distinct functional domains of human immunodeficiency virus type 1 Vpr. J Virol 1997; 71:6339–47.

The env/vpu was also mutated by site-specific mutagenesis to delete the env initiation AUG codon and part of the vpu reading frame.

These mutations were first made individually and then combined.

Construction of Gi (generation one, deletion of vpu, vif, vpr) and G2 (deletion of tat, rev) pHP vectors based on pHP-dl.28 (nef deleted and env partially deleted):

1. Construction of env AUG and Vpu deletion mutant pHP-dl.env/vpu I and pHP-dl.env/vpu II: the mutant I has a long deletion from nt 6195 at the vpu amino acid codon 45 to nt. 6330 at the 38th amino acid codon of env gene and a stop codon TAA inserted in the sequence. The primer used was a forward primer: —GTTAATTGATAGACTAGTCTAATATGGGGTACCTG (SEQ ID NO:32)—. The mutant II has a small deletion from nt. 6216 at vpu a.a. codon 52 to nt. 6237 at vpu a.a. codon 59 and env a.a. codon 6 which also has a stop codon mutation TAA at the vpu a. al. codon 50. Note that although these mutations are G1 mutations, they are made into the G2 vector pHP-dl.28 backbone.

2. Construction of vpr mutants of pHP: two vpr mutants were made, one with frameshift mutation which inactivate the entire vpr function and the other with one amino acid substitution which inactive the cell cycle arrest function of vpr but not the nuclear localization function which can assist transduction of non-dividing cells:

pHP-dl.vpr is a frame-shift mutant which was made by EcoRI digestion at nt. 5745, near vpr amino acid codon #62, and resulted in a 4 bp insertion which caused a frameshift.

pHP-vpr/ala/leu: this is a point mutation which has changed alanine to leucine at a.a. #30. This mutation deleted the cell cycle arrest function but not the nuclear localization function of vpr as reported before [Zhang, 1997 #3492; Mahalingam, 1997 #3791]. The primer used for mutagenesis is:

—-CCTAGGAAAATGTCTAACTAGTTCACTCTTAAG-TTCCTC(SEQ ID NO:33)—. Note that although these mutations are G1 mutations, they were made with the G2 vector pHP-dl.28 backbone.

3. Combination of dl.env/vpu I and dl.env/vpuII with vpr/ala/leu mutations to generate pHP-vpr/env/vpu I and pHP-vpr/env/vpu II. These two combination mutants were made by ligating the two designated mutant fragments, SpeI (in gag) to EcoRI (in vpr) containing the vpr mutation, and EcoRI to NdeI (in env) containing the env/vpu mutation, into NdeI and SpeI digested pHP-dl.28. Note that although these mutations are G1 mutations, they are made into the G2 vector pHP-dl.28 backbone.

4. Construction of a G2 vector, pHP-dl.NdeI, which has deletion of the following genes, vif/vpr/tat/rev/env/vpu: this mutant was made by deleting nt. 5122 to nt. 6399 via NdeI digestion of pHP-dl.28, and resulted in a packaging vector with all the accessory gene functions deleted and the env gene partially deleted. This NdeI-NdeI deletion also included the 3' splice sites SA4, SA5, SA6 and SA7, used for the syntheses of vpr, tat, rev, vpu and env.

Example 1D

Construction of HIV-1 Transducing Vectors (TV)

Two families of transducing vectors were constructed. In the pTVψ vectors, the major packaging signal was modified relative to the source HIV-1 signal. In the pTVΔ vectors, the source major packaging signal was used.

Figure 8:
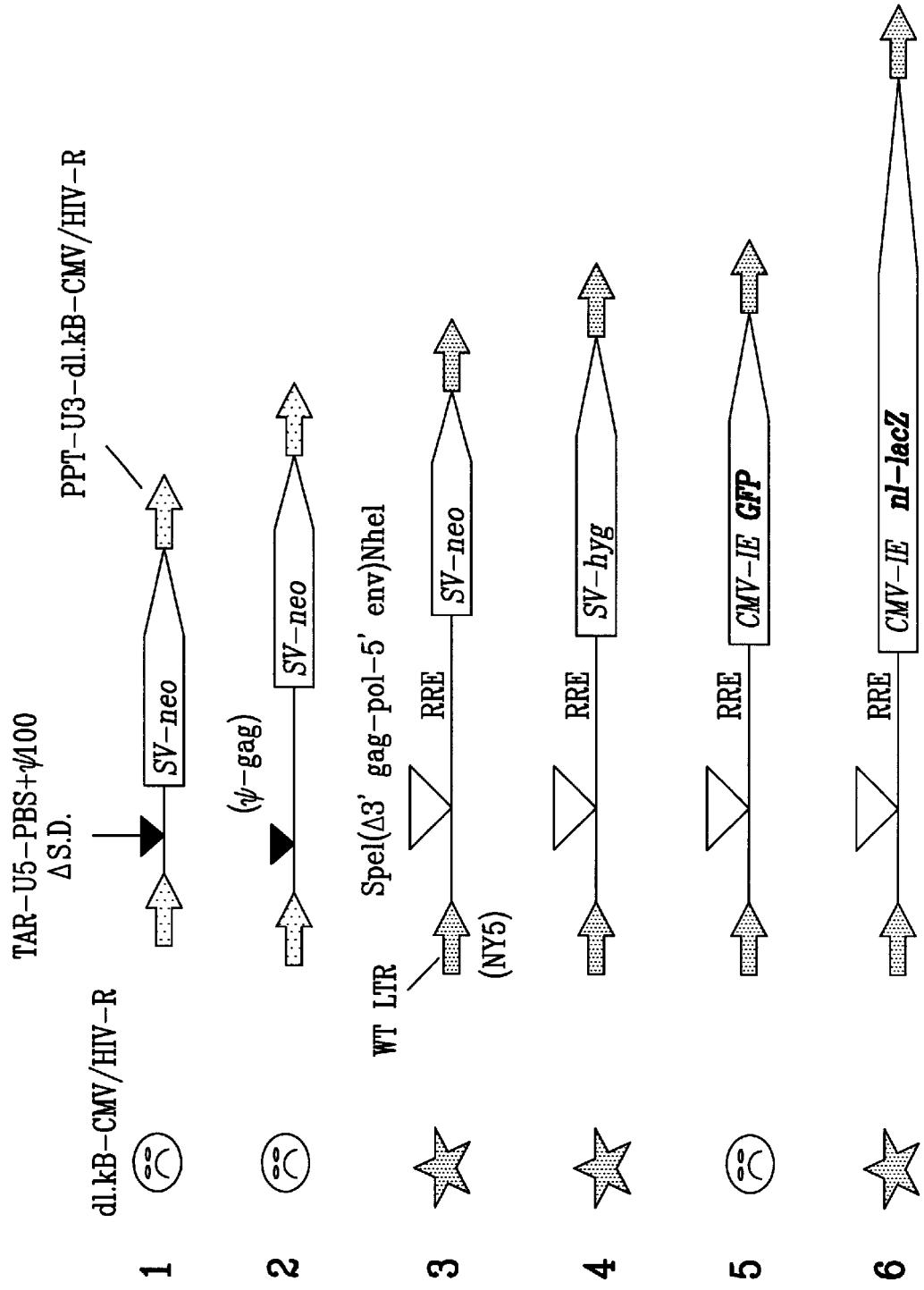
FIG. 8 shows six pTV-derived transducing vector constructs.

FIG. 8 provides a diagram of six HIV-1 transducing vectors, in which the vector backbone is derived from pNL4-3 and different LTRs. The IRES element shown in this Figure was derived from poliovirus, which could allow bicistronic gene expression.

To engineer a packaging signal for the construction of HIV-1 transducing vectors (TV), an artificial HIV-1ψ sequence using four synthetic oligonucleotides was synthesized, which comprised sequences between the PBS and the gag AUG (referred to as "ψ100" or "PAK100") and sequences extending into the gag ORF (referred to as "ψ140" or "PAK140"). These synthetic HIV-1ψ sequences contained a mutated SD site (three nucleotides changed in PAK100 and PAK140, GAGTA→CATTC) and a mutated gag AUG (HindIII and BamHI sites inserted upstream of gag AUG in both; PAK100 stopped just upstream of gag AUG; PAK 140 changed gag AUG to UAG and second codon from GGT to GCC) to avoid possible adverse effects in gene expression. PAK100 and PAK140 both started at nt 690 of provirus, i.e., 5' base of U3=1. The synthetic ψ signals were cloned into the pTVψ vector as shown in FIG. 8, which is comprised of two recombinant LTRs ("dl.kB-CMV/HIV-TAR"), the PBS and 5' leader sequences, an SV40-driven neo resistance gene, and the 3' PPT.

The packaging efficiencies of pTVψ100 and pTVψ140 (FIG. 8, constructs 1 and 2) were tested in a co-transfection experiment. HeLa cells were transfected with pHP-1 and pTVψ100 or pTVψ140 and 48 hours later, the culture supernatants were harvested and used to transduce CD4 HeLa cells (not VSV-G pseudotyped). G418 resistant colonies were counted 10 days later. As a control, HeLa cells were transfected with wild-type HIV-1 DNA; 48 hours later, the culture supernatant was used to infect CD4 HeLa cells. The titer of the wild-type HIV-1 was determined by a sensitive immunohistochemical staining method using anti-Gag p24 mAb as described by Chang and Zhang (L.-J. Chang and C. Zhang, Virol., 211:157–169 [1995]). Results of this study showed that both pTVψ100 and pTVψ140 were packaged at a very low efficiency (approximately 3 logs of magnitude less than the wild-type HIV-1).

Figure 9A:
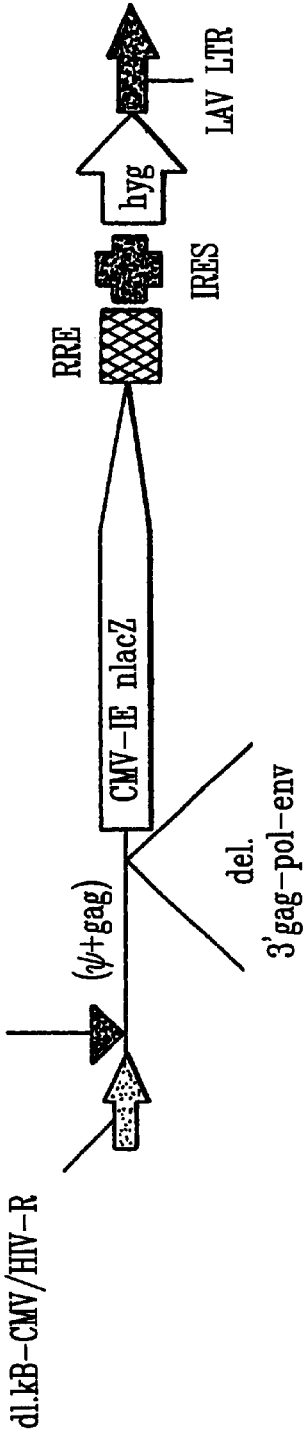
FIG. 9A shows a pTVψ-derived construct.

This result indicated that additional HIV-1 sequences are needed to improve the packaging function of pTVψ100 and pTVψ140. Therefore, more HIV-1 sequences, including an additional gag sequence and an RRE element, were cloned into pTVψ140. One such example is shown in FIG. 9A (pTVψ+CMV-nlacZ-hyg). Again, the pTVψ+ was not packaged efficiently, indicating the splice donor site and Gag AUG mutations in pTVψ100 and pTVψ140 are detrimental to HIV packaging. While the tested pTVψs cannot be used as efficient transducing vectors, pTVΔs can be efficiently packaged and transduced, as shown below.

Thus, site-specific mutagenesis was performed to change 1–2 nucleotides in the splice donor site, and the Gag AUG in pTVΔs using primers:

5'-GCGGCGACTGGGGAGGACGCCAA-3' (SEQ ID NO:7) and

5'-GAAGGAGAGAGTTGGGTGCGAG-3' (SEQ ID NO:8), to generate pTVΔSM vectors.

It is desirable to avoid sequence homology between the packaging construct and the transducing vector construct so as to reduce the probability of recombination. However, cotransfection with additional accessory genes such as vpr, nef and vpu may also help to increase the vector titer and the transduction efficiency. Inclusion of accessory genes in the transducing vector does not increase the probability of recombination, provided that such genes are omitted from the packaging vectors. The homology between the preferred pHP and pTV constructs is sufficiently low so that recombination was not detected in our study.

In order to generate a replication-competent HIV-1, the major SD site, the gag AUG and the env sequences must be restored, because they are deleted from the modified pHP and pTV constructs.

In an alternative approach for the construction of an efficient transducing vector the wild-type genome was gradually deleted (pTVΔ). In this embodiment, the two replication-competent HIV-1 vectors, "HIV-1-SVneo" and "HIV-1-SVhyg" (See, FIG. 4) were used as a starting point. These two constructs are nef-minus, and exhibited up to 50–70% of the wild-type HIV-1 replication efficiency. A deletion was made starting from the middle of the gag ORF to the middle of the env ORF. This did not delete the RRE element.

First, pTVΔSVneo was created by digesting pNL-SV with NheI (with a site located in the middle of the env gene), and SpeI (with a site in the middle of the gag gene), and then self-ligated to delete the gag-pol-env, and vif, vpu, vpr, tat, and rev genes. pNLSV was created by inserting SVneo in between the nef AUG and the XhoI site in the N-terminus of nef. pTVΔCMVnlacZ was made by digesting pTVΔSVneo with XhoI-KpnI as the vector, which deleted SVneo and part of the nef sequences near the 5' end of the PPT of HIV-1, the product was then ligated with a SalI-KpnI fragment containing CMV-nlacZ sequence from pcDNAzeo-nlacZ. pcDNAzeo-nlacZ was generated by inserting nlacz of pSP72nlacZ into pcDNA3.1zeo(+).

The two deletion vectors, "pTVΔSVneo" and "pTVΔSVhyg," (See, FIG. 8, constructs 3 and 4) were examined for their transduction efficiencies in cotransfection experiments.

Figure 9B:
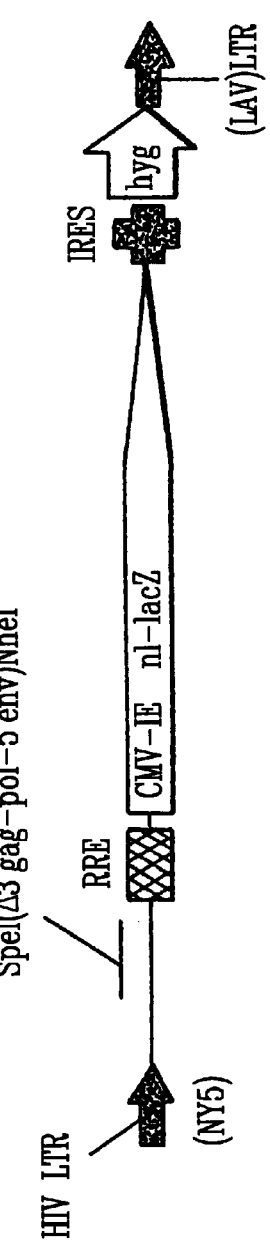
FIG. 9B shows a pTVΔ-derived construct.

Three additional pTVΔ vectors were also constructed, each containing a different reporter gene: CMV-GFP (green fluorescent protein, PTVΔCMV-GFP), CMV-nlacZ (pTVΔCMV-nlacZ) and CMV-nlacZ-hyg (pTVΔCMV-nlacZ-hyg), as illustrated in FIG. 8 (See, FIG. 8, constructs 5 and 6, as well as FIG. 9B).

Example 2

Detection of Synthesis of HIV-1 Proteins by Packaging Cell Lines

Western Blot analysis:

In this Example, Western analyses of HIV-1 proteins in HeLa cells transfected with various vector constructs were tested. In this Example, cell lysates were prepared and analyzed by Western blotting and compared with a wild-type HIV-1 construct (pNL4-3), in order to determine the level of viral proteins synthesized by pHP-1 and pHP-VSVG (with and without Tat), in comparison with wild-type HIV-1. In this Example, the Western blots were performed using serum obtained from an HIV-infected individual, and methods known in the art (See e.g., Ausubel et al. (eds.) Short Protocols in Molecular Biology, 2d ed., John Wiley & Sons, New York, N.Y. [1992], pp. 10.33–10.35).

Figure 6:
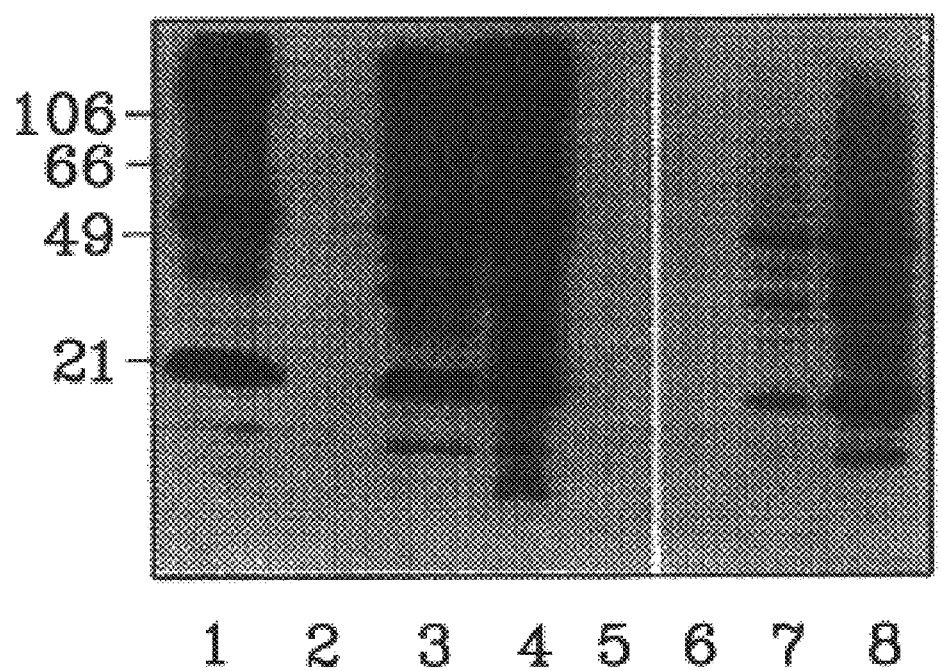
FIG. 6 shows a Western analysis of HIV-1 proteins in HeLa cells.

FIG. 6 shows the results of the Western analyses. In this Figure, lane 1 contains cell lysate from MT4 cells infected with HIV-1; lane 2 contains control HeLa cell lysate; lane 3 contains lysate from HeLa cells with pHP-1; lane 4 contains wild-type HIV-1 pNL4-3 cell lysates; lanes 5 and 6 contain pHP-VSVG-transfected cell lysates; lane 7 contains pHP-VSVG+Tat cell lysate; and lane 8 contains pHP-VSVG+Vpr cell lysate. As indicated in FIG. 3, the results showed that the level of viral proteins synthesized by pHP-1 was similar to that of the wild-type pNL4-3 (gee, lanes 3 and 4, respectively, in FIG. 6). Similar results were obtained when pHP.1.dl constructs were used.

These results indicated that in the absence of Tat, the recombinant LTR of pHP-VSVG is inactive. Thus, it is likely that the TAR element in the LTR down-regulates transcriptional elongation. These results led to the generation of an inducible packaging cell line using the pHP-VSVG construct as described in Example 4.

Reverse Transcriptase Activity

Analysis of reverse transcriptase (RT) activity in the transfected culture supernatants indicated that the level of active RT production was reduced 40% for pHP-1 compared with the wild-type construct pNL4-3. RT synthesis of pHP vs. wild type HIV-1NL4-3.

| Packaging construct | *RT (cpm/µl) exp.1/exp.2 |
|---|---|
| pNL4-3 | 12,094/9,120 |
| pHP-1 | 8,400/8,678 |
| pHP-1dl.2 | 7,250/4,682 |
| pHP-1dl.28 | 6,436/8,682 |

*RT, two independent transfection and assay results are shown; the RT background activity of 50 cpm/µl was not subtracted.

The expression of Gag-Pol function indicates that tat and rev are functional. Thus, the artificially engineered splice donor (SD) site in the pHP-1 construct, which is unrelated to HIV sequences, works like the wild-type SD site (i.e., allowing partition of spliced and unspliced mRNAs into the cytoplasm).

The packaging vector pHP-dl.28 expressed RT at 50–90% of the wild type level, indicating that the mutations in pHP-dl. did not affect the synthesis and function of Gag-Pol.

Comments

Analyses of RNA expression and packaging function by pHP-CMV and pHP-EF were performed in order to compare these vectors directly with the wild-type HIV-1. These experiments showed that pHP-CMV and pHP-EF do not express Gag-Pol protiens at high efficiencies, indicating that the pHP-1-derived vectors have important viral sequences that are necessary for efficient vector production. pHP-VSVG did not express HIV-1 proteins unless the Tat trans-activating protein is also present (See, FIG. 6, lane 6 vs. 7). Thus, although expression of VSV-G and Gag may be cytotoxic, an inducible packaging cell line could be established using pHP-VSVG without a tat plasmid.

PHEF-VSVG: human elongation factor 1 alpha promoter driven VSV-G envelope and pHEF-A-env: EF1a promoter driven amphotropic MLV envelope, were also constructed in our laboratory and shown to express high levels of envelope proteins; better than the CMV-IE promoter driven construct.

It should also be noted that overexpression of Gag-Pol may not increase the vector titer because earlier studies have shown that overexpression of Gag-Pol induces protease activation and prevents virus assembly and budding (V. Karacostas et al., Virol., 193:661–671 [1993]; J. Park and C. D. Morrow, J. Virol., 65:5111–5117 [1991]). The present examples describe vectors that produce measurable amounts of Gag-Pol (e.g., pHP-1, pHP-1del, and pHP-VSVG), as well as vectors that do not express detectable amounts of Gag-Pol (e.g., pHP-CMV and its derivatives). The latter require further mutation to be useful as vectors.

Example 3

Requirement for HIV-1 Tat for Efficient Gal-Pol Protein Processing

In this Example, the requirement of Tat for efficient Gag-Pol processing and HIV-1 vector production in certain packaging systems was demonstrated.

1. Western Analysis of Tat+ and Tat− HIV-1 Particles and Infected Cells

Virus pellets ("P") and cell lysates ("L") were prepared from Tat+ (tat WT) and Tat− (tat-B and tat-C) virus-infected cells, and the protein contents were separated by a 10% SDS protein gel, and detected in Western analysis using AIDS patient's serum. The signals were amplified using the Amersham ECL chemiluminescence kit.

Figure 11:
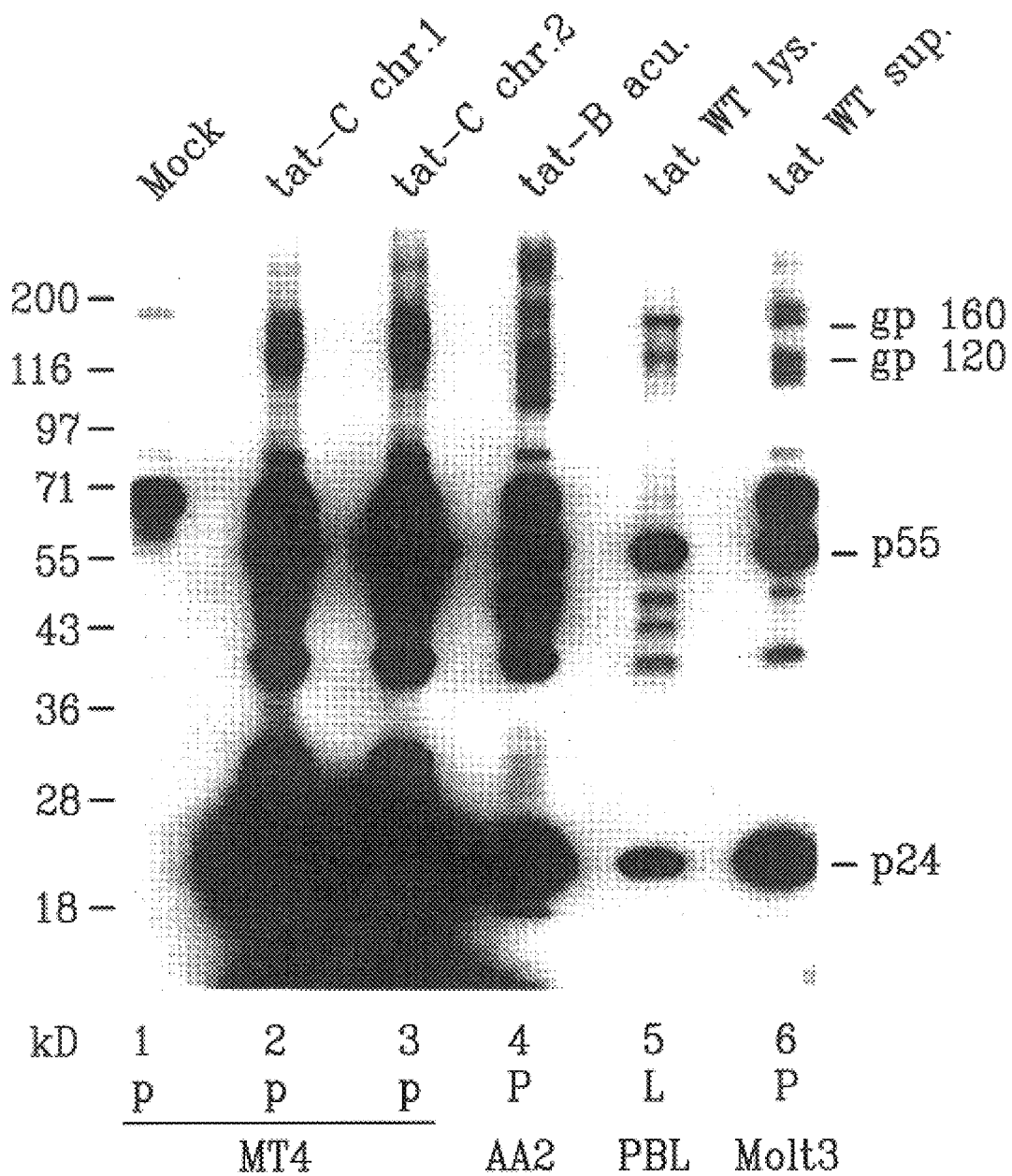
FIG. 11 shows a Western analysis of expression of Tat$^+$ and Tat$^-$ HIV particles and infected cells.

In FIG. 11, the first three lanes (1–3) indicate the results for mock-infected cells (lane 1), and virus pellets harvested from MT4 cells (lanes 2 and 3 contain viral pellet from cells chronically infected with tatc), and AA2 cells (i.e., CD4+ hybridoma human T and B cells, available from the AIDS Research and Reference Reagent Program) lane 4 contains viral pellet harvested from AA2 cells acutely infected with tatB. Cell lysates and pelleted particles of Tat+ viruses grown in PBL and Molt3 cells, are shown for comparison on lanes 5 and 6 of FIG. 11. In this Figure, protein markers are shown on the left and representative structure proteins of HIV-1 are indicated on the right.

Figure 14:
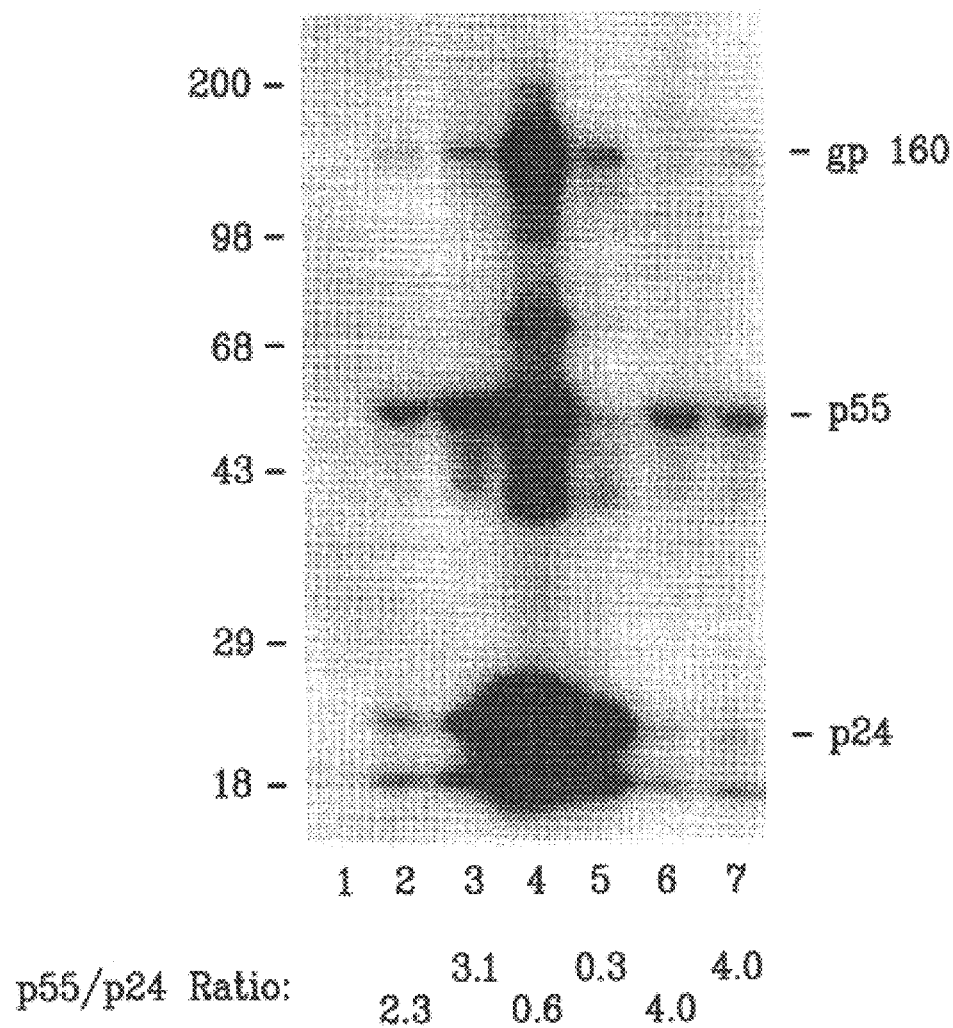
FIG. 14 shows a Western analysis of Gag processing in wild-type or tat HIV-1 infected cell cultures.
Figure 15:
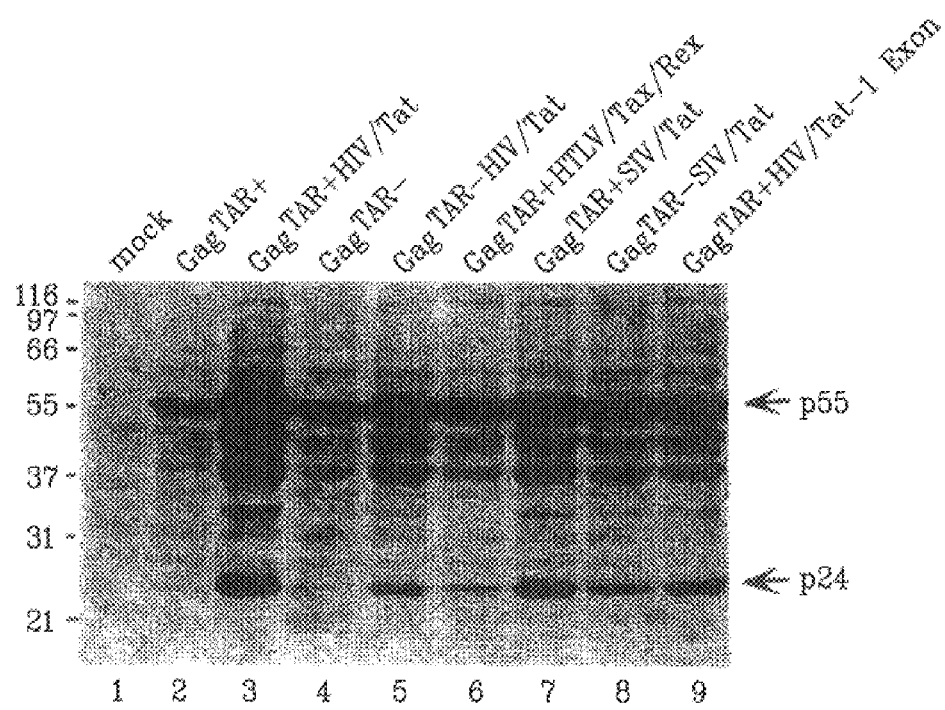
FIG. 15 shows a Western analysis indicating the effect of Tat on Gag processing in infected HeLa cells.

2. Gag Processing Deficiency of Tat-minus HIV-1 Demonstrated by Metabolic Labeling of Chronically Infected Cells WT or tat-minus HIV-1 chronically infected cultures were metabolically labeled with $^3$H-leucine overnight, immunoprecipitated with pooled HIV patient sera, and analyzed by SDA-PAGE (10%). The relative ratio of Gag p55:p24 is shown at the bottom. Processing of the envelope gp160 to gp120 was not significantly different between different samples. The $^3$H-labeled protein bands were quantified using a phosphoimager (BAS1000). The results are shown in FIG. 14: Lane 1, control MT4; lane 2 &3, MT4 chronically infected with dl.Sp1 CMV tat-C; lane 4, MT4 acutely infected with WT HIV-1; lane 5, C8166 chronically infected with WT HIV-1; lane 6, MT4 chronically infected with dl.Sp1 CMV tat-B; lane 7, AA2 chronically infected with dl.Sp1 CMV tat-C.

Figure 10:
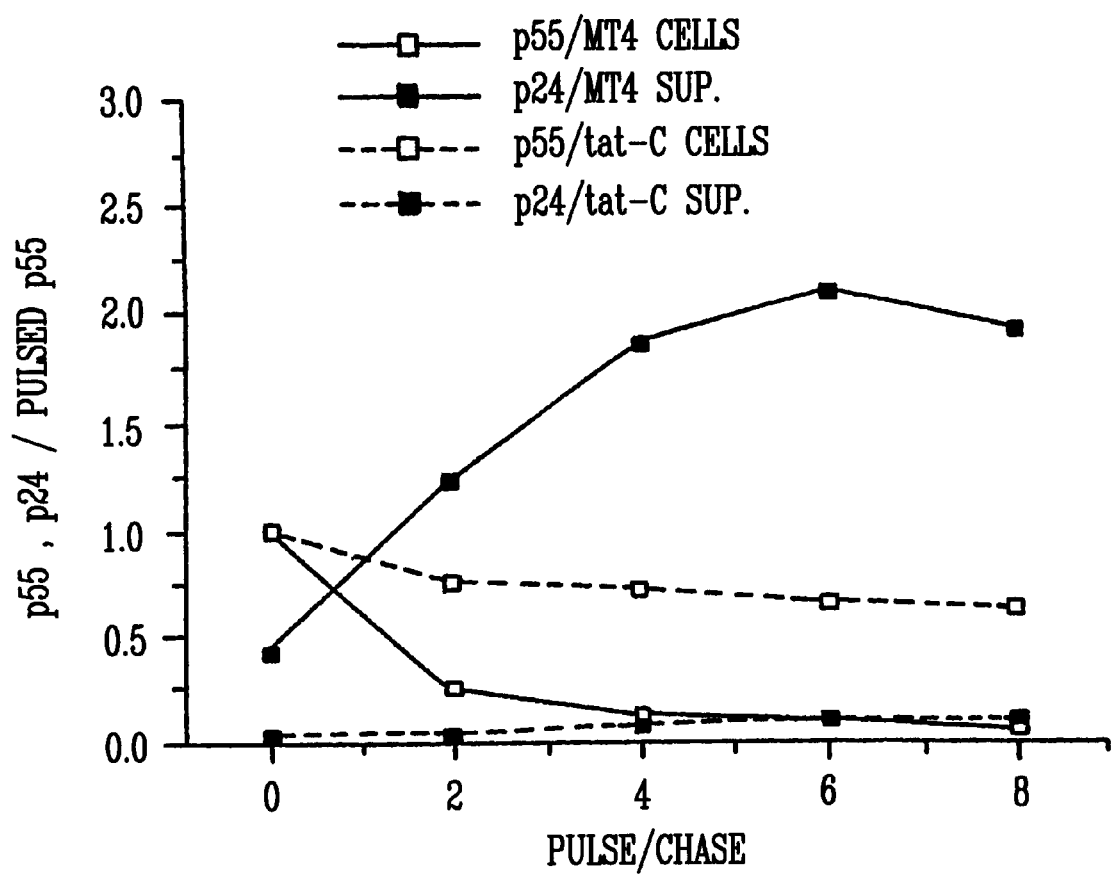
FIG. 10 shows the Gag processing rates of wild-type HIV-infected MT4 compared with tat-C HIV chronic high producing cells.

3. Cells Chronically Infected with Tat-minus RIV-1 are Deficient in Gag Protein Processing Demonstrated by Pulse-Chase Metabolic Labeling The same number of viable cells (3×10$^6$) was used in each lane of a 10% SDS-PAGE gel system. Cells were labeled with medium containing bands for HIV-1 Env gp120, and Gag p55 and p24. A Fuji phosphoimager was used for quantitation of Gag p55 and p24of WT-infected MT4 and tat-C chronic high producer. In FIG. 10, the resultant decrease of p55 and increase of p24 (p55, p24/pulse-labeled p55) with time (P, 2, 4, 6, 8 hours) were shown and plotted. In FIG. 10, the solid curves demonstrate efficient processing of p55 of HIV$_{NL4-3}$ with steady increase of p24 and decrease of p55; the dashed curves demonstrate that the amounts of p55 and p24 are not significantly changed with time in the tat-C high producer cells, indicating a deficiency in Gag processing.

4. Tat Enhances Gag Processing in HeLa cells

Figure 16:
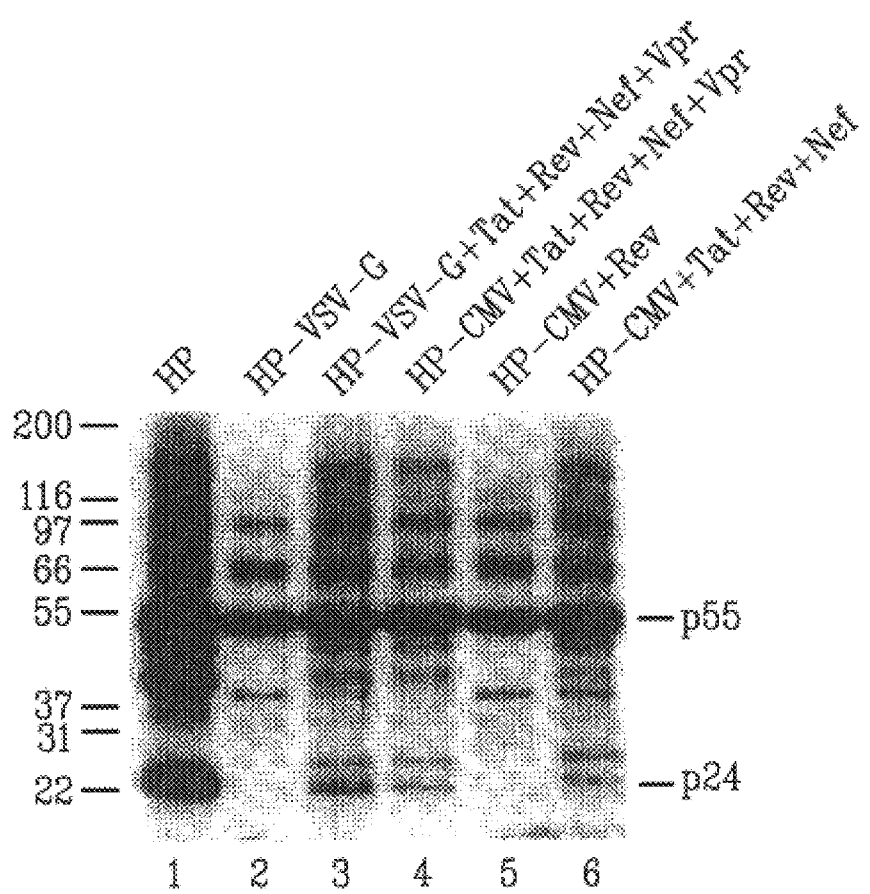
FIG. 16 shows a Western analysis of the effect of Tat on Gag processing in infected TE671 cells.
Figure 18:
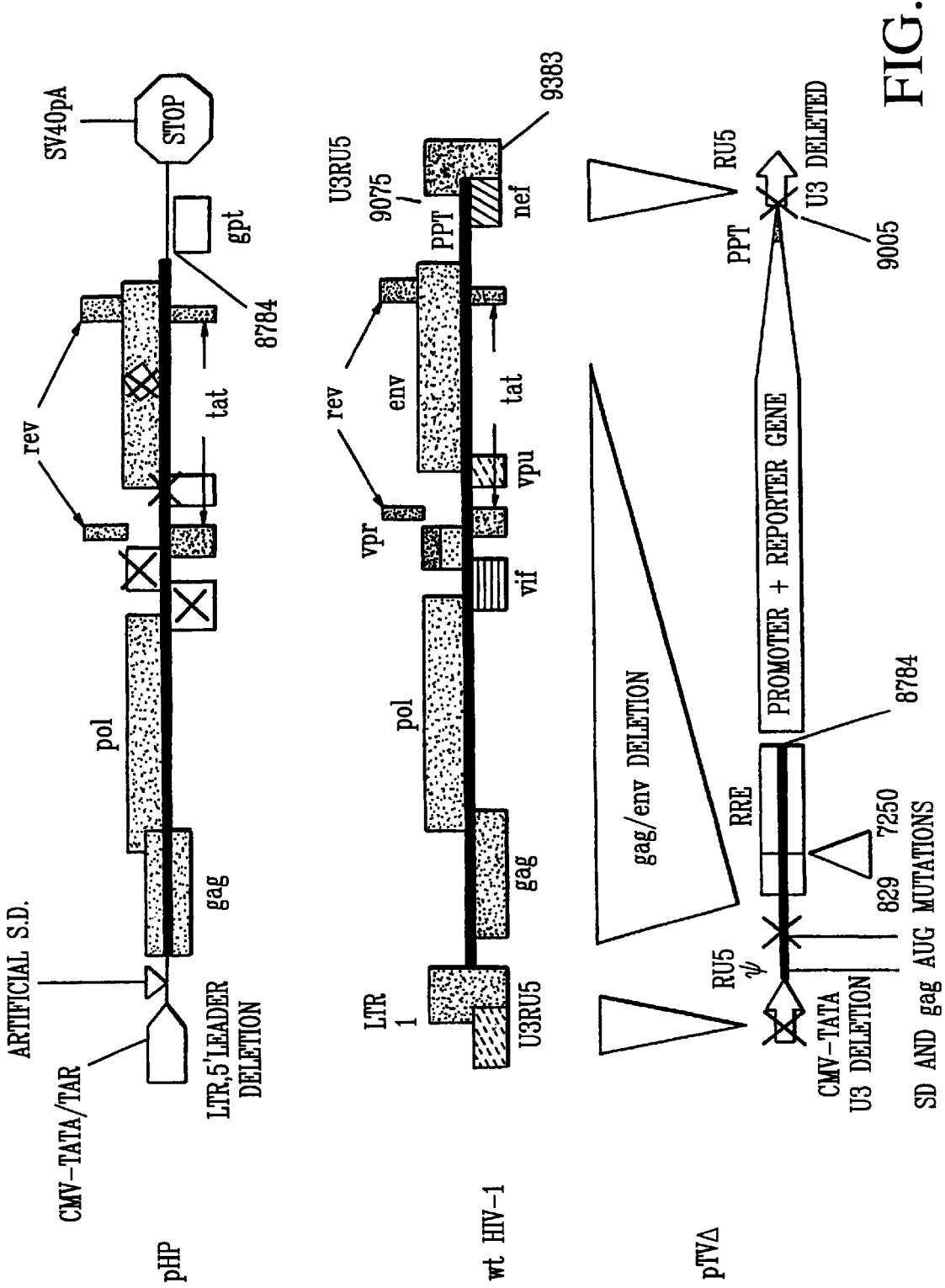
FIG. 18 compares the strucutres of pHP, wt HIV-1 and pTVΔ.
Figure 19A:
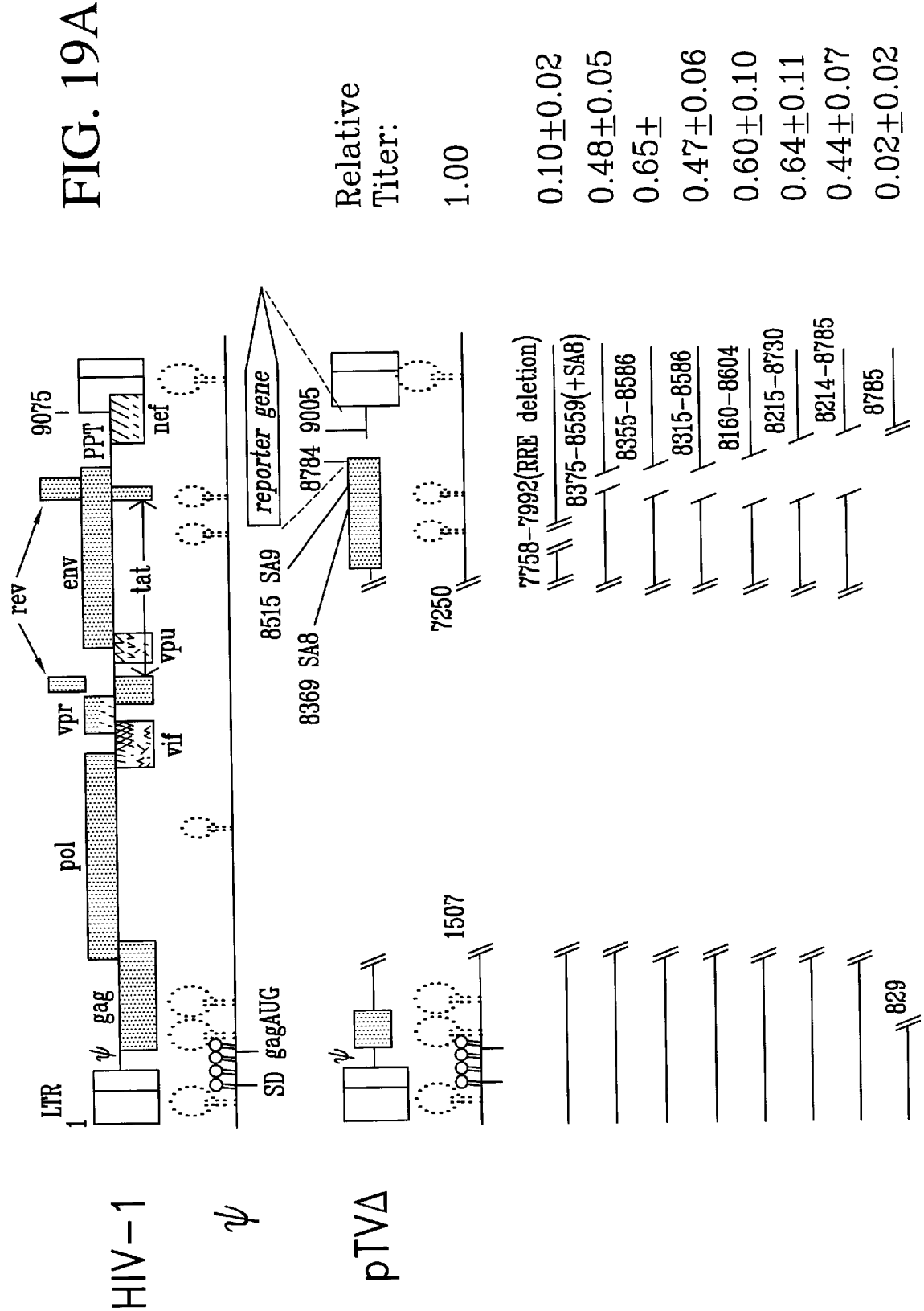
FIGS. 19A–19C show the structures of HIV-1 and numerous transducing vector variants, together with the viral titers relative to pTVΔ set at unity. The locations of the SD, the gagAUG, and various known or potential packaging signals (stem-loops) are indicated.
Figure 19B:
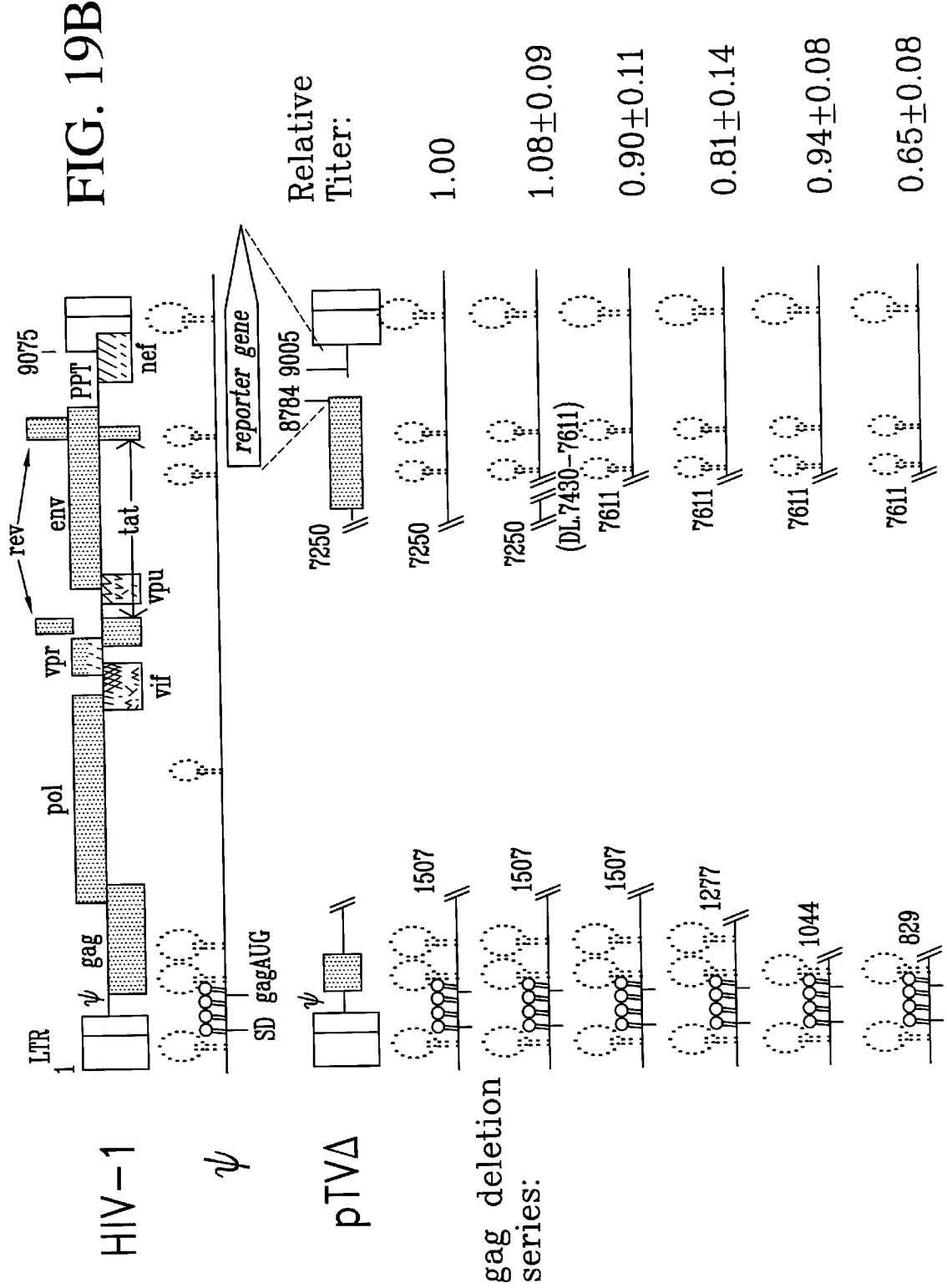
Figure 19C:
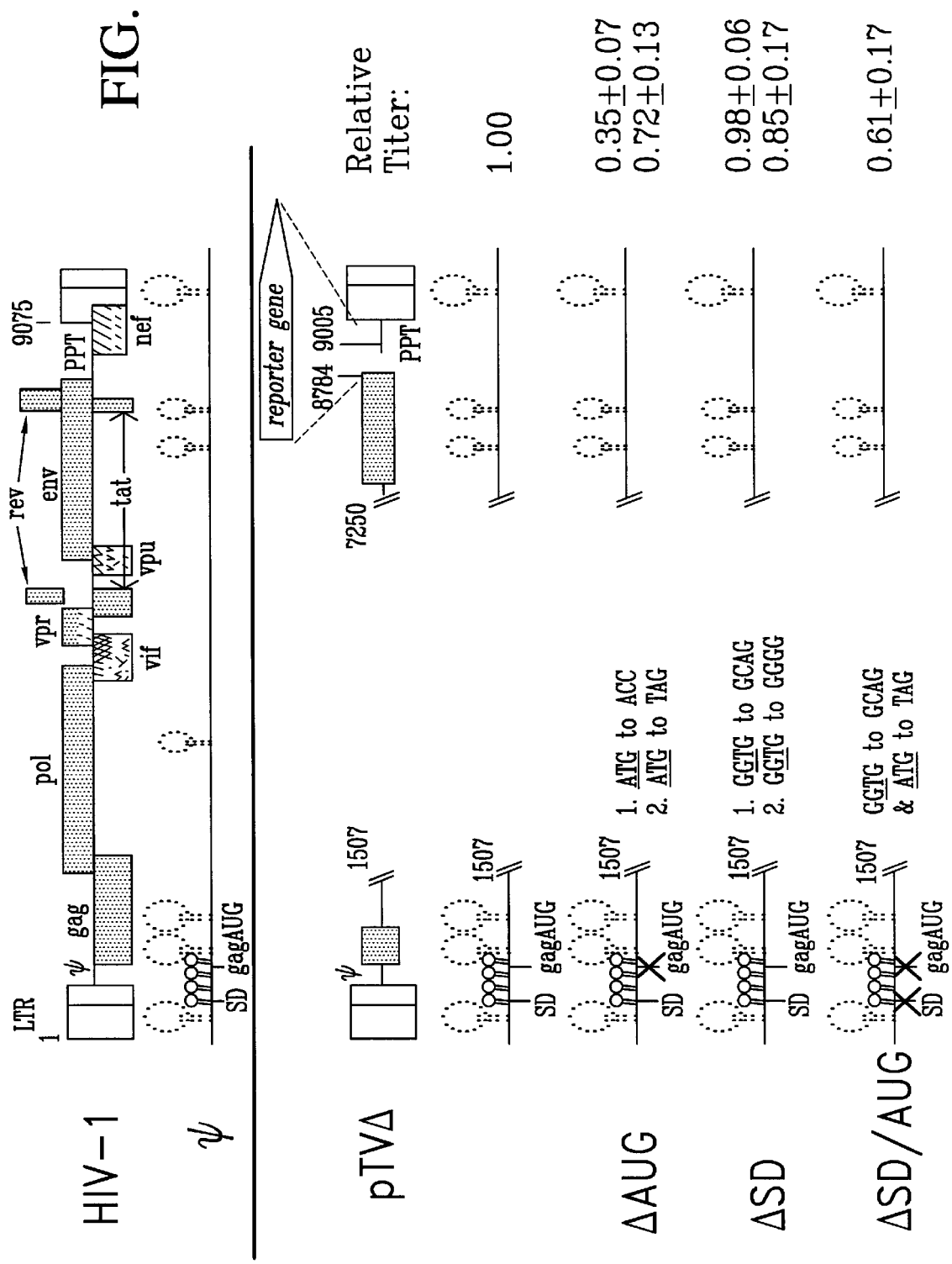

HeLa cells were transfected with plasmid DNA encoding HIV-1 Gag, Rev, Tat, HTLV Tax/Rex, SIV Tat, or HIV Tat exon 1 as indicated in FIG. 16. The results shown in FIG. 16, clearly demonstrate that Tat enhances p55 to p24 Gag processing. The effect of Tat on Gag processing is TAR-independent as GagTAR-construct which has TAR deletion is also sensitive to this Tat effect. This function of Tat resides in the exon 1 which can be partially restored by SIVTat and HTLV Tax/Rex.

5. Tat Enhances Gag Processing From the pHP-VSV-G Packaging Construct

TE671 cells were transfected with plasmids as described above. Cell lysates were harvested 24 hours after DNA removal and analyzed by SDS-PAGE and Western blotting as described using anti-p24 MAb. The result indicated that Gag processing is enhanced by the presence of Tat (See, lane 2 vs. lane 3, and lane 5 vs. lane 6 in FIG. 16).

Example 4

Generation of an Inducible Packaging Cell Line

In this Example, an inducible packaging cell line was generated using the pHP-VSVG, and its derivative construct. First, pHP-VSVG was linearized and transfected into human TE671 cells by electroporation, together with a selective marker. After selection, individual cell clones were tested for Gag-Pol expression by direct extracellular RT assay in the presence or absence of a transfected tat plasmid. The expression of VSV-G protein was detected by immunohistochemical staining.

Briefly, the pHP-VSVG linearized by digestion with NotI, and transfected into the TE671 cells along with pSV2-neo (i.e., with G-418 as the selectable marker). Transfection was accomplished by electroporation, using methods known in the art. Transfected cells were grown in 1 mg/ml of G418 culture in DMEM containing 10% FBS. The induced gag-pol Gag-Pol expression was then determined by direct extracellular RT assays with and without transfected tat plasmid. HIV-1 Gag and RT expression were detected by p24 antigen ELISA or RT (See, co-pending U.S. patent application. Ser. Nos. 08/791,994 and 08/838,702; See also, L. J. Chang and C. Zhang, Virol., 211:157–169 [1995]; and L. J. Chang et al., J Virol., 67:743–752 [1993]).

The expression of Gag-Pol in this inducible cell line still requires Tat function. To make a user-friendly packaging cell line, vpr and tat genes can also be expressed by an inducible promoter. The vpr gene is included because of its function in promoting transduction of nondividing cells. Vpr is a virion-associated protein, and the vpr gene is therefore assigned to the packaging vector so that equivalents of Vpr, like those of Gag, Pol and Env, are produced only in the packaging cell line. A tetracycline-inducible expression vector (a TET-OFF system, suppression of expression in the presence of tetracycline or doxycycline) has been chosen for this purpose. An inducible tat-vpr expression vector has been constructed into the pcDNA3.1/Zeo plasmid with genes arranged in the following order-tetOP-tat-IRES-vpr-IRES-tetR.VP16-SVpA-(inverted tk-zeo-pA). Preliminary studies of this construct showed co-expression of Tat and Vpr in the absence of tetracycline or doxycycline, indicating that the two internal ribosomal entry site (IRES) are functional. However, even in the presence of tetracycline or doxycycline, this inducible construct still expresses Tat function, indicating a leaky expression of the tetR.VP16. As a result, this construct was only used for coexpression of Tat and Vpr in the co-transfection experiments.

A second construct, -tetOP-tat-P2-vpr-SVpA-(inverted tk-zeo-pA), which is up-regulated by a separate tetR.VP16 expression plasmid, has been constructed and used to generate an inducible cell line. tetOP-tat-P2-vpr-P2-tetR-VP16-SVpA-(inverted tk-zeo-pA) is a clone that expresses HIV-1 Tat and Vpr and the tet tTA operon inducer tetR-VP16 which was made by ligation of the following fragments: tetop, HIV-1 Tat, internal ribosomal entry site (IRES) P2, HIV-1 Vpr, IRES P2, tetR-VP16, and the vector pREP9 with EBNA1 gene sequence deleted. The two tTA plasmids were obtainable from Display Systems Biotechnology, Inc. (now distributed by Clontech). This clone is auto-inducible by the removal of tetracycline or doxycycline (2–10 microgram/ ml) from the culture media (a Tet-OFF system) (See, M. Gossen and H. Bujard, Proc. Natl. Acad. Sci. USA. 89:5547–5551 [1992]).

As these plasmids use different selective markers (neo, zeo, and hyg) it was possible to co-select them in the same cell. However, a large number of cell clones had to be screened before a stable inducible packaging cell line could be established.

Example 5

Internal CMV-IE in pTVΔCMVnlacZ Promoter Exhibits Higher Promoter Activity Than Native CMV-IE In this Example, the expression of the reporter lacZ gene from the pTV-ΔCMVnlacZ was compared with pcDNAn-lacZ (i.e., CMV-IE promoter-driven), 48 hours after transfection of TE671 cells. TE671 cells were transfected with 5 μg of pcDNA3-nlacZ or pTVΔCMVnlacZ, as described above. Following transfection and growth, cells were fixed and stained for β-galactosidase actvity, as described below.

The beta-galactosidase activity was detected by the following protocol as published by Kimpton and Emerman (J. Kimpton and M. Emerman, J Virol., 66:2232–2239 [1992]). Briefly, cells were fixed in culture plate at room temperature, with 1% formaldehyde (1.33 ml of 37.6% for final 50 ml) and −0.2% glutaraldehyde (0.4 ml of 25% for final 50 ml) in PBS for 5 minutes. The cells were then washed three times with PBS, and incubated with 500 μl ddH$_2$O containing 4 mM potassium ferrocyanide (100 μl of 0.4 M for final 10 ml), 4 mM potassium ferricyanide (100 μl of 0.4 M), 2 mM MgCl$_2$ (20 μl of 1 M), 0.4 mg/ml X-Gal (200 μl of 2Omg/ml) at 37° C. for 50 minutes to several hours. The blue-staining (i.e., β-galactosidase positive) cells were counted under an inverted microscope. These results indicated greater expression by the pTVΔCMVnlacZ vector, as compared with the pcDNA3-nlacZ. Table 2 shows the results, with more "+" indicating the presence of a relatively greater number of blue-staining cells.

TABLE 2

| β-Galactosidase Activity | |
|---|---|
| Plasmid | Cells Stained (Blue) |
| Mock | − |
| pcDNAnlacZ | + + |
| pTVΔCMVnlacZ | + + + |

Example 6

Production Efficiency of Transducing Vectors

Example 6A

Production Efficiency of VSV-G Pseudotyped Vectors

In this Example, TE671 cells were transfected with certain packaging and transducing vectors, as identified in the table below.

In this experiment, VSV-G pseudotyped vectors were produced and the target cells were CD4-minus human cell lines. pHP-VSVG was co-transfected with a pTVΔ plasmid and a tat plasmid (pCEP4tat) into TE671 cells. Culture supernatant was harvested 48 hours later. Tat was included to transactivate both pHP-VSVG and pTVΔ. The production of virus was confirmed by RT assay, and expression of HIV-1 p24 and VSV-G was confirmed by immunohistochemical staining. Virus produced from the transfected cells were harvested without further concentration, and used to infect TE671 cells. After selection with either G418 or hygromycin for 7–10 days, cell colonies were counted under an inverted microscope. The VSV-G pseudotyped pTVΔSVneo and pTVΔSVhyg both produced transducing titers up to $10^3$/ml without further concentration. This titer was increased to $10^5$/ml without concentration, when pHP-dl.2 or pHP-dl.28 were co-transfected with pHEP-VSV-G. This result indicated that pHP-VSVG does not function efficiently.

Culture supernatants were harvested 24 hours after removal of transfection solution. HIV RT activity was detected by an in vitro RT assay and vector titers were determined by transduction and beta-galactosidase assay of TE671 cells 48 hours later.

TE671 cells were also transfected (as described above) with the packaging vector pHP-1 or an env-deletion mutant pHP-1dl.2, and compared to the wild-type HIV-1 molecular clone pNL4-3 for their packaging efficiencies. Culture supernatants were collected for RT assay and for vector titering after 48 hours. The vectors were pseudotyped with the VSV-G envelope and titered on TE671 cells. X-gal stained blue cells were counted after 48 hours.

TABLE 3

Production of High-Titer HIV-1 Derived Vectors

| Packaging Construct | Pseudo-typed Envelope | Transducing Vector | Additional Genes | RT (cpm/μl) | Titer (cfu/ml) |
|---|---|---|---|---|---|
| pNL4-3 | pHEF-VSVG | pTVΔCMV nlacZ | | $1.1 \times 10^5$ | $7.9 \times 10^4$ |
| pNL-4-3 | pHEF-VSVG | pTVψCMV-nlacZ-hyg-dl.SmaI | | $7.9 \times 10^4$ | 24 |
| pHP-1 | pHEF-VSVG | pTVΔCMV nlacZ | pCEP-tat | $3.7 \times 10^4$ | $2.5 \times 10^5$ |
| pHP-1 | pHEF-VSVG | pTVψCMV-nlacZ-hyg-dl.SmaI | pCEP-tat | $3.1 \times 10^4$ | 100 |
| pHP-2dl.2 | pHEF-VSVG | pTVΔCMV nlacZ | pCEP-tat | $3.9 \times 10^4$ | $1.7 \times 10^5$ |
| pHP-1dl.2 | pHEF-VSVG | pTVψCMV-nlacZ-hyg-dl.SmaI | pCEP-tat | $3.6 \times 10^4$ | 90 |

These results indicated that pHP-1 or pHP-1dl.2 could produce HIV proteins at near the wild-type levels. In addition, both pHP constructs produced higher vector titers than did the wild-type $HIV_{NL4-3}$, suggesting that the wild-type HIV-1 genome might have interfered with the transducing vector genome for packaging. Also, the presence of additional Tat appears to enhance the vector production. This experiment also showed that the pTVψ vector was poorly packaged and need further modifications. TE671 cells transduced with the VSV-G pseudotyped pTVΔCMV-nlacZ vector stained strongly by X-gal and exhibited nuclear β-galactosidase activity. The pTVΔCMV-nlacZ-hyg and pTVΔCMV-GFP did not express the reporter genes efficiently, whereas pTVΔCMV-nlacZ did. These transducing vectors were further characterized using dividing and nondividing tissue culture models and a small animal model.

Example 6C
Production efficiency of Second Generation Constructs

Comparison of vector titer of different pHP packaging constructs using pTVdeltaCMVnlacZ or pTVdeltaEFnlacZ as transducing reporter gene:

Methods: TE671 cells were co-transfected with pHP construct (8 microgram per well in a 6-well plate), pTV construct (8 microgram per well), PHEFVSV-G (5 microgram per well as envelope pseudotype) with a tat expression plasmid pCEP-tat (0.5–1 microgram) and a rev expression plasmid pCMV-rev (0.5–1 microgram). The tat and rev expression plasmids were included because we have shown that they could enhance the vector titers for most of the pHP constructs and they were necessary for pHP-dl.NdeI which has a tat and rev deletion and for pHP-VSVG which has a tat deletion.

We have shown that the original construct pHP-dl.28 (a G1 construct) expressed RT at 50–90% of the wild type level indicating that the mutations in pHP-dl. did not affect the synthesis and function of Gag-Pol. The relative titers of different pHP mutants are shown below: (all included a co-transfected pTV reporter transgene)

pHP-dl.28 (env, nef deletion, relative titer: 1.00);
pNL4-3 (wild type HIV-1 control which in fact produce less vector than pHP-dl.28, relative titer: 0.40);
pHP-VSVG (vpr, tat, env and nef deletion, relative titer: 0.014); pHP-dl.env/vpu I (vpu, env, nef deletion, relative titer: 0.43); pHP-dl.env/vpu II (vpu, env, nef deletion, relative titer: 0.38); pHP-dl.vpr (vpr, env, nef deletion, relative titer: 0.85); pHP-vpr/ala/leu (vpr functional mutation, env, nef deletion, relative titer: 0.85);
pHP-vpr/env/vpu I (vpr functional mutation and vpu, env, nef deletion, relative titer: 0.24);
pHP-vpr/env/vpu II (vpr functional mutation and vpu, env, nef deletion, relative titer: 0.50)
pHP-dl.NdeI (vif, vpr, tat, rev, vpu, env, and nef deletion, relative titer: 0.006).

Thus, as more and more of the essential genes were deleted, such as tat and rev, and seqeunces such as major splice acceptor sites SA4 at nt. 5390, SA5 at nt. 5777, SA6 at nt. 5960, and SA7 at nt. 5976 and the 5' of env coding sequence, the vector efficiency gradually or drastically decreased. Nevertheless, the date showed that the second generation pHP construct such as pHP-vpr/env/vpu II can be made with relative titer still at 50% level of the pHP-dl.28 and this is about the same efficiency as using a wild type HIV-1 as the packaging vector (pNL4-3 titer=40% of pHP-dl.28).

In theory, a G2 pHP construct should contain only gag-pol open reading frames and the RRE regulatory sequences such as the pHP-CMV, pHP-CMVdel.TAR/SD, pHP-CMVEFla-intron, or pHP-EF constructs (although the vif gene is still present in all of them). However, these constructs exhibited reduced levels of gag-pol activity as shown by the following summary table:
methods: TE671 cells were transfected with 5 microgram of each test HP plasmid and 0.5 microgram of pCEPtat (except for one construct, pHP-CMVEF1a-intron, we tested both with and without Tat) and 1 microgram of pCMVrev. The culture supernatant was harvested and p24 level was determined by ELISA as described before.

(The relative level of p24 shown with pHP-dl.28 set at 1.00)
pHP-1 (1.00)
pHP-dl.28 (1.00)
pHP-VSVG (0.008)
pHP-dl.vpr (0.34)
pHP-dl.env/vpu I (0.43)
pHP-dl.env/vpu II (1.41)
pHP-dl.NdeI (0.007)
pHP-CMV (0.05)

pHP-CMVdel. TAR/SD (0.03)
pHP-CMVEF1a-intron (0.21, with Tat))
pHP-CMVEF1a-intron (0.04, without Tat)
pHP-EF (0.27)

It was thus shown that deleting TAR in the 5' LTR as seen in pHP-CMVEF1a-intron did not make the pHP construct Tat-independent, suggesting that Tat has alternative effects on gag-pol expression besides promotor transactivation via TAR. In addition, the EF1a enhancer promoter and intron construct exhibited the highest level of p24 expression suggesting that the EF-1a promoter is a better choice than the CMV promoter in later pHP modifications.

Example 7

Production of RC-HIV

In order to determine whether an RC-HIV recombinant could be generated, the transfected human TE671 cells (ATCC CRL 8805) were co-cultured with the human lymphoma cell line MT4. MT4 cells are an HTLV-1 transformed human CD4+ lymphoma cell line, that are very sensitive to HIV-1 infection. These cells are available from the National Institutes of Health AIDS Reagents and Reference Program. Uninfected MT4 cells were added into the co-culture every week during these experiments.

In this Example, it was found that the pHP1 packaging construct, but not the env-deleted constructs pHP-1dl.2 (2 nt deletion) and pHP-1dl.28 28 nt deletion), produced replication-competent HIV-1 (RCV) after co-transfection with pTV plasmid. Infectious virus was detected from pHP+pTVΔCMVnlacZ MT4 co-culture in 8 days. In addition, no infectious virus was detected from pHP.dl.2 or pHP.dl.28+pTVΔCMVnlacZ MT4 co-culture in 60 days (See, Table 4, below).

TE671 cells were co-transfected with pHP+pTV+pHEF-VSV-G as shown in the Table below (Table 4), and the culture supernatants were harvested 48 hours after DNA removal for RT assay and vector titer was determined as described before. To detect RCV, the transfected cells were co-cultured with the human MT-4 lymphoblastoid cell line, which is very sensitive to HIV-1 infection, for up to 2 months. The culture supernatants were harvested at different time points after co-culture. To detect replication-competent HIV-1 (RCV), the supernatant from the co-culture was assayed for HIV-1 RT activity and for infectious RCV by passage onto CD4+HeLa cells or uninfected MT4 culture. Infection of CD4+HeLa cells was examined by anti-p24 immunohistochemical staining using pooled AIDS patients' sera, and infection of MT4 cells by cytopathic effects of RCV and the RT production. A very sensitive assay which would detect cell-cell transmission of poor replicative virus was also used. After four months of co-culture, the MT4 cells were removed and added to fresh MT4 cells and further cultured for 4 days. The co-cultured MT4 cells were fixed and immunostained with HIV patients' sera. The results showed that both pHP-1dl.2 and pHP-1dl.28 were incapable of producing RC-HIV. In sum, these results indicated that pHP-1 transfected cultures produced replication-competent HIV-l after 8 days of co-culture. However, no RCV was detected after a 60-day co-culture for either pHP-1dl.2 or pHP-1dl.28 cotransfection. The vector titers produced by pHP-1dl.2 and pHP-1dl.28 were as high as that produced by pHP-1. The 28 nt deletion vector pHP-1dl.28 was shown to be as efficient as pHP-1, and did not produce RCV, based on the sensitive HIV infection assay. Thus, the deletion does not affect vector production efficiency and the env-deleted pHP constructs are safe for vector production without generating RCV.

Figure 12:
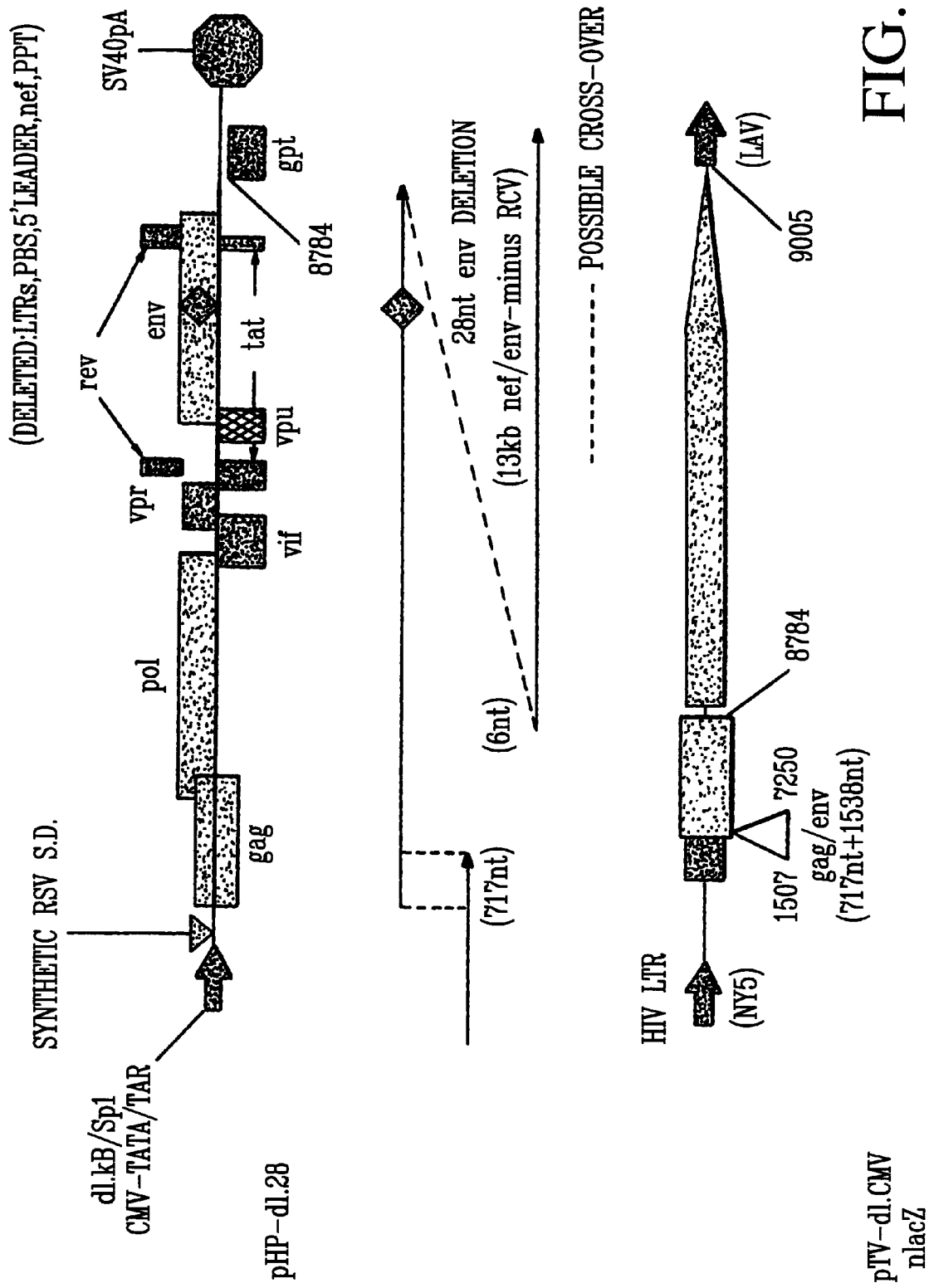
FIG. 12 illustrates the possible cross-over to generate RCV from co-transfection of pHP-dl.28 and pTV-dl.CMVnlacZ.

FIG. 12 illustrates the possible cross-over between pHP-dl.28 and pTV-dl.CMVnlacZ, to generate RCV during co-transfection. These results clearly indicate that the recombinants are not infectious, due to the deletion in env and the LTR mutation, and requires two homologous recombination events.

TABLE 4

Detection of Replication-Competent HIV (RCV)

| Packaging Construct | Pseudotyped Envelope | Transducing Vector | Additional Genes | Days After Co-Culture 8 | 28 | 60# |
|---|---|---|---|---|---|---|
| pNL4-3 (Control) | pHEF-VSVG | pTVΔCMV-nlacZ | | +++ + | +* | +++ |
| pHP-1 | pHEF-VSVG | pTVΔCMV-nlacZ | pCEP-tat | ++ | +++ | +++ |
| pHP-1dl.2 | pHEF-VSVG | pTVΔCMV-nlacZ | PCEP-tat | – | – | – |
| pHP-1dl.28 | pHEF-VSVG | PTVΔCMV-nlacZ | pCEP-tat | – | – | – |

*Results of rapid cell death and loss of MT4 cells.
'+ to ++++', approximately 10 to 40% of the reporter CD4-HeLa cells were HIV-positive after infection using 1 ml of supernatant.
The MT4 cells in the TE671/MT4 co-culture were transferred into a fresh MT4 culture on day 46 after co-culture; 12 days later, the MT4 cells were directly immunostained with HIV patients' sera.
'–', no infectious virus was detected.

Example 8

Transduction of Target Cells

Example 8A

In Vitro Transduction of Mitomycin-C-Treated Human Cells

In this Example, two cell cultures were transduced with HP-TV and observed for its transduction efficiency. TE671 or HeLa cells were treated with the DNA synthesis inhibitor, mitomycin C, at 10 µg/ml for 4 hours, trypsinized and plated into a 6-well culture plate. The cells were transduced with HP-TV HIV vector carrying a nlacZ marker gene in the presence of 4–8 µg/ml polybrene in a total volume of 0.5 ml for 2–3 hours and fed with growth media (DMEM containing 10% FBS). After 48 hours, the expression of the transduced lacZ gene was detected by X-gal staining as described above. The results indicated that the HP-TV vector was capable of efficiently transducing mitomycin-C-treated, non-dividing human cells.

The HP/TV lentiviral vectors transduce cells with different efficiencies depending on the cell cycle stage at the time of transduction. To demonstrate this, TE671 was treated with 5 microgram/ml of mitomycin C in DMEM growth media for 2.5 hr and the treated cells were transduced with the pTVdeltaEFnlacZ vector and 48 h later, the transduction efficiency was determined by x-gal staini assay. The result demonstrated that cells were most efficiently transduced at 24–48 hr after mitomycin C treatment, at which time, the cells were arrested at S or G2/M phases. At later stage, when cells entered high chromosomal content (>4N) stage the transduction efficiency became reduced. This result suggests that although HP/TV lentiiral vector transduces post-mitotic cells, the efficiency of gene transduction is still dependent on the cell cycle stage.

Example 8B

In Vitro Transduction of Primary Neuronal Cells

In this Example, rat neuronal cells were isolated from the brains of Fisher rats according to the method of Ure et al.

(Ure et al., Develop. Biol., 154:388–395 [1992]). The cells were grown in culture medim containing L15CO$_2$ (GIBCO, Grand Island, N.Y.), containing 200 ng/ml 2.5 S nerve growth factor (NGF), 2.55 rat serum, 1 mg/ml ascorbic acid, and 10 µM cytosine arabinose (Sigma), to inhibit divisions of non-neuronal cells.

In addition to rat neuronal cells, human neurons and astrocytes were obtained from differentiated embryonal neural stem cells provided by Neurospheres, Ltd (Calgary, Alberta, Canada). These cells were infected with the HP-TV vectors carrying the nlacz reporter gene as described above. Briefly, cells were incubated in culture media containing the HP-TV vector. After two hours of incubation, conditioned media (i.e., supernatant medium harvested from cultured neuronal cells after 24 hours of culture) were added, and the culture continued to incubate for five days. The cells were then fixed with formaldehyde and glutaraldehyde, and incubated with X-gal substrate as described in the β-galactosidase assay described above. The results indicated that the HP-TV vector efficiently transduces primary neuronal cells obtained from rat brains, and human neuronal stem cells (neurons and astrocytes).

Example 8C
In Vivo Transduction of Muscle Cells

In this Example, the HP-TV HIV vector was used to transduce muscle cell in vivo. The hind-legs of mice CB-17 SCID/beige mice (Taconic) were intramuscularly injected with 50–100 µl of vectors carrying the nlacZ reporter gene as unconcentrated ($10^5$/ml) or microcentrifuge concentrated ($30\times10^5$/ml) stocks in the presence of 4 µg/ml of polybrene. The mice were sacrificed two days later and the injected tissue was prepared for frozen section and for β-galactosidase analysis. The results showed that HP-TV vector transduced muscle cells efficiently in vivo. In particular, tissues exposed to the concentrated vector stock were transduced at near 100% efficiency at the site of injection. It was also noticed that microcentrifuge concentration increased the infectious virus titer, but not in proportion to the fold of concentration.

Example 8D
HIV Vectors are More Efficent than MLV Vectors

In this Example, HIV vectors were compared with the standard MLV vectors commonly in use. The results obtained in these experiments indicated that HIV vector is more efficient than the MLV vector. In this example, a MLV-derived vector (MFGnlacZ, obtainable from Dr. Richard Mulligan) and the HIV-1 derived pHP-1dl.28+ pTVΔCMVnlacZ vectors were involved in a long term transduction and gene expression study. Three different human cells lines (TE671, 293, and HepG2) were used in these experiments. The cells were transduced as described, three times in three days using virus stocks prepared from vector producing cells (transfection of PA317 for MFGnlacZ, approximately $10^5$ cfu/ml and transfection of 293 for HIV-1 vector, approximate $10^5$ cfu/ml). The cells were transduced three times and propagated once before staining for beta-galactosidase expression.

Briefly, the transduced cells were grown for 3 days and trypsinized, the number of cells was determined, the cells were then plated into 6-well culture plates and one day later, the cells were stained for beta-galactosidase activity. The number of blue cells were counted and the percentages of blue cell in the wells were determined under an inverted microscope. The results suggest that the HIV-1 derived vectors can transduce all three cell types at higher efficiencies than the MLV vector, at ranges from 3 to 10 folds. These cells were also passaged for 48 days, and stained for β-galactosidase activity again. The results showed that in the long term culture, the HP+TV HIV vectors exhibited gene expression stability.

Table 5 below, shows a direct comparison of the transduction efficiencies observed at 48 hours and 48 days. As previously mentioned, TE671 are rhabdomyosarcoma cells, 293 are kidney cells, and HepG2 are hepatoma cells. In this table, the numbers indicate the percent of cells transduced after one passage or multiple passages (for the 48 hour samples, the cells were transduced three times and propagated once, before staining for β-galactosidase activity as previously described in Example 6.

TABLE 5

5. Comparison of Long-Term Transduction Efficiencies

| Cell Lines | Transduction Efficiencies of MLV vs. HIV nlacZ Vectors | | | |
|---|---|---|---|---|
| | 48 Hours | | 48 Days | |
| | MLV | HIV | MLV | HIV |
| HepG2 | 3 ± 2 | 29 ± 7 | 15 ± 0.2 | 27 ± 4 |
| TE671 | 20 ± 4 | 60 ± 2 | 12 ± 2 | 45 ± 2 |
| 293T | 7 ± 0.1 | 46 ± 2 | 1.2 ± 0.2 | 13 ± 3 |

Example 8E
Gene transduction into CD34+ human hematopoietic procursor cells

Gene transfer into the human hematopoietic stem cells (HSCs) has encountered with problems of vector transduction efficiency and long term expression stability. See Barranger JA. Hematopoietic stem cell gene transfer. Gene Therapy 1996; 3:379–380; Brenner MK. Gene transfer to hematopoietic cells. N. Engl. J. Med. 1996; 335:337–339. Amphotropic MLV vectors transduce mouse HSCs quite efficiently but human HSCs poorly due to the low level of cell surface MLV-env receptor expression; see Orlic D, Girard L J, Jordan C T, Anderson S M, Cline A P, Bodine D M., The level of mRNA encoding the amphotropic retrovirus receptor in mouse and human hematopoietic stem cells is low and correlates with the efficiency of retrovirus transduction. Proc. Natl. Acad. Sci. USA 1996; 93:11097–11102; Sabatino DE, Do BQ, Pyle LC, et al. Amphotropic or gibbon ape leukemia virus retrovirus binding and transduction correlates with the level of receptor mRNA in human hematopoietic cell lines, Blood Cells Mol Dis 1997; 23:422–33; and possible cis-repressive elements in the MLV LTRs.Challita P M, Skelton D, El-Khoueiry A, Yu X J, Weinberg K, Kohn D B, Multiple modifications in cis elements of the long terminal repeat of retroviral vectors lead to increased expression and decreased DNA methylation in embryonic carcinoma cells. J Virol 1995; 69:748–755. In particular, transduction of HSCs in clinical trials has been very difficult. See Dunbar CE. Gene transfer to hematopoietic stem cells: implications for gene therapy of human disease. Annu Rev Med 1996; 47:11–20. Adeno-associated virus vector has been demonstrated capable of transducing hematopoeitic stem cell-derived erythroid cells but only works at extremely high titer. See Nienhuis A W, Bertran J, Hargrove P, Vanin E, Yang Y. Gene transfer into hematopoietic cells. Stem Cells 1997; 1:123–34. To overcome the problem with low amphotropic MLV env receptor on CD34 cells, infectious HIV-1 constructs have been pseudotyped with vesicular stomatitis G envelope proteins (VSV-G) and shown to infect CD34 cells quite efficiently. See Akkina R, Walton R M, Chen M L, Li Q-X, Planelles V, Chen ISY. High-efficiency gene transfer into CD34+ cells with a human immunodeficiency virus type-1-based retroviral vector pseudotyped with vesicular stomatitis virus envelope glycoprotein G. J. Virol. 1996; 70:2581–2585. However, for obious safety reasons, such replication-competent HIV-1 constructs would never be used in gene therapy application.

The HP/TV vector efficiently transduces actively dividing human cell lines including TE671 (rhabdomyosarcoma), 293T (kidney carcinoma) HepG2 (hepatoma), and HeLa (cervical carcinoma) cells. Non-dividing and terminally differentiated cells such as mitomycin C-treated TE671 or HeLa cells, neruons, monocyte-derived macrophages and muscles can also be efficiently transduced by the HP/TV vectors. In contrast, transduction of metabolically quiescent human peripheral blood lymphocytes or bone marrow mobilized blood CD34 stem cells with lentiviral vectors have not been reported, and in our experience, transduction of these cells with viral vectors including AAV, retroviral vectors or lentiviral vectors is extremely inefficient, probably because in the absence of growth factor activation these cells have very low metabolic enzyme and transcriptional activities, and accordingly, viral integration and gene expression do not proceed efficiently.

Nevertheless, we have demonstrated transduction of human CD34 derived hematopoietic precursor cells with the HP/TV vectors carrying either nuclear lacZ or green fluorescent protein (GFP) reporter gene. This has been demonstrated using pTV vector containing human elongation factor 1a (EF1a) promoter as an internal promoter possibly because EF1a promoter has very high transcriptional activity even in quiescent human hematopoietic precursor cells.

To demonstrate transduction of HSC-derived precursor cells, human peripheral blood lymphocytes (PBLs) were collected from patients treated with G-CSF (granulocyte-colony stimulating factor) to mobolize bone marrow stem cells and purified through an anti-CD34 antibody affinity column. The collected C34+ cells were washed 2–3 times with RPMI medium containing 10% fetal bovine serum without-growth factor supplements, centrifuged at 800 g for 5 min, and resuspended in the same growth medium at 1×105 cells/100 microliter.

To prepare HP/TV vectors, TE671 cells were transfected with pHP-1dl.28 (8 microgram/well), pTVdl.EFnlacZ or pTVdl.EFGFP (8 microgram/well), pHEF-VSVG (5 microgram/well) and pCEP-tat (0.2 microgram/well) plasmid DNA in a 6-well culture plate, and 48 hr after DNA was added, culture supernatant was collected and centrifuged at 1000 g for 5 min. The clear supernatant was stored at −80° C. for future use. The human CD34 cells were transduced 2–3 times with TV vectors at a multiplicity of infection (MOI) of 10, i.e. approximately 10E5 cells were transduced with 10E6 infectious units (iu) of pTV vectors in a final volume of 100 ul in DMEM or RPMI growth medium supplemented with 8 microgram/ml of polybrene for 3–4 h each time. The 10E6 iu of pTV vectors were prepared from two ml of vector stocks containing 5×105 iu/ml which can be concentrated 30–40 fold in a microfuge spun at 20,800 g at room temperature for 90–120 min. The transduced CD34 cells could be maintained in RPMI supplemented with growth factors for 1–4 days before they were plated into semi-solid methylcellulose colony assay media. The plated hematopoietic precursor cells grew and formed colonies in 3–4 weeks and the expression of transduced nlacz and GFP genes were assayed by x-gal colorimetric staining and observed under an inverted fluorescent microscope.

For the x-gal staining, the reaction substrate was prepared in phosphate buffered saline adjusted to pH 8.5 using 150 mM Tris containing 4 mM K-ferrocyanide, 4 mM K-ferricyanide, 2 mM MgCl2, 0.8 mg/ml X-Gal. One ml of the x-gal substrate was added to each 30 mm dish containing HSC-derived colonies and the dish was incubated at 37 deg. C. in a 5% CO2 incubator for 24–72 hr. The total colonies and the dark blue-stained colonies were counted under an inverted microscope. The GFP expression was observed directly under an inverted fluorescent microscope. The expression efficiency of transduction was determined to be less than 1% at 3–4 weeks after CD34 cells were plated. However, after 5–6 weeks, the efficiency of expression of the transgene (e.g. GFP gene) increased to more than 20%. To determine the efficiency of transduction of the CD34 cells by the pTV vector, the colonies formed in methylcellulose agar were individually picked up and the genomic DNA extracted and subjected to polymerase chain reaction (PCR) using primers specific to the pTV vector. We found twenty out of the twenty colonies picked were positive for pTV sequence suggesting that the transduction efficiency had been near 100%. This study suggests that the CD34 cells can be efficiently transduced by the VSV-G pseudotyped HP/TV vectors but gene expression is delayed and the level of expression is very low which must also depend on the promoter used in the vectors.

Example 9

An innovative Short-term Stromal-type HP/TV Producer Cells (SSPC)—a Novel Protocol for Efficient HSC Transduction with HP/TV Vectors Retroviral vectors transduce HSCs poorly due to reasons including low number of receptors on HSCS, low vector titers, and possible blocks to reverse transcription after entry, see Sinclair A M, Agrawal Y P, Elbar E, Agrawal R, Ho A D, Levine F. Interaction of vesicular stomatitis virus-G pseudotyped retrovirus with CD34(+) and CD34(+)CD38(−) hematopoietic progenitor cells. Gene Therapy 1997; 4:918–927. Protocols to improve transduction efficiency have been developed for retroviral gene transfer into HSCs, for examples, coating culture plates with fibronectin fragment FN30/35, see Moritz T, Dutt P, Xiao X, et al. Fibronectin improves transduction of reconstituting hematopoietic stem cells by retroviral vectors: evidence of direct viral binding to chymotryptic carboxy-terminal fragments. Blood 1996; 88:855–862, or adding a pretreatment step using medium containing 5 ng/ml of anti-TGF-beta for 10–20 h, see Hatzfeld A, Batard P, Panterne B, Taieb F, Hatzfeld J. Increased stable retroviral gene transfer in early hematopoietic progenitors released from quiescence. Human Gene Therapy 1996; 7:207–213., and applying centrifugal force during infection to increases the reversible binding of virus to the cells, see Bahnson A B, Dunigan J T, Baysal B E, et al. Centrifugal enhancement of retroviral mediated gene transfer. J Virol Methods 1995; 54:131–43. These protocols may or may not improve the poor transduction efficiencies of lentiviral vectors on HSCs as we showed in the preliminary studies. Co-culturing target cells with retroviral producer cells has been shown to improve retroviral transduction efficiency. To improve the efficiency of transducing HSCs with lentiviral vectors, a modified protocol is proposed which combines the growth factor stimulation step with the lentiviral producer cell co-culture step. This protocol will also eliminate the vector concentration step which involves the use of a ultracentrifuge. The cells used for lentiviral production, TE671, can be modified to express human IL-3, SCF, and flt3 ligand via cDNA co-transfection for the purpose of supporting long term culture and transduction of CD34+/CD38− HSCs. Alternatively, freshly prepared human stromal cells can be modified to become lentiviral vector producer cells by co-transfection using HP/TV vectors plus pHEF-VSV-G or pHEV-GALV-env (Gibbon ape leukemia virus) constructs.

Thus, TE671 (or other human cell line) transfectants expressing human IL-3, SCF, and flt3 ligand via transfection, or freshly prepared human stromal cells are co-transfected with HP/TV vector plus pHEF-VSV-G or PHEV-GALV-env (Gibbon ape leukemia virus) constructs and 24–48 hr later, or when the cells become 100% confluent, the transfected cells were treated with mitomycin C (5 microgram/ml) for 2.5 hr, washed and refed with RPMI growth media.

Human IL-3 cDNA was amplified using primers:
—TTTCTAGACCACCATGAGCCGCCTGCCCGTC-C—(SEQ ID NO:34) and
—AAGGATCCCTAAAAGATCGCGAGGCTC—(SEQ ID NO:35),
per Otsuka T, Miyajima A, Brown N, et al. Isolation and characterization of an expressible cDNA encoding human IL-3. Induction of IL-3 mRNA in human T cell clones. J. Immunol. 1988; 140:2288–2295.

Human SCF cDNA was amplified using primers:
—TTTCTAGACCACCATGAAGAAGACACAAACT-TG—(SEQ ID NO:36) and
—AAGGATCCTTACACTTCTTGAAACTC—(SEQ ID NO:37),
per Martin F H, et al., Primary structure and functional expression of rat and human stem cell factor DNAs. Cell 1990; 63:203–211.

Human flt3 ligand CDNA was amplified using primers:
—TTTCTAGACCACCATGACAGTGCTGGCGCCA-G—(SEQ ID NO:38) and
—AAGGATCCTCAGTGCTCCACAAGCAGC—(SEQ ID NO:39),
per Lyman S D, James L, Johnson L, et al. Cloning of the human homologue of the murine flt3 ligang: a growth factor for early hematopoietic progenitor cells. Blood 1994; 83:2795–2801.

Example 101

G2 Transducing Vectors

Towards construction of G2 pTV:

Gag AUG, SD, gag coding sequence, env coding sequence, RRE and gag/env/RRE deletion mutants: To see if the highly conserved packaging signal, i.e. sequences spanning the gag AUG and the 5' major splice donor, can be changed without affecting packaging function of pTV, the following mutants were constructed and tested for cytoplasmic RNA synthesis (exported from nucleus), and packaging function by virion RNA slot-blot assay, and transduction functions by vector titration.

A. Mutant construction:

All mutants were made by the megaprimer site-specific mutagenesis method described before or by direct DNA molecular cloning.

A-1: 5' splice site (SD at nt. 744) and Gag AUG (at nt. 790) mutations. The two gag AUG mutants and the two SD mutants were made using primers containing the mutation sequences as listed below:

1.pTVdeltaAUG1: —CTC TCG CAC CGG TCT CTC TCC TTC—(SEQ ID NO:40)

2.pTVdeltaAUG2: —CTC TCG CAC CCT ACT CTC TCC TTC—(SEQ ID NO:41)

3.pTVdeltaSD1: —GGC GGC GAC TGC AGA GTA CGC CAA—(SEQ ID NO:42)

4.pTVdeltaSD2: —GGC GGC GAC TGG GGA GTA CGC CAA—(SEQ ID NO:43)

A-2: Gag coding sequence mutations. pTV has a gag-pol-env deletion from nt. 1507–7250. The series of additional gag coding sequence mutants were made by site-specific mutagenesis using primers designed to delete specific lengths of gag coding region as shown in FIG. and described below:

1. pTVgag dl.1, deletion of 180 bp, from nt 7430–7611. using the following primer:
—CTC CAG GTC TGA AGA TCT TTG ACC CTT CAG TAC TC—

2. pTVgag dl.2, deletion of 361 bp, from nt 7250–7611. using the following primer:
—CTC CAG GTC TGA AGA TCT ACT AGT AGT TCC TGC TAT G—(SEQ ID NO:45)

3. pTVgag dl. 3 deletion of 591 bp, from nt. 1277–1507 and nt.7250–7611 using primer:
—CTC CAG GTC TGA AGA TCT GCC TTC TCT TCT ACT ACT—(SEQ ID NO:46)

4. pTVgag dl. 4 deletion of 824 bp, from nt. 1044–1507 and nt. 7250–7611 using primer:
—CTC CAG GTC TGA AGA TCT GAG GAC TGC TAT TGT ATT—(SEQ ID NO:47)

5. pTVgag dl. 5 deletion of 1039 bp, from nt. 829–1507 and 7250–7611 using primer:
—CTC CAG GTC TGA AGA TCT CTA ATT CTC CCC CGC TT—(SEQ ID NO:48)

A3. Env coding sequence and splice acceptor 8 (SA8 at nt. 8369) and SA9 (at nt. 8515) mutations. The series of env mutants, some of which contained splice acceptor site 8 & 9 deletion, were made by Bal3l deletion at the BamHI site at nt. 8465 and six deletion mutants were isolated and sequenced and their deletions were confirmed as follows:

1. pTVenv dl.1, BamHI 2'-12, from nt 8375–8559, between RRE and the CMV promoter but SA8 site (splice acceptor site 8 at nt. 8369) is intact.

2. pTVenv dl.2, BamHI 2'-6: from nt 8355–858659, between RRE and the CMV promoter.

3. pTVenv dl.3, BamHI 2'-8: from nt 8315–8586, between RRE and the CMV promoter.

4. pTVenv dl.4, BamHI 5'-3 from nt. 8160–8604, between RRE and the CMV promoter.

5. pTVenv dl.5, BamHI 5'-8 from nt. 8215–8730, between RRE and the CMV promoter.

6. pTVenv dl.6, BamHI 5'-10 from nt. 8214–8785, between RRE and the CMV promoter.

A. 4. RRE and RRE/gag/env deletion mutations. The RRE deletion mutant and the RRE/gag/env deletion mutant were constructed using the following methods and primers:

1. RRE deletion mutant, deletion pTVdl.RRE: a primer flanking both end of RRE with the following sequence was used to construct pTVdl.RRE. AACCCCAAATCCCCAT-TCCCACTGCTCTTTTT (SEQ ID NO:49). The first round PCR generated a 1.3 kbp product which was used as megaprimer to amplify a 2.3 kbp fragment which was digested with SphI and NotI sites for cloning into pTV vectors. The SphI-NotI 1350 bp was ligated with SphI and NotI-XbaI 4025 bp and XbaI-SphI 7332 bp of pTVΔnlacZ to generate the RRE deletion mutant.

2. RRE/gag/env deletion mutant, pTVdl.gag/env/RRE: This deletion starts from gag nt. 829 to env nt. 8785 which was constructed using three fragment ligation approach. The three fragments are: BssHII to BglII 125 bp of pTV gag dl.5 containing 5' leader-gag-env, BglII to XbaI 4016 bp from pTVDnlacZ, and XbaI to BssHII 6600 bp from pTVDnlacZ as plasmid backbone.

A. 5. Combination of SD1 (GGTG to GCAG)/gag AUG (AUG to TAG) or SD1/env coding sequence/SA deletion, or SD1/RRE/gag/env deletion mutations. To make generation 2 pTVs, deletion of more essential sequences such as the SD site coupled with gag AUG, or gag or env coding sequences in the pTV constructs will make the vector system even safer. Surprisingly, in some cases, the combination of mutations did not further decrease vector titer, instead, the combination of mutations increased vector titers (see below).

a). pTVdeltaSD1/AUG2: this mutant was made by site-specific mutagenesis using the existing AUG2 primer: —CTC TCG CAC CCT ACT CTC TCC TTC— (AUG to TAG) and using the pTVdeltaSD1 as backbone.

b). pTVdeltaSD1/env dl.6: this mutant was made by restriction enzyme digestion and isolation of DNA fragments containing either the SD1 mutation or the env dl.6 mutation and ligated with the pTVdeltaCMVnlacZ backbone.

c). pTVdeltaSD1/dl.gag/env/RRE: this mutant was made by megaprimer mutagenesis as described before using the SD1 primer: —GGC GGC GAC TGC AGA GTA CGC CAA— (SEQ ID NO:51) and a primer resided in the CMV-IE promoter downstream of the dl.gag/env/RRE region. The amplified fragment containing both SD1 mutation and the dl.gag/env/RRE sequence was ligated with two fragments obtained from pTVdeltaCMVnlacZ to generate pTVdeltaSD1/dl.gag/env/RRE.

Results and Discussion: The results of analyses of vector RNA, packaging function and vector titer are summarized in the table below:

(full-length/spliced RNAs; Virion RNA levels; relative titers)

Control pTVdeltaCMVnlacZ: (+++++/+++++; +++++; 1.00)
1. pTVdeltaAUG1: (++++/++++; ++; 0.35) translation void, steady-state RNA less than wt.
2. pTVdeltaAUG2: (++++/++++; ++; 0.72) translation void, stead-state RNA less than wt.
3. pTVdeltaSD1: (++/−; ++; 0.98) less RNA made and less detected in virions, but wt titer.
4. pTVdeltaSD2: (++/−; ++; 0.85) less RNA made and less detected in virions, but wt titer.
5. pTVgag dl.1: (+++++/+++++; ++++++; 1.08)
6. pTVgag dl.2: (+++++/+++++; +++++; 0.90)
7. pTVgag dl. 3: (+++++/+++++; +++++; 0.81)
8. pTVgag dl. 4: (+++++/+++++; +++++; 0.94)
9. pTVgag dl. 5: (+++++/+++++; +++++; 0.65)
10. pTVenv dl.1: (++/−; +++; 0.48) no spliced RNA.
11. pTVenv dl.2: (n.d.; n.d.; 0.65) no spliced RNA.
12. pTVenv dl.3: (++/−; +++; 0.47) no spliced RNA.
13. pTVenv dl.4: (++/−; +++; 0.60) no spliced RNA.
14. pTVenv dl.5: (n.d.; +++; 0.64) no spliced RNA.
15. pTVenv dl.6: (+++/−; +++; 0.44) more full-length RNA but less titer than other env dl.
16. pTVdl.RRE: (++/+++++;+; 0.10) detected 20% virion RNA but less titer.
17. pTVdl.gag/env/RRE: (++/−; +; 0.02) detected 20% virion RNA but much less titer.
18. pTVdeltaSD1/AUG2: (n.d.; ++; 0.61)
19. pTVdeltaSD1/env dl.6: (n.d.; +++++; 1.00)
20. pTVdeltaSD1/dl.gag/env/RRE: (n.d.; ++++; 0.30) detected 80% virion RNA but less titer.

footnote: +++++ represents 100% level with each "+" representing 20%, "−" representing undetected; n.d., not determined.

The results showed that:

1. Northern analyses of cytoplasmic RNA indicated that neither the gag AUG mutants nor the gag deletion mutants have much detrimental effects on mRNA synthesis and the transduction functional analysis showed, as determined by vector titration of vectors on TE671 cells, that one of the two gag AUG mutants (AUG2), and all of the gag coding sequence mutants exhibited no significant effects on vector titers (less than 50% reduction compared with original pTV vector). However, the gag AUG1 mutant pTVdeltaAUG1 showed more reduction one of the gag AUG mutants showed more detrimental effects on vector titer compared with wild type construct (35% of the wild type vector level).

2. Analyses Northern analyses of cytoplasmic polyA+ RNA indicated that the two SD mutants expressed less amount of the full-length vector RNA. However, the titration study showed that both SD mutants showed and the env deletion series have little to no significant effects on vector titers compared with wild type vector, suggesting that the two SD mutations either enhanced the RNA packaging function, or enhanced the efficiency of the transgene expression.

3. Northern analyses of cytoplasmic polyA+ RNA showed that the env conding sequence deletion mutations (SA mutations as well) have some minor effects (50%) on steady-state level of RNA synthesis which correlated well with the vector titer results. Therefore, this region of env and the SA sites are dispensable for vector construction. The env deletion series, all have the splice acceptor function deleted but maintained an intact SD site, exhibited less cytoplasmic mRNA and less virion RNA than wild type which correlated well with the titer data. Interestingly, the pTVenv dl.6 mutant exhibited more full-length RNA but less titer than other env dl. suggesting that a minot packaging signal may reside in the region between nt 8730 and nt 8785.

4. Northern analyses of cytoplasmic polyA+ RNA showed that the RRE mutant and the RRE/gag/env mutant were both were suppressed in full-length cytoplasmic RNA synthesis, suggesting that the deletedse sequences are necessary for RNA nuclear export. However, the titer study showed that the RRE/gag/env mutant is more defective than the RRE mutant although both the latter mutants expressed similar levels ofless full-length RNA in the cytoplasm, suggesting that the RRE/gag/pol sequence has additional functionseffects on vector packaging or transduction efficiency. Interestingly, the levels of virion RNA detected in the RRE mutants did not correlate with the titer reduction, suggesting that the RRE sequence has additional functions besides nuclear transport of the full-length RNA. This finding indicates that RRE is necessary not only for vector RNA export to the cytoplasm, but also for high vector transduction efficiency.

5. The observation that the internal CMV promoter activity was affected when the SD site was mutated suggesting that the splicing machinary has some effects on the internal enhancer/promoter function, possibly through interfering with transcriptional factor binding to the CMV-IE enhancer/promoter elements.

A.6., Construction of 3' U3 deletion mutants and assay for vector titer.

To generate U3 deletion in the vector system, both the 5' U3 and the 3' U3 will be deleted except for the att site in the 3' U3 region which is needed for provirus integration. The 5' U3 was deleted using the same CMV-TATA-HIV-TAR promoter as illustrated in the construction of pHP-1. The 3' U3 was deleted by megaprimer directed site-specific mutagenesis. We established 5 different deletion mutants as described below: a.pTVdl.kB/Sp1: this construct was made using a kB/Sp1 deleted HIV-1 construct as reported by Chang et al. 1993 (J. Virology) to replace the 3' LTR of pTVdeltaCMVnlacZ. The kB/Sp1 deleted HIV-1 construct was digested with KpnI (in the nef region of the genome, nt. 9005) and NgomI (NaeI, nt. 10349) and ligated with KpnI to NotI and NotI to NgomI fragments from pTVdeltaCMVnlacZ to generate pTVdl.kB/Sp1.

b. pTV-U3dl.1, pTV-U3dl.2, pTV-U3dl.3, and pTV-U3dl.4 were made by megaprimer mutagenesis to generate deletions from nt.9098–9528 (entire U3 deletion to the beginning of R except for the 5' 24 nt att site), nt.9154–9528 (the 5' sequence of U3 from 9098–9154 was retained), nt. 9098–9512 (the extended 5' TAR sequence in the U3 is retained), and nt. 9154 to 9512 (both 5' and 3' extra sequences in the U3 were retained). These mutants were made using the following primers:

primer U3dl.1:
—GTCTAACCAGAGAGACCCTGGGAGTGAAT-TAGCCCTTC—(SEQ ID NO:52)

primer U3dl.2:
—GTCTAACCAGAGAGACCCCAGGGAAGTAG-CCTTGTG—(SEQ ID NO:53)

primer U3dl.3:
—CCAGTACAGGCAAAAAGCTGGGAGTGAATT-AGCCCTTC— primer U3dl.4:
—CCAGTACAGGCAAAAAGCCAGGGAAGTAG-CCTTGTG—(SEQ ID NO:55)

and using a 5' primer annealed to the ECORI site of the nlacZ gene: 5' RI primer:
—GTCTAACCAGAGAGACCCTGGGAGTGAATTA-GCCCTTC—(SEQ ID NO:56)

and a 3' primer next to the NgoMI site:
3' NgoMI primer: —ATAGAACTCCGTTCTCC—(SEQ ID NO:57)

The PCR amplified fragment was digested with EcoRI and NgoMI and ligated into EcoRI and NgoMI digested pTVdeltaCMVnlacZ to generate the four U3 mutants.

Results and Discussion:
The relative vector titer of these mutants was determined by co-transfection with pHP-dl.28 and pHEF-VSVG as described above and the transfected culture supernatant was harvested 48 hr later and used to infect TE671 and 48 hr after infection, the lacZ gene expression was assay by X-gal staining and the blue nucleated cells were counted. The relative vector titer was shown with the pTVdeltaCMVnlacZ set at 1.00.

Table: (relative vector titer)
1. pTVdeltaCMVnlacZ: (1.00+/−0.00)
2. pTVdl.kB/Sp1: (1.00+/−0.10)
3. pTV-U3dl.1: (0.80+/−0.24)
4. pTV-U3dl.2: (0.91+/−0.24)
5. pTV-U3dl.3: (1.22+/−0.06)
6. pTV-U3dl.4: (0.84+/−0.27)

Summary: The results showed that the 3' U3, except for the att site, can be deleted from the transducing vector pTV construct without affecting vector titer. The 5' U3 deletion had no effect on vector promoter function as shown in the past. The elimination of U3 sequence from the vector system greatly improved the safety of our HP/TV vector system because U3 is an essential HIV replication element and may play important pathogenesis roles during viral infection.

Therefore, in combination, we have deleted the following HIV-1 essential elements, U3, SD, gag AUG, gag-pol, env, tat, rev and 3' SA sites, and all the accessory genes from the pTV construct. To generate a RCV from our HP/TV vector system, a non-homologous recombination must occur at the gag AUG site to bring the pTV leader sequence into pHP gag-pol and to cross back to pTV at the 3' env/RRE region which is about 1106 nt (nt. 7250–8355) and into the inserted reporter gene cassette and the 3' U3-deleted LTR. Although the overlap in the env region including the RRE is still quite long, the recombined product will be lacking 5' U3, SD, gag AUG, env, all accessory genes, and 3' U3. This recombinant will not be replication competent and will not exhibit any viral function.

Example 102

Cystic Fibrosis

This example is a mixture of preliminary studies and hypothetical experiments.

1. Study of the effects of HIV-1 Vpr on human bronchial epithelial cells. A key to long term therapy in CF is to avoid repeated vector administration and to transduce CFTR functional gene into undifferentiated, proliferating airway epithelial cells. HIV-1 Vpr is virion-associated which participates in the nuclear translocation of the preintegration core. Vpr has also been shown to arrest cell cycle and cause cell differentiation. Thus, on one hand, Vpr may be necessary to improve transduction and expression efficiencies of HIV vectors but on the other hand, its presence may block proliferation. To see if HIV-1 Vpr has any biological effects on human bronchial epithelial cells, two human airway epithelial cell lines, IB3-1 and BEAS-2B, will be transfected with a vpr expression eukaryotic vector, pHEF-vpr (driven by a strong human elongation factor 1a promoter). The differentiation and cytotoxic effects of Vpr will be evaluated after transfection. Transfected cells will be monitored by a co-transfected green fluorescent protein (GFP) marker. Morphologic and functional features of differentiated epithelial cells will be characterized as described [Engelhardt, 1995 #3704]. The apoptotic effects of vpr on epithelial cells will be examined by Hoechst dye staining. This preliminary examination of Vpr function in human epithelial cells will be useful for later evaluation of various HIV-1 vector constructs and their effects on airway epithelial cells.

2. Transduction of human respiratory epithelial cells in vitro. We have transduced IB3-1 cell line, which is a human CF bronchial epithelial cell line (CFTR genotype is dlF508/W1282X), with HIV-1 vector pTVΔCMV-nlacZ. These cells retain all of the ion channel and cytokeratin expression characteristics of bronchial epithelial cells.

In this preliminary transduction, vectors with or without HIV-1 Vpr were prepared using two different HIV-1 packaging pHP constructs, one with wild type vpr gene and the other with an in-frame stop codon mutation. Both vectors transduced IB3-1 at expected efficiencies.

Our preliminary studies with human rhabdomyosarcoma cell line TE671 indicate that repeated transduction with high titer ($>10^5$ transducing units/ml) of Vpr+ HIV-1 vectors causes TE671 differentiation into muscle cells. To see if this is true to human airway epithelial cells, IB3-1 cells will be transduced with high titer Vpr+ or Vpr− pTVΔCMV-nlacZ vector. The transduced culture will be monitored for differentiation, apoptosis, and proliferation. The nuclear lacZ gene expression will also be quantitatively recorded with time. If expression of Vpr induces differentiation of human airway epithelial cells, these differentiated cells will be used as target cells for Vpr+ and Vpr− HIV vector transduction. The latter experiment will answer whether HIV vector can efficiently transduce differentiated airway epithelial cells. Characterization of cell differentiation will be performed in collaboration with Dr. Flotte's laboratory.

3. Transduction of mouse lung tracheal epithelial cells. A recent study by Goldman et al. suggests that HIV vector does not transduce well-differentiated bronchial epithelium xenografts. In contrast, with poorly differentiated xenografts, substantial transduction was observed. It is not clear whether lentiviral vector can efficiently transduce airway epithelial cells or whether the presence of HIV-1 Vpr has an effect on such transduction. We propose to transduce mouse lungs via intracheal instillation with either Vpr+ or Vpr− pTVΔCMV-nlacZ vector, VSV-G pseudotyped and concentrated at $10^7$–$10^8$ transducing units/ml. The mouse lungs will be studied at 1 week, 8 weeks, or 6 months after transduction. The nuclear beta-galactosidase expression will be detected by X-gal staining. The transduced airway epithelial cells will be collected, and un-integrated and integrated proviral DNA will be harvested by a Hirt method coupled with a genomic DNA extraction protocol used routinely in our laboratory. If the pilot study demonstrates long term gene transduction in adult mouse lungs, further study will be performed in neonatal rabbit to evaluate whether lentiviral vector gene expression persists throughout the alveolar phase of lung development as described by Rubenstein et al.[Rubenstein, 1997 #3705].

3. Generation of different DTV-CFTR HIV vectors. Although the study of pTVΔCMV-nlacZ showed that the internal CMV promoter is a strong promoter after HIV vector transduction, some vector constructs, such as those carrying reporter genes such as GFP or placenta alkaline phosphatase (PLAP) exhibited undetectable amount of gene products in our preliminary studies. Therefore, the optimal CFTR HIV vector will have to be empirically established. pTV constructs containing either CMV or human elongation factor 1a internal promoter will be used to generate CFTR vectors. The upstream HIV major splice donor site and the gag AUG initiation codon have both been deleted without affecting vector titers. These different CFTR HIV vector constructs will be generated and used to transduce IB3-1 epithelial cells. The expression of apical CFTR will be immunostained with a monoclonal antibody MATG1031 [Demolombe, 1996 #3706], specific to the first extracellular loop sequence of the CFTR protein which is absent in IB3-1 cells. The level of expression will be determined under a confocal microscope.

4. Functional study of pTV-CFTR HIV vector transduction of CF respiratory epithelial cells. IB3-1 epithelial cells will be transduced with high titer pTV-CFTR, using pTVΔCMV-nlacZ as control, and 2, 7, 30, and 60 days later, the $^{36}$Cl- isotope tracer efflux profiles will be assayed in the presence and absence of forskolin, CPT-cAMP, and IBMX (to increase intracellular cAMP). A statistically significant increase in the rate of efflux in the presence of increased cAMP as compared with the basal rate is indicative of functional CFTR expression. Once the optimal CFTR construct is chosen based on the expression study, the electro-chemical properties of the transduced CFTR gene will be studied in CF patient's respiratory epithelial cells.All of the amplified fragments have XbaI site at the 5' end and BamHI site at the 3' end so they are digested with XbaI and BamHI and cloned into XbaI and BamHI digested vector pHEF. HSCs are then added on top of the TV producers (stromal cell transfectants) and co-cultured for 1–5 days (or longer) to allow infection of HSCs by the vectors via direct contact with producer cells. This protocol greatly improve the transduction efficiency of HSCs with the lentiviral HP/TV vector (up to more than 50%) which can be determined by the methylcellulose colony (LTC-IC, long term culture initiating colony assay). See Glimm H, Kiem H P, Darovsky B, et al. Efficient gene transfer in primitive CD34+/CD38lo human bone marrow cells reselected after long-term exposure to GALV-pseudotyped retroviral vector. Hum Gene Ther 1997; 8:2079–86.

Example 103

Retro- and Lenti-viral Transduction and in Vitro Culture of Established and Primary Breast Cancer Cells Like Example 102, this example is a mixture of preliminary studies and planned experiments.

The ultimate goal of gene therapy for treating breast cancer is to generate a cancer vaccine to prevent the growth of abnormal breast or mammary tumors. A cancer vaccine can be generated by genetically modifying cancer cells using appropriate gene therapy vectors. For therapeutic purposes, efficient in vitro or in vivo delivery of therapeutic genes to the cancer targets is essential. We have tested two breast cancer cell lines, MCF7 and MDA468, for retro- and lentiviral gene transfer. Since many tumor cells lose major histocompatibility complex (MHC) surface markers which are essential to immune recognition, we first examined these molecules by FACS analyses. MCF7 cells expressed neither class I or class II MHC molecules, whereas MDA468 expressed class I strongly but not class II MHC. It is known that cytokines such as interferon gamma (IFN-g) induces or up-regulates cellular class I or II MHC expression. To test this, we constructed three retroviral (non-lentiviral) vectors encoding IFN-g, GM-CSF and IL-12 (bicistronic A and B chains of human IL-12), respectively, and transduced both cell lines with all three retroviral vectors and re-examined the cell surface MHC expression following transduction. The results showed that there was an up-regulation of both class I and II MHC expression for MCF7 but not for MDA468 cells following transduction of all three cytokine genes. To see whether lentiviral vector could transduce these two breast cancer cell lines, cells were transduced with a green fluorescent protein (GFP) reporter vector, pTVE'EF-GFP, and the GFP expression was analyzed by FACS 48–72 hr after transduction. Following the lenti-TV transduction, more than 50% of MDA468 and MCF7 cells expressed the lentiviral GFP gene as illustrated by the green fluorescent shift of the transduced cells.

To see how efficiently primary breast tumor cells could be transduced with retro- or lentiviral vectors, a total of 8 primary breast cancer specimens were processed by mincing, digesting with collagenase, hyaluronidase, and DNase, and passing through a stainless steel mesh. Single cell suspension and small chunks of tumor tissue were plated onto Falcon Primaria tissue culture flasks or regular tissue flasks coated with collagen. Six of the eight specimens attached to the flask and expanded into small colonies. Five of the six samples had been cultured for longer than one month and three of the six for longer than two months. The overall growth rate of the breast cancer cells was slow in vitro. Nevertheless, we were able to keep them in culture long enough for the gene transduction study. Using conventional MLV-derived retroviral vectors, we observed poor transduction efficiencies in the primary breast tumor culture. In contrast, the primary breast tumor cells showed GFP expression after they were transduced with the lentiviral GFP reporter vector. Although preliminary, these results demonstrated the feasibility and certain advantages of lentiviral vectors over retroviral vectors for the transduction of primary breast cancer cells.

Establishment of a scid/beige mouse-human tumor model. In vivo study of human tumors requires appropriate immunodeficiency animals so to minimize xenograft rejection. Nude mice and scid/scid mice have both been used in such xenograft studies but the human tumor take rate is often less than satisfactory in these animals likely due to the remaining immune functions within these animals which can reject foreign tissues. Alternative strains of scid mice have been considered for the in vivo human tumor transplantation study. It has been reported that the SCID/beige mice, lacking all the T, B and natural killer (NK) cell functions, are severely immunodeficient. To test if this strain of mice are suitable for human tumor engraftment, we injected different human tumor cells into this strain of mice and studied the success rate for engraftment. The results showed that all the human tumor lines tested including breast tumor, melanoma, hepatoma, and glioblastoma, were successfully engrafted into the scid/beige mice. In addition, most of the tumors were tangible within one week. The same melanoma tumor line was reported to have a 60% tumor take rate in the scid/scid mice. The breast cancer cell line MCF7 has been reported to be engraftable only in the presence of estrogen in scid/scid mice. We have successfully engrafted MCF7 in the scid/beige mice without external supplies of estrogen. Therefore, the scid/beige mice might be useful as an in vivo human breast cancer model.

In addition to the use of established tumor cell lines, engraftment of primary human tumors into scid/beige mice was also studied. The study, however, was restricted to primary melanoma, glioblastoma and hepatoma. Our results demonstrated that all three surgical melanoma tumors were successfully engrafted in the scid/beige mice, although at a slower growth rate than that of the established melanoma cell lines. The engraftment of primary glioblastoma and hepatoma in the scid/beige mice has not been successful, i.e. no palpable tumor detectable in 3 months. The success rate of primary human tumor engraftment largely depends on the condition and the stage of the cancer cells obtained at surgery, as well as the tissue or cell types. As our sample size is still small, no firm conclusion can be made before more primary tumor specimens are examined.

Comparing transduction efficiencies off lentiviral vs. retroviral vectors in breast cancer cell lines and primary breast tumor culture.

Experimental design and methodology: Viral vectors including retroviral vectors pMFG-nlacZ, PMFG-GFP and lentiviral vectors pTVDEFnlacZ, PTVDEFGFP, carrying either nlacz or GFP reporter gene cassette, will be prepared by DNA co-transfection using relevant packaging plasmids, pHEF-gag-pol for the MLV vector, and pHP for the lentiviral vector. These vectors will be pseudotyped with VSV-G envelope protein by cotransfection with a VSV-G plasmid and the vector titer will be determined on human HeLa or TE671 cells. Both established breast cancer cell lines and primary tumor specimens will be used for this study. We plan to culture 20 primary breast cancer specimens plus the two breast tumor cell lines, MCF7 and MDA468. The primary tumor tissues will be processed as described above and transduced after plated out in tissue culture for 24 h. The cells will be transduced three times using an infectious dose between 104–106/ml with vectors carrying either nlacz or GFP reporter gene. Transduction efficiency will be determined using the X-Gal calorimetric staining method for nlacz expression or using a fluorescent microscope or FACS flow cytometry for GFP expression. For long term expression study, the transduced cells will be maintained in culture for six months and assayed for gene expression and stability.

Gene integration will be determined by Southern analysis. The percentage of transduced cells will be determined after each 5–10 passages. Long term study of the primary culture will depend on their culturing efficiency. The surgical tumor specimens will also be transduced with viral vectors as soon as they are processed into single cell suspension. The efficiency of transduction can be improved by using concentrated vector preparations as the VSV-G pseudotyped lenti- or retro-viral vectors can be concentrated to 10E8–10E9 transducing units/ml by ultracentrifugation. The transduction efficiency will be determined at different time points after the surgical tissues being cultured. This study will determine whether it is possible to generate gene-modified tumor cells and whether or not the transgene will continue to express at high efficiency.

Targeted Transgene Expression in Breast Cancer Cells using Lentiviral Vectors.

Rationale: A major concern with human gene therapy practice has been the specificity of the transgene to be accurately delivered to the target tissue. The therapeutic genes can be engineered to contain tissue specific enhancer/promoter so to restrict its expression in specific cells or tissues. The DF3/MUC1 gene has been shown to contain breast cancer specific promoter by Kovarik et al. and Manome et al. Using adenoviruses containing the DF3 promoter, Chen et al. have further demonstrated the tissue specificity of DF3/MUC1 promoter using the Ad-tk gene transduction approach. The generation of a breast tumor specific lentiviral vector with increased specificity and possibly improved expression efficiency will be useful for future breast cancer gene therapy application. We propose to test the DF3 tumor specific promoter using the lentiviral vector in this study.

Experimental design and methodology: To generate a breast tumor specific lentiviral vector the DF3 promoter, from nucleotide −725 to +31 in the DF3/MUC1 gene, will be amplified from chromosomal DNA prepared from MCF7 tumor cells by using the following two primers:

5' primer —ATA AGA ATG CGG CCG CTA AGT GA AAT TTC TTC CC—(SEQ ID NO:5), and

3' primer —CTA GCT AGC GGA AGA AAG AGA CGG—(SEQ ID NO:6).

The amplified DNA will be cloned into pTVDEFnlacZ and pTVDEFGFP using the Not I and Nhe I restriction sites to replace the EF-1a promoter to generate pTVDDF3nlacZ and pTVDDF3GFP. Transduction efficiencies of these newly constructed vectors will be compared with those of the CMV or the EF-1a driven vectors in breast tumor cell lines. The tissue specificity will be determined by comparing reporter gene expression in the breast tumor cells with non-breast tumor cell lines such as HeLa and TE671 cells and normal human tissues like foreskin fibroblasts. Tissue specific expression will be quantitatively determined by Northern analysis of the transgene mRNA, and by reporter gene assay.

Assessing Lentiviral Gene Transduction in vivo Following Intratumoral Injection.

Rationale: In vivo gene transduction using lentiviral vectors have been successfully demonstrated in rat brains, eyes, and lungs 47–49. Using the HP/TV lentiviral vector system, we have demonstrated efficient in vivo transduction of muscles of rats. Our preliminary studies also showed that the HP/TV vectors transduced tissue culture cell lines such as HeLa, TE671 and HepG2 cells more efficiently than the MFG retroviral vectors both short term and long term (more than 6 months).

Transduction via intratumoral injection using retroviral vectors have been very inefficient. It is possible that the center of the solid tumor may grow slowly or stop growing totally and therefore retroviral transduction becomes inefficient. Since the HP/TV vectors transduce non-dividing cells, they may also transduce solid tumors more efficiently than retroviral vectors. To prove this, we will evaluate the in vivo transduction efficiency of the HP/TV lentiviral vectors using the human breast tumor scid/beige mouse model.

Experimental design and methodology: We will first use the s.c. established breast tumors in scid/beige mice for the intratumoral injection. The mice will be injected s.c., on both flanks, with 5×106 MCF7 (or MDA) cells on each side. It normally takes two weeks to establish palpable solid breast tumor in the mice. Once palpable, the tumor nodules will receive three times of vector injection, either unconcentrated (usually 105 tu/ml) or concentrated (106–107 tu/ml), one time each day for 3 days. For side-by-side comparison, one frank of the mice will receive HP/TV vectors and the other retroviral vectors. The mice will be terminated after three days and the injected tumors will be fixed in 4% paraformaldehyde and sectioned for reporter gene assay. The initial short term study will determine the efficiency of transduction using different concentrations of vectors. Once the short term expression is demonstrated, long term study will be initiated. The breast tumor will be established in mice and vectors will be injected and at different time intervals, from 1 week to 2 months, mice will be terminated for analysis.

To see if the lentiviral vectors can transduce primary tumors in vivo, scid/beige mice implanted with tumors in the mammary fatpad will be injected with either retro- or lentiviral vectors and the mice will be sacrificed at different time points. The analyses of reporter gene transduced tumors will determine the efficiency of transduction. At the same time, micrometastasis of the primary breast tumors to other organ sites will be studied.

These in vivo studies will determine the efficiency of intratumoral transduction of lentiviral vectors. Further experiments will test the breast tumor-targeting vectors pTVDDF3nlacZ and pTVDDF3GFP. These vectors should exhibit tumor specific gene expression and therefore the surrounding normal tissue should have minimal transgene expression. To determine the specificity of these DF3 vectors, both the breast tumor cell lines and the primary tumors established in the scid/beige mice will be transduced and studied. Tumor specific gene expression will be examined carefully in the metastasis sites to evaluate the vector specificity. For quantitative determination of viral transduction efficiency, in situ hybridization will be performed on tissue section using biotinylated DNA probes. The efficiency of DNA integration will be compared with the relevant transgene expression to determine if all transgenes are expressed in the target tissue.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

```
The entire 12479 nt pHP-1 sequence (corrected SEQ ID NO: 13):

GATgtgGCCCGAGAGCTGCATCCGGAGTAtctagaTGGAGTTCCGCGTTACATAACTTACGGTAAATGGCCCGCCTGGCT

GACCGCCCAACGACCCCCGCCCATTGACGTCAATAATGACTGATGTTCCCATAGTAACGCCAATAGGGACTTTCCATTGA

CGCtAATGGGAGTTTGTTTTGgcaccaaaatcaacgggactttccaaaatgtcgtaataacccgccccgttgacgcaaa tgggcggtaggcgtgtactctagaAGGTCTATATAAGCAGAGCTCGTTTAGTGAACCGttTATACtacttatctGGTCTC TCTGGTTAGACCAGATCTGAGCCTGGGAGCTCTCTGGCTAACTAGGGAACCCACTGCTTAAGCCTCAATAaagctttGGT CGCCCGGTGGATCAAGACCGGTAGCCGTCATAAAGGTGATTTCGTCggatCCACCATGGGTGCGAGAGCGTCGGTATTAA

GCGGGGGAGAATTAGATAAATGGGAAAAAATTCGGTTAAGGCCAGGGGGAAAGAAACAATATAAACTAAAACATATAGTA

TGGGCAAGCAGGGAGCTAGAACGATTCGCAGTTAATCCTGGCCTTTTAGAGACATCAGAAGGCTGTAGACAAATACTGGG

ACAGCTACAACCATCCCTTCAGACAGGATCAGAAGAACTTAGATCATTATATAATACAATAGCAGTCCTCTATTGTGTGC

ATCAAAGGATAGATGTAAAAGACACCAAGGAAGCCTTAGATAAGATAGAGGAAGAGCAAAACAAAAGTAAGAAAAAGGCA

CAGCAAGCAGCAGCTGACACAGGAAACAACAGCCAGGTCAGCCAAAATTACCCTATAGTGCAGAACCTCCAGGGGCAAAT

GGTACATCAGGCCATATCACCTAGAACTTTAAATGCATGGGTAAAAGTAGTAGAAGAGAAGGCTTTCAGCCCAGAAGTAA

TACCCATGTTTTCAGCATTATCAGAAGGAGCCACCCCACAAGATTTAAATACCATGCTAAACACAGTGGGGGGACATCAA

GCAGCCATGCAAATGTTAAAAGAGACCATCAATGAGGAAGCTGCAGAATGGGATAGATTGCATCCAGTGCATGCAGGGCC

TATTGCACCAGGCCAGATGAGAGAACCAAGGGGAAGTGACATAGCAGGAACTACTAGTACCCTTCAGGAACAAATAGGAT

GGATGACACATAATCCACCTATCCCAGTAGGAGAAATCTATAAAAGATGGATAATCCTGGGATTAAATAAAATAGTAAGA

ATGTATAGCCCTACCAGCATTCTGGACATAAGACAAGGACCAAAGGAACCCTTTAGAGACTATGTAGACCGATTCTATAA

AACTCTAAGAGCCGAGCAAGCTTCACAAGAGGTAAAAAATTGGATGACAGAAACCTTGTTGGTCCAAAATGCGAACCCAG

ATTGTAAGACTATTTTAAAAGCATTGGGACCAGGAGCGACACTAGAAGAAATGATGACAGCATGTCAGGGAGTGGGGGGA
```

-continued

```
CCCGGCCATAAAGCAAGAGTTTTGGCTGAAGCAATGAGCCAAGTAACAAATCCAGCTACCATAATGATACAGAAAGGCAA
TTTTAGGAACCAAAGAAAGACTGTTAAGTGTTTCAATTGTGGCAAAGAAGGGCACATAGCCAAAAATTGCAGGGCCCCTA
GGAAAAAGGGCTGTTGGAAATGTGGAAAGGAAGGACACCAAATGAAAGATTGTACTGAGAGACAGGCTAATTTTTTAGGG
AAGATCTGGCCTTCCCACAAGGGAAGGCCAGGGAATTTTCTTCAGAGCAGACCAGAGCCAACAGCCCCACCAGAAGAGAG
CTTCAGGTTTGGGGAAGAGACAACAACTCCCTCTCAGAAGCAGGAGCCGATAGACAAGGAACTGTATCCTTTAGCTTCCC
TCAGATCACTCTTTGGCAGCGACCCCTCGTCACAATAAAGATAGGGGGCAATTAAAGGAAGCTCTATTAGATACAGGAG
CAGATGATACAGTATTAGAAGAAATGAATTTGCCAGGAAGATGGAAACCAAAAATGATAGGGGGAATTGGAGGTTTTATC
AAAGTAGGACAGTATGATCAGATACTCATAGAAATCTGCGGACATAAAGCTATAGGTACAGTATTAGTAGGACCTACACC
TGTCAACATAATTGGAAGAAATCTGTTGACTCAGATTGGCTGCACTTTAAATTTTCCCATTAGTCCTATTGAGACTGTAC
CAGTAAAATTAAAGCCAGGAATGGATGGCCCAAAAGTTAAACAATGGCCATTGACAGAAGAAAAAATAAAAGCATTAGTA
GAAATTTGTACAGAAATGGAAAAGGAAGGAAAAATTTCAAAAATTGGGCCTGAAAATCCATACAATACTCCAGTATTTGC
CATAAAGAAAAAGACAGTACTAAATGGAGAAAATTAGTAGATTTCAGAGAACTTAATAAGAGAACTCAAGATTTCTGGG
AAGTTCAATTAGGAATACCACATCCTGCAGGGTTAAAACAGAAAAAATCAGTAACAGTACTGGATGTGGGCGATGCATAT
TTTTCAGTTCCCTTAGATAAAGACTTCAGGAAGTATACTGCATTTACCATACCTAGTATAAACAATGAGACACCAGGGAT
TAGATATCAGTACAATGTGCTTCCACAGGGATGGAAAGGATCACCAGCAATATTCCAGTGTAGCATGACAAAAATCTTAG
AGCCTTTTAGAAAACAAAATCCAGACATAGTCATCTATCAATACATGGATGATTTGTATGTAGGATCTGACTTAGAAATA
GGGCAGCATAGAACAAAAATAGAGGAACTGAGACAACATCTGTTGAGGTGGGGATTTACCACACCAGACAAAAAACATCA
GAAAGAACCTCCATTCCTTTGGATGGGTTATGAACTCCATCCTGATAAATGGACAGTACAGCCTATAGTGCTGCCAGAAA
AGGACAGCTGGACTGTCAATGACATACAGAAATTAGTGGGAAAATTGAATTGGGCAAGTCAGATTTATGCAGGGATTAAA
GTAAGGCAATTATGTAAACTTCTTAGGGGAACCAAAGCACTAACAGAAGTAGTACCACTAACAGAAGAAGCAGAGCTAGA
ACTGGCAGAAAACAGGGAGATTCTAAAAGAACCGGTACATGGAGTGTATTATGACCCATCAAAAGACTTAATAGCAGAAA
TACAGAAGCAGGGGCAAGGCCAATGGACATATCAAATTTATCAAGAGCCATTTAAAAATCTGAAAACAGGAAAATATGCA
AGAATGAAGGGTGCCCACACTAATGATGTGAAACAATTAACAGAGGCAGTACAAAAAATAGCCACAGAAAGCATAGTAAT
ATGGGGAAAGACTCCTAAATTTAAATTACCCATACAAAAGGAAACATGGGAAGCATGGTGGACAGAGTATTGGCAAGCCA
CCTGGATTCCTGAGTGGGAGTTTGTCAATACCCCTCCCTTAGTGAAGTTATGGTACCAGTTAGAGAAAGAACCCATAATA
GGAGCAGAAACTTTCTATGTAGATGGGGCAGCCAATAGGGAAACTAAATTAGGAAAAGCAGGATATGTAACTGACAGAGG
AAGACAAAAAGTTGTCCCCCTAACGGACACAACAAATCAGAAGACTGAGTTACAAGCAATTCATCTAGCTTTGCAGGATT
CGGGATTAGAAGTAAACATAGTGACAGACTCACAATATGCATTGGGAATCATTCAAGCACAACCAGATAAGAGTGAATCA
GAGTTAGTCAGTCAAATAATAGAGCAGTTAATAAAAAAGGAAAAAGTCTACCTGGCATGGGTACCAGCACACAAAGGAAT
TGGAGGAAATGAACAAGTAGATGGGTTGGTCAGTGCTGGAATCAGGAAAGTACTATTTTTAGATGGAATAGATAAGGCCC
AAGAAGAACATGAGAAATATCACAGTAATTGGAGAGCAATGGCTAGTGATTTTAACCTACCACCTGTAGTAGCAAAAGAA
ATAGTAGCCAGCTGTGATAAATGTCAGCTAAAAGGGGAAGCCATGCATGGACAAGTAGACTGTAGCCCAGGAATATGGCA
GCTAGATTGTACACATTTAGAAGGAAAAGTTATCTTGGTAGCAGTTCATGTAGCCAGTGGATATATAGAAGCAGAAGTAA
TTCCAGCAGAGACAGGGCAAGAAACAGCATACTTCCTCTTAAAATTAGCAGGAAGATGGCCAGTAAAAACAGTACATACA
GACAATGGCAGCAATTTCACCAGTACTACAGTTAAGGCCGCCTGTTGGTGGGCGGGGATCAAGCAGGAATTTGGCATTCC
CTACAATCCCCAAAGTCAAGGAGTAATAGAATCTATGAATAAAGAATTAAAGAAAATTATAGGACAGGTAAGAGATCAGG
CTGAACATCTTAAGACAGCAGTACAAATGGCAGTATTCATCCACAATTTTAAAAGAAAAGGGGGGATTGGGGGGTACAGT
GCAGGGGAAGAATAGTAGACATAATAGCAACAGACATACAAACTAAAGAATTACAAAAACAAATTACAAAAATTCAAAA
TTTTCGGGTTTATTACAGGGACAGCAGAGATCCAGTTTGGAAAGGACCAGCAAAGCTCCTCTGGAAAGGTGAAGGGGCAG
TAGTAATACAAGATAATAGTGACATAAAAGTAGTGCCAAGAAGAAAAGCAAAGATCATCAGGGATTATGGAAAACAGATG
```

-continued

```
GCAGGTGATGATTGTGTGGCAAGTAGACAGGATGAGGATTAACACATGGAAAAGATTAGTAAAACACCATATGTATATTT

CAAGGAAAGCTAAGGACTGGTTTTATAGACATCACTATGAAAGTACTAATCCAAAAATAAGTTCAGAAGTACACATCCCA

CTAGGGGATGCTAAATTAGTAATAACAACATATTGGGGTCTGCATACAGGAGAAAGAGACTGGCATTTGGGTCAGGGAGT

CTCCATAGAATGGAGGAAAAAGAGATATAGCACACAAGTAGACCCTGACCTAGCAGACCAACTAATTCATCTGCACTATT

TTGATTGTTTTTCAGAATCTGCTATAAGAAATACCATATTAGGACGTATAGTTAGTCCTAGGTGTGAATATCAAGCAGGA

CATAACAAGGTAGGATCTCTACAGTACTTGGCACTAGCAGCATTAATAAAACCAAAACAGATAAAGCCACCTTTGCCTAG

TGTTAGGAAACTGACAGAGGACAGATGGAACAAGCCCCAGAAGACCAAGGGCCACAGAGGGAGCCATACAATGAATGGAC

ACTAGAGCTTTTAGAGGAACTTAAGAGTGAAGCTGTTAGACATTTTCCTAGGATATGGCTCCATAACTTAGGACAACATA

TCTATGAAACTTACGGGGATACTTGGGCAGGAGTGGAAGCCATAATAAGAATTCTGCAACAACTGCTGTTTATCCATTTC

AGAATTGGGTGTCGACATAGCAGAATAGGCGTTACTCGACAGAGGAGAGCAAGAAATGGAGCCAGTAGATCCTAGACTAG

AGCCCTGGAAGCATCCAGGAAGTCAGCCTAAAACTGCTTGTACCAATTGCTATTGTAAAAAGTGTTGCTTTCATTGCCAA

GTTTGTTTCATGACAAAAGCCTTAGGCATCTCCTATGGCAGGAAGAAGCGGAGACAGCGACGAAGAGCTCATCAGAACAG

TCAGACTCATCAAGCTTCTCTATCAAAGCAGTAAGTAGTACATGTAATGCAACCTATAATAGTAGCAATAGTAGCATTAG

TAGTAGCAATAATAATAGCAATAGTTGTGTGGTCCATAGTAATCATAGAATATAGGAAAATATTAAGACAAAGAAAAATA

GACAGGTTAATTGATAGACTAATAGAAAGAGCAGAAGACAGTGGCAATGAGAGTGAAGGAGAAGTATCAGCACTTGTGGA

GATGGGGTGGAAATGGGGCACCATGCTCCTTGGGATATTGATGATCTGTAGTGCTACAGAAAAATTGTGGGTCACAGTC

TATTATGGGGTACCTGTGTGGAAGGAAGCAACCACCACTCTATTTTGTGCATCAGATGCTAAAGCATATGATACAGAGGT

ACATAATGTTTGGGCCACACATGCCTGTGTACCCACAGACCCCAACCCACAAGAAGTAGTATTGGTAAATGTGACAGAAA

ATTTTAACATGTGGAAAAATGACATGGTAGAACAGATGCATGAGGATATAATCAGTTTATGGGATCAAAGCCTAAAGCCA

TGTGTAAAATTAACCCCACTCTGTGTTAGTTTAAAGTGCACTGATTTGAAGAATGATACTAATACCAATAGTAGTAGCGG

GAGAATGATAATGGAGAAGGAGAGATAAAAAACTGCTCTTTCAATATCAGCACAAGCATAAGAGATAAGGTGCAGAAAG

AATATGCATTCTTTTATAAACTTGATATAGTACCAATAGATAATACCAGCTATAGGTTGATAAGTTGTAACACCTCAGTC

ATTACACAGGCCTGTCCAAAGGTATCCTTTGAGCCAATTCCCATACATTATTGTGCCCCGGCTGGTTTTGCGATTCTAAA

ATGTAATAATAAGACGTTCAATGGAACAGGACCATGTACAAATGTCAGCACAGTACAATGTACACATGGAATCAGGCCAG

TAGTATCAACTCAACTGCTGTTAAATGGCAGTCTAGCAGAAGAAGATGTAGTAATTAGATCTGCCAATTTCACAGACAAT

GCTAAAACCATAATAGTACAGCTGAACACATCTGTAGAAATTAATTGTACAAGACCCAACAACAATACAAGAAAAAGTAT

CCGTATCCAGAGGGGACCAGGGAGAGCATTTGTTACAATAGGAAAAATAGGAAATATGAGACAAGCACATTGTAACATTA

GTAGAGCAAAATGGAATGCCACTTTAAAACAGATAGCTAGCAAATTAAGAGAACAATTTGGAAATAATAAAACAATAATC

TTTAAGCAATCCTCAGGAGGGGACCCAGAAATTGTAACGCACAGTTTTAATTGTGGAGGGGAATTTTTCTACTGTAATTC

AACACAACTGTTTAATAGTACTTGGTTTAATAGTACTTGGAGTACTGAAGGGTCAAATAACACTGAAGGAAGTGACACAA

TCACACTCCCATGCAGAATAAAACAATTTATAAACATGTGGCAGGAAGTAGGAAAAGCAATGTATGCCCCTCCCATCAGT

GGACAAATTAGATGTTCATCAAATATTACTGGGCTGCTATTAACAAGAGATGGTGGTAATAACAACAATGGGTCCGAGAT

CTTCAGACCTGGAGGAGGCGATATGAGGGACAATTGGAGAAGTGAATTATATAAATATAAAGTAGTAAAAATTGAACCAT

TAGGAGTAGCACCCACCAAGGCAAAGAGAAGAGTGGTGCAGAGAGAAAAAAGAGCAGTGGGAATAGGAGCTTTGTTCCTT

GGGTTCTTGGGAGCAGCAGGAAGCACTATGGGCGCACGGTCAATGACGCTGACGGTACAGGCCAGACAATTATTGTCTGA

TATAGTGCAGCAGCAGAACAATTTGCTGAGGGCTATTGAGGCGCAACAGCATCTGTTGCAACTCACAGTCTGGGGCATCA

AACAGCTCCAGGCAAGAATCCTGGCTGTGGAAAGATACCTAAAGGATCAACAGCTCCTGGGGATTTGGGGTTGCTCTGGA

AAACTCATTTGCACCACTGCTGTGCCTTGGAATGCTAGTTGGAGTAATAAATCTCTGGAACAGATTTGGAATAACATGAC

CTGGATGGAGTGGGACAGAGAAATTAACAATTACACAAGCTTAATACACTCCTTAATTGAAGAATCGCAAAACCAGCAAG

AAAAGAATGAACAAGAATTATTGGAATTAGATAAATGGGCAAGTTTGTGGAATTGGTTTAACATAACAAATTGGCTGTGG
```

```
TATATAAAATTATTCATAATGATAGTAGGAGGCTTGGTAGGTTTAAGAATAGTTTTTGCTGTACTTTCTATAGTGAATAG
AGTTAGGCAGGGATATTCACCATTATCGTTTCAGACCCACCTCCCAATCCCGAGGGGACCCGACAGGCCCGAAGGAATAG
AAGAAGAAGGTGGAGAGAGAGACAGAGACAGATCCATTCGATTAGTGAACGGATCCTTAGCACTTATCTGGGACGATCTG
CGGAGCCTGTGCCTCTTCAGCTACCACCGCTTGAGAGACTTACTCTTGATTGTAACGAGGATTGTGGAACTTCTGGGACG
CAGGGGGTGGGAAGCCCTCAAATATTGGTGGAATCTCCTACAGTATTGGAGTCAGGAACTAAAGAATAGTGCTGTTAACT
TGCTCAATGCCACAGCCATAGCAGTAGCTGAGGGACAGATAGGGTTATAGAAGTATTACAAGCAGCTTATAGAGCTATT
CGCCACATACCTAGAAGAATAAGACAGGGCTTGGAAAGGATTTTGCTATaagctttAtatatAGtgttatAGTGCGCCAG
ATCTCTATAATCTCGCGCAACCTATTTTCCCCTCGAACACTTTTTAAGCCGTAGATAAACAGGCTGGGACACTTCACATG
AGCGAAAAATACATCGTCACCTGGACATGTTGCAGATCCATGCACGTAAACTCGCAAGCCGACTGATGCCTTCTGAACA
ATGGAAAGGCATTATTGCCGTAAGCCGTGGCGGTCTGGTACCGGGTGCGTTACTGGCGCGTGAACTGGGTATTCGTCATG
TCGATACCGTTTGTATTTCCAGCTACGATCACGACAACCAGCGCGAGCTTAAAGTGCTGAAACGCGCAGAAGGCGATGGC
GAAGGCTTCATCGTTATTGATGACCTGGTGGATACCGGTGGTACTGCGGTTGCGATTCGTGAAATGTATCCAAAAGCGCA
CTTTGTCACCATCTTCGCAAAACCGGCTGGTCGTCCGCTGGTTGATGACTATGTTGTTGATATCCCGCAAGATACCTGGA
TTGAACAGCCGTGGGATATGGGCGTCGTATTCGTCCCGCCAATCTCCGGTCGCTAActcgagActcgagGCCGGCAAGGC
CGGATCCAGACATGATAAGATACATTGATGAGTTTGGACAAACCACAACTAGAATGCAGTGAAAAAAATGCTTTATTTGT
GAAATTTGTGATGCTATTGCTTTATTTGTAACCATTATAAGCTGCAATAAACAAGTTAACAACAACAATTGCATTCATTT
TATGTTTCAGGTTCAGGGGGAGGTGGGGAGGTTTTTTAAAGCAAGTAAAACCTCTACAAATGTGGTATGGCTGATTATGA
TCCGGCTGCCTCGCGCGTTTCGGTGATGACGGTGAAAACCTCTGACACATGCAGCTCCCGGAGACGGTCACAGCTTGTCT
GTAAGCGGATGCCGGGAGCAGACAAGCCCGTCAGGGCGCGTCAGCGGGTGTTGGCGGGTGTCGGGGCGCAGCCATGACCG
GTCGActgcagtctctgcagGAATTCGATATCAAGCTTATCGATACCGTCGACCTCGAGGGGGGGCCCGGTACCCAATTC
GCCCTATAGTGAGTCGTATTACAATTCACTGGCCGTCGTTTTACAACGTCGTGACTGGGAAAACCCTGGCGTTACCCAAC
TTAATCGCCTTGCAGCACATCCCCCTTTCGCCAGCTGGCGTAATAGCGAAGAGGCCCGCACCGATCGCCCTTCCCAACAG
TTGCGCAGCCTGAATGGCGAATGGAAATTGTAAGCGTTAATATTTTGTTAAAATTCGCGTTAAATTTTTGTTAAATCAGC
TCATTTTTTAACCAATAGGCCGAAATCGGCAAAATCCCTTATAAATCAAAAGAATAGACCGAGATAGGGTTGAGTGTTGT
TCCAGTTTGGAACAAGAGTCCACTATTAAAGAACGTGGACTCCAACGTCAAAGGGCGAAAAACCGTCTATCAGGGCGATG
GCCCACTACGTGAACCATCACCCTAATCAAGTTTTTTGGGGTCGAGGTGCCGTAAAGCACTAAATCGGAACCCTAAAGGG
AGCCCCCGATTTAGAGCTTGACGGGGAAAGCCGGCGAACGTGGCGAGAAAGGAAGGGAAGAAAGCGAAAGGAGCGGGCGC
TAGGGCGCTGGCAAGTGTAGCGGTCACGCTGCGCGTAACCACCACACCCGCCGCGCTTAATGCGCCGCTACAGGGCGCGT
CAGGTGGCACTTTTCGGGGAAATGTGCGCGGAACCCCTATTTGTTTATTTTTCTAAATACATTCAAATATGTATCCGCTC
ATGAGACAATAACCCTGATAAATGCTTCAATAATATTGAAAAAGGAAGAGTATGAGTATTCAACATTTCCGTGTCGCCCT
TATTCCCTTTTTTGCGGCATTTTGCCTTCCTGTTTTTGCTCACCCAGAAACGCTGGTGAAAGTAAAAGATGCTGAAGATC
AGTTGGGTGCACGAGTGGGTTACATCGAACTGGATCTCAACAGCGGTAAGATCCTTGAGAGTTTTCGCCCCGAAGAACGT
TTTCCAATGATGAGCACTTTTAAAGTTCTGCTATGTGGCGCGGTATTATCCCGTATTGACGCCGGGCAAGAGCAACTCGG
TCGCCGCATACACTATTCTCAGAATGACTTGGTTGAGTACTCACCAGTCACAGAAAAGCATCTTACGGATGGCATGACAG
TAAGAGAATTATGCAGTGCTGCCATAACCATGAGTGATAACACTGCGGCCAACTTACTTCTGACAACGATCGGAGGACCG
AAGGAGCTAACCGCTTTTTTGCACAACATGGGGGATCATGTAACTCGCCTTGATCGTTGGGAACCGGAGCTGAATGAAGC
CATACCAAACGACGAGCGTGACACCACGATGCCTGTAGCAATGGCAACAACGTTGCGCAAACTATTAACTGGCGAACTAC
TTACTCTAGCTTCCCGGCAACAATTAATAGACTGGATGGAGGCGGATAAAGTTGCAGGACCACTTCTGCGCTCGGCCCTT
CCGGCTGGCTGGTTTATTGCTGATAAATCTGGAGCCGGTGAGCGTGGGTCTCGCGGTATCATTGCAGCACTGGGGCCAGA
TGGTAAGCCCTCCCGTATCGTAGTTATCTACACGACGGGGAGTCAGGCAACTATGGATGAACGAAATAGACAGATCGCTG
```

-continued

AGATAGGTGCCTCACTGATTAAGCATTGGTAACTGTCAGACCAAGTTTACTCATATATACTTTAGATTGATTTAAAACTT

CATTTTTAATTTAAAAGGATCTAGGTGAAGATCCTTTTTGATAATCTCATGACCAAAATCCCTTAACGTGAGTTTTCGTT

CCACTGAGCGTCAGACCCCGTAGAAAAGATCAAAGGATCTTCTTGAGATCCTTTTTTTCTGCGCGTAATCTGCTGCTTGC

AAACAAAAAAACCACCGCTACCAGCGGTGGTTTGTTTGCCGGATCAAGAGCTACCAACTCTTTTTCCGAAGGTAACTGGC

TTCAGCAGAGCGCAGATACCAAATACTGTCCTTCTAGTGTAGCCGTAGTTAGGCCACCACTTCAAGAACTCTGTAGCACC

GCCTACATACCTCGCTCTGCTAATCCTGTTACCAGTGGCTGCTGCCAGTGGCGATAAGTCGTGTCTTACCGGGTTGGACT

CAAGACGATAGTTACCGGATAAGGCGCAGCGGTCGGGCTGAACGGGGGGTTCGTGCACACAGCCCAGCTTGGAGCGAACG

ACCTACACCGAACTGAGATACCTACAGCGTGAGCTATGAGAAAGCGCCACGCTTCCCGAAGGGAGAAAGGCGGACAGGTA

TCCGGTAAGCGGCAGGGTCGGAACAGGAGAGCGCACGAGGGAGCTTCCAGGGGAAACGCCTGGTATCTTTATAGTCCTG

TCGGGTTTCGCCACCTCTGACTTGAGCGTCGATTTTTGTGATGCTCGTCAGGGGGCGGAGCCTATGGAAAAACGCCAGC

AACGCGGCCTTTTTACGGTTCCTGGCCTTTTGCTGGCCTTTTGCTCACATGTTCTTTCCTGCGTTATCCCCTGATTCTGT

GGATAACCGTATTACCGCCTTTGAGTGAGCTGATACCGCTCGCCGCAGCCGAACGACCGAGCGCAGCGAGTCAGTGAGCG

AGGAAGCGGAAGAGCGCCCAATACGCAAACCGCCTCTCCCCGCGCGTTGGCCGATTCATTAATGCAGCTGGCACGACAGG

TTTCCCGACTGGAAAGCGGGCAGTGAGCGCAACGCAATTAATGTGAGTTAGCTCACTCATTAGGCACCCCAGGCTTTACA

CTTTATGCTTCCGGCTCGTATGTTGTGTGGAATTGTGAGCGGATAACAATTTCACACAGGAAACAGCTATGACCATGATT

ACGCCAAGCTCGAAATTAACCCTCACTAAAGGGAACAAAAGCTGGAGCTCCACCGCGGTggcggccgctctagaactagt ggatccccgggctgcaggaattcgataacCTGGCTTATCGAAATTAATACGACTCACTATAGGGAGACCGGCAGATCT

---

What is claimed is:

1. A packaging vector comprising a nucleotide sequence encoding Gag and Pol proteins of a reference lentivirus, said packaging vector differing from said reference lentivirus at least in that
   (a) its major splice donor site, while functional, differs in sequence from that of said reference lentivirus sufficiently so that said major splice donor site is not a potential site for homologous recombination between said packaging vector and said reference lentivirus, and
   (b) it lacks a functional major packaging signal, which vector, after introduction into a suitable host cell, is capable of causing such cell, either through expression from said vector alone, or through co-expression from said vector and a second vector providing for expression of a compatible envelope protein, to produce packaging vector particles comprising functional Gag and Pol proteins and having a normal or a pseudotyped envelope, where said particles are free of the RNA form of said packaging vector as a result of (b) above,
      where said cell, as a result of said expression or co-expression, produces particles encapsulating the RNA form of a transducing vector possessing a compatible and functional packaging signal if said transducing vector is introduced into said cell
   where said reference lentivirus is selected from the group consisting of HIV-1, HIV-2 and SIV.

2. The packaging vector of claim 1 in which the reference lentivirus is HIV-1.

3. The packaging vector of claim 1 in which the reference lentivirus is HIV-2.

4. The packaging vector of claim 1 in which the reference lentivirus is SIV.

5. The packaging vector of claim 1 which encodes one or more envelope proteins.

6. The packaging vector of claim 1 which does not encode a functional envelope protein.

7. The packaging vector of claim 1 wherein the major splice donor site of said vector differs in sequence from that of any lentivirus major splice donor site sufficiently so that said major splice donor site is not a potential site for homologous recombination between said packaging vector and said lentivirus.

8. The packaging vector of claim 1 which comprises a sequence encoding lentivirus Env proteins.

9. The packaging vector of claim 1 which comprises a sequence encoding the VSV-G envelope protein.

10. The packaging vector of claim 1 which further differs from said reference lentivirus in that at least portions of at least one gene selected from the group consisting of the env, vpr, vif, and vpu genes of said reference lentivirus is or are deleted.

11. The packaging vector of claim 1 which lacks the native primer binding site of said reference lentivirus.

12. The packaging vector of claim 1 which lacks the native polypurine tract of said reference lentivirus.

13. The packaging vector of claim 1 which lacks a functional nef gene.

14. The packaging vector of claim 1 which further differs from said lentivirus in that the 5' LTR has been modified.

15. The packaging vector of claim 1 in which the 5'LTR is a chimera of a lentivirus LTR and a CMV enhancer/promoter.

16. The packaging vector of claim 1 comprises a tat gene and a TAR sequence.

17. The packaging vector of claim 1 which comprises a rev gene and an RRE element.

18. The packaging vector of claim 1 which further differs from the reference lentivirus in that at least a portion of the tat gene and the TAR sequence are deleted.

19. The packaging vector of claim 1 which further differs from the reference lentivirus in that at least a portion of the env gene and the RRE element are deleted.

20. A packaging cell which comprises the packaging vector of claim 1 and is suitable for production of infectious transducing vector particles encapsulating the RNA form of a transducing vector possessing a compatible and functional packaging signal if said transducing vector is introduced into said cell.

21. A method of producing a transducing vector comprising a remedial gene, in the form of infectious particles, which comprises (a) transfecting a cell with a packaging vector according to claim 1, and, if said packaging vector does not itself provide for expression of a compatible envelope protein, a pseudotyping vector which does provide expression, so said cell is capable of producing packaging vector particles, (b) transfecting said cell with a transducing vector comprising said remedial gene, and a functional packaging signal, but which by itself is incapable of causing a cell to produce transducing vector particles, and (c) causing the cell to produce infectious transducing vector particles comprising said transducing vector in RNA form, said Gag and Pol proteins, and said envelope protein.

22. A kit comprising a packaging vector according to claim 1 and a transducing vector comprising a functional and compatible packaging signal, said transducing vector being incapable by itself of causing a cell transfected by said transducing vector to encapsulate the RNA form of said transducing vector into a lentivirus-like particle.

23. The packaging vector of claim 1 in which the major splice donor site is a modified RSV major splice donor site corresponding to the splice donor site included in SEQ ID NO:9 and SEQ ID NO:10.

24. The packaging vector of claim 1 which is vector pHP-1.

25. The packaging vector of claim 7 wherein the major splice donor site of said vector is substantially identical major splice donor site of said vector is substantially identical to the RSV splice donor site.

26. The cell of claim 20, which further comprises a pseudotyping vector.

27. The cell of claim 20 which further comprises a transducing vector which by itself is incapable of coding for expression of infectious transducing vector particles, but which cell, as a result of the expression of genes of said packaging vector, packages the RNA form of said transducing vector into infectious transducing vector particles.

28. The cell of claim 20 where said transducing vector further comprises a remedial gene.

29. The cell of claim 20 wherein packaging is inducible.

30. The cell of claim 20 in which the major packaging signal of said transducing vector is at least 50% identical to the major packaging signal of said reference lentivirus.

31. A method of delivering a remedial gene to target cells which comprises producing the particles by the method of claim 21 and then (d) infecting the target cells with an effective amount of the particles of step (c).

32. The method of claim 31 in which the cells are nondividing cells.

33. The method of claim 31 in which the target cells are cells in a target mammal.

34. The kit of claim 22, said packaging vector comprising a gene encoding a compatible envelope protein.

35. The kit of claim 22, further comprising a pseudotyping vector comprising a gene encoding a non-lentiviral envelope protein incorporatable into said particles.

36. The method of claim 21 in which the major packaging signal of said transducing vector is at least 50% identical to the major packaging signal of said reference lentivirus.

37. The kit of claim 22 in which the major packaging signal of said transducing vector is at least 50% identical to the major packaging signal of said reference lentivirus.

* * * * *

SEQUENCE LISTING (1) GENERAL INFORMATION:

(iii) NUMBER OF SEQUENCES: 62

(2) INFORMATION FOR SEQ ID NO: 1:

(i) SEQUENCE CHARACTERISTICS:
       (A) LENGTH: 140 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO: 1:

AGGCGTTACT CGACAGAGGA GAGCAAGAAA TGGAGCCAGT AGATCCTAGA CTATAGGCCT    60

GGAAGCATCC AGGAAGTTAG CCTTAAACTG CTTGTACCAA TTGCTATTGT AAAAAGTGTT   120

GCTTTCATTG CCAAGTTTGT    140

(2) INFORMATION FOR SEQ ID NO: 2:

(i) SEQUENCE CHARACTERISTICS:
       (A) LENGTH: 31 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO: 2:

CTCAGGTACC TTTAAGACCA ATGACTTACA A    31

(2) INFORMATION FOR SEQ ID NO: 3:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 3:

CTCAGGTACC TTTAAGACTC TAGATCTAGA A                                  31

(2) INFORMATION FOR SEQ ID NO: 4:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 4:

AAAAATTTTG ACTAGCGGA                                             19

(2) INFORMATION FOR SEQ ID NO: 5:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

ATAAGAATGC GGCCGCTAAG TGAAATTTCT TCCC                              34

(2) INFORMATION FOR SEQ ID NO: 6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

GGCAGAGAAA GAAGGCGATC GATC                                        24

(2) INFORMATION FOR SEQ ID NO: 7:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

GCGGCGACTG GGGAGGACGC CAA                                         23

(2) INFORMATION FOR SEQ ID NO: 8:

(i) SEQUENCE CHARACTERISTICS:

(A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

GAAGGAGAGA GTTGGGTGCG AG                                            22

(2) INFORMATION FOR SEQ ID NO: 9:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

AGCTTGGTCG CCCGGTGGAT CAAGACCGGT AGCCGTCATA AAGGTGATTT CGTCG        55

(2) INFORMATION FOR SEQ ID NO: 10:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

GATCCGACGA AATCACCTTT ATGACGGCTA CCGGTCTTGA TCCACCGGGC GACCA        55

(2) INFORMATION FOR SEQ ID NO: 11:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 11:

CGGGATCCAC CATGGGTGCG AGAGCGTC                                      28

(2) INFORMATION FOR SEQ ID NO: 12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 12:

ATCCTATTTG TTCCTGAAGG                                               20

(2) INFORMATION FOR SEQ ID NO: 13:

(i) SEQUENCE CHARACTERISTICS:
        (A) LENGTH: 12479 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 13:

```
GATGTGGCCC GAGAGCTGCA TCCGGAGTAT CTAGATGGAG TTCCGCGTTA CATAACTTAC    60
GGTAAATGGC CCGCCTGGCT GACCGCCCAA CGACCCCCGC CCATTGACGT CAATAATGAC   120
TGATGTTCCC ATAGTAACGC CAATAGGGAC TTTCCATTGA CGCTAATGGG AGTTTGTTTT   180
GGCACCAAAA TCAACGGGAC TTTCCAAAAT GTCGTAATAA CCCCGCCCCG TTGACGCAAA   240
TGGGCGGTAG GCGTGTACTC TAGAAGGTCT ATATAAGCAG AGCTCGTTTA GTGAACCGTT   300
TATACTACTT ATCTGGTCTC TCTGGTTAGA CCAGATCTGA GCCTGGGAGC TCTCTGGCTA   360
ACTAGGGAAC CCACTGCTTA AGCCTCAATA AAGCTTTGGT CGCCCGGTGG ATCAAGACCG   420
GTAGCCGTCA TAAAGGTGAT TTCGTCGGAT CCACCATGGG TGCGAGAGCG TCGGTATTAA   480
GCGGGGGAGA ATTAGATAAA TGGGAAAAAA TTCGGTTAAG GCCAGGGGGA AGAAACAAT   540
ATAAACTAAA ACATATAGTA TGGGCAAGCA GGGAGCTAGA ACGATTCGCA GTTAATCCTG   600
GCCTTTTAGA GACATCAGAA GGCTGTAGAC AAATACTGGG ACAGCTACAA CCATCCCTTC   660
AGACAGGATC AGAAGAACTT AGATCATTAT ATAATACAAT AGCAGTCCTC TATTGTGTGC   720
ATCAAAGGAT AGATGTAAAA GACACCAAGG AAGCCTTAGA TAAGATAGAG GAAGAGCAAA   780
ACAAAAGTAA GAAAAAGGCA CAGCAAGCAG CAGCTGACAC AGGAAACAAC AGCCAGGTCA   840
GCCAAAATTA CCCTATAGTG CAGAACCTCC AGGGGCAAAT GGTACATCAG GCCATATCAC   900
CTAGAACTTT AAATGCATGG GTAAAAGTAG TAGAAGAGAA GGCTTTCAGC CCAGAAGTAA   960
TACCCATGTT TTCAGCATTA TCAGAAGGAG CCACCCCACA AGATTTAAAT ACCATGCTAA  1020
ACACAGTGGG GGGACATCAA GCAGCCATGC AAATGTTAAA AGAGACCATC AATGAGGAAG  1080
CTGCAGAATG GGATAGATTG CATCCAGTGC ATGCAGGGCC TATTGCACCA GGCCAGATGA  1140
GAGAACCAAG GGGAAGTGAC ATAGCAGGAA CTACTAGTAC CCTTCAGGAA CAAATAGGAT  1200
GGATGACACA TAATCCACCT ATCCCAGTAG GAGAAATCTA TAAAAGATGG ATAATCCTGG  1260
GATTAAATAA AATAGTAAGA ATGTATAGCC CTACCAGCAT TCTGGACATA AGACAAGGAC  1320
CAAAGGAACC CTTTAGAGAC TATGTAGACC GATTCTATAA AACTCTAAGA GCCGAGCAAG  1380
CTTCACAAGA GGTAAAAAAT TGGATGACAG AAACCTTGTT GGTCCAAAAT GCGAACCCAG  1440
ATTGTAAGAC TATTTTAAAA GCATTGGGAC CAGGAGCGAC ACTAGAAGAA ATGATGACAG  1500
CATGTCAGGG AGTGGGGGGA CCCGGCCATA AGCAAGAGT TTTGGCTGAA GCAATGAGCC  1560
AAGTAACAAA TCCAGCTACC ATAATGATAC AGAAAGGCAA TTTTAGGAAC CAAAGAAAGA  1620
CTGTTAAGTG TTTCAATTGT GGCAAAGAAG GGCACATAGC CAAAAATTGC AGGGCCCCTA  1680
GGAAAAAGGG CTGTTGGAAA TGTGGAAAGG AAGGACACCA AATGAAAGAT TGTACTGAGA  1740
GACAGGCTAA TTTTTTAGGG AAGATCTGGC CTTCCCACAA GGGAAGGCCA GGGAATTTTC  1800
TTCAGAGCAG ACCAGAGCCA ACAGCCCCAC CAGAAGAGAG CTTCAGGTTT GGGGAAGAGA  1860
CAACAACTCC CTCTCAGAAG CAGGAGCCGA TAGACAAGGA ACTGTATCCT TTAGCTTCCC  1920
TCAGATCACT CTTTGGCAGC GACCCCTCGT CACAATAAAG ATAGGGGGC AATTAAAGGA  1980
AGCTCTATTA GATACAGGAG CAGATGATAC AGTATTAGAA GAAATGAATT TGCCAGGAAG  2040
ATGGAAACCA AAAATGATAG GGGGAATTGG AGGTTTTATC AAAGTAGGAC AGTATGATCA  2100
GATACTCATA GAAATCTGCG GACATAAAGC TATAGGTACA GTATTAGTAG GACCTACACC  2160
TGTCAACATA ATTGGAAGAA ATCTGTTGAC TCAGATTGGC TGCACTTTAA ATTTTCCCAT  2220
```

```
TAGTCCTATT GAGACTGTAC CAGTAAAATT AAAGCCAGGA ATGGATGGCC CAAAAGTTAA      2280

ACAATGGCCA TTGACAGAAG AAAAAATAAA AGCATTAGTA GAAATTTGTA CAGAAATGGA      2340

AAAGGAAGGA AAAATTTCAA AAATTGGGCC TGAAAATCCA TACAATACTC CAGTATTTGC      2400

CATAAAGAAA AAAGACAGTA CTAAATGGAG AAAATTAGTA GATTTCAGAG AACTTAATAA      2460

GAGAACTCAA GATTTCTGGG AAGTTCAATT AGGAATACCA CATCCTGCAG GGTTAAAACA      2520

GAAAAAATCA GTAACAGTAC TGGATGTGGG CGATGCATAT TTTTCAGTTC CCTTAGATAA      2580

AGACTTCAGG AAGTATACTG CATTTACCAT ACCTAGTATA AACAATGAGA CACCAGGGAT      2640

TAGATATCAG TACAATGTGC TTCCACAGGG ATGGAAAGGA TCACCAGCAA TATTCCAGTG      2700

TAGCATGACA AAAATCTTAG AGCCTTTTAG AAAACAAAAT CCAGACATAG TCATCTATCA      2760

ATACATGGAT GATTTGTATG TAGGATCTGA CTTAGAAATA GGGCAGCATA GAACAAAAAT      2820

AGAGGAACTG AGACAACATC TGTTGAGGTG GGGATTTACC ACACCAGACA AAAAACATCA      2880

GAAAGAACCT CCATTCCTTT GGATGGGTTA TGAACTCCAT CCTGATAAAT GGACAGTACA      2940

GCCTATAGTG CTGCCAGAAA AGGACAGCTG GACTGTCAAT GACATACAGA AATTAGTGGG      3000

AAAATTGAAT TGGGCAAGTC AGATTTATGC AGGGATTAAA GTAAGGCAAT TATGTAAACT      3060

TCTTAGGGGA ACCAAAGCAC TAACAGAAGT AGTACCACTA ACAGAAGAAG CAGAGCTAGA      3120

ACTGGCAGAA AACAGGGAGA TTCTAAAAGA ACCGGTACAT GGAGTGTATT ATGACCCATC      3180

AAAAGACTTA ATAGCAGAAA TACAGAAGCA GGGGCAAGGC CAATGGACAT ATCAAATTTA      3240

TCAAGAGCCA TTTAAAAATC TGAAAACAGG AAAATATGCA AGAATGAAGG GTGCCCACAC      3300

TAATGATGTG AAACAATTAA CAGAGGCAGT ACAAAAAATA GCCACAGAAA GCATAGTAAT      3360

ATGGGGAAAG ACTCCTAAAT TTAAATTACC CATACAAAAG GAAACATGGG AAGCATGGTG      3420

GACAGAGTAT TGGCAAGCCA CCTGGATTCC TGAGTGGGAG TTTGTCAATA CCCCTCCCTT      3480

AGTGAAGTTA TGGTACCAGT TAGAGAAAGA ACCCATAATA GGAGCAGAAA CTTTCTATGT      3540

AGATGGGGCA GCCAATAGGG AAACTAAATT AGGAAAAGCA GGATATGTAA CTGACAGAGG      3600

AAGACAAAAA GTTGTCCCCC TAACGGACAC AACAAATCAG AAGACTGAGT TACAAGCAAT      3660

TCATCTAGCT TTGCAGGATT CGGGATTAGA AGTAAACATA GTGACAGACT CACAATATGC      3720

ATTGGGAATC ATTCAAGCAC AACCAGATAA GAGTGAATCA GAGTTAGTCA GTCAAATAAT      3780

AGAGCAGTTA ATAAAAAAGG AAAAAGTCTA CCTGGCATGG GTACCAGCAC ACAAAGGAAT      3840

TGGAGGAAAT GAACAAGTAG ATGGGTTGGT CAGTGCTGGA ATCAGGAAAG TACTATTTTT      3900

AGATGGAATA GATAAGGCCC AAGAAGAACA TGAGAAATAT CACAGTAATT GGAGAGCAAT      3960

GGCTAGTGAT TTTAACCTAC CACCTGTAGT AGCAAAAGAA ATAGTAGCCA GCTGTGATAA      4020

ATGTCAGCTA AAAGGGGAAG CCATGCATGG ACAAGTAGAC TGTAGCCCAG GAATATGGCA      4080

GCTAGATTGT ACACATTTAG AAGGAAAAGT TATCTTGGTA GCAGTTCATG TAGCCAGTGG      4140

ATATATAGAA GCAGAAGTAA TTCCAGCAGA GACAGGGCAA GAAACAGCAT ACTTCCTCTT      4200

AAAATTAGCA GGAAGATGGC CAGTAAAAAC AGTACATACA GACAATGGCA GCAATTTCAC      4260

CAGTACTACA GTTAAGGCCG CCTGTTGGTG GGCGGGGATC AAGCAGGAAT TTGGCATTCC      4320

CTACAATCCC CAAAGTCAAG GAGTAATAGA ATCTATGAAT AAAGAATTAA AGAAAATTAT      4380

AGGACAGGTA AGAGATCAGG CTGAACATCT TAAGACAGCA GTACAAATGG CAGTATTCAT      4440

CCACAATTTT AAAAGAAAAG GGGGGATTGG GGGGTACAGT GCAGGGGAAA GAATAGTAGA      4500

CATAATAGCA ACAGACATAC AAACTAAAGA ATTACAAAAA CAAATTACAA AAATTCAAAA      4560

TTTTCGGGTT TATTACAGGG ACAGCAGAGA TCCAGTTTGG AAAGGACCAG CAAAGCTCCT      4620
```

-continued

```
CTGGAAAGGT GAAGGGGCAG TAGTAATACA AGATAATAGT GACATAAAAG TAGTGCCAAG    4680

AAGAAAAGCA AAGATCATCA GGGATTATGG AAAACAGATG GCAGGTGATG ATTGTGTGGC    4740

AAGTAGACAG GATGAGGATT AACACATGGA AAAGATTAGT AAAACACCAT ATGTATATTT    4800

CAAGGAAAGC TAAGGACTGG TTTTATAGAC ATCACTATGA AAGTACTAAT CCAAAAATAA    4860

GTTCAGAAGT ACACATCCCA CTAGGGGATG CTAAATTAGT AATAACAACA TATTGGGGTC    4920

TGCATACAGG AGAAAGAGAC TGGCATTTGG GTCAGGGAGT CTCCATAGAA TGGAGGAAAA    4980

AGAGATATAG CACACAAGTA GACCCTGACC TAGCAGACCA ACTAATTCAT CTGCACTATT    5040

TTGATTGTTT TTCAGAATCT GCTATAAGAA ATACCATATT AGGACGTATA GTTAGTCCTA    5100

GGTGTGAATA TCAAGCAGGA CATAACAAGG TAGGATCTCT ACAGTACTTG GCACTAGCAG    5160

CATTAATAAA ACCAAAACAG ATAAAGCCAC CTTTGCCTAG TGTTAGGAAA CTGACAGAGG    5220

ACAGATGGAA CAAGCCCCAG AAGACCAAGG GCCACAGAGG GAGCCATACA ATGAATGGAC    5280

ACTAGAGCTT TTAGAGGAAC TTAAGAGTGA AGCTGTTAGA CATTTTCCTA GGATATGGCT    5340

CCATAACTTA GGACAACATA TCTATGAAAC TTACGGGGAT ACTTGGGCAG GAGTGGAAGC    5400

CATAATAAGA ATTCTGCAAC AACTGCTGTT TATCCATTTC AGAATTGGGT GTCGACATAG    5460

CAGAATAGGC GTTACTCGAC AGAGGAGAGC AAGAAATGGA GCCAGTAGAT CCTAGACTAG    5520

AGCCCTGGAA GCATCCAGGA AGTCAGCCTA AAACTGCTTG TACCAATTGC TATTGTAAAA    5580

AGTGTTGCTT TCATTGCCAA GTTTGTTTCA TGACAAAAGC CTTAGGCATC TCCTATGGCA    5640

GGAAGAAGCG GAGACAGCGA CGAAGAGCTC ATCAGAACAG TCAGACTCAT CAAGCTTCTC    5700

TATCAAAGCA GTAAGTAGTA CATGTAATGC AACCTATAAT AGTAGCAATA GTAGCATTAG    5760

TAGTAGCAAT AATAATAGCA ATAGTTGTGT GGTCCATAGT AATCATAGAA TATAGGAAAA    5820

TATTAAGACA AAGAAAAATA GACAGGTTAA TTGATAGACT AATAGAAAGA GCAGAAGACA    5880

GTGGCAATGA GAGTGAAGGA GAAGTATCAG CACTTGTGGA GATGGGGGTG GAAATGGGGC    5940

ACCATGCTCC TTGGGATATT GATGATCTGT AGTGCTACAG AAAAATTGTG GGTCACAGTC    6000

TATTATGGGG TACCTGTGTG GAAGGAAGCA ACCACCACTC TATTTTGTGC ATCAGATGCT    6060

AAAGCATATG ATACAGAGGT ACATAATGTT TGGGCCACAC ATGCCTGTGT ACCCACAGAC    6120

CCCAACCCAC AAGAAGTAGT ATTGGTAAAT GTGACAGAAA ATTTTAACAT GTGGAAAAAT    6180

GACATGGTAG AACAGATGCA TGAGGATATA ATCAGTTTAT GGGATCAAAG CCTAAAGCCA    6240

TGTGTAAAAT TAACCCCACT CTGTGTTAGT TTAAAGTGCA CTGATTTGAA GAATGATACT    6300

AATACCAATA GTAGTAGCGG GAGAATGATA ATGGAGAAAG GAGAGATAAA AAACTGCTCT    6360

TTCAATATCA GCACAAGCAT AAGAGATAAG GTGCAGAAAG AATATGCATT CTTTTATAAA    6420

CTTGATATAG TACCAATAGA TAATACCAGC TATAGGTTGA TAAGTTGTAA CACCTCAGTC    6480

ATTACACAGG CCTGTCCAAA GGTATCCTTT GAGCCAATTC CCATACATTA TTGTGCCCCG    6540

GCTGGTTTTG CGATTCTAAA ATGTAATAAT AAGACGTTCA ATGGAACAGG ACCATGTACA    6600

AATGTCAGCA CAGTACAATG TACACATGGA ATCAGGCCAG TAGTATCAAC TCAACTGCTG    6660

TTAAATGGCA GTCTAGCAGA AGAAGATGTA GTAATTAGAT CTGCCAATTT CACAGACAAT    6720

GCTAAAACCA TAATAGTACA GCTGAACACA TCTGTAGAAA TTAATTGTAC AAGACCCAAC    6780

AACAATACAA GAAAAAGTAT CCGTATCCAG AGGGGACCAG GGAGAGCATT TGTTACAATA    6840

GGAAAAATAG GAAATATGAG ACAAGCACAT TGTAACATTA GTAGAGCAAA ATGGAATGCC    6900

ACTTTAAAAC AGATAGCTAG CAAATTAAGA GAACAATTTG GAAATAATAA AACAATAATC    6960
```

-continued

```
TTTAAGCAAT CCTCAGGAGG GGACCCAGAA ATTGTAACGC ACAGTTTTAA TTGTGGAGGG   7020

GAATTTTTCT ACTGTAATTC AACACAACTG TTTAATAGTA CTTGGTTTAA TAGTACTTGG   7080

AGTACTGAAG GGTCAAATAA CACTGAAGGA AGTGACACAA TCACACTCCC ATGCAGAATA   7140

AAACAATTTA TAAACATGTG GCAGGAAGTA GGAAAAGCAA TGTATGCCCC TCCCATCAGT   7200

GGACAAATTA GATGTTCATC AAATATTACT GGGCTGCTAT TAACAAGAGA TGGTGGTAAT   7260

AACAACAATG GGTCCGAGAT CTTCAGACCT GGAGGAGGCG ATATGAGGGA CAATTGGAGA   7320

AGTGAATTAT ATAAATATAA AGTAGTAAAA ATTGAACCAT TAGGAGTAGC ACCCACCAAG   7380

GCAAAGAGAA GAGTGGTGCA GAGAGAAAAA AGAGCAGTGG GAATAGGAGC TTTGTTCCTT   7440

GGGTTCTTGG GAGCAGCAGG AAGCACTATG GGCGCACGGT CAATGACGCT GACGGTACAG   7500

GCCAGACAAT TATTGTCTGA TATAGTGCAG CAGCAGAACA ATTTGCTGAG GGCTATTGAG   7560

GCGCAACAGC ATCTGTTGCA ACTCACAGTC TGGGGCATCA AACAGCTCCA GGCAAGAATC   7620

CTGGCTGTGG AAAGATACCT AAAGGATCAA CAGCTCCTGG GGATTTGGGG TTGCTCTGGA   7680

AAACTCATTT GCACCACTGC TGTGCCTTGG AATGCTAGTT GGAGTAATAA ATCTCTGGAA   7740

CAGATTTGGA ATAACATGAC CTGGATGGAG TGGGACAGAG AAATTAACAA TTACACAAGC   7800

TTAATACACT CCTTAATTGA AGAATCGCAA AACCAGCAAG AAAAGAATGA ACAAGAATTA   7860

TTGGAATTAG ATAAATGGGC AAGTTTGTGG AATTGGTTTA ACATAACAAA TTGGCTGTGG   7920

TATATAAAAT TATTCATAAT GATAGTAGGA GGCTTGGTAG GTTTAAGAAT AGTTTTTGCT   7980

GTACTTTCTA TAGTGAATAG AGTTAGGCAG GGATATTCAC CATTATCGTT TCAGACCCAC   8040

CTCCCAATCC CGAGGGGACC CGACAGGCCC GAAGGAATAG AAGAAGAAGG TGGAGAGAGA   8100

GACAGAGACA GATCCATTCG ATTAGTGAAC GGATCCTTAG CACTTATCTG GACGATCTG    8160

CGGAGCCTGT GCCTCTTCAG CTACCACCGC TTGAGAGACT TACTCTTGAT TGTAACGAGG   8220

ATTGTGGAAC TTCTGGGACG CAGGGGGTGG GAAGCCCTCA AATATTGGTG GAATCTCCTA   8280

CAGTATTGGA GTCAGGAACT AAAGAATAGT GCTGTTAACT TGCTCAATGC CACAGCCATA   8340

GCAGTAGCTG AGGGGACAGA TAGGGTTATA GAAGTATTAC AAGCAGCTTA TAGAGCTATT   8400

CGCCACATAC CTAGAAGAAT AAGACAGGGC TTGGAAAGGA TTTTGCTATA AGCTTTATAT   8460

ATAGTGTTAT AGTGCGCCAG ATCTCTATAA TCTCGCGCAA CCTATTTTCC CCTCGAACAC   8520

TTTTTAAGCC GTAGATAAAC AGGCTGGGAC ACTTCACATG AGCGAAAAAT ACATCGTCAC   8580

CTGGGACATG TTGCAGATCC ATGCACGTAA ACTCGCAAGC CGACTGATGC CTTCTGAACA   8640

ATGGAAAGGC ATTATTGCCG TAAGCCGTGG CGGTCTGGTA CCGGGTGCGT TACTGGCGCG   8700

TGAACTGGGT ATTCGTCATG TCGATACCGT TTGTATTTCC AGCTACGATC ACGACAACCA   8760

GCGCGAGCTT AAAGTGCTGA AACGCGCAGA AGGCGATGGC GAAGGCTTCA TCGTTATTGA   8820

TGACCTGGTG GATACCGGTG GTACTGCGGT TGCGATTCGT GAAATGTATC CAAAAGCGCA   8880

CTTTGTCACC ATCTTCGCAA AACCGGCTGG TCGTCCGCTG GTTGATGACT ATGTTGTTGA   8940

TATCCCGCAA GATACCTGGA TTGAACAGCC GTGGGATATG GGCGTCGTAT TCGTCCCGCC   9000

AATCTCCGGT CGCTAACTCG AGACTCGAGG CCGGCAAGGC CGGATCCAGA CATGATAAGA   9060

TACATTGATG AGTTTGGACA AACCACAACT AGAATGCAGT GAAAAAAATG CTTTATTTGT   9120

GAAATTTGTG ATGCTATTGC TTTATTTGTA ACCATTATAA GCTGCAATAA ACAAGTTAAC   9180

AACAACAATT GCATTCATTT TATGTTTCAG GTTCAGGGGG AGGTGGGGAG GTTTTTTAAA   9240

GCAAGTAAAA CCTCTACAAA TGTGGTATGG CTGATTATGA TCCGGCTGCC TCGCGCGTTT   9300

CGGTGATGAC GGTGAAAACC TCTGACACAT GCAGCTCCCG GAGACGGTCA CAGCTTGTCT   9360
```

```
GTAAGCGGAT GCCGGGAGCA GACAAGCCCG TCAGGGCGCG TCAGCGGGTG TTGGCGGGTG    9420

TCGGGGCGCA GCCATGACCG GTCGACTGCA GTCTCTGCAG GAATTCGATA TCAAGCTTAT    9480

CGATACCGTC GACCTCGAGG GGGGGCCCGG TACCCAATTC GCCCTATAGT GAGTCGTATT    9540

ACAATTCACT GGCCGTCGTT TTACAACGTC GTGACTGGGA AAACCCTGGC GTTACCCAAC    9600

TTAATCGCCT TGCAGCACAT CCCCCTTTCG CCAGCTGGCG TAATAGCGAA GAGGCCCGCA    9660

CCGATCGCCC TTCCCAACAG TTGCGCAGCC TGAATGGCGA ATGGAAATTG TAAGCGTTAA    9720

TATTTTGTTA AAATTCGCGT TAAATTTTTG TTAAATCAGC TCATTTTTTA ACCAATAGGC    9780

CGAAATCGGC AAAATCCCTT ATAAATCAAA AGAATAGACC GAGATAGGGT TGAGTGTTGT    9840

TCCAGTTTGG AACAAGAGTC CACTATTAAA GAACGTGGAC TCCAACGTCA AAGGGCGAAA    9900

AACCGTCTAT CAGGGCGATG GCCCACTACG TGAACCATCA CCCTAATCAA GTTTTTTGGG    9960

GTCGAGGTGC CGTAAAGCAC TAAATCGGAA CCCTAAAGGG AGCCCCCGAT TTAGAGCTTG   10020

ACGGGGAAAG CCGGCGAACG TGGCGAGAAA GGAAGGGAAG AAAGCGAAAG GAGCGGGCGC   10080

TAGGGCGCTG GCAAGTGTAG CGGTCACGCT GCGCGTAACC ACCACACCCG CCGCGCTTAA   10140

TGCGCCGCTA CAGGGCGCGT CAGGTGGCAC TTTTCGGGGA AATGTGCGCG GAACCCCTAT   10200

TTGTTTATTT TTCTAAATAC ATTCAAATAT GTATCCGCTC ATGAGACAAT AACCCTGATA   10260

AATGCTTCAA TAATATTGAA AAAGGAAGAG TATGAGTATT CAACATTTCC GTGTCGCCCT   10320

TATTCCCTTT TTTGCGGCAT TTTGCCTTCC TGTTTTTGCT CACCCAGAAA CGCTGGTGAA   10380

AGTAAAAGAT GCTGAAGATC AGTTGGGTGC ACGAGTGGGT TACATCGAAC TGGATCTCAA   10440

CAGCGGTAAG ATCCTTGAGA GTTTTCGCCC CGAAGAACGT TTTCCAATGA TGAGCACTTT   10500

TAAAGTTCTG CTATGTGGCG CGGTATTATC CCGTATTGAC GCCGGGCAAG AGCAACTCGG   10560

TCGCCGCATA CACTATTCTC AGAATGACTT GGTTGAGTAC TCACCAGTCA CAGAAAAGCA   10620

TCTTACGGAT GGCATGACAG TAAGAGAATT ATGCAGTGCT GCCATAACCA TGAGTGATAA   10680

CACTGCGGCC AACTTACTTC TGACAACGAT CGGAGGACCG AAGGAGCTAA CCGCTTTTTT   10740

GCACAACATG GGGGATCATG TAACTCGCCT TGATCGTTGG GAACCGGAGC TGAATGAAGC   10800

CATACCAAAC GACGAGCGTG ACACCACGAT GCCTGTAGCA ATGGCAACAA CGTTGCGCAA   10860

ACTATTAACT GGCGAACTAC TTACTCTAGC TTCCCGGCAA CAATTAATAG ACTGGATGGA   10920

GGCGGATAAA GTTGCAGGAC CACTTCTGCG CTCGGCCCTT CCGGCTGGCT GGTTTATTGC   10980

TGATAAATCT GGAGCCGGTG AGCGTGGGTC TCGCGGTATC ATTGCAGCAC TGGGGCCAGA   11040

TGGTAAGCCC TCCCGTATCG TAGTTATCTA CACGACGGGG AGTCAGGCAA CTATGGATGA   11100

ACGAAATAGA CAGATCGCTG AGATAGGTGC CTCACTGATT AAGCATTGGT AACTGTCAGA   11160

CCAAGTTTAC TCATATATAC TTTAGATTGA TTTAAAACTT CATTTTTAAT TTAAAAGGAT   11220

CTAGGTGAAG ATCCTTTTTG ATAATCTCAT GACCAAAATC CCTTAACGTG AGTTTTCGTT   11280

CCACTGAGCG TCAGACCCCG TAGAAAAGAT CAAAGGATCT TCTTGAGATC CTTTTTTTCT   11340

GCGCGTAATC TGCTGCTTGC AAACAAAAAA ACCACCGCTA CCAGCGGTGG TTTGTTTGCC   11400

GGATCAAGAG CTACCAACTC TTTTTCCGAA GGTAACTGGC TTCAGCAGAG CGCAGATACC   11460

AAATACTGTC CTTCTAGTGT AGCCGTAGTT AGGCCACCAC TTCAAGAACT CTGTAGCACC   11520

GCCTACATAC CTCGCTCTGC TAATCCTGTT ACCAGTGGCT GCTGCCAGTG GCGATAAGTC   11580

GTGTCTTACC GGGTTGGACT CAAGACGATA GTTACCGGAT AAGGCGCAGC GGTCGGGCTG   11640

AACGGGGGGT TCGTGCACAC AGCCCAGCTT GGAGCGAACG ACCTACACCG AACTGAGATA   11700
```

```
CCTACAGCGT GAGCTATGAG AAAGCGCCAC GCTTCCCGAA GGGAGAAAGG CGGACAGGTA    11760

TCCGGTAAGC GGCAGGGTCG AACAGGAGA GCGCACGAGG GAGCTTCCAG GGGGAAACGC    11820

CTGGTATCTT TATAGTCCTG TCGGGTTTCG CCACCTCTGA CTTGAGCGTC GATTTTTGTG    11880

ATGCTCGTCA GGGGGGCGGA GCCTATGGAA AAACGCCAGC AACGCGGCCT TTTTACGGTT    11940

CCTGGCCTTT TGCTGGCCTT TTGCTCACAT GTTCTTTCCT GCGTTATCCC CTGATTCTGT    12000

GGATAACCGT ATTACCGCCT TTGAGTGAGC TGATACCGCT CGCCGCAGCC GAACGACCGA    12060

GCGCAGCGAG TCAGTGAGCG AGGAAGCGGA AGAGCGCCCA ATACGCAAAC CGCCTCTCCC    12120

CGCGCGTTGG CCGATTCATT AATGCAGCTG GCACGACAGG TTTCCCGACT GGAAAGCGGG    12180

CAGTGAGCGC AACGCAATTA ATGTGAGTTA GCTCACTCAT TAGGCACCCC AGGCTTTACA    12240

CTTTATGCTT CCGGCTCGTA TGTTGTGTGG AATTGTGAGC GGATAACAAT TTCACACAGG    12300

AAACAGCTAT GACCATGATT ACGCCAAGCT CGAAATTAAC CCTCACTAAA GGGAACAAAA    12360

GCTGGAGCTC CACCGCGGTG GCGGCCGCTC TAGAACTAGT GGATCCCCCG GCTGCAGGA    12420

ATTCGATAAC CTGGCTTATC GAAATTAATA CGACTCACTA TAGGGAGACC GGCAGATTCT    12479

(2) INFORMATION FOR SEQ ID NO: 14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 14:

TAAGAATTCT AGTAGGTTGC TTTCATTGCC                                         30

(2) INFORMATION FOR SEQ ID NO: 15:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 15:

CTTCTCCTTC ACTCTCGAGT GATCACTGTC TTCTGCTCTT TC                            42

(2) INFORMATION FOR SEQ ID NO: 16:

(i) SEQUENCE CHARACTERISTICS:
        (A) LENGTH: 290 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 16:

TATAAGCTTG GTGGCAAGTG GTCAAAAAGT AGTGTGATTG GATGGCCTGC TGTAAGGGAA        60

AGAATGAGAC GAGCTGAGCC AGCAGCAGAT GGGGTGGGAG CAGTATCTCG AGACCTAGAA       120

AAACATGGAG CAATCACAAG TAGCAATACA GCAGCTAACA ATGCTGCTTG TGCCTGGCTA       180

GAAGCACAAG AGGAGGAAGA GGTGGGTTTT CCAGTCACAC CTCAGGTACC TTTAAGACCA       240

ATGACTTACA AGGCAGCTGT AGATCTTAGC CACTTTTTAA AAGAAAAGGG                  290
```

(2) INFORMATION FOR SEQ ID NO: 17:

(i) SEQUENCE CHARACTERISTICS:
        (A) LENGTH: 290 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 17:

```
TATAAGCTTG GTGGCAAGTG GTCAAAAAGT AGTGTGATTG GATGGCCTGC TGTAAGGGAA      60

AGAATGAGAC GAGCTGAGCC AGCAGCAGAT GGGGTGGGAG CAGTATCTCG AGACCTAGAA     120

AAACATGGAG CAATCACAAG TAGCAATACA GCAGCTAACA ATGCTGCTTG TGCCTGGCTA     180

GAAGCACAAG AGGAGGAAGA GGTGGGTTTT CCAGTCACAC CTCAGGTACC TTTAAGACTC     240

TAGATCTAGA AGGCAGCTGT AGATCTTAGC CACTTTTTAA AAGAAAAGGG                290
```

(2) INFORMATION FOR SEQ ID NO: 18:

(i) SEQUENCE CHARACTERISTICS:
        (A) LENGTH: 140 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 18:

```
AGGCGTTACT CGACAGAGGA GAGCAAGAAA TGGAGCCAGT AGATCCTAGA CTATAGGCCT      60

GGAAGCATCC AGGAAGTCAG CCTAAAACTG CTTGTACCAA TTGCTATTGT AAAAAGTGTT     120

GCTTTCATTG CCAAGTTTGT                                                 140
```

(2) INFORMATION FOR SEQ ID NO: 19:

(i) SEQUENCE CHARACTERISTICS:
        (A) LENGTH: 118 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 19:

```
AGGCGTTACT CGACAGAGGA GAGCAAGAAA CGGCGCCTCG CGTAGCTAGC GGCCGCCCGG      60

GATCGATACG CGTACCAATT GCTATTGTAA AAAGTGTTGC TTTCATTGCC AAGTTTGT      118
```

(2) INFORMATION FOR SEQ ID NO: 20:

(i) SEQUENCE CHARACTERISTICS:
        (A) LENGTH: 113 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 20:

```
AAGCTTTGGT CGCCCGGTGG ATCAAGACCG GTAGCCGTCA TAAAGGTGAT TCGTCGGAT       60

CCATGGGTGC GAGAGCGTCG GTATTAAGCG GGGAGAATT AGATAAATGG GAA             113
```

(2) INFORMATION FOR SEQ ID NO: 21:

(i) SEQUENCE CHARACTERISTICS:
    (A) LENGTH: 300 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 21:

```
AAGCTTGCCT TGAGTGCTCA AAGTAGTGTG TGCCCGTCTG TTGTGTGACT CTGGTAACTA    60

GAGATCCCTC AGACCCTTTT AGTCAGTGTG GAAAATCTCT AGCAGTGGCG CCCGAACAGG   120

GACTTGAAAG CGAAAGTAAA GCCAGAGGAG ATCTCTCGAC GCAGGACTCG GCTTGCTGAA   180

GCGCGCACGG CAAGAGGCGA GGGGCGGCGA CTGCAGAGTA CGCCAAAAAT TTTGACTAGC   240

GGAGGCTAGA AGGAGAGAGT AGGGTGCGAG AGCGTCGGTA TTAAGCGGGG GAGAATTAGA   300
```

(2) INFORMATION FOR SEQ ID NO: 22:

(i) SEQUENCE CHARACTERISTICS:
    (A) LENGTH: 14 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 22:

```
YYYYYYYYYY NYAG                                                      14
```

(2) INFORMATION FOR SEQ ID NO: 23:

(i) SEQUENCE CHARACTERISTICS:
    (A) LENGTH: 59 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 23:

```
AGCTTGGTCG CCCGGTGGAT CAAGACCGGT AGCCGTCATA AAGGTGATTT CGTCGGATC     59
```

(2) INFORMATION FOR SEQ ID NO: 24:

(i) SEQUENCE CHARACTERISTICS:
    (A) LENGTH: 59 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 24:

```
ATTCTGGTCG CCCGGTGGAT CAAGCATGGA AGCCGTCATA AAGGTGATTT CGTCCGCGT     59
```

(2) INFORMATION FOR SEQ ID NO: 25:

(i) SEQUENCE CHARACTERISTICS:
    (A) LENGTH: 63 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 25:

```
GGCTTGCTGA GGTGCNCACA GCAAGAGGCG AGAGCGGCGA CTGGTGAGTA CGCCNNAAAT    60
```

```
TTT                                                                        63

(2) INFORMATION FOR SEQ ID NO: 26:

(i) SEQUENCE CHARACTERISTICS:
         (A) LENGTH: 270 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO: 26:

GCCTTGAGNT GCTTNAAGTA GTGTGTGCCC GTCTGNTTNT NTGACTCTGG TAACTAGAGA         60

TCCCTCAGAC CACTNTAGAC TGTGTAAAAA TCTCTAGCAG TGGCGCCCGA ACAGGNNNNN        120

NNNNNNNNNN NGACTCGAAA GCGAAAGTTC CAGAGAAGNT CTCTCGACGC ANGGACTCGG        180

CTTGCTGAGG TGCNCACAGC AAGAGGCGAG AGCGGCGACT GGTGAGTACG CCNNAAATTT        240

TNNGACTAGC GGAGGCTAGA AGGAGAGANA                                         270

(2) INFORMATION FOR SEQ ID NO: 27:

(i) SEQUENCE CHARACTERISTICS:
         (A) LENGTH: 61 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO: 27:

CAAAAACTGT AGCCGAAAGG GCTTGCTATC CTACCTTTAG ACAGGTAGAA GATTGTGGGA         60

G                                                                        61

(2) INFORMATION FOR SEQ ID NO: 28:

(i) SEQUENCE CHARACTERISTICS:
         (A) LENGTH: 111 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO: 28:

ACGGCGTGAG GAGCGGGAGA GGAAGAGGCC TCCGGTTGCA GGTAAGTGCA ACACAAAAAA         60

GAAATAGCTG TCTTTTATCC AGGAAGGGGT AATAAGATAG AGTGGGAGAT G                111

(2) INFORMATION FOR SEQ ID NO: 29:

(i) SEQUENCE CHARACTERISTICS:
         (A) LENGTH: 44 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO: 29:

GAATTGGGTG TCGACATAGC GGCCGCTTGT ACCAATTGCT ATTG                          44

(2) INFORMATION FOR SEQ ID NO: 30:

(i) SEQUENCE CHARACTERISTICS:
```

(A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 30:

GGTACAAGCA GTTTAAGGCT AACTTCCTGG ATGCTTCC                                38

(2) INFORMATION FOR SEQ ID NO: 31:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 31:

CGACAGAGGA GAGCAAGAAA CGGCGCCTCG CGTAGCTAGC GG                           42

(2) INFORMATION FOR SEQ ID NO: 32:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 32:

GTTAATTGAT AGACTAGTCT AATATGGGGT ACCTG                                   35

(2) INFORMATION FOR SEQ ID NO: 33:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 33:

CCTAGGAAAA TGTCTAACTA GTTCACTCTT AAGTTCCTC                               39

(2) INFORMATION FOR SEQ ID NO: 34:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 34:

TTTCTAGACC ACCATGAGCC GCCTGCCCGT CC                                      32

(2) INFORMATION FOR SEQ ID NO: 35:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 35:

AAGGATCCCT AAAAGATCGC GAGGCTC                                    27

(2) INFORMATION FOR SEQ ID NO: 36:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 36:

TTTCTAGACC ACCATGAAGA AGACACAAAC TTG                             33

(2) INFORMATION FOR SEQ ID NO: 37:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 37:

AAGGATCCTT ACACTTCTTG AAACTC                                     26

(2) INFORMATION FOR SEQ ID NO: 38:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 38:

TTTCTAGACC ACCATGACAG TGCTGGCGCC AG                              32

(2) INFORMATION FOR SEQ ID NO: 39:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 39:

AAGGATCCTC AGTGCTCCAC AAGCAGC                                    27

(2) INFORMATION FOR SEQ ID NO: 40:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 40:

CTCTCGCACC GGTCTCTCTC CTTC                                24

(2) INFORMATION FOR SEQ ID NO: 41:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 41:

CTCTCGCACC CTACTCTCTC CTTC                                24

(2) INFORMATION FOR SEQ ID NO: 42:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 42:

GGCGGCGACT GCAGAGTACG CCAA                                24

(2) INFORMATION FOR SEQ ID NO: 43:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 43:

GGCGGCGACT GGGGAGTACG CCAA                                24

(2) INFORMATION FOR SEQ ID NO: 44:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 44:

CTCCAGGTCT GAAGATCTTT GACCCTTCAG TACTC                    35

(2) INFORMATION FOR SEQ ID NO: 45:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 45:

CTCCAGGTCT GAAGATCTAC TAGTAGTTCC TGCTATG                  37

(2) INFORMATION FOR SEQ ID NO: 46:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 46:

CTCCAGGTCT GAAGATCTGC CTTCTCTTCT ACTACT                        36

(2) INFORMATION FOR SEQ ID NO: 47:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 47:

CTCCAGGTCT GAAGATCTGA GGACTGCTAT TGTATT                        36

(2) INFORMATION FOR SEQ ID NO: 48:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 48:

CTCCAGGTCT GAAGATCTCT AATTCTCCCC CGCTT                         35

(2) INFORMATION FOR SEQ ID NO: 49:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 49:

AACCCCAAAT CCCCATTCCC ACTGCTCTTT TT                            32

(2) INFORMATION FOR SEQ ID NO: 50:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 50:

CTCTCGCACC CTACTCTCTC CTTC                                     24

(2) INFORMATION FOR SEQ ID NO: 51:

(i) SEQUENCE CHARACTERISTICS:
        (A) LENGTH: 24 base pairs (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 51:

GGCGGCGACT GCAGAGTACG CCAA                                              24

(2) INFORMATION FOR SEQ ID NO: 52:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 52:

GTCTAACCAG AGAGACCCTG GGAGTGAATT AGCCCTTC                                38

(2) INFORMATION FOR SEQ ID NO: 53:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 53:

GTCTAACCAG AGAGACCCCA GGGAAGTAGC CTTGTG                                  36

(2) INFORMATION FOR SEQ ID NO: 54:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 54:

CCAGTACAGG CAAAAAGCTG GGAGTGAATT AGCCCTTC                                38

(2) INFORMATION FOR SEQ ID NO: 55:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 55:

CCAGTACAGG CAAAAAGCCA GGGAAGTAGC CTTGTG                                  36

(2) INFORMATION FOR SEQ ID NO: 56:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 56:

GTCTAACCAG AGAGACCCTG GGAGTGAATT AGCCCTTC                          38

(2) INFORMATION FOR SEQ ID NO: 57:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 57:

ATAGAACTCC GTTCTCC                                                 17

(2) INFORMATION FOR SEQ ID NO: 58:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 58:

GGGACTTTCC                                                         10

(2) INFORMATION FOR SEQ ID NO: 59:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 59:

GCCACTTTAA AACAGATAGC TAGCAAATTA AGA                               33

(2) INFORMATION FOR SEQ ID NO: 60:

(i) SEQUENCE CHARACTERISTICS:
            (A) LENGTH: 140 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 60:

AGGCGTTACT CGACAGAGGA GAGCAAGAAA TGGAGCCAGT AGATCCTAGA CTAGAGCCCT   60

GGAAGCATCC AGGAAGTCAG CCTAAAACTG CTTGTACCAA TTGCTATTGT AAAAAGTGTT  120

GCTTTCATTG CCAAGTTTGT                                             140

(2) INFORMATION FOR SEQ ID NO: 61:

(i) SEQUENCE CHARACTERISTICS:
            (A) LENGTH: 140 base pairs
            (B) TYPE: nucleic acid
            (C) STRANDEDNESS: single
            (D) TOPOLOGY: linear -continued

```
    (ii) MOLECULE TYPE: cDNA (xi) SEQUENCE DESCRIPTION: SEQ ID NO: 61:

TATAAGATGG GTGGCAAGTG GTCAAAAAGT AGTGTGATTG GATGGCCTGC TGTAAGGGAA         60

AGAATGAGAC CTCAGGTACC TTTAAGACCA ATGACTTACA AGGCAGCTGT AGATCTTAGC        120

CACTTTTTAA AAGAAAAGGG                                                   140

(2) INFORMATION FOR SEQ ID NO: 62:

(i) SEQUENCE CHARACTERISTICS:
        (A) LENGTH: 310 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 62:

AAGCTTGCCT TGAGTGCTCA AAGTAGTGTG TGCCCGTCTG TTGTGTGACT CTGGTAACTA         60

GAGATCCCTC AGACCCTTTT AGTCAGTGTG GAAAATCTCT AGCAGTGGCG CCCGAACAGG        120

GACTTGAAAG CGAAAGTAAA GCCAGAGGAG ATCTCTCGAC GCAGGACTCG GCTTGCTGAA        180

GCGCGCACGG CAAGAGGCGA GGGGCGGCGA CTGGTGAGTA CGCCAAAAAT TTTGACTAGC        240

GGAGGCTAGA AGGAGAGAGA TGGGTGCGAG AGCGTCGGTA TTAAGCGGGG GAGAATTAGA        300

TAAATGGGAA                                                              310
```